(12) United States Patent
Manning et al.

(10) Patent No.: US 10,793,514 B2
(45) Date of Patent: Oct. 6, 2020

(54) GLUTAMINE TRANSPORT INHIBITORS AND METHODS FOR TREATING CANCER

(71) Applicant: Vanderbilt University, Nashville, TN (US)

(72) Inventors: H. Charles Manning, Franklin, TN (US); Michael Schulte, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/435,169

(22) Filed: Jun. 7, 2019

(65) Prior Publication Data

US 2020/0095190 A1   Mar. 26, 2020

Related U.S. Application Data

(63) Continuation-in-part of application No. PCT/US2017/065641, filed on Dec. 11, 2017.

(60) Provisional application No. 62/432,198, filed on Dec. 9, 2016, provisional application No. 62/596,021, filed on Dec. 7, 2017.

(51) Int. Cl.
| | |
|---|---|
| *C07C 229/26* | (2006.01) |
| *A61P 35/00* | (2006.01) |
| *C07D 207/16* | (2006.01) |
| *C07D 211/60* | (2006.01) |
| *C07D 401/12* | (2006.01) |

(52) U.S. Cl.
CPC ............ *C07C 229/26* (2013.01); *A61P 35/00* (2018.01); *C07D 207/16* (2013.01); *C07D 211/60* (2013.01); *C07D 401/12* (2013.01)

(58) Field of Classification Search
CPC ..... C07C 229/26; A61P 35/00; C07D 207/16; C07D 211/60; C07D 401/12
See application file for complete search history.

(56) References Cited

FOREIGN PATENT DOCUMENTS

WO   WO2007/017093 A1 *   2/2007

* cited by examiner

*Primary Examiner* — Timothy R Rozof
(74) *Attorney, Agent, or Firm* — Stites & Harbison PLLC; Richard S. Myers, Jr.

(57) ABSTRACT

The present disclosure provides compounds of formula:

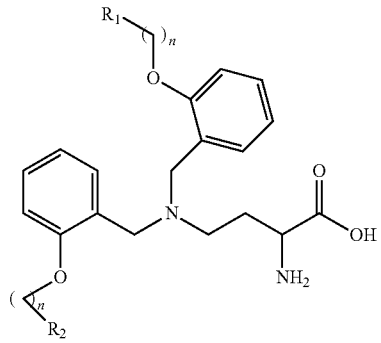

wherein $R_1$, $R_2$, and n are defined as set forth in the specification, and related aminobutanoic acids. The present disclosure also provides compositions comprising these compounds and methods for modulating ASCT2 function in a patient in need thereof.

20 Claims, 27 Drawing Sheets

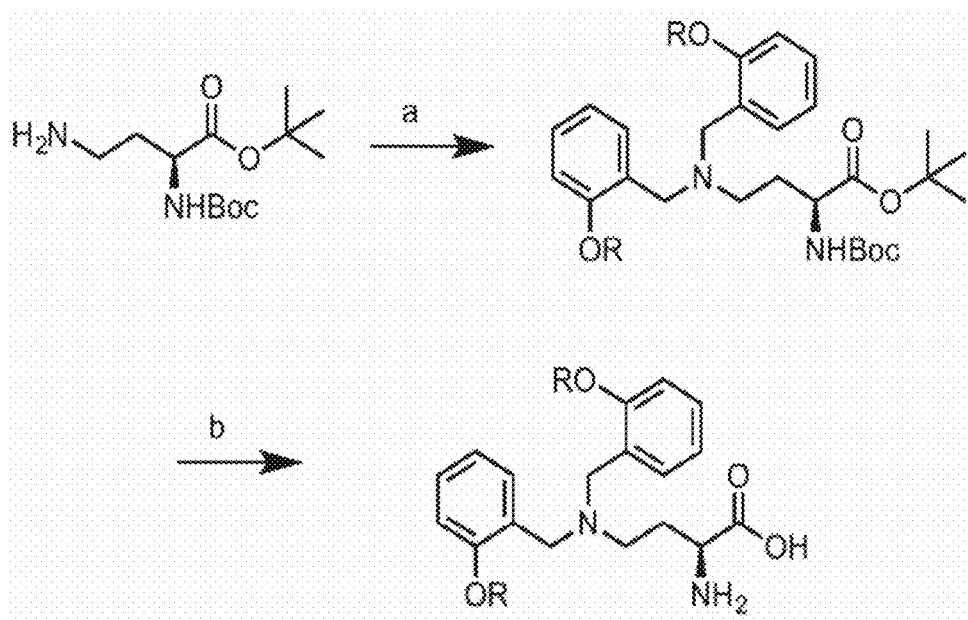
Figure 1
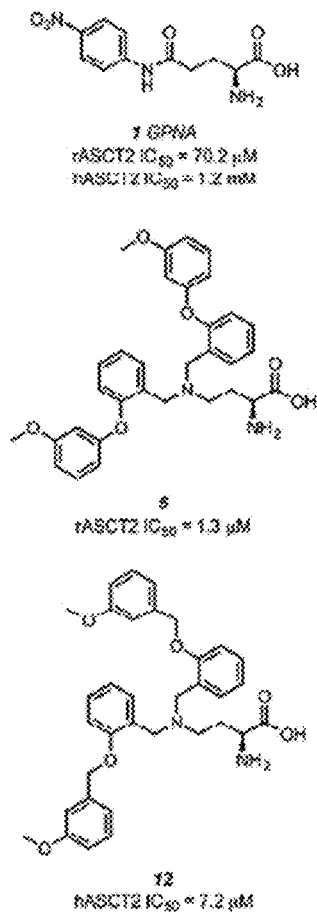 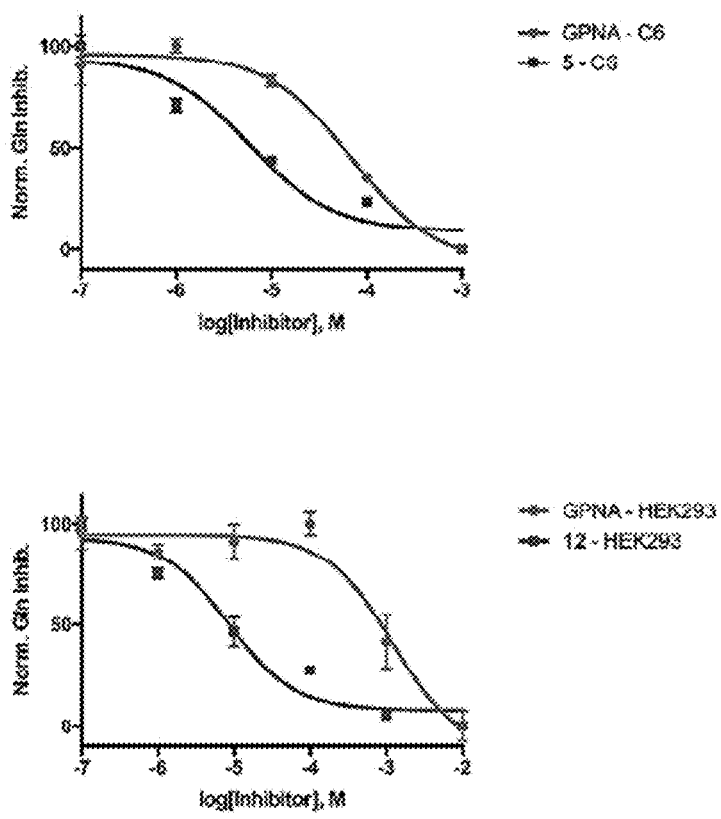
Figure 2

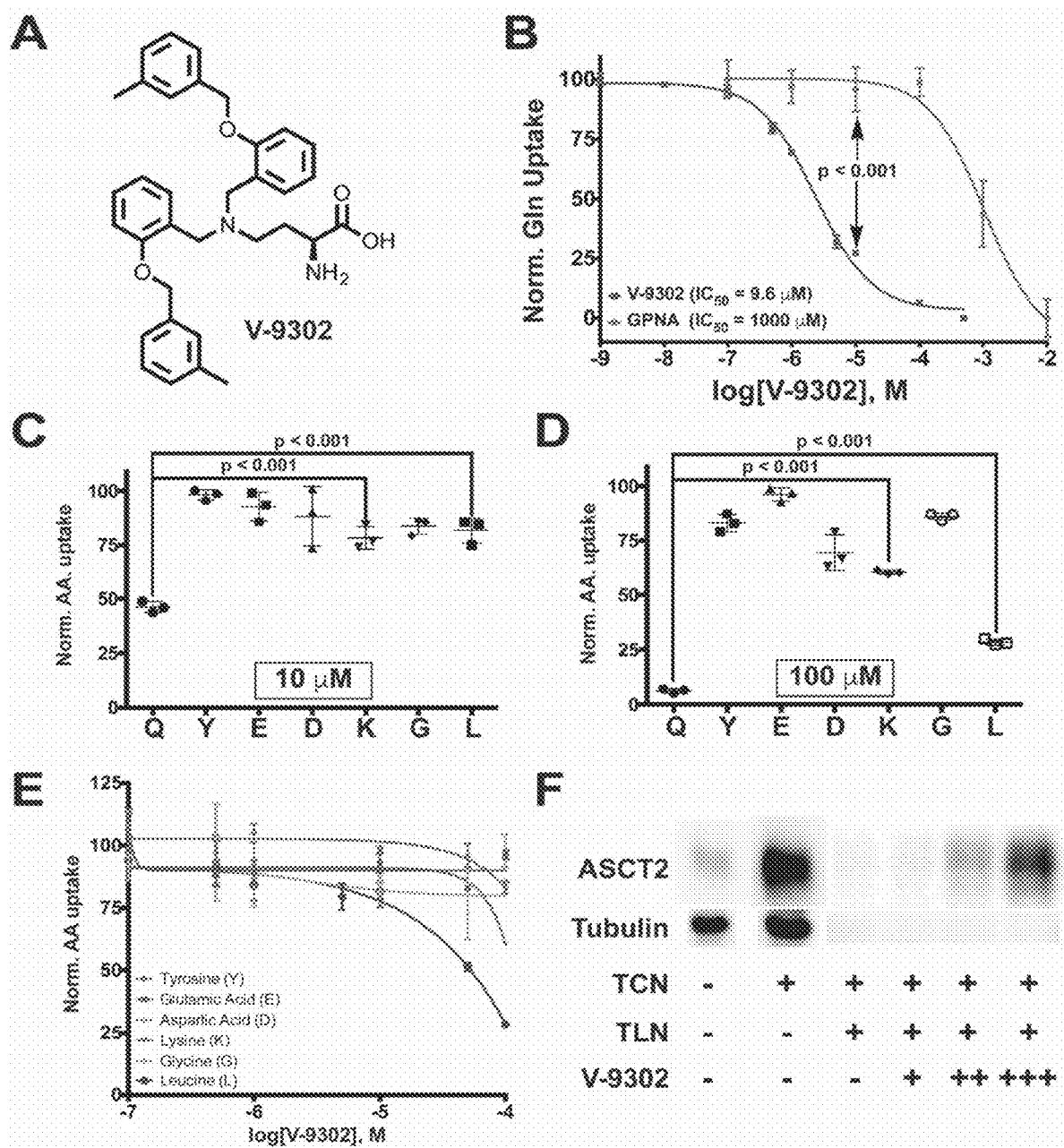
Figure 3A-F

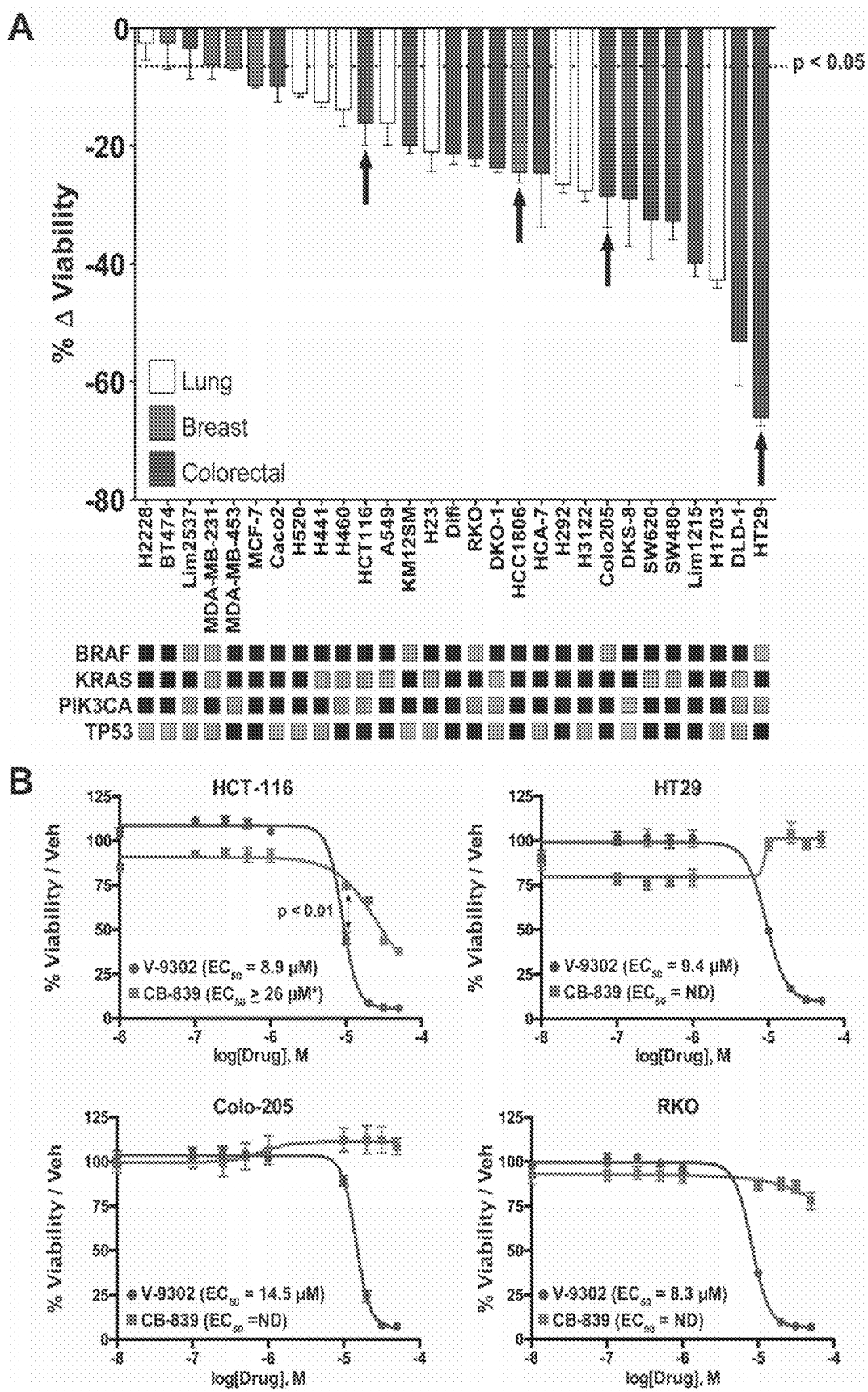
Figure 5A-B

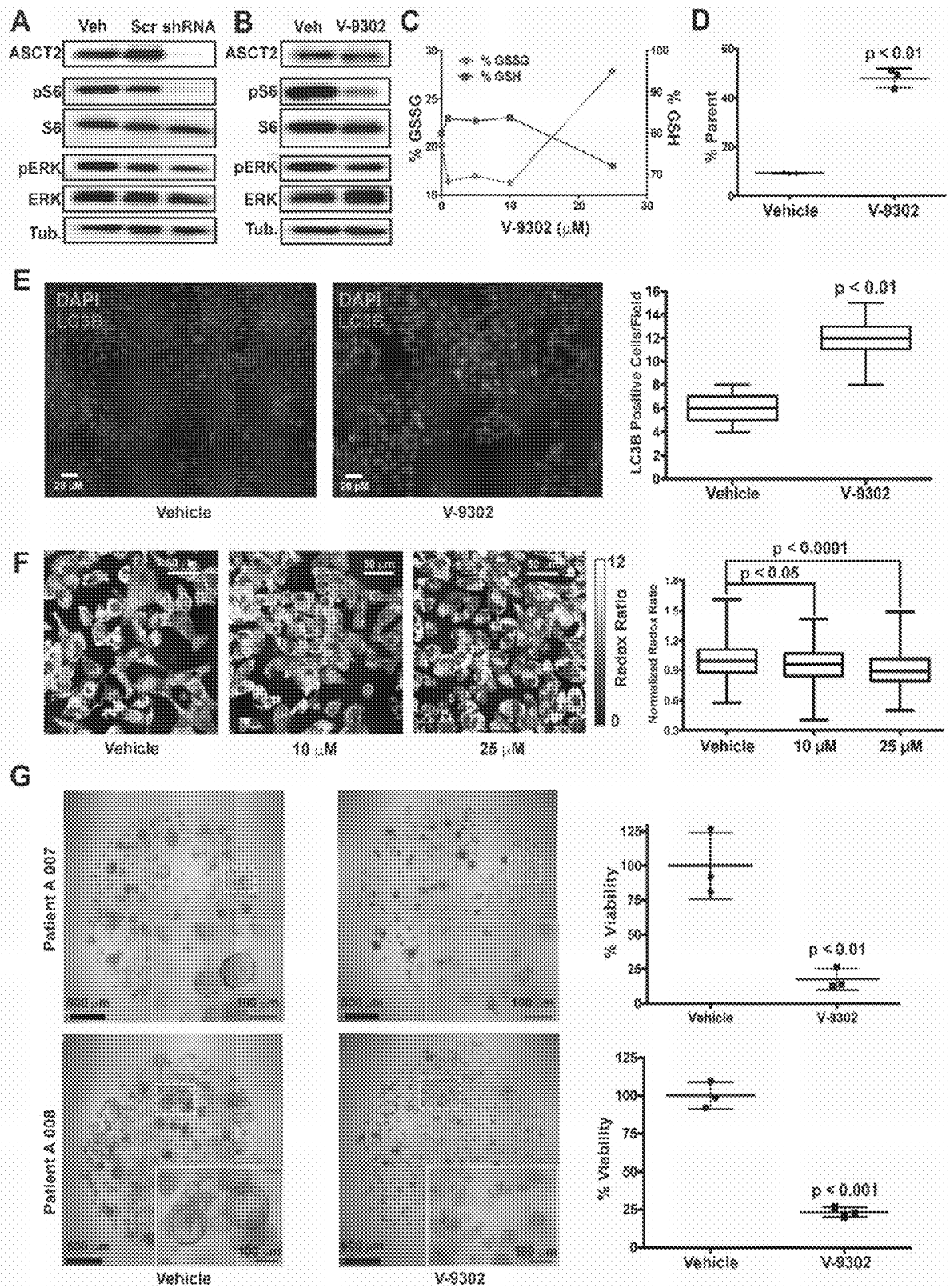
Figure 6A-G

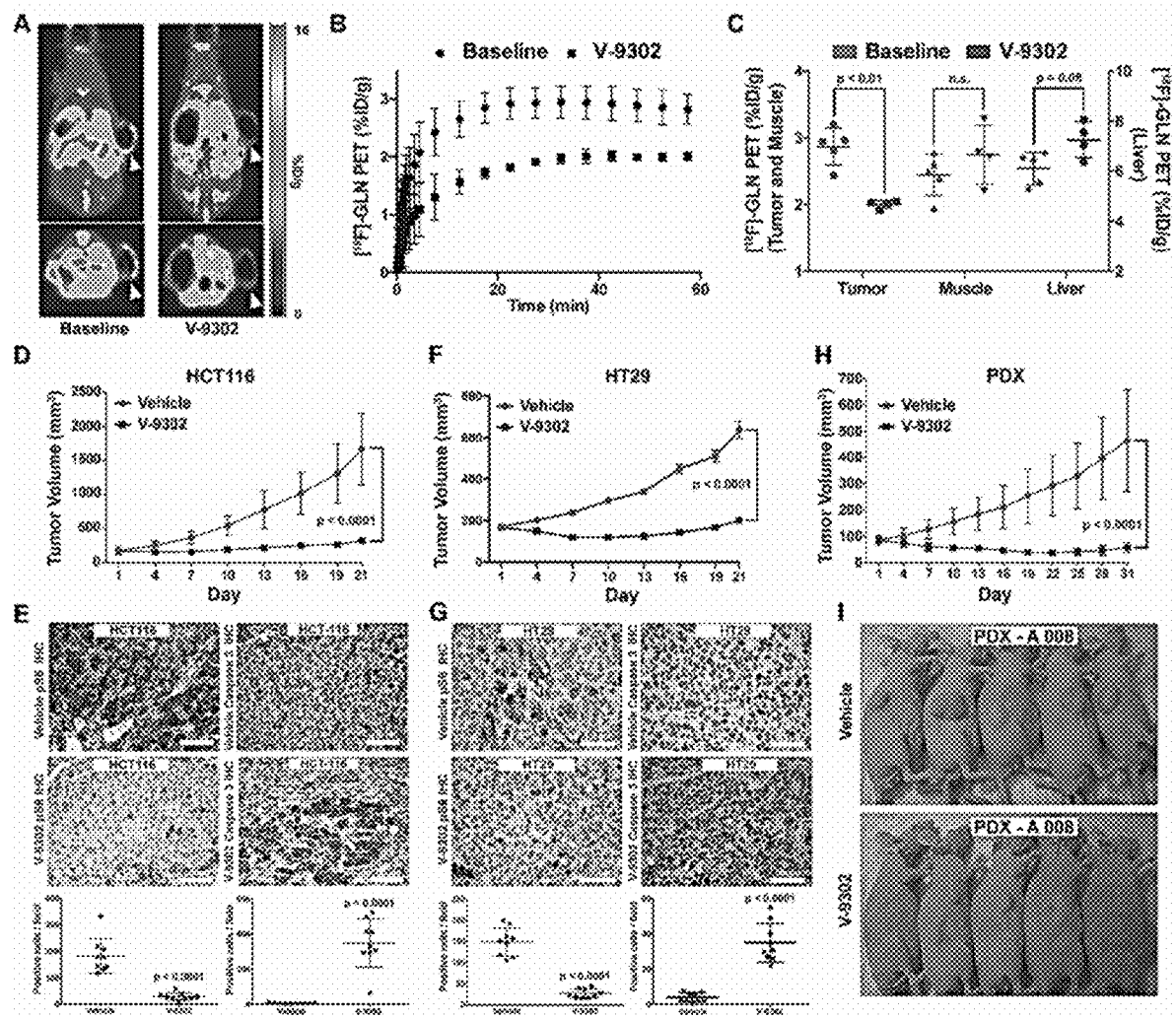
Figure 7A-I.

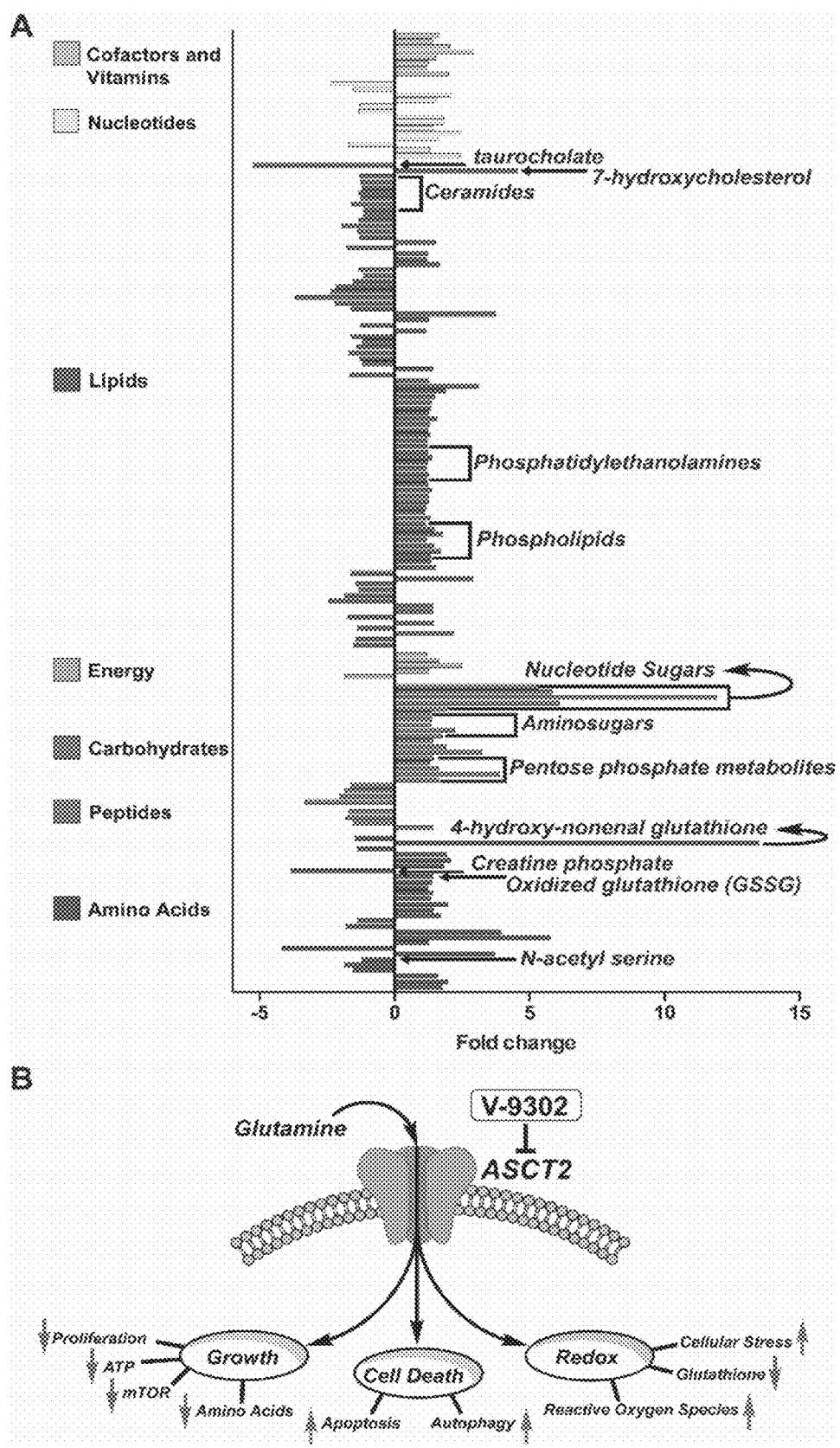
Figure 8A-B

| Gene | Protein | Substrates |
|---|---|---|
| SLC1A5 | ASCT2 | A,N,C,G,M,S,T,V |
| SLC1A3 | EAAT1 | D,E |
| SLC1A2 | EAAT2 | D,E |
| SLC1A1 | EAAT3 | D,C,E |
| SLC1A6 | EAAT4 | D,E |
| SLC1A7 | EAAT5 | D,E |
| SLC7A5 | LAT1 | H,I,M,F,W,V |
| SLC7A8 | LAT2 | A,N,C,H,I,M,F,S,T,W,V |
| SLC7A11 | xCT | E |
| SLC6A9 | GlyT1 | G |
| SLC6A5 | GlyT2 | G |
| SLC38A1 | SNAT1 | A,N,C,H,M,P,S,T,V |
| SLC38A2 | SNAT2 | A,N,M,F,P,S,T |
| SLC38A4 | SNAT4 | A,R,N,H,F,P,S |
| SLC38A3 | SNAT3 | A,N,H |
| SLC38A5 | SNAT5 | A,N,H,S |

Figure 9

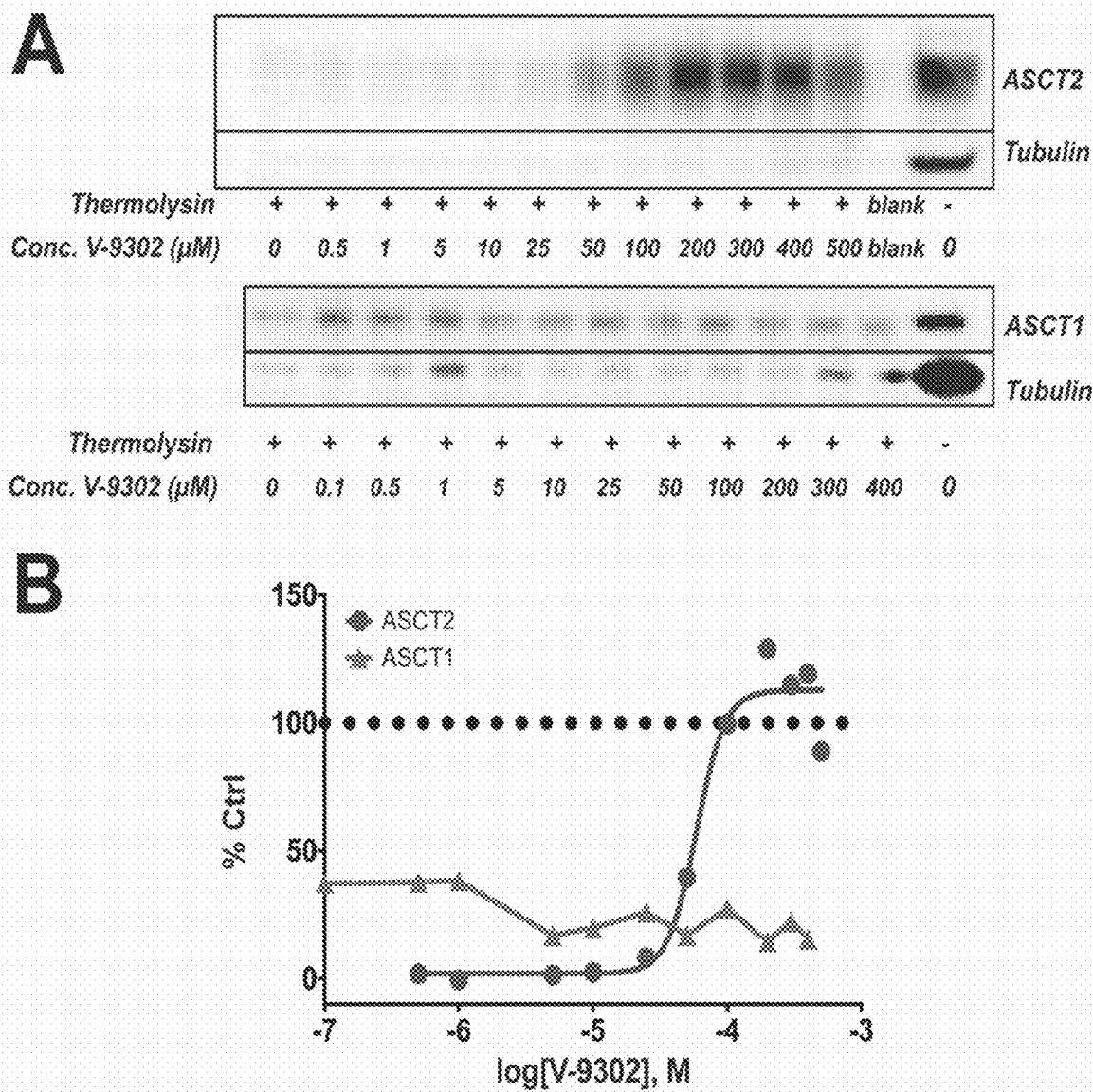
Figure 10A-B

| Cell Line | Cancer Type | Select Mutations | % Δ Viability Rel. Veh. | +/- SD |
|---|---|---|---|---|
| H2228 | Lung | TP53 | -2.46 | 5.08 |
| BT474 | Breast | TP53 | -2.51 | 6.29 |
| Lim2537 | Colorectal | BRAF, PIK3CA, TP53 | -3.38 | 9.08 |
| MDA-MB-231 | Breast | BRAF, KRAS, TP53 | -6.20 | 4.24 |
| MDA-MB-453 | Breast | PIK3CA | -6.78 | 0.69 |
| MCF-7 | Breast | | -9.79 | 0.56 |
| Caco-2 | Colorectal | TP53 | -9.92 | 4.60 |
| H520 | Lung | TP53 | -11.01 | 1.19 |
| H441 | Lung | KRAS, TP53 | -12.62 | 1.35 |
| H460 | Lung | KRAS, PIK3CA | -13.81 | 4.97 |
| HCT-116 | Colorectal | KRAS, PIK3CA | -16.06 | 6.63 |
| A549 | Lung | KRAS | -16.06 | 6.50 |
| KM12SM | Colorectal | BRAF, TP53 | -19.91 | 2.39 |
| H23 | Lung | KRAS, TP53 | -21.00 | 5.80 |
| DiFi | Colorectal | | -21.34 | 3.13 |
| RKO | Colorectal | BRAF, PIK3CA | -22.16 | 2.13 |
| DKO-1 | Colorectal | KRAS, PIK3CA, TP53 | -23.73 | 0.79 |
| HCC1806 | Breast | | -24.44 | 3.13 |
| HCA-7 | Colorectal | TP53 | -24.58 | 16.0 |
| H292 | Lung | | -26.50 | 2.46 |
| H3122 | Lung | TP53 | -27.60 | 3.05 |
| Colo-205 | Colorectal | BRAF | -28.57 | 9.12 |
| DKS-8 | Colorectal | PIK3CA, TP53 | -28.92 | 8.02 |
| SW620 | Colorectal | KRAS | -32.46 | 11.6 |
| SW480 | Colorectal | KRAS | -32.80 | 5.35 |
| Lim1215 | Colorectal | | -39.81 | 4.02 |
| H1703 | Lung | TP53 | -42.79 | 2.34 |
| DLD-1 | Colorectal | KRAS, PIK3CA, TP53 | -53.09 | 13.08 |
| HT29 | Colorectal | BRAF, PIK3CA | -66.09 | 2.42 |

Fig. 11

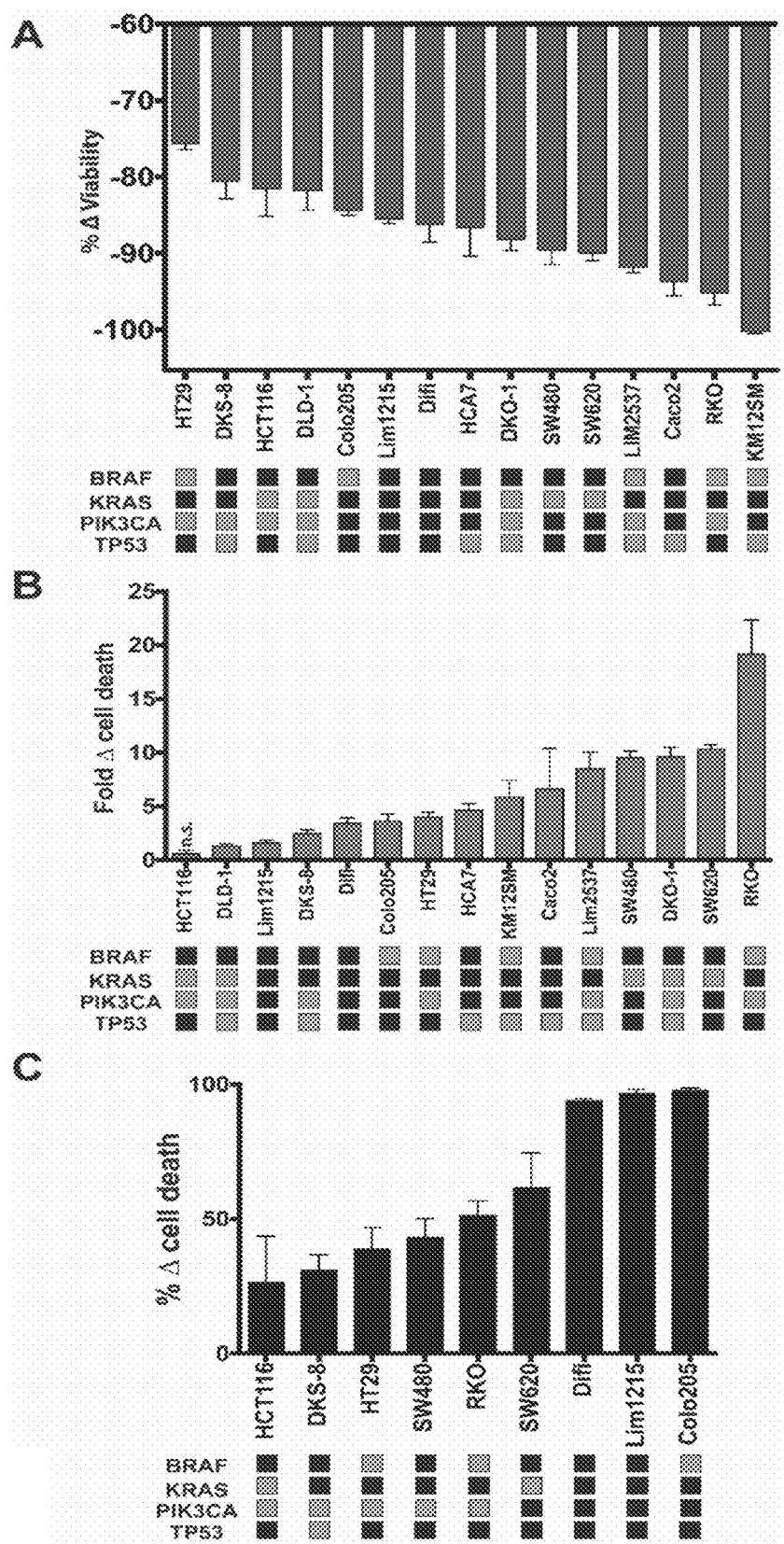
Figure 12A-C

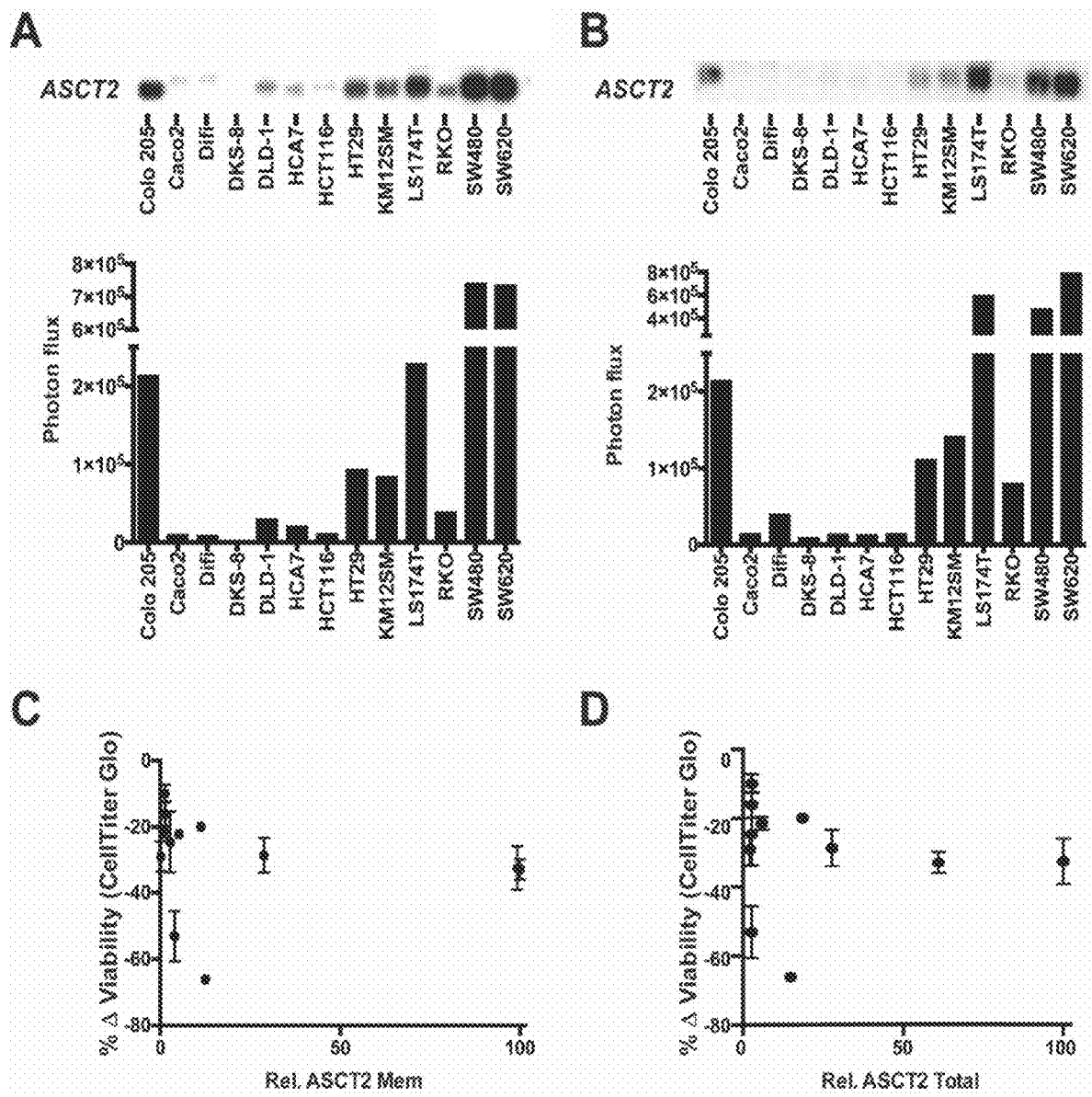
Figure 13A-D

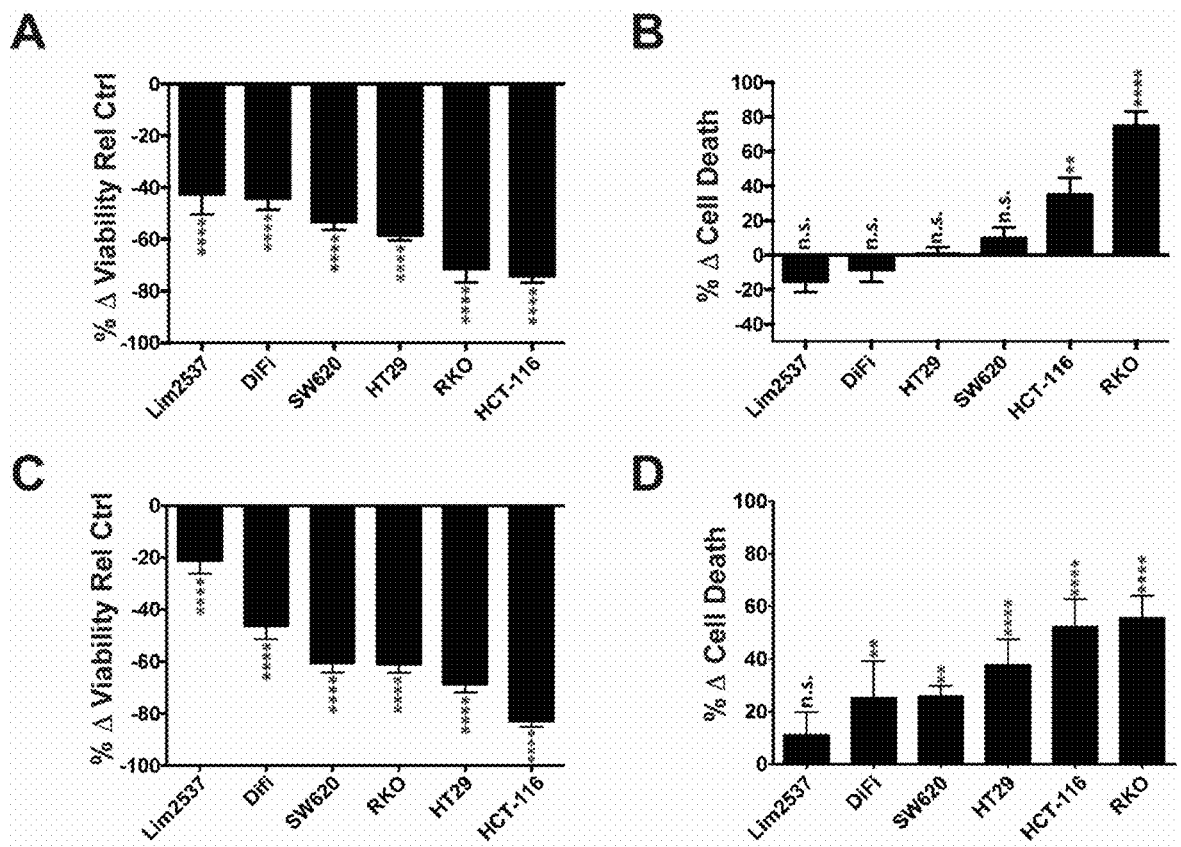
Figure 14A-D
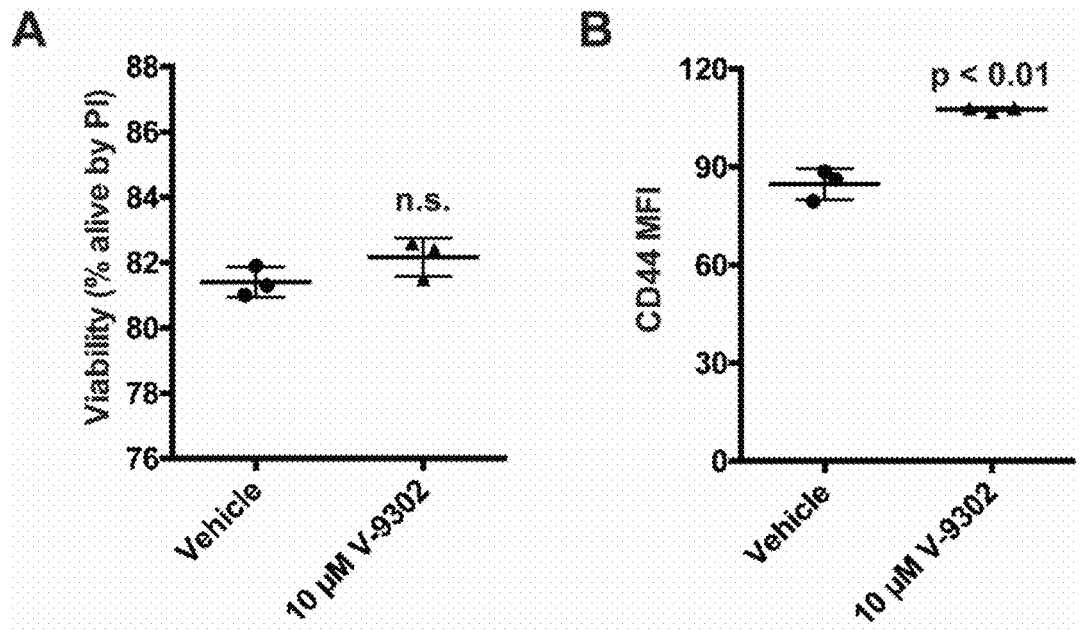
Figure 15A-B

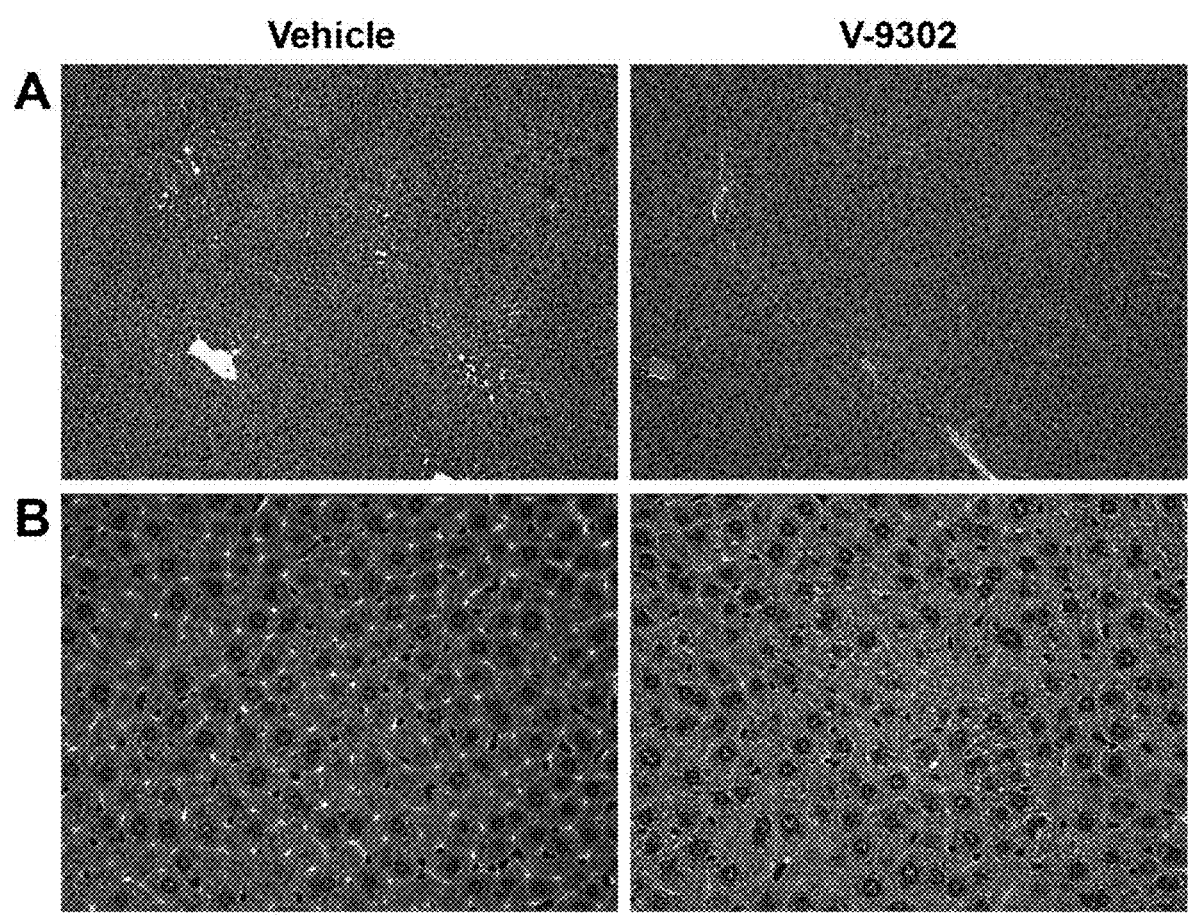
Fig. 28A-B

GLUTAMINE TRANSPORT INHIBITORS AND METHODS FOR TREATING CANCER

GOVERNMENT SUPPORT

This invention was made with government support under grant numbers P30CA068485, P50CA095103, and P30DK058404 awarded by the National Institutes of Health. The government has certain rights in the invention.

BACKGROUND OF THE INVENTION

Healthy mammalian cells sequester the amino acid glutamine through an evolutionarily redundant family of cell-surface transporters known as the solute carrier family of proteins (SLC). The alanine-serine-cysteine transporter, type-2 (ASCT2, gene symbol SLC1A5), is a sodium-dependent solute carrier protein responsible for the import of neutral amino acids and is the primary transporter of glutamine in cancer cells. Elevated ASCT2 levels have been linked to poor survival in many human cancers, including those of the lung, breast, and colon. Furthermore, several studies have attributed signal transduction and oncogene expression with increased demand for glutamine. For example, MYC is responsible for transcribing the machinery of glutaminolysis, including SLC1A5, while a link has also been established between oncogenic RAS and glutamine dependency.

The critical role of glutamine in cancer cell growth and homeostasis suggests the potential of novel therapies targeting glutamine metabolism; however, efforts thus far have been met with limited success. One strategy currently being evaluated in early phase clinical trials targets mitochondrial glutaminase (GLS1; CB-839 (Calithera Biosciences)), an enzyme responsible for converting glutamine to glutamate. While promising, a limitation of this strategy is that targeting GLS1 does not fully address extra-mitochondrial roles of glutamine, which include RAS-independent activation of MAPK signaling. The present inventors have shown that antagonizing cell-surface glutamine transport, which abrogates multiple facets of glutamine metabolism, may represent a more efficacious approach. Prior genetic studies silencing ASCT2 in cancer cells resulted in dramatic anti-tumor effects.

However, to date few compounds that target ASCT2 have been reported and most are derivatives of endogenous ASCT2 substrates. As an early entrant to the field, in 2004 Esslinger and co-workers described a series of glutamine analogs that explored pKa effects on the amide NH bond to probe the ASCT2 amino acid binding site through the addition of electron-donating and electron-withdrawing aryl groups to the terminal amide of glutamine. L-γ-glutamyl-p-nitroanilide (GPNA), exhibited modest potency in the low millimolar range and no observations were made regarding steric requirements for binding to ASCT2. The present inventors were able to expand upon this class of inhibitors by exploring the steric requirements for binding to ASCT2 and found that while SAR was flat, 2-substituted glutamylanilides were preferred. The present inventors described N-(2-(morpholinomethyl)phenyl)-L-glutamine as a novel glutamyl-anilide with three-fold improved activity against ASCT2 compared to GPNA. In 2011, Albers et al. described a series of ASCT2 inhibitors based on the ASCT2 substrate serine. Using an in silico approach along with experimental validation, they found that side chain aromaticity was required for high-affinity interaction. This lead to the discovery of O-(4-phenylbenzoyl)-L-serine, an inhibitor of ASCT2 with an apparent affinity of 30 μM. In 2012, Oppedisano et al. identified the first small molecule lacking an amino acid that blocked glutamine uptake in ASCT2 reconstituted in proteoliposomes. This series of 1,2,3-dithiazoles likely inhibited uptake of glutamine non-competitively through formation of mixed sulfides at Cys-207 or Cys-210 with the most potent compound exhibiting an $IC_{50}$ of 3.7 μM.

Towards this end, the present inventors have developed the first small molecule antagonist of a glutamine transporter evaluated its use in the setting of oncology.

SUMMARY OF THE INVENTION

The unique metabolic demands of cancer cells underscore potentially fruitful opportunities for drug discovery. Surprisingly, however, therapeutic targeting of cancer metabolism remains largely unexplored. The neutral amino acid glutamine serves as a key intermediate in numerous metabolic processes leveraged by cancer cells including biosynthesis, cell signaling, and oxidative protection.

The present invention includes a novel strategy to block transmembrane glutamine flux. Compounds of the present invention include competitive antagonists of glutamine transport, and are the first selective and potent small molecule inhibitor of the amino acid transporter ASCT2 (SLC1A5). Widely-expressed in numerous solid tumors, ASCT2 activity has been previously associated with oncogenic MYC and KRAS. Representing a new class of targeted therapy, the present invention demonstrates the utility of a pharmacological inhibitor of glutamine transport in oncology.

Embodiments of the present invention include 2-amino-4-bis(aryloxybenzyl)aminobutanoic acids, novel inhibitors of ASCT2-mediated glutamine transport.

In one aspect of the present invention, the inhibitor is the following compound:

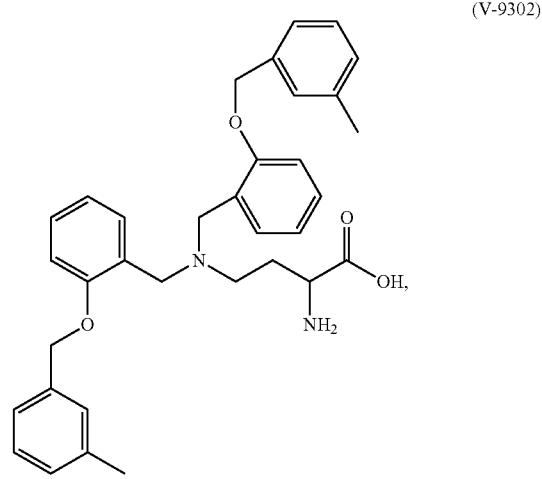 [SMILES: Cc1cccc(COc2ccccc2CN(CCC(N)C(=O)O)Cc2ccccc2OCc2cccc(C)c2)c1]

(V-9302)

and pharmaceutically acceptable salts and pharmaceutically acceptable derivatives thereof.

The 2-amino-4-bis(aryloxybenzyl)aminobutanoic acids compounds of the present invention are novel inhibitors of ASCT2(SLC1A5)-mediated glutamine accumulation in mammalian cells. Embodiments of the present invention exhibit significantly improve potency compared with prior art in C6 (rat) and HEK293 (human) cells. The potency of embodiments of the present invention represent a superior and unexpected improvement over previously reported inhibitors and represents potent pharmacological inhibitors of ASCT2-mediated glutamine accumulation in live cells. These and other compounds in this novel series exhibit tractable chemical properties for further development as potential therapeutic leads.

Thus, embodiments of the present invention include compounds disclosed herein. The present invention also includes pharmaceutical compounds that comprise compounds of the present invention.

Other embodiments of the present invention include methods of modulating and/or inhibiting ASCT2-mediated glutamine accumulation in a patient in need thereof.

Other embodiments include methods of modulating angiogenesis, tumor progression, and/or metastasis, comprising the step of administering to a tissue or a subject associated with a disease condition a therapeutically effective amount of a compound of the present invention. In certain embodiments, said modulating inhibits angiogenesis, tumor progression, and/or metastasis. Also, in certain embodiments, said inhibiting involves inhibiting cellular glutamine uptake via ASCT2.

Other embodiments of the present invention include methods of treating cancers that overexpress ASCT2, including cancers of the lung, pancreas, breast, liver, colon, prostate as well as many leukemias. In embodiments of the invention, a companion imaging probe could allow for improved diagnosis of these diseases and serve as a marker to track therapeutic response. The compounds of the present invention can be used as chemotherapeutic agents alone or in combination with other chemotherapeutic agents to treat various human or mammalian tumors or cancers.

The present invention also includes methods for sensitizing cancer treatment.

The present invention also includes methods of treating microbial infection.

The present invention also includes methods of treating ischemia-related central nervous system injury.

The present invention also includes methods of medical imaging. Thus, embodiments of the present invention include a compound described herein and an imaging agent coupled thereto. In certain embodiments, the imaging agent is a radionuclide.

BRIEF DESCRIPTION OF THE FIGURES

FIG. 1 shows a two-step synthesis of 2-amino-4-bis (aryloxybenzyl)-aminobutanoic acids. Reagents and conditions: a) RCHO, NaBH(OAc)$_3$, CH$_2$Cl$_2$, RT, 12 h. b) HCl, dioxane, 40° C., 5 h.

FIG. 2 shows structures and activities of examples of compounds of the present invention in C6 cells (compound 5) and HEK293 cells (compound 12).

FIG. 3A-F shows aspects of the present invention, including the embodiment V-9302, an inhibitor of glutamine transport. (A) Chemical structure of V-9302. (B) Concentration-dependent inhibition of glutamine uptake in live HEK-293 cells; V-9302 ("left" curve), GPNA ("right" curve). Cellular glutamine accumulation normalized to vehicle control. Normalized amino acid uptake (relative to vehicle) in HEK-293 cells with V-9302 exposure at the IC$_{50}$ (10 μM, (C)) and 10× the IC$_{50}$ for glutamine inhibition (100 μM, (D)). Q=glutamine, Y=tyrosine, E=glutamic acid, D=aspartic acid, K=lysine, G=glycine, L=leucine. (E) Normalized uptake of $^3$H-labeled amino acids in HEK293 cells evaluated in the presence of increasing concentrations of V-9302. Normalization relative to vehicle control. (F) Drug Affinity Responsive Target Stability (DARTS) assay visualized by immunoblot; tetracycline (TCN)-inducible ASCT2 HEK293 cells. ASCT2 is protected from proteolytic degradation by thermolysin (TLN) in the presence of increasing concentrations of V-9302 (veh=−, +=50 μM, ++=100 μM, +++=200 μM. Error bars represent ±std. dev.

FIG. 5A-B shows in vitro efficacy of the present invention, including the embodiment V-9302. (A) A panel of 29 human cancer cell lines exposed to a single concentration of V-9302 (25 μM, 48 hrs); assay of ATP-dependent viability (CellTiter Glo). Select mutational status highlighted (green squares). Cell lines derived from lung cancer, breast cancer, and colorectal cancer shown. Specific cell lines representing a range of in vitro sensitivities prioritized for further evaluation in vivo indicated by arrows. (B) Direct comparison of V-9302 or CB-839 on the viability of human CRC cell lines. Drug incubated at concentrations shown for 48 hrs. Percent viability relative to vehicle control (MultiTox Glo assay). Error bars represent ±std. dev. *Estimated EC$_{50}$. Error bars represent ±std. dev.

FIG. 6A-G shows molecular determinants of ASCT2-antagonism in vitro. (A) Silencing ASCT2 (shRNA; HCC1806 cells; immunoblot shown) resulted in significantly attenuated pS6 and modestly decreased pERK. (B) V-9302 exposure (25 μM, 48 hrs) exhibited a similar inhibition profile to silencing ASCT2 with shRNA in HCC1806 cells. (C) V-9302-dependent increase in oxidized glutathione (GSSG, left y-axis) and depletion of reduced glutathione (GSH, right y-axis) and (D) corresponding assay of reactive oxygen species (ROS); HCC1806 cells. (E) Effect of V-9302 exposure (25 μM, 48 hrs) on LC3B, a marker of autophagy, in HCC1806 cells. Immunofluorescence photomicrographs (left panels) showing cellular LC3B localization (pink fluorescence). Quantified numbers of LC3B-positive cells per field shown in right panel; quantification reflects mean cell counts of three independent biological replicates. Magnification 40×. (F) Effect of V-9302 exposure on optical redox-ratio ([FAD]/[NAD(P)H]) in HCC1806 cells. Representative photomicrographs (left) and quantification (right); concentration shown, 48 hr exposure. Magnification 40×. (G) Effects of V-9302 exposure (25 μM, 96 hrs) on viability of two human colorectal cancer organoids (A007—

Figures 4A, 4B, 4C:
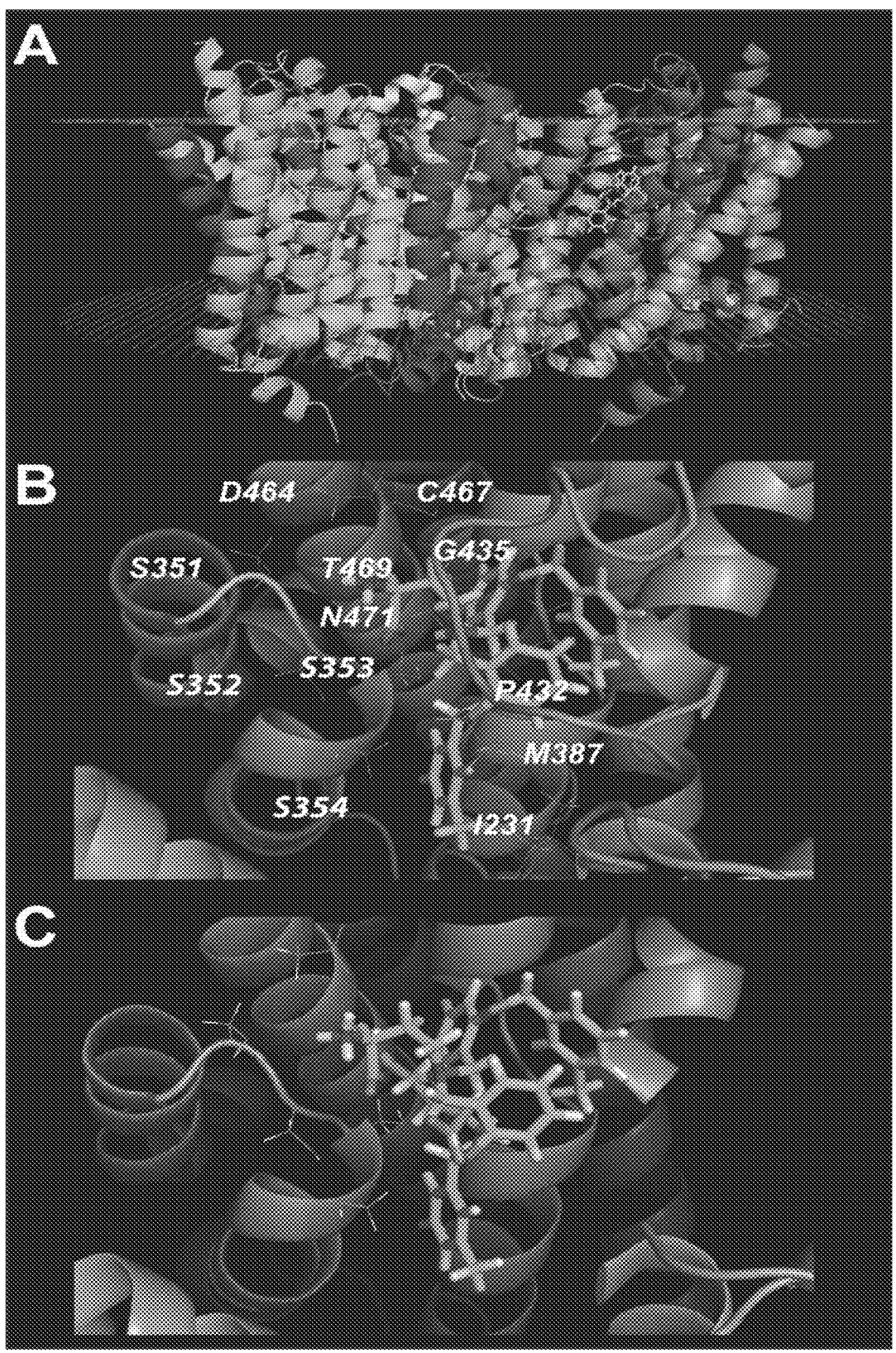
FIG. 4A-F shows in silico modeling of V-9302 interactions with human ASCT2 (hASCT2). (A) Homology model of hASCT2 (trimer shown) with V-9302 docked into the orthosteric binding site within the transmembrane region of the protein (extracellular membrane and intracellular membrane). (B) Expanded view of residues proximal to V-9302 within the orthosteric binding site. Top scoring pose shown. (C) Overlay of V-9302 and ASCT2 substrate, glutamine, docked into the orthosteric binding site. (D) In silico alanine scan of the hASCT2 binding pocket. Positive values indicate alanine substitution interacts less favorably with V-9302 relative to the native residue. The total interface score is a weighted summation of the hydrogen bonding scores, repulsion penalties, solvation energies, and electrostatic potential. Glutamine and V-9302 were evaluated in a homology model of LAT1. (E) Ligand interaction diagram of glutamine or V-9302 in LAT1 visualized in the MOE molecular modeling and simulation package. Steric clash with the surrounding residues is only seen with V-9302). (F) Docking scores for glutamine and V-9302 into LAT1; similar fit observed for glutamine in LAT1 and ASCT2, while V-9302 only fits the ASCT2 binding pocket. For box plots, center line is plotted at the median; the box spans from the first quartile to the third quartile; whiskers represent min to max.

BRAF$^{V600E}$; A008—KRAS$^{G12V}$; p53$^{R248Q}$; PTEN$^{L140Y}$.) Representative brightfield photomicrographs (left) and quantified organoid viability (right). Error bars represent ±std. dev. For box plots, center line is plotted at the median; the box spans from the first quartile to the third quartile; whiskers represent min to max.

FIG. 7A-I shows and evaluation of V-9302 in vivo. (A) Pharmacodynamic [$^{18}$F]-4F-Gln PET imaging prior to and 4 h following a single administration of V-9302 (75 mg/kg) in HCC1806 cell line xenograft-bearing mice (arrows indicate xenograft tumor on right flank*). (B) Mean time activity curves (TACs) from tumor regions of interest (n=4 measurements per condition); data prior to and following V-9302 administration. (C) Quantified tracer accumulation in xenograft tumors, muscle, and liver (n=4 measurements per condition). Volumetric analysis over 21 day treatment regimen (Vehicle or V-9302; 75 mg/kg, daily) of HCT-116 (D) and HT29 (F) cell line xenografts propagated in athymic nude mice (n=10 mice per group). Immunohistochemistry for pS6 in vehicle-treated or V-9302-treated HCT-116 (E) and HT29 (G) xenografts. Representative photomicrographs shown; magnification 20×. (H) Volumetric analysis over 31 day treatment regimen (Vehicle or V-9302; 75 mg/kg, daily) on athymic nude mice bearing patient-derived xenograft tumors (PDX A 008, KRAS$^{G12V}$; p53$^{R248Q}$; PTEN$^{L140Y}$; n=10 mice per group). (I) Photographs of A 008 PDX-bearing mice treated with V-9302 or vehicle; day 16 of 31. (Error bars represent ±std. dev. *Central photopenia observed.)

FIG. 8A-B shows a summary of cancer cell programs modulated by V-9302. (A) Global metabolomic analysis of HT-29 cell-line xenograft tumor-bearing mice treated with V-9302 or vehicle (n=5 per condition). Individual statistically significant (p<0.05) metabolites spanning seven distinct metabolic families highlighted. Select metabolites involved in glutamine-centric biological processes indicated (see text for details). (B) ASCT2 blockade with V-9302 results in attenuated cancer cell Growth and Proliferation, increased Cell Death, and increased Oxidative Stress. Arrows indicate V-9302-induced phenotypes relative to baseline homeostasis. Additional substrates transported by ASCT2 include Alanine, Serine, Cysteine, Threonine, Leucine, and Asparagine.

FIG. 9 shows amino acid transporters and substrates used for selectivity screening. (A) Common transporters and amino acid substrates shown. Amino acids designated by one-letter codes. Transporters responsible for glutamine uptake are shaded. Amino acid substrates utilized to evaluate the selectivity of V-9302 are lighter grey.

FIG. 10 A-B shows a Drug Affinity Responsive Target Stability (DARTS) assay comparing the stabilization of ASCT2 and ASCT1 by V-9302. (A) Immunoblots for ASCT2 and ASCT2 illustrating concentration dependent stabilization of ASCT2 in the presence of the protease thermolysin by V-9302. ASCT1 is not similarly protected by V-9302. (B) Immunoblot densitometry analysis DARTS immunoblots for ASCT2 and ASCT1. Percent control (Ctrl) relative to ASCT2 or ASCT1 immunoreactivity, respectively, without thermolysin.

FIG. 11 shows a summary and annotation of human cancer cell lines utilized in CellTiter Glo viability screen of V-9302 activity (graph shown in FIG. 5). Percent change in viability relative to vehicle control following 25 μM V-9302 exposure for 48 h (% Δviability relative to vehicle); standard deviation (SD).

FIG. 12A-C shows follow-up viability screening of V-9302 activity in human CRC cells. In vitro multiplex assay (MultiTox Glo) of 15 colorectal cancer cell lines exposed to V-9302 (25 μM, 48 h). V-9302-dependent changes in the number of live cells (A) and dead cells (B) relative to vehicle control. (C) V-9302 Sulforhodamine B assay evaluating V-9302-dependent cell death in 9 colorectal cancer cell lines in vitro. Data for each assay relative to vehicle control. Select mutational status (squares) shown. All data is p<0.05 unless otherwise indicated. n.s.=not statistically significant. Error bars represent ±std. dev.

FIG. 13 A-D shows the lack of correlation between ASCT2 protein levels and sensitivity to V-9302. (A) Membranous and (B) total ASCT2 levels evaluated by western blotting in thirteen human CRC cell lines. Neither membranous (C) nor total (D) ASCT2 levels quantified by densitometry correlated with V-9302 sensitivity. Immunoblots normalized to total protein gel loading control.

FIG. 14A-D shows the effect of glutamine withdrawal (A/B) or combinatorial ASCT2 substrate withdrawal (C/D) on cellular viability and cell death in V-9302 sensitive human CRC cell lines. Cell lines propagated for 48 hrs in either glutamine-depleted or ASCT2-substrate-depleted media; Multi-Tox Glo assay. (A) Cell viability and (B) cell death with glutamine withdrawal (C) Cell viability and (D) cell death with ASCT2-substrate (alanine, serine, cysteine, threonine, glutamine, asparagine, methionine, glycine, leucine, valine, glutamate) withdrawal. Percent change relative to standard media control. n.s.=not statistically significant; =p<0.01; **=p<0.0001. Error bars represent ±std. dev.

FIG. 15A-B shows viability and activation of mouse T-cells following V-9302 exposure for 96 hrs. (A) Viability analyzed by propidium iodide flow cytometry. (B) Activation of T-cells as measured by flow cytometry for CD44 expressions; mean fluorescence intensity (MFI).

Figure 16:
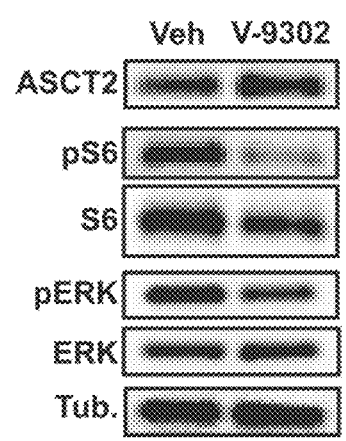

FIG. 16 shows the effects of V-9302 exposure (25 μM, 48 h) on pS6 and pERK in HT29 cells.

FIG. 17A-B shows validation of V-9302-dependent decrease in pERK levels in HCC1806 and HT29 cells; SureFire biochemical assay. Comparison of V-9302 and glutaminase inhibitor, CB839. (A) HCC1806 and (B) HT-29 cells. Drug concentrations shown; treatment duration 48 h. Error bars represent ±std. dev.

FIG. 18A-B shows evaluation of oxidized glutathione (GSSG) levels in HT-29 cells with V-9302 or CB-839 exposure. (A) Oxidized glutathione (GSSG) and (B) reactive oxygen species (ROS). Drug concentrations shown, cells treated for 48 h. Error bars represent ±std. dev.

Figure 19:
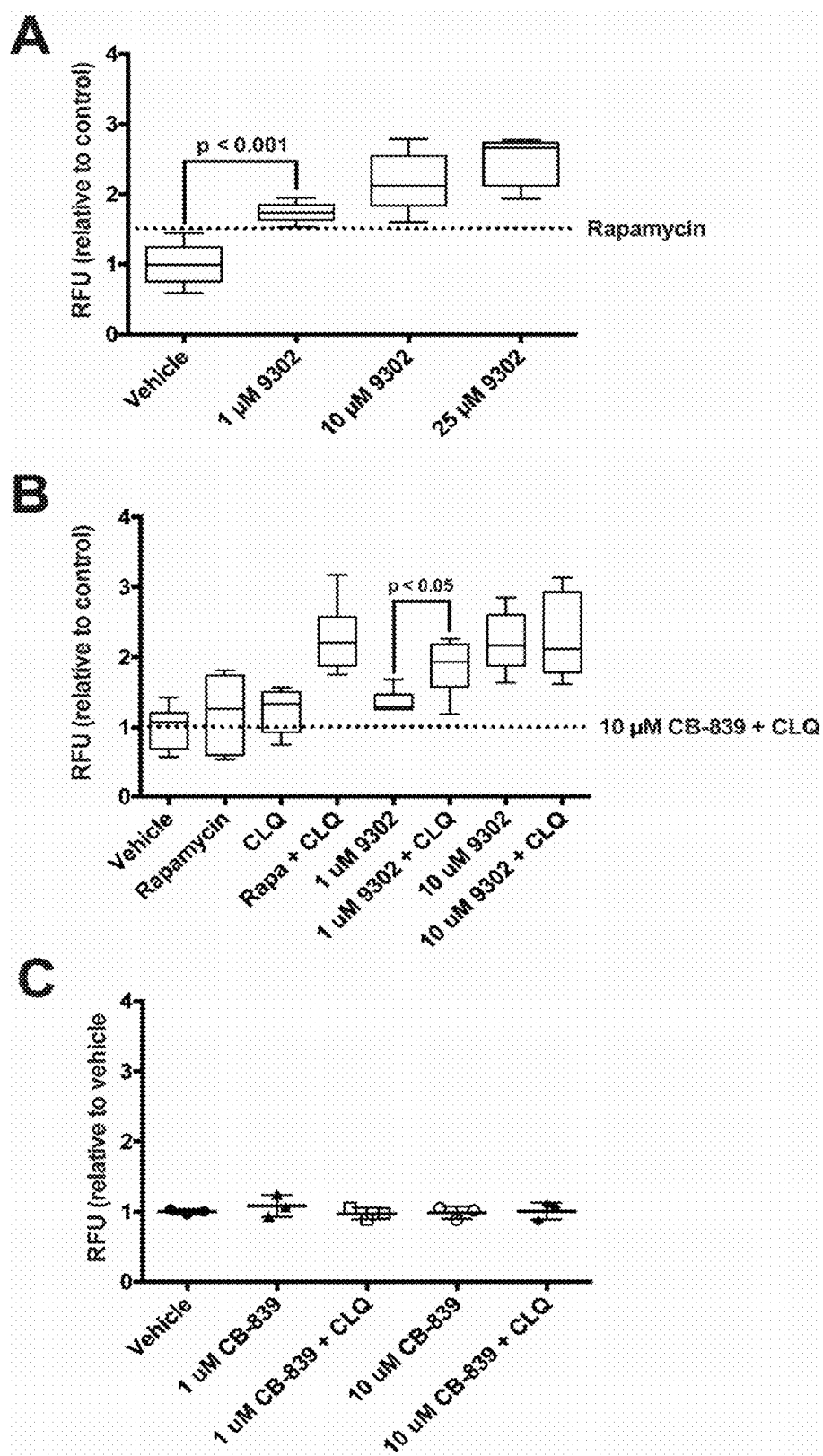

FIG. 19A-C shows an analysis of autophagic flux with V-9302 exposure. (A) Autophagic vesicles in HCC1806 cells with exposure to increasing concentrations of V-9302; 8 h treatment duration, concentrations shown. Vesicles induced by rapamycin (dotted line, 500 nM, positive control). Combination of lysosomal inhibitor chloroquine (10 μM) and V-9302 (B) or CB-839 (C) in HT29 cells. CLQ=chloroquine. For box plots, center line is plotted at the median; the box spans from the first quartile to the third quartile; whiskers represent min to max. Error bars represent ±std. dev.

FIG. 20A-B shows the additive effect on cellular viability between V-9302 and chloroquine but not CB-839 and chloroquine. HT29 cells (A) and HCT-116 cells (B) exposed to V-9302 (concentrations shown), CB-839 (concentrations shown), chloroquine (CLQ, 10 μM), and the combinations thereof for 48 h. Error bars represent ±std. dev.

Figure 21:
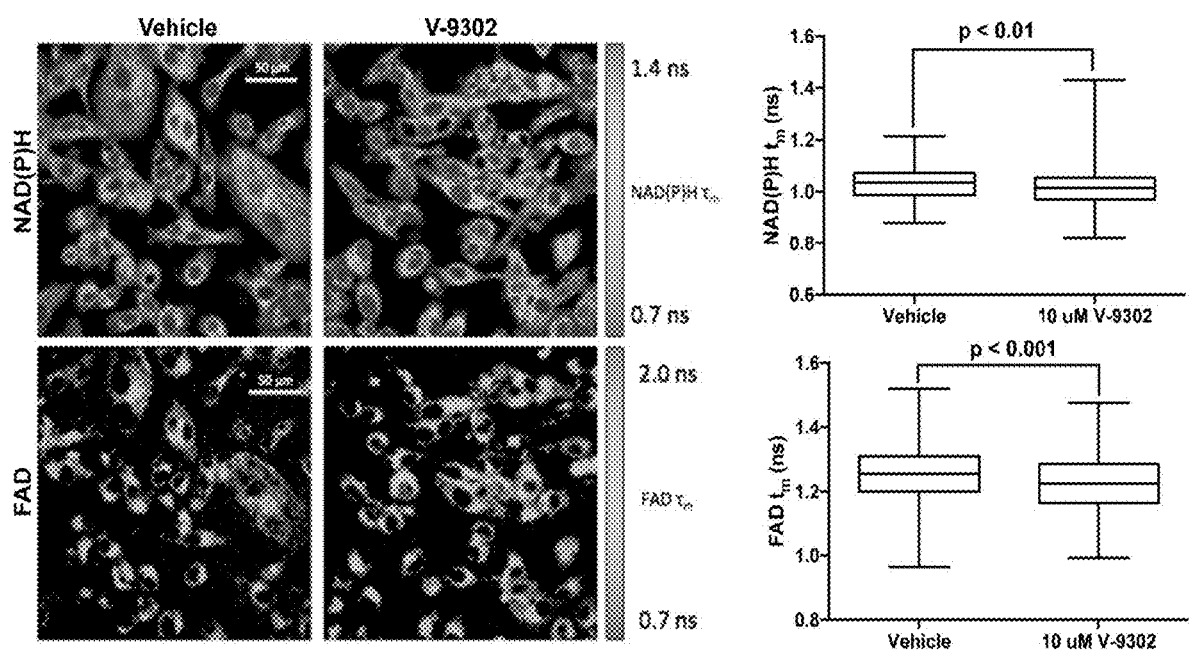

FIG. 21 shows fluorescence lifetimes of NAD(P)H and FAD measured by optical spectroscopy were reduced with exposure to V-9302 (10 μM) in HCC1806 cells. Drug exposure 48 h, magnification 40×. For box plots, center line is plotted at the median; the box spans from the first quartile to the third quartile; whiskers represent min to max Error bars represent ±std. dev.

FIG. 22A-B shows viability of human CRC organoids A 007 (BRAF$^{V600E}$) (A) and A 008 (KRAS$^{G12V}$; p53$^{R248Q}$; PTEN$^{L140Y}$) (B) with exposure to CB-839 (35 µM, 96 h). Error bars represent ±std. dev.

Figure 23:
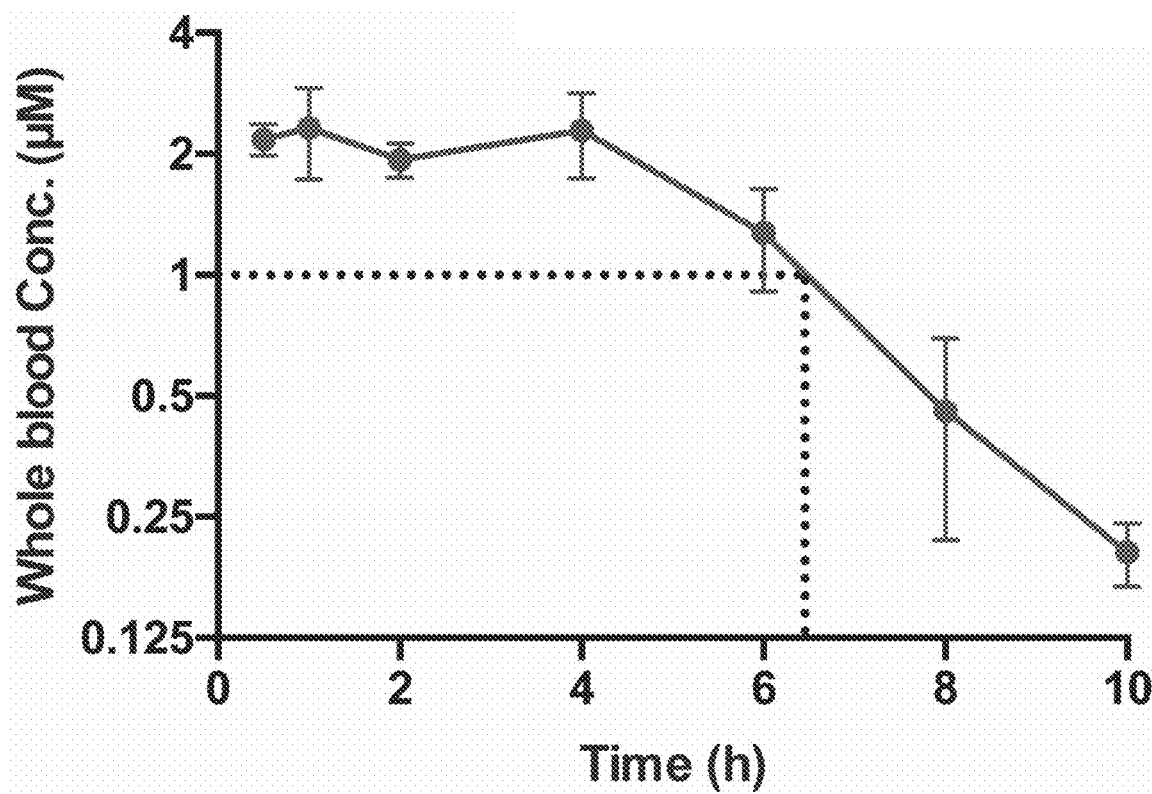

FIG. 23 shows an longitudinal assay of V-9302 concentration in whole blood following a single dose (75 mg/kg) in healthy C57BL/6 mice (n=5 replicates at each time point). Error bars represent ±std. dev.

FIG. 24A-D shows an evaluation of acute (A/B) and chronic (C/D) V-9302 exposure on plasma glucose (A/C) and glutamine (B/D) in mice. Acute exposure consisted of a single dose (75 mg/kg) with metabolites assayed 4 h post-treatment. Chronic exposure analysis at the conclusion of 21 day treatment course (75 mg/kg daily), with metabolites assayed 4 h following the final V-9302 dose.

FIG. 25A-C shows an evaluation of V-9302 in vivo in HCC1806 cell line xenograft-bearing mice. (A) Tumor volumetric analysis of mice treated with vehicle or V-9302 (75 mg/kg per day) for 10 days. (B) Immunofluorescence analysis of tumor tissues harvested from vehicle- or V-9302-treated mice; LC3B and pAKT (Ser473) shown (pink). CD-31 positive vessels shown in green and nuclei in blue (DAPI). 20× magnification. (C) Effects of V-9302 treatment on pS6-positive cells and caspase 3-positive cells by immunohistochemistry. Quantitative analysis consisted of the mean counts of at least three representative fields from three vehicle and three V-9302-treated mice. For box plots, center line is plotted at the median; the box spans from the first quartile to the third quartile; whiskers represent min to max. Error bars represent ±std. dev.

FIG. 26A-C shows an evaluation of V-9302 in vivo in colo-205 cell line xenograft bearing mice. (A) Tumor volumetric analysis of mice treated with vehicle or V-9302 (75 mg/kg per day) for 10 days. (B) Immuno dot-blot assay of markers of cellular response to V-9302 in colo-205 cell line xenograft tumors; change in marker immunoreactivity relative to vehicle control. (C) Immnunofluorescence assay of LC3B-, pS6-, pAKT (Ser473)-, and BRDU-positive cells by immunofluorescence (pink). CD-31 positive vessels shown in green and nuclei in blue (DAPI). 20× magnification. Representative images shown. Quantitative analysis consisted of the mean counts of at least three representative fields from three vehicle and three V-9302 treated mice. For box plots, center line is plotted at the median; the box spans from the first quartile to the third quartile; whiskers represent min to max. Error bars represent ±std. dev.

Figure 27:
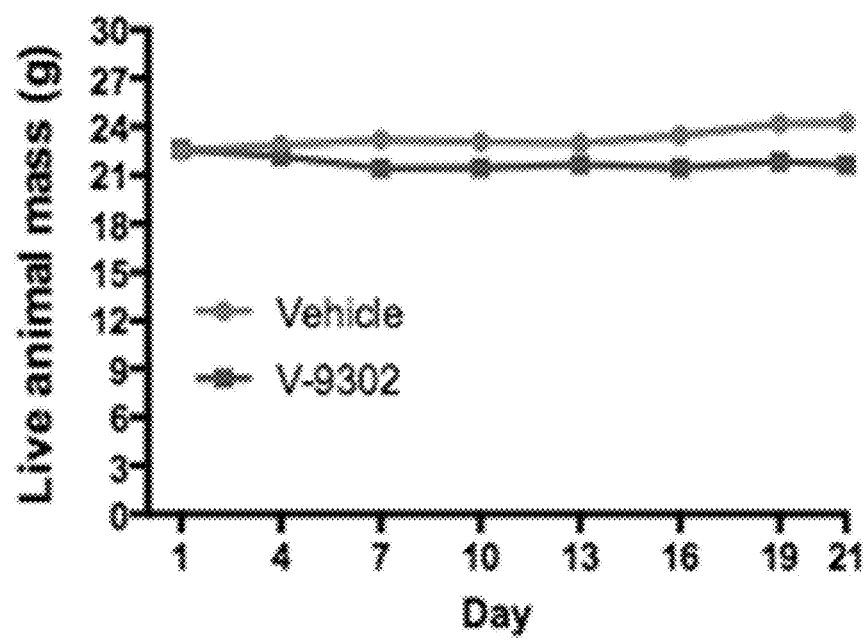

FIG. 27 shows a longitudinal assessment of the mass of live athymic nude mice treated daily with V-9302 (75 mg/kg per day) or vehicle over 21 days.

FIG. 28A-B shows representative photomicrographs of H&E stained liver sections from athymic nude mice chronically treated with 75 mg/kg per day V-9302 or vehicle over 21 days. Magnification 20× (A) and 40× (B) shown. An experienced GI pathologist (MKW) found no discernible difference between liver pathology in mice treated with V-9302 or vehicle (n=5).

DESCRIPTION OF THE INVENTION

As indicated herein, embodiments of the present invention include the discovery of ASCT2 inhibitors. The compounds of the present invention accomplish that need. As such, the compounds of the present invention can be used as modulators of ASCT2 transporters.

The compounds of the present invention can also be used to treat patients (e.g., humans) suffering from diseases, conditions, disorders, or syndromes caused or influenced by abnormal ASCT2 transporter dysfunction. Such diseases, conditions, disorders, and syndromes include, e.g., cancer, microbial infections, and ischemia-related central nervous system (CNS) injuries.

The compounds of the present invention can also be used to treat ASCT2 functional abnormalities.

The compounds of the present invention can also contain a radionuclide, such as fluorine-18, for use in radiographic medical imaging applications in a patient (e.g., human) to diagnose or follow the progression of diseases, disorders, conditions, or symptoms related to a disease, disorder, condition, or symptom caused or related to ASCT2 functional abnormality, including, but not limited to, cancer, microbial infections, and ischemia-related central nervous symptom injuries.

In summary, embodiments of the present invention includes novel Nγ-glutamylanilides as inhibitors of cellular glutamine uptake via ASCT2 with significantly greater potency than GPNA. Evaluation of this chemical series within the context of ligand docking to a homology model of human ASCT2 revealed compatibility with the ASCT2 binding site based on SurflexDock Total Scores. The data show that compounds of the present invention interact with multiple structural elements within the ASCT2 binding site, including the amino acid zwitter ion binding site and the adjacent hydrophobic pocket. Uniquely, previous work in the Nγ-glutamylanilide series suggested that reduction of the glutamine amide pK$_a$ was required for ASCT2 inhibition; the present inventors did not observe this trend.

Unless defined otherwise, all technical and scientific terms used herein have the meaning commonly understood by a person skilled in the art.

As used herein, the singular form "a," "an," and "the" include plural references unless the context clearly dictates otherwise. For example, the term "a cell" includes a plurality of cells, including mixtures thereof.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3SH$, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." Unless specifically stated otherwise, the compounds of the present invention and variable groups described in connection with the compounds of the present invention are presumed to be optionally substituted.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

Optical isomers are compounds with the same molecular formula but differ in the way they rotate plane polarized light. There are two types of optical isomers. The first type of optical isomers are compounds that are mirror images of one another but cannot be superimposed on each other. These isomers are called "enantiomers." The second type of optical isomers are molecules that are not mirror images but each molecule rotates plane polarized light and are considered optically-active. Such molecules are called "diastereoisomers." Diasteroisomers differ not only in the way they rotate plane polarized light, but also their physical properties. The term "optical isomer" comprises more particularly the enantiomers and the diastereoisomers, in pure form or in the form of a mixture.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "cancer" refers to or describes the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer. Particular, but non-limiting examples of the present invention is lung, colon, and pancreatic cancer.

The terms "combination therapy" or "co-administration" mean the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The term "imaging agent" as used herein refers to any moiety useful for the detection, tracing, or visualization of a compound of the invention when coupled thereto. Imaging agents include, e.g., an enzyme, a fluorescent label (e.g., fluorescein), a luminescent label, a bioluminescent label, a magnetic label, a metallic particle (e.g., a gold particle), a nanoparticle, an antibody or fragment thereof (e.g., a Fab, Fab', or F(ab')$_2$ molecule), and biotin. An imaging agent can be coupled to a compound of the invention by, for example, a covalent bond, ionic bond, van der Waals interaction or a hydrophobic bond. An imaging agent of the invention can be a radiolabel coupled to a compound of the invention, or a radioisotope incorporated into the chemical structure of a compound of the invention. Methods of detecting such imaging agents are well known to those having skill in the art.

The phrase "therapeutically effective" is intended to qualify the amount of active ingredients used in the treatment of a disease or disorder. This amount will achieve the goal of reducing or eliminating the disease or disorder.

The term "therapeutically acceptable" refers to those compounds (or salts, esters, prodrugs, tautomers, zwitterionic forms, etc. thereof) which are suitable for use in contact with the tissues of patients without undue toxicity, irritation, and allergic response, are commensurate with a reasonable benefit/risk ratio, and are effective for their intended use.

As used herein, the term "subject" refers to a target of administration. The subject of the herein disclosed methods can be a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibiting ASCT2-mediated glutamine accumulation" means having been subjected to a physical examination by a person of skill, for example, a physician, and found to have a condition that can be diagnosed or treated by a compound or composition that can inhibit ASCT2 activity. Such a diagnosis can be in reference to a disorder, such as cancer, and the like, as discussed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "cancer" refers to disorders characterized by cellular proliferation, evasion of programmed cell death, altered cellular metabolism, induction of angiogenesis, enhancement of cellular invasion and metastasis, alterations to tumor suppressor genes causing a reduction in activity, alterations to oncogenes casing enhancement of activity, or evasion of immunological destruction. Cancer can refer to a tissue or organ type and can also spread from one tissue or organ to another tissue type or organ. Cancer can occur in any cell of any type including but not limited to breast, prostate, skin, lung, pancreatic, stomach, brain, kidney, uterine, ovarian, testicular, endothelial, colon, bladder, bone as well as cells of the blood to produce various forms of leukemia.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents. Unless otherwise specified, the substituents are all independent from one another.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, thioether, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

The term "alkoxy" The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —OA-$(OA^2)_a$-$OA^3$, where "a" is an integer of from 1 to 200 and $A^1$, $A^2$, and $A^3$ are alkyl and/or cycloalkyl groups.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compounds disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

In some aspects, a structure or part of a structure of a compound can be represented by a formula:

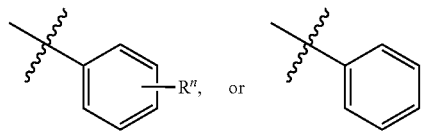

which is understood to be equivalent to a formula:

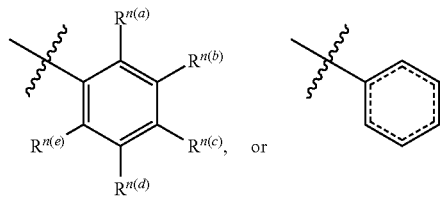

wherein n is typically an integer. That is, $R^n$ is understood to represent live independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance. Likewise, when a group R is defined as four substituents, R is understood to represent four independent substituents, $R^a$, $R^b$, $R^c$, and $R^d$. Unless indicated to the contrary, the substituents are not limited to any particular order or arrangement.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

In one aspect, the invention relates to compounds, or pharmaceutically acceptable derivatives thereof, useful as inhibitors of ASCT2 activity.

One embodiment is a compound of the following formula:

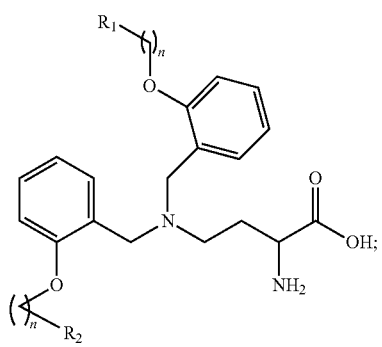

wherein:

$R_1$ is phenyl (optionally substituted with at least one $R_3$), benzyl (optionally substituted with at least one $R_3$), pyridinyl (optionally substituted with at least one $R_3$);

$R_2$ is phenyl (optionally substituted with at least one $R_3$), benzyl (optionally substituted with at least one $R_3$), pyridinyl (optionally substituted with at least one $R_3$);

$R_3$ is independently H, Me, alkyl, methoxy, alkoxy, halogen, $CF_3$; and n is 0-6;

and pharmaceutically acceptable salts and pharmaceutically acceptable derivatives thereof.

Examples of these compounds include, but are not limited to, the following:

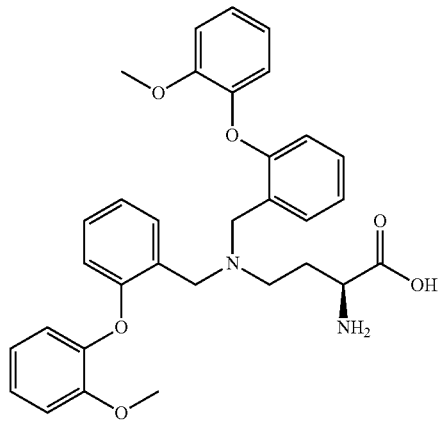

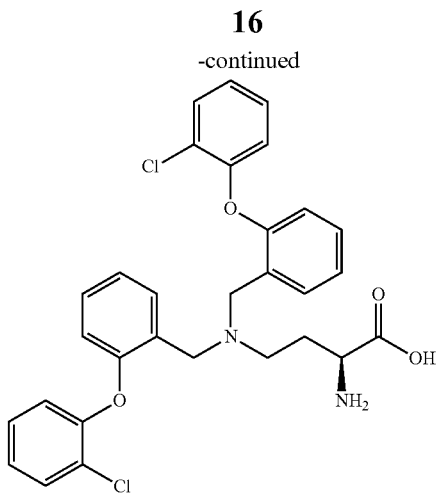

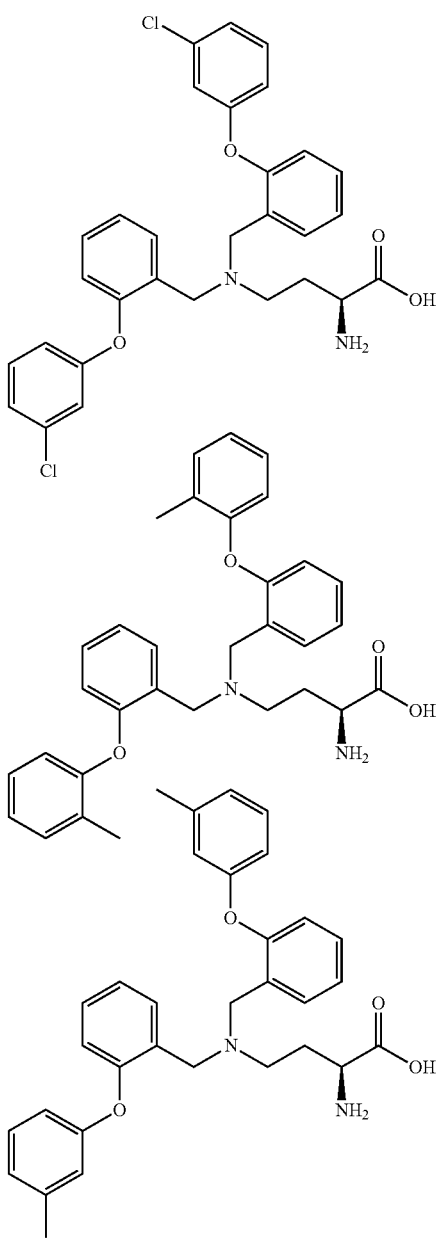

17
-continued
18
-continued
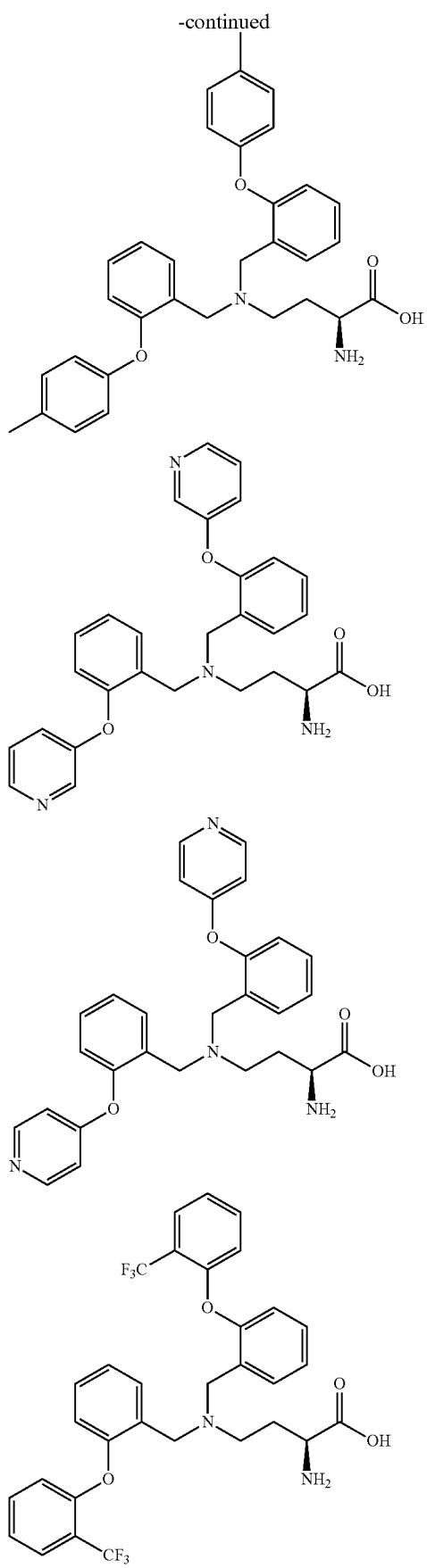
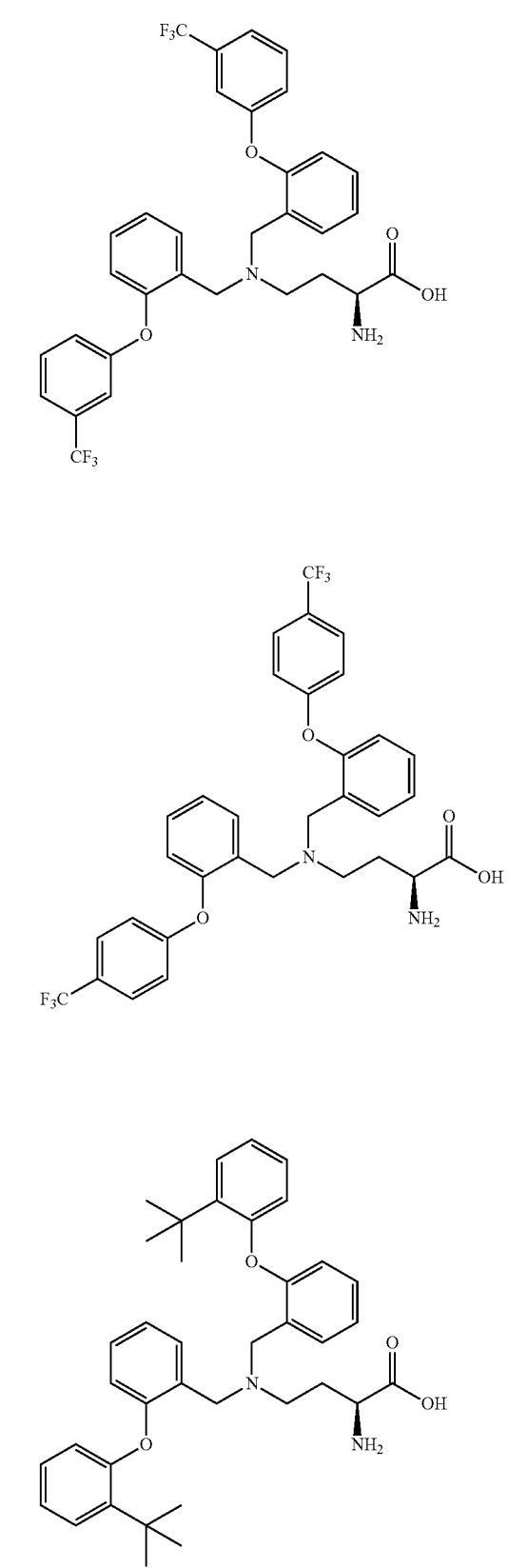

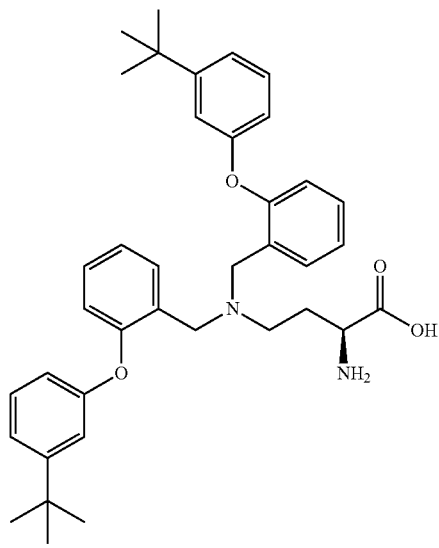
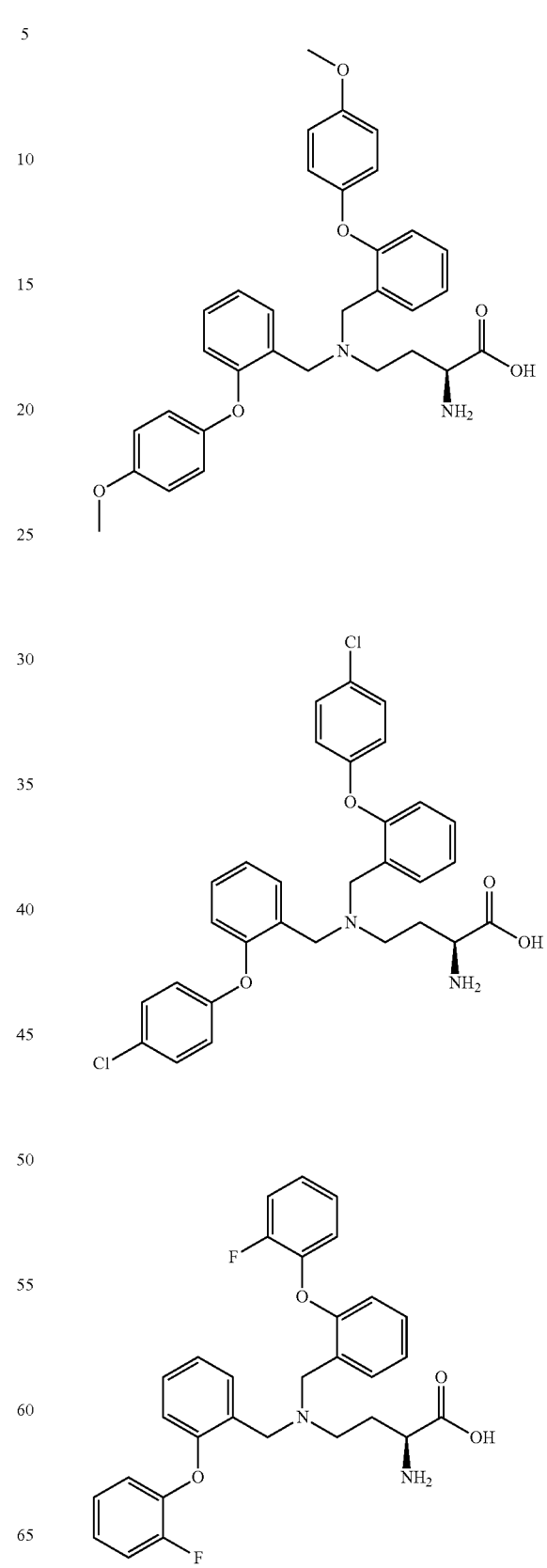

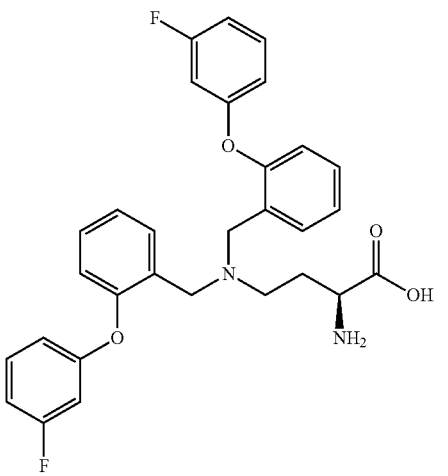

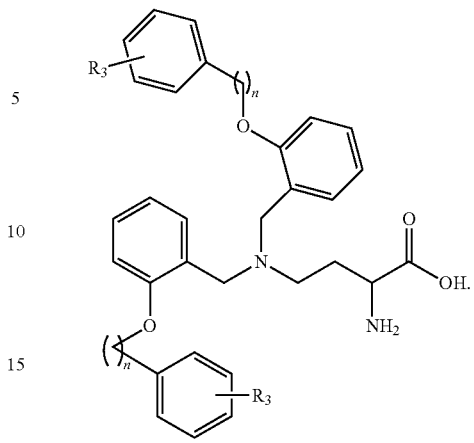

Another embodiment is a compound of the following formula:

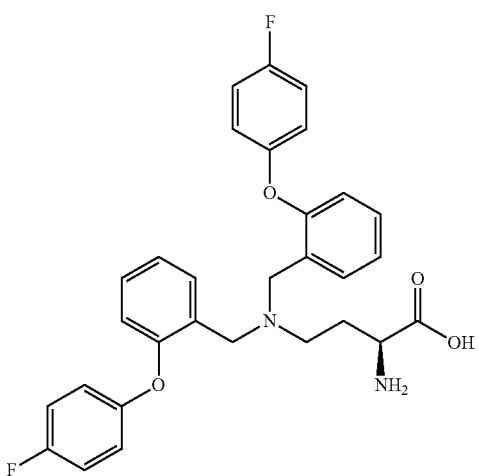

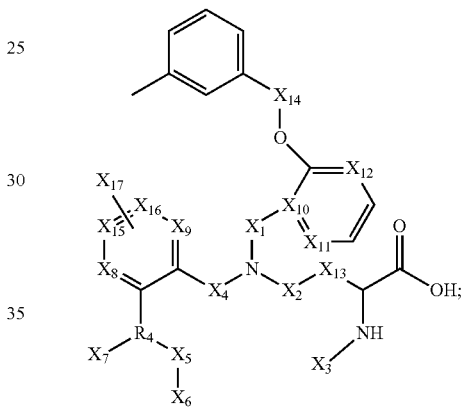

wherein:

$R_4$ is O r N;

$X_1$ is $CH_2$, or is CH and forms a ring with $X_9$ (substituted or unsubstituted), or is absent when $X_9$ forms a ring with $X_{10}$ and at the same time $X_{11}$ forms a ring with $X_2$;

$X_2$ is $CH_2$, or forms a ring with $X_3$ (substituted or unsubstituted), $X_3$ is H, or forms a ring with $X_2$ (substituted or unsubstituted), $X_4$ is $CH_2$, or forms a ring with $X_5$ or $X_7$ (substituted or unsubstituted), $X_5$ is absent; $CH_2$; or forms a ring with $X_4$ (substituted or unsubstituted);

$X_6$ is absent, H, or phenyl (substituted or unsubstituted), $X_7$ is H, absent, benzyl (substituted or unsubstituted) or forms a ring or bicyclic ring with $X_8$ or $X_4$ (substituted or unsubstituted);

$X_8$ is C, CH, $CH_2$, N, or forms a ring or bicyclic ring with $X_7$ (substituted or unsubstituted);

$X_9$ is C, CH, $CH_2$, N, or forms a ring or bicyclic ring with $X_1$, $X_{10}$, or $X_{11}$ (substituted or unsubstituted);

$X_{10}$ is CH, or forms a ring with $X_1$ or $X_9$ (substituted or unsubstituted);

$X_{11}$ is CH, or $CH_2$, or forms a ring with $X_2$ or $X_{13}$ (substituted or unsubstituted);

$X_{12}$ is CH or $CH_2$, or forms a ring with $X_{14}$ (substituted or unsubstituted);

Another embodiment of the present invention is a compound of the following formula:

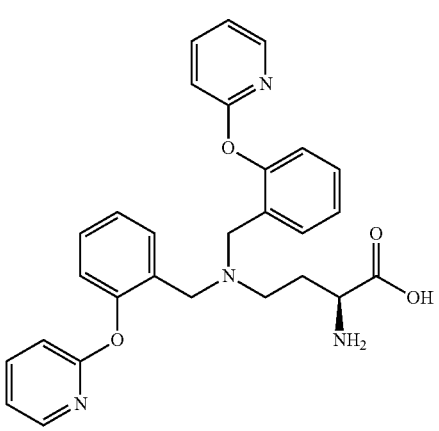

$X_{13}$ is $CH_2$, or forms a ring with $X_{11}$ (substituted or unsubstituted);

$X_{14}$ is $CH_2$, or forms a ring with $X_{12}$ (substituted or unsubstituted);

$X_{15}$ is C, CH, $CH_2$, N;

$X_{16}$ is C, CH, $CH_2$, N;

$X_{17}$ is optionally present and is H, methyl, alkyl, halogen, methoxy, alkoxy, CN, —$CF_3$, —$OCF_3$, or Cyc;

and pharmaceutically acceptable salts and pharmaceutically acceptable derivatives thereof.

Another embodiment is a compound of the following formula:

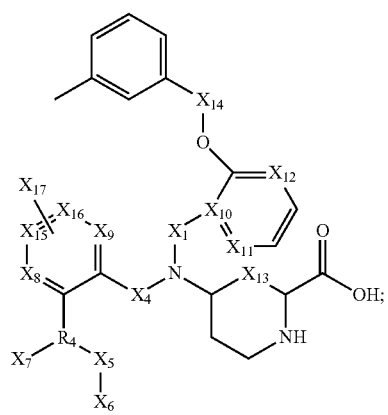

wherein:

$R_4$ is O;

$X_1$ is $CH_2$;

$X_4$ is $CH_2$;

$X_5$ is $CH_2$;

$X_6$ is phenyl (substituted or unsubstituted);

$X_7$ is absent;

$X_8$ is CH;

$X_9$ is CH;

$X_{10}$ is C;

$X_{11}$ is CH;

$X_{12}$ is CH;

$X_{13}$ is $CH_2$;

$X_{14}$ is $CH_2$;

$X_{15}$ is CH;

$X_{16}$ is CH; and $X_{17}$ is H, alkyl, halogen, alkoxy, CN, —$CF_3$, or —$OCF_3$;

or pharmaceutically acceptable salt thereof.

Another embodiment is a compound of the following formula:

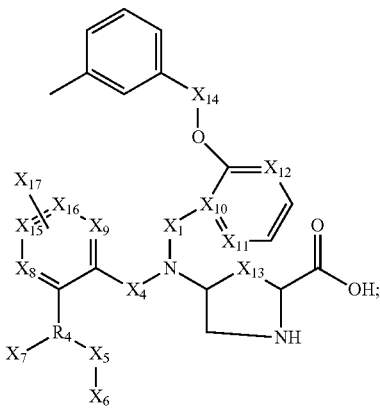

wherein:

$R_4$ is O;

$X_1$ is $CH_2$;

$X_4$ is $CH_2$;

$X_5$ is $CH_2$;

$X_6$ is phenyl (substituted or unsubstituted);

$X_7$ is absent;

$X_8$ is CH;

$X_9$ is CH;

$X_{10}$ is C;

$X_{11}$ is CH;

$X_{12}$ is CH;

$X_{13}$ is $CH_2$;

$X_{14}$ is $CH_2$;

$X_{15}$ is CH;

$X_{16}$ is CH; and $X_{17}$ is H, alkyl, halogen, alkoxy, CN, —$CF_3$, or —$OCF_3$;

or pharmaceutically acceptable salt thereof.

Examples of these compounds include, but are not limited to, the following:

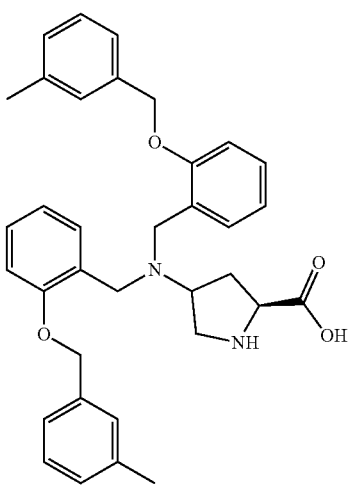

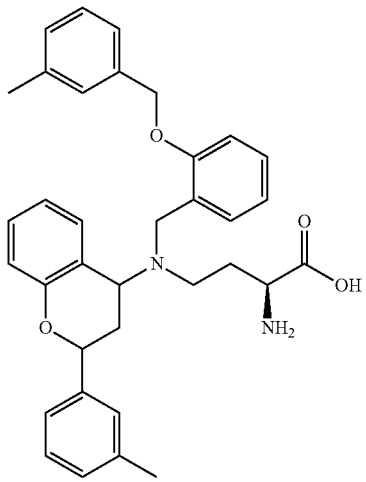
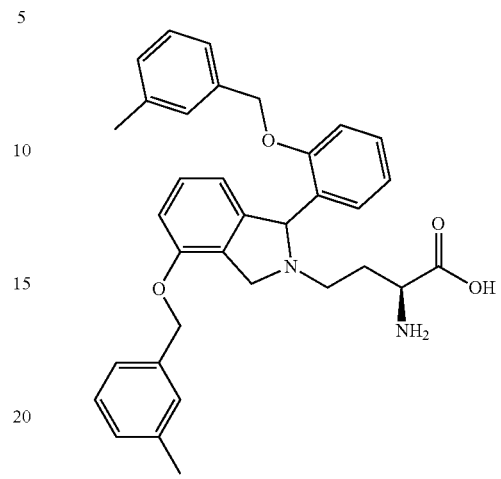
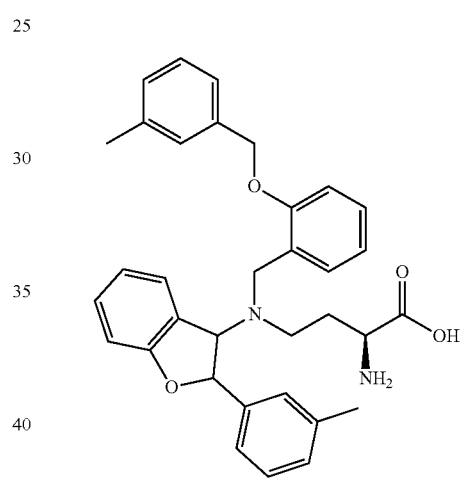
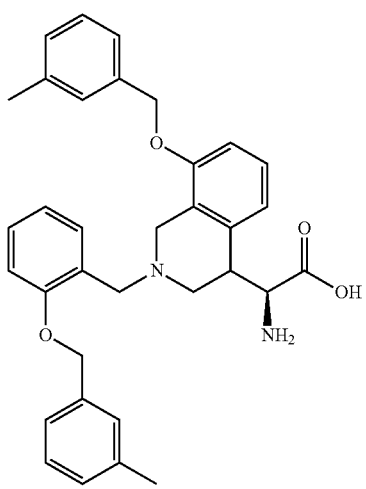
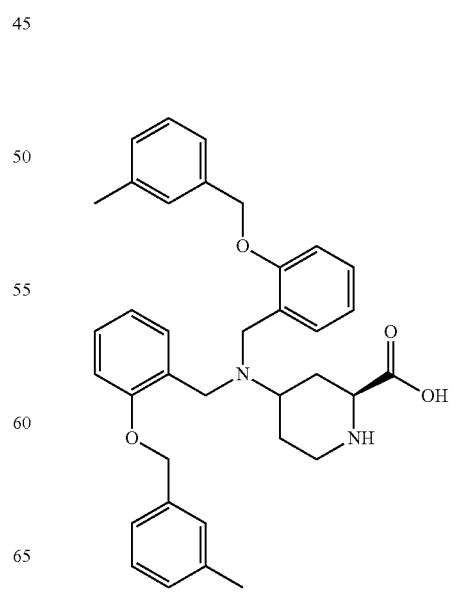

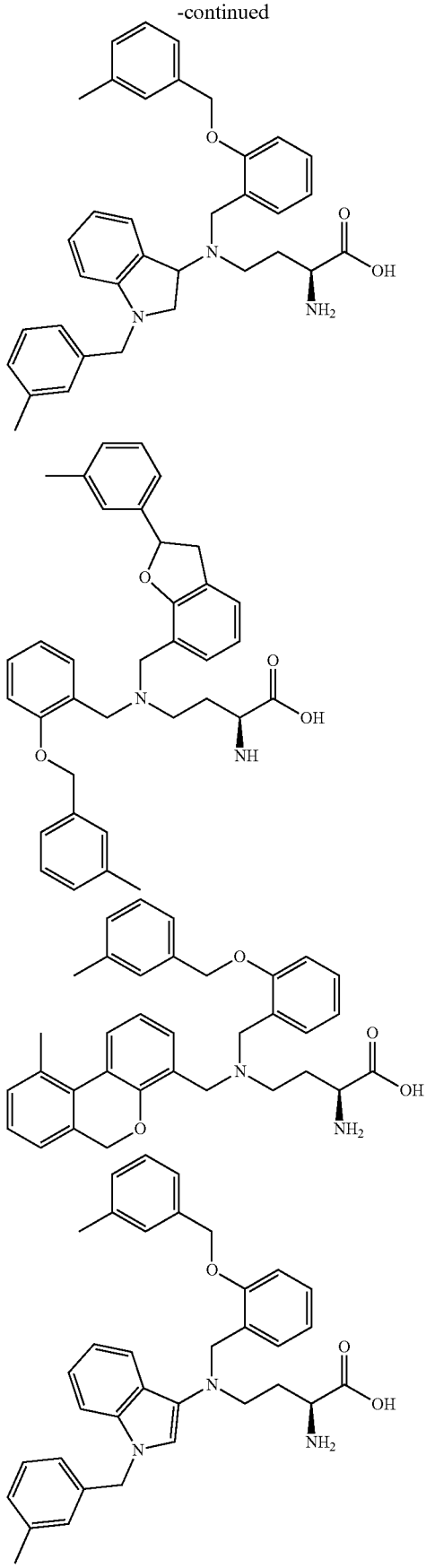
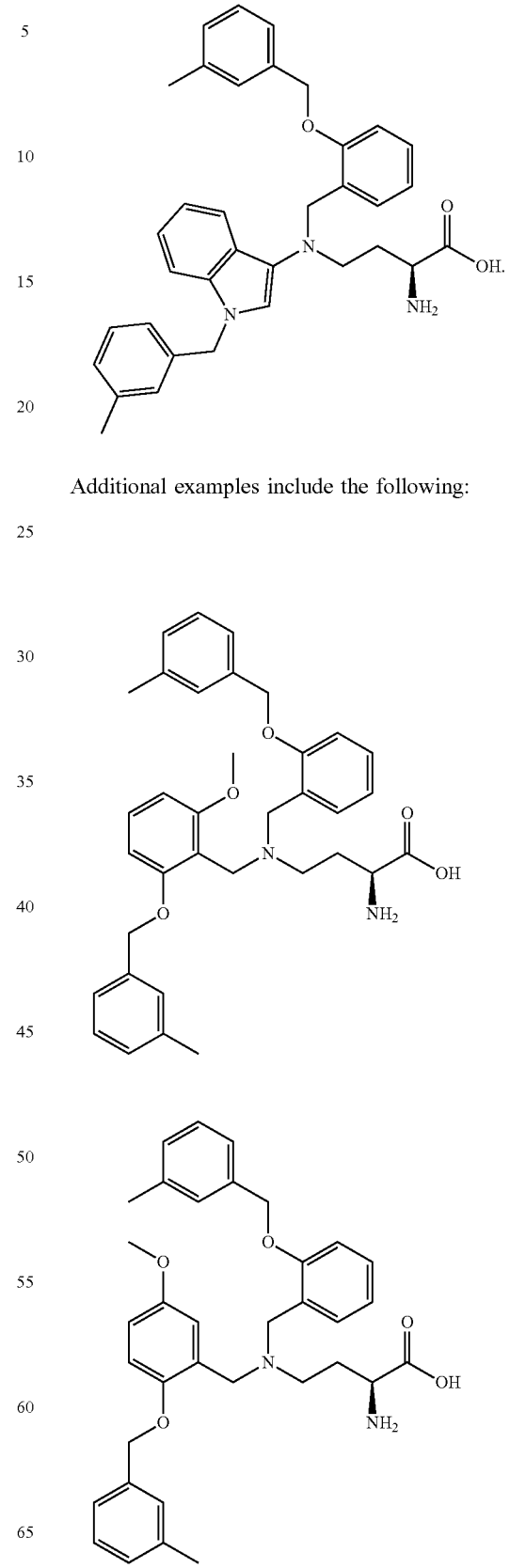
Additional examples include the following:

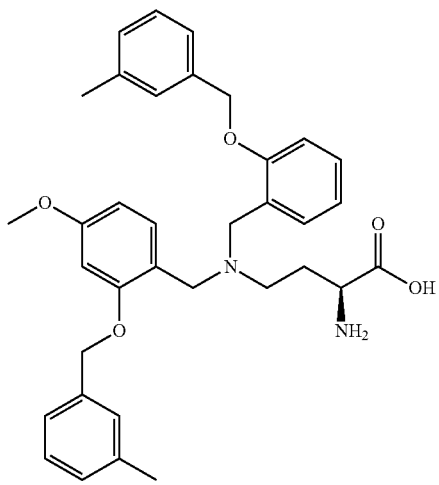
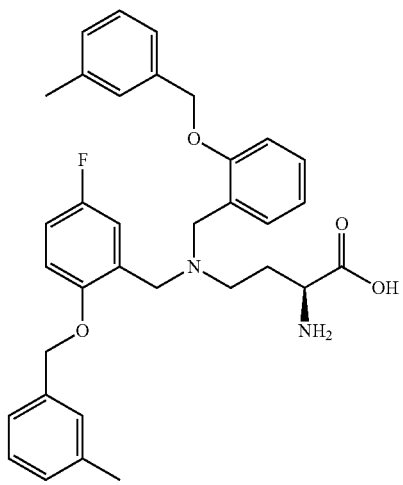
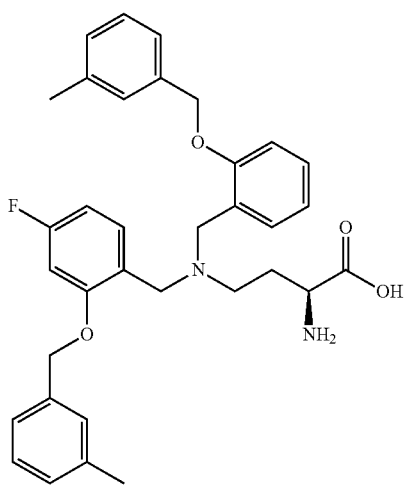
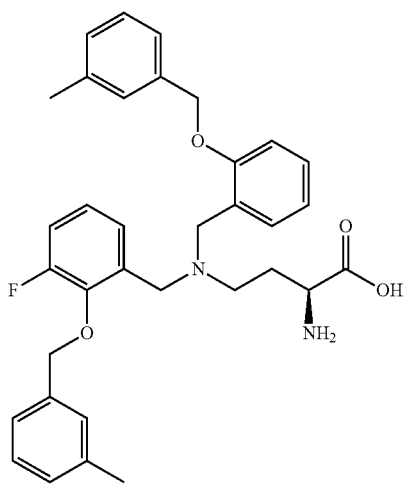

31
-continued
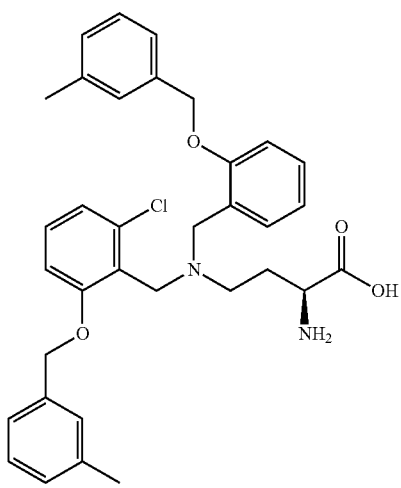
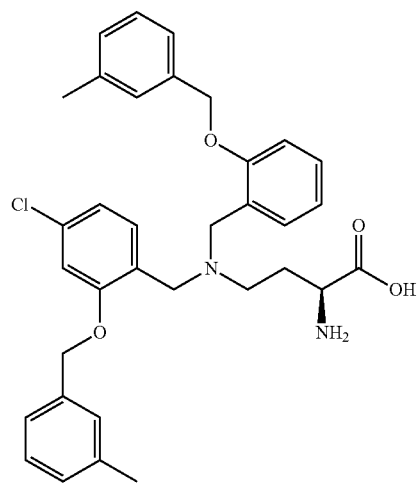
32
-continued
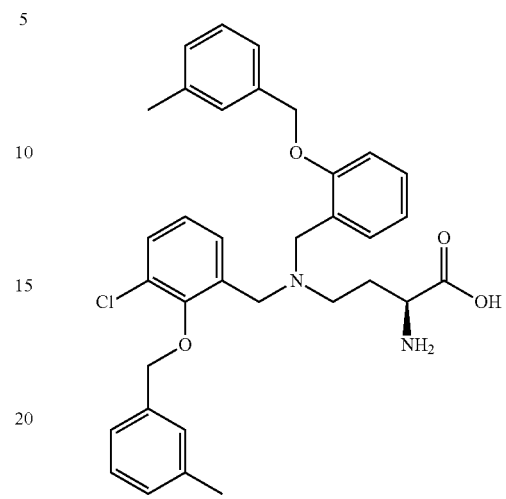

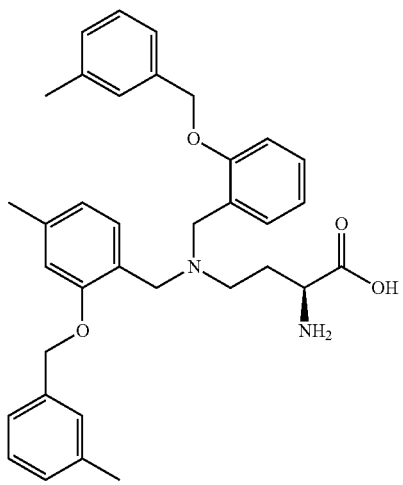
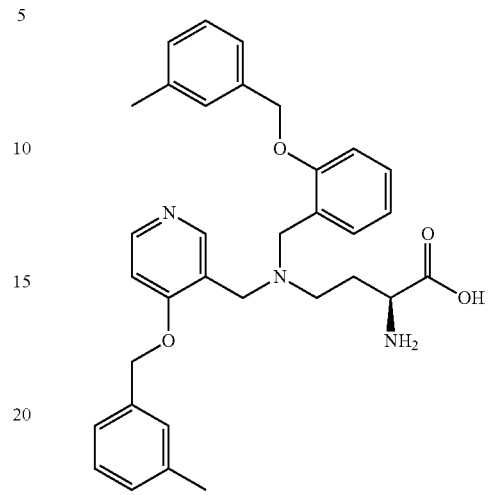
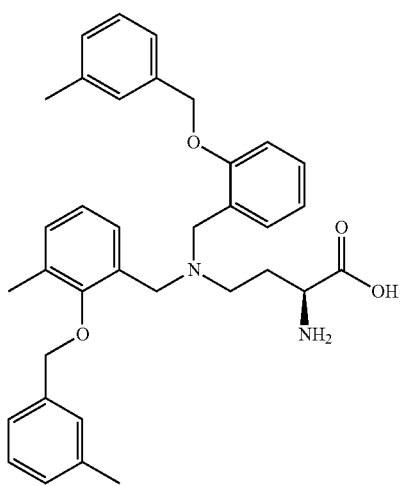
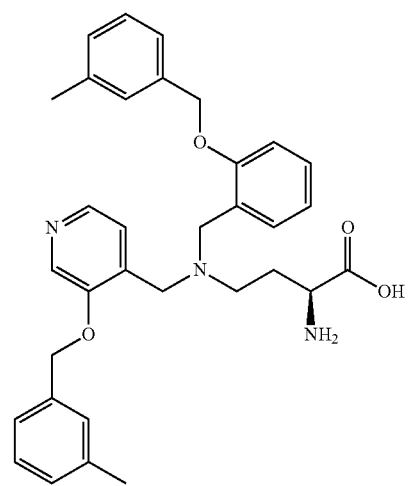
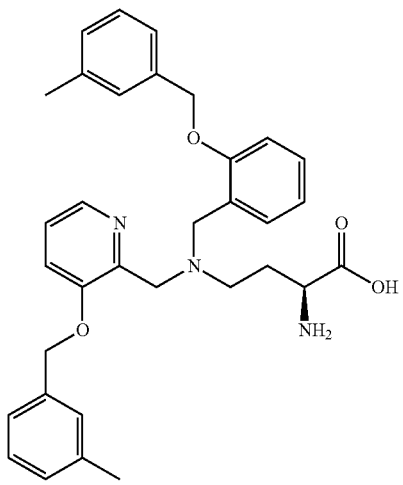
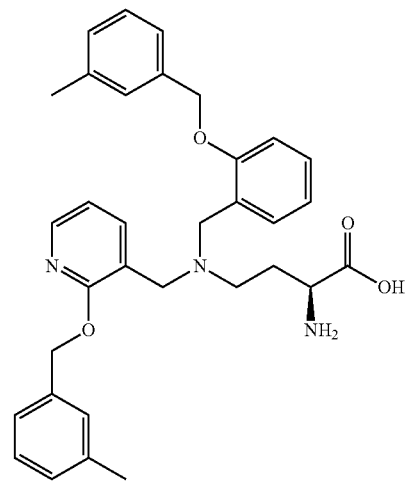

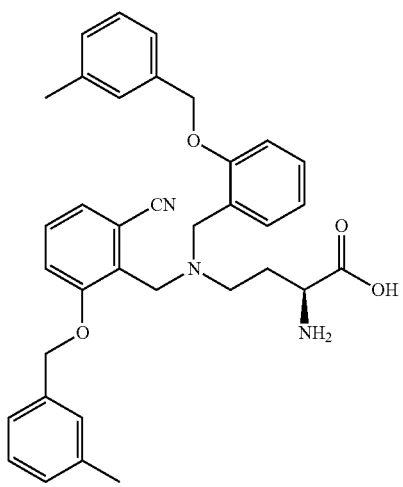
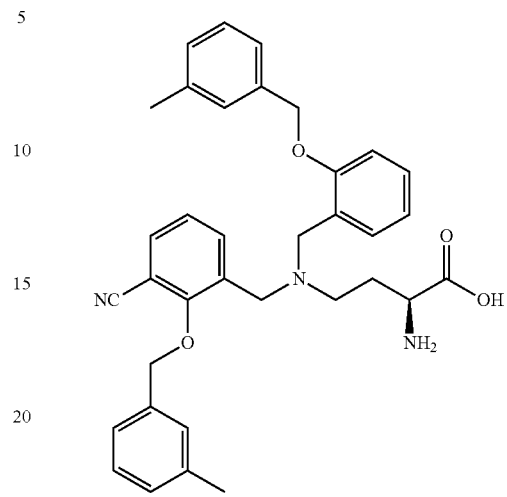
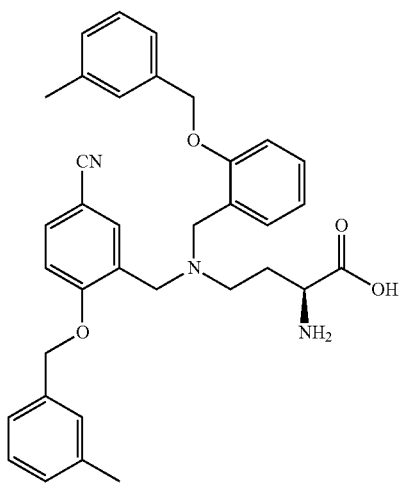
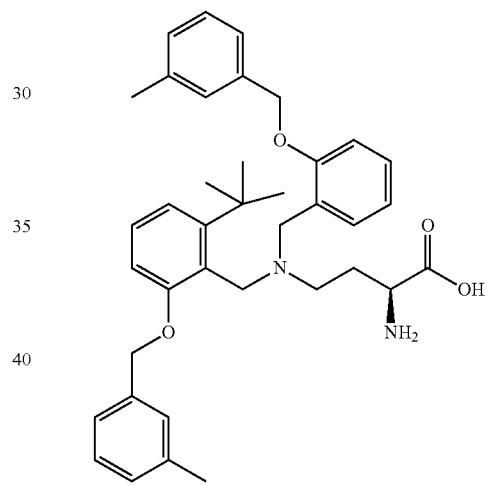
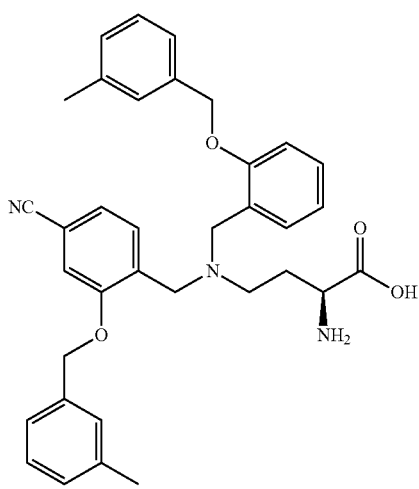
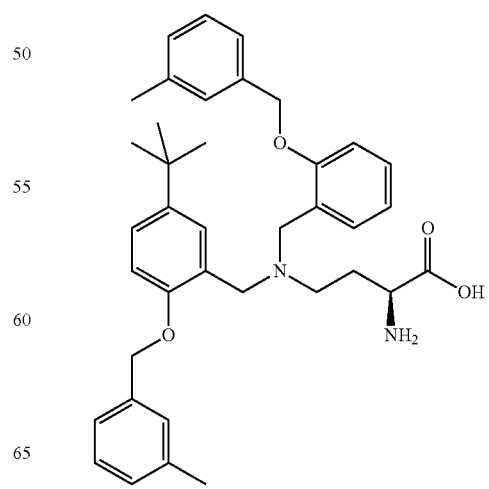

37
-continued
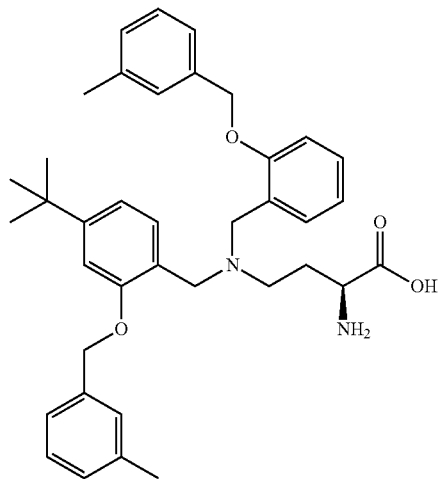
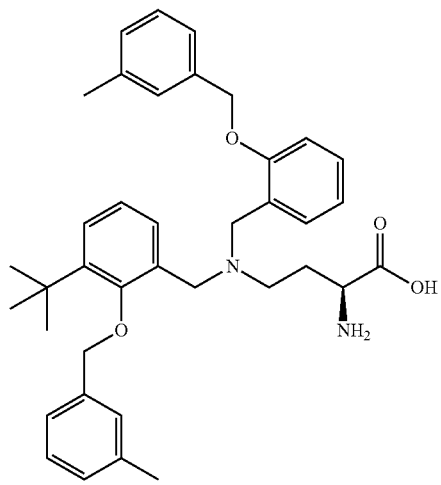
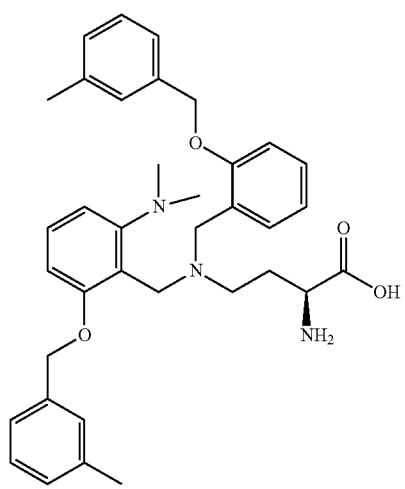
38
-continued
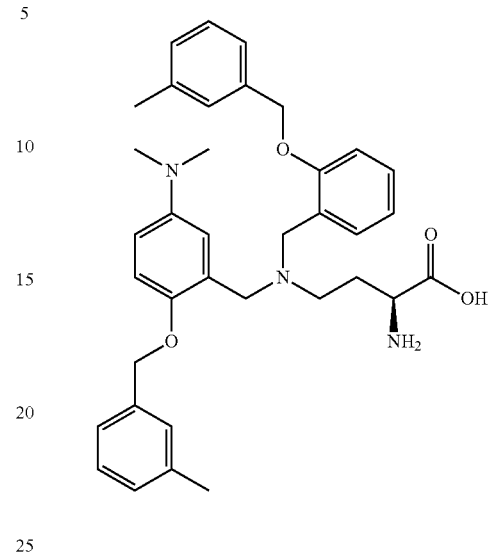
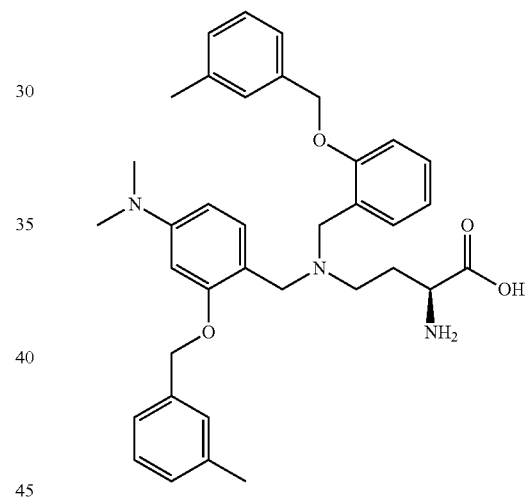
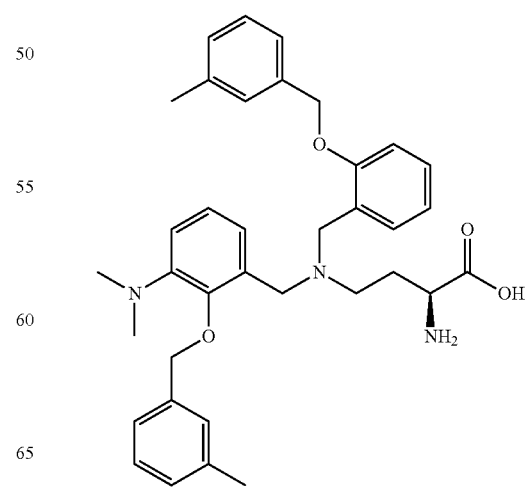

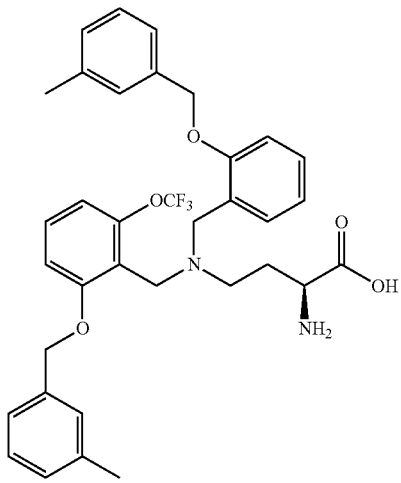
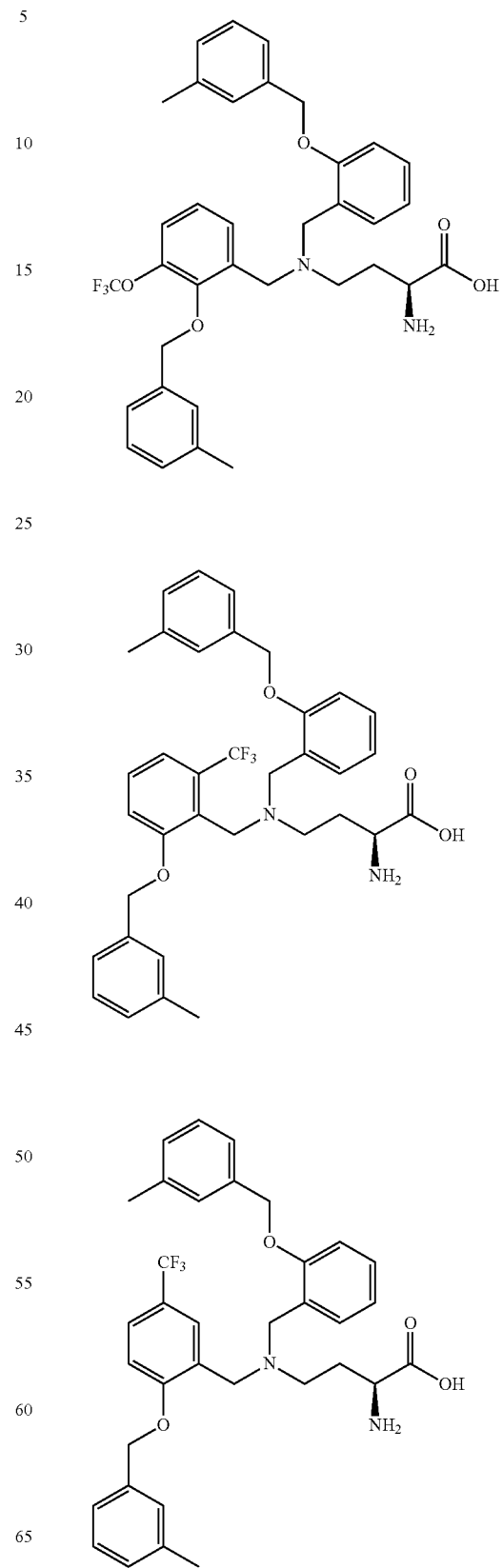

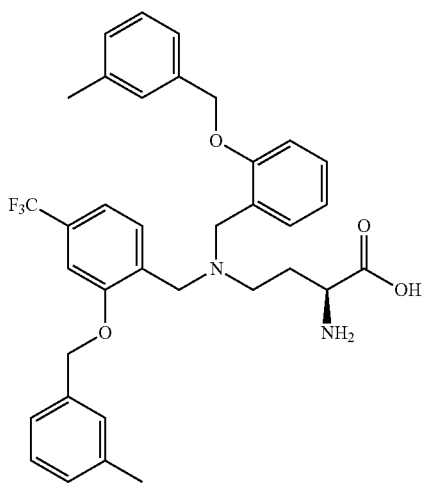
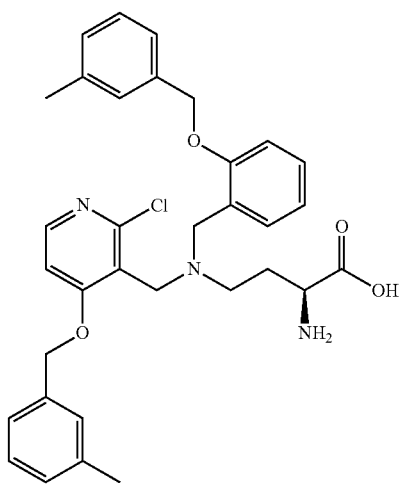
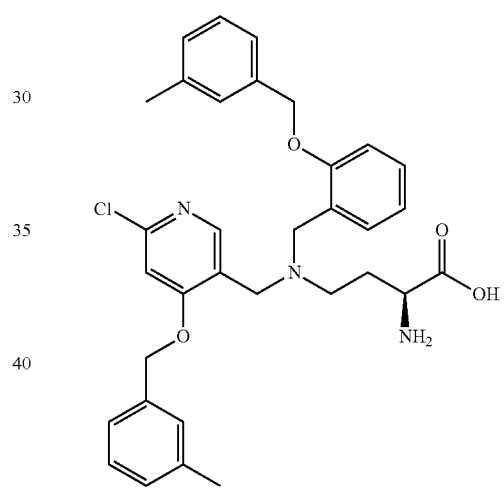
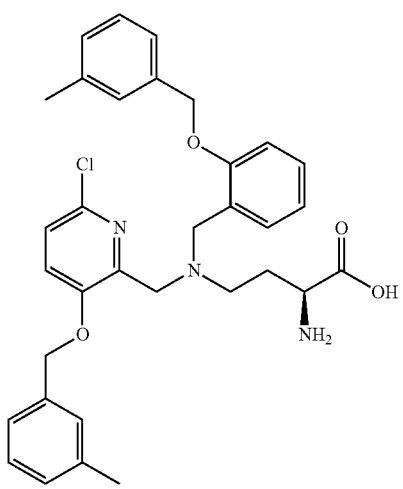

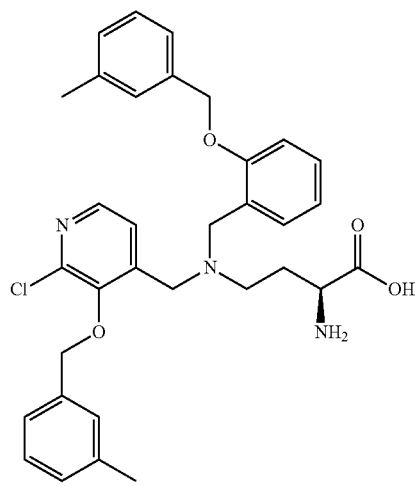
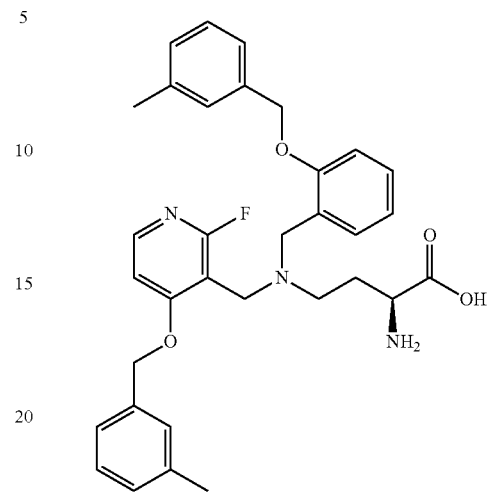
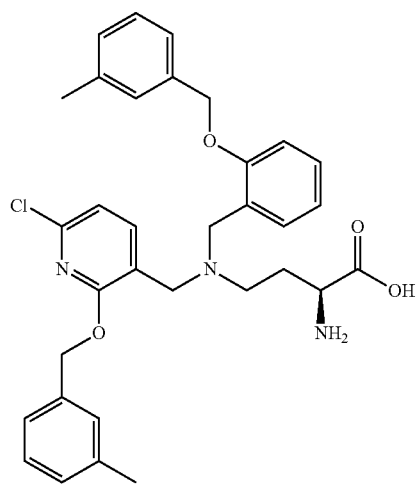
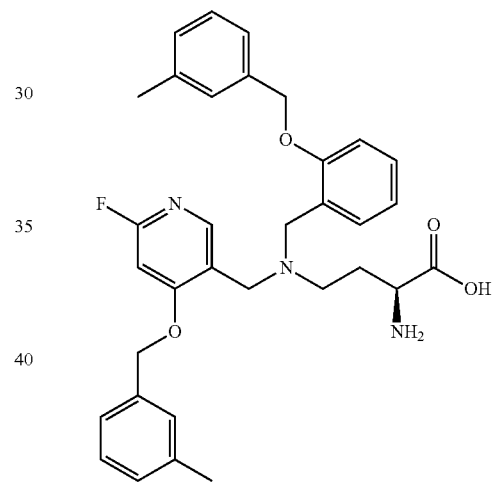
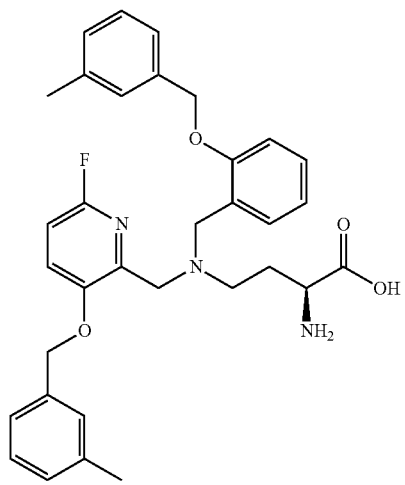
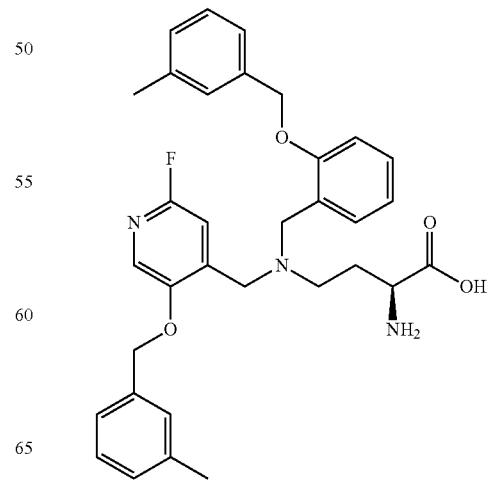

-continued
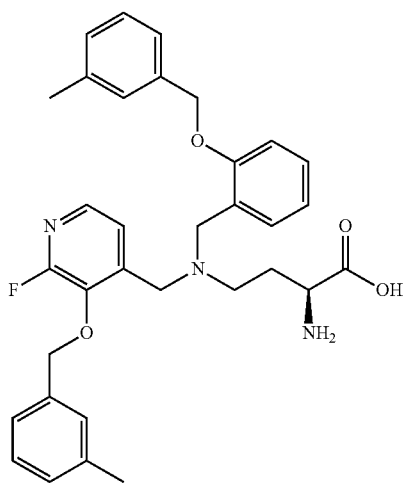
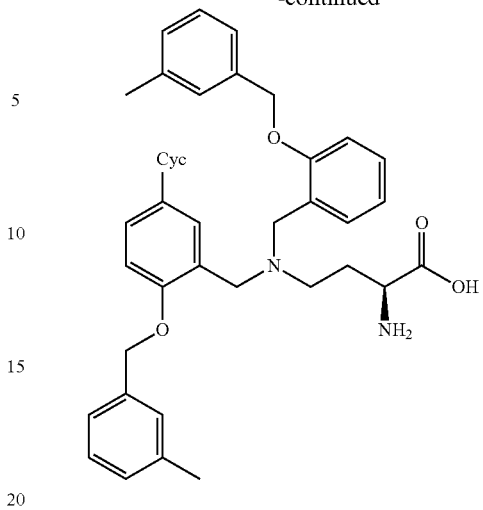
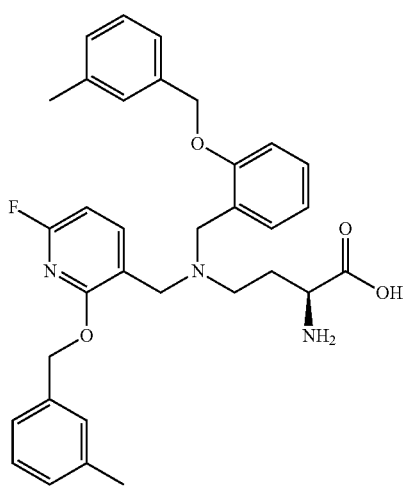
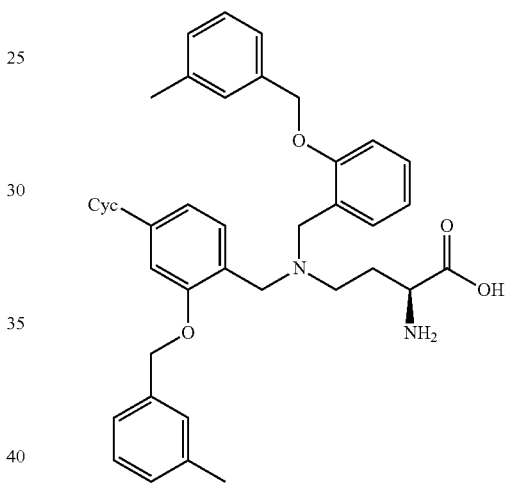
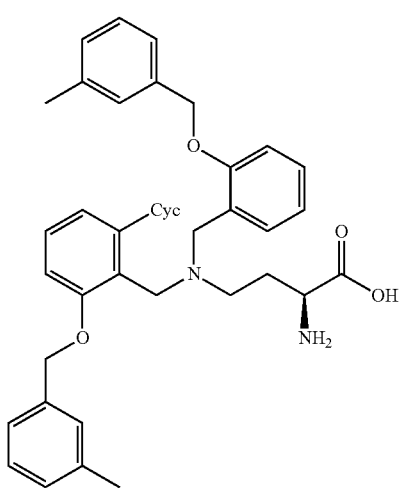
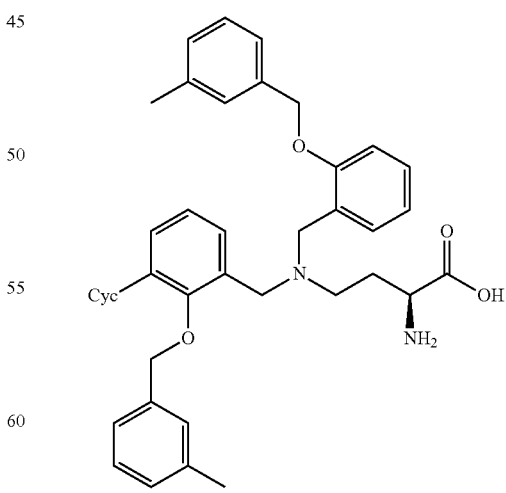
Cyc = cycles(eamples: cycloalkyl, heterocycles)
Another embodiment of the present is a compound of the following formula:

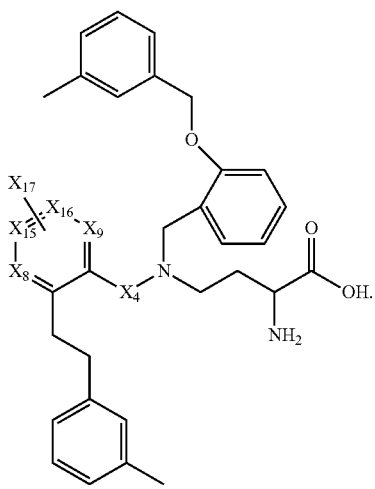

Another embodiment is a compound of the following formula:

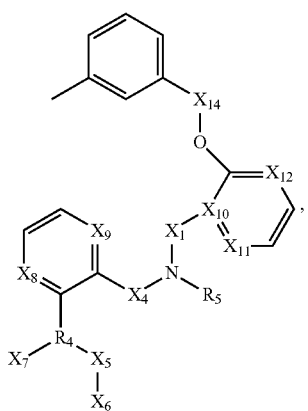

wherein:
$R_4$ is O or N;
$X_1$ is $CH_2$;
$X_4$ is $CH_2$;
$X_5$ is $CH_2$;
$X_6$ is phenyl (substituted or unsubstituted),
$X_7$ is H or absent;
$X_8$ is CH, $CH_2$;
$X_9$ is CH, $CH_2$;
$X_{10}$ is CH;
$X_{11}$ is CH, or $CH_2$;
$X_{12}$ is CH or $CH_2$;
$X_{14}$ is $CH_2$;
$R_5$ is chosen from:

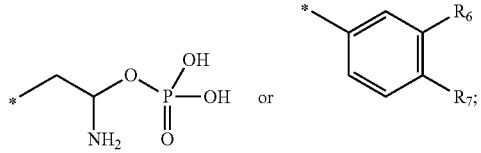

$R_6$ is NH C, CH, or $CH_2$;
$R_7$ is NH C, CH, or $CH_2$; and $R_6$ and $R_7$ form a 5 or 6-membered heteroring optionally substituted by H, OH, amino, phosphonic acid, carbonyl, acetic acid;

and pharmaceutically acceptable salts and pharmaceutically acceptable derivatives thereof.

Examples of these compounds include, but are not limited to, the following:

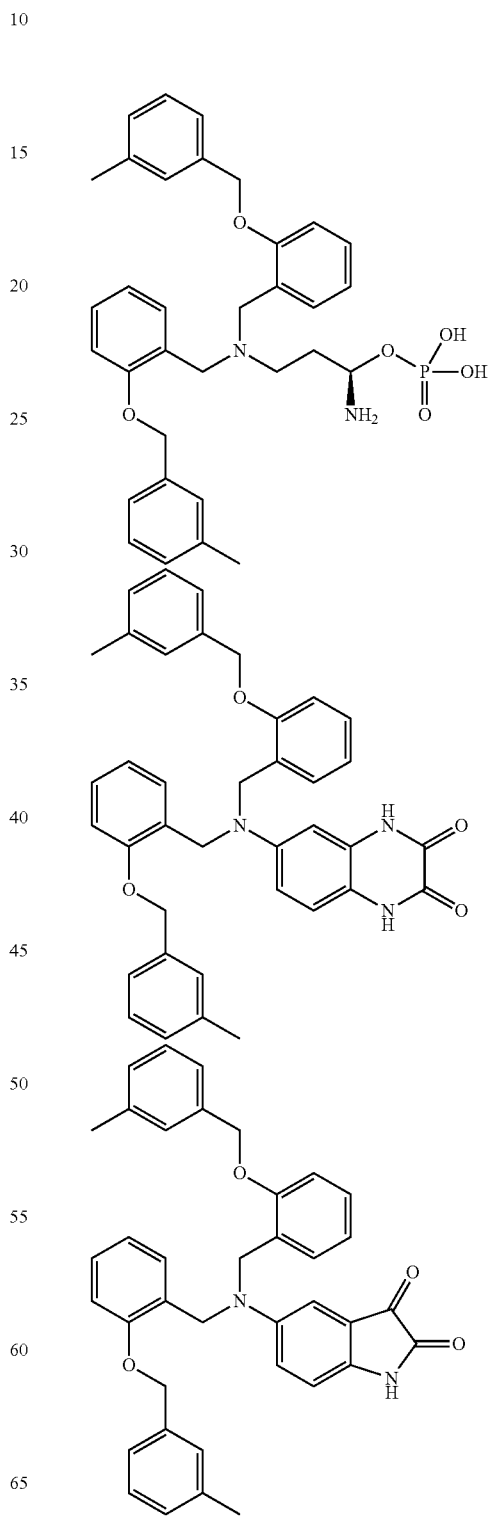

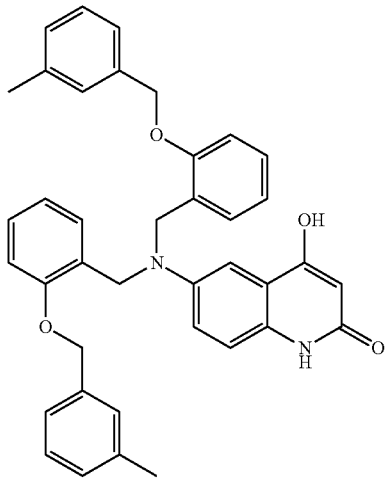
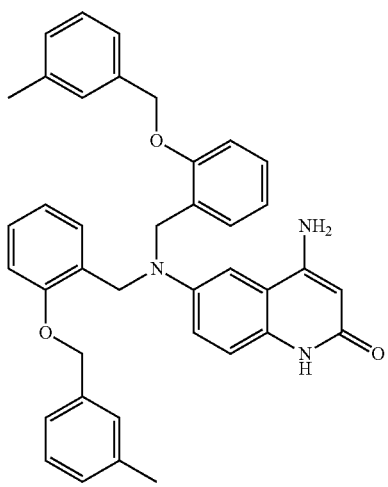
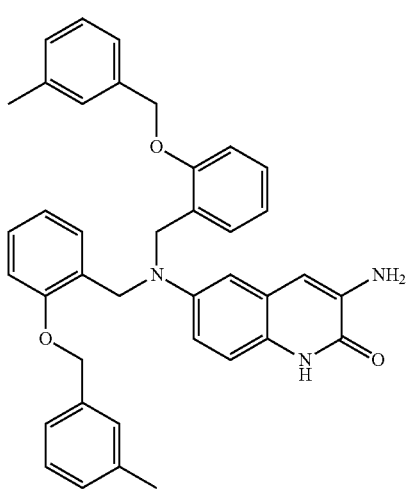
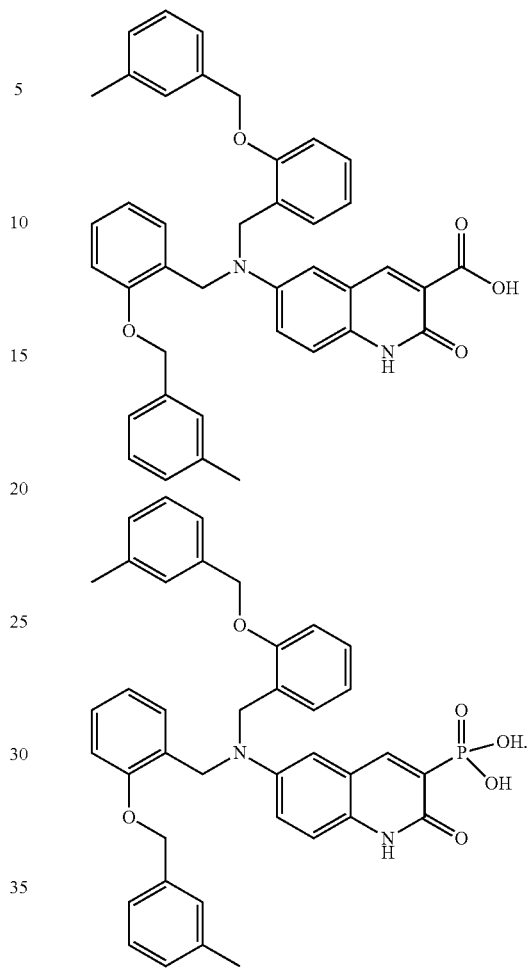
In other embodiments, $R_6$ and $R_7$ are C, CH, $CH_2$, N, or NH, and form a ring. In other embodiments, $R_6$ and $R_7$ are both NH and form ring.
Another embodiment of the present invention is a compound of the following formula:
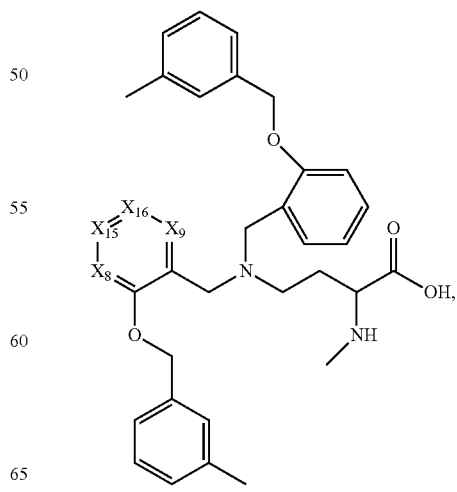

wherein:

$X_{16}$ and $X_9$ join to form a bicyclic ring (substituted or unsubstituted);

$X_{15}$ and $X_8$ join to form a bicyclic ring (substituted or unsubstituted); or $X_{16}$ and $X_{15}$ join to form a bicyclic ring (substituted or unsubstituted);

and pharmaceutically acceptable salts and pharmaceutically acceptable derivatives thereof.

In other embodiments, $X_{16}$ and $X_9$, $X_{15}$ and $X_8$, or $X_{16}$ and $X_{15}$ join together to form pyrazole, pyrrole, pyridine, pyrrolidine, piperidine, phenyl, cyclohexane, cyclopentene, tetrahydropyran, pyran, furan, dioxolane, dioxane, oxazole, imidazole, thiophene, oxathiolane, dioxepane, dioxepine.

Examples of the above compounds include the following:

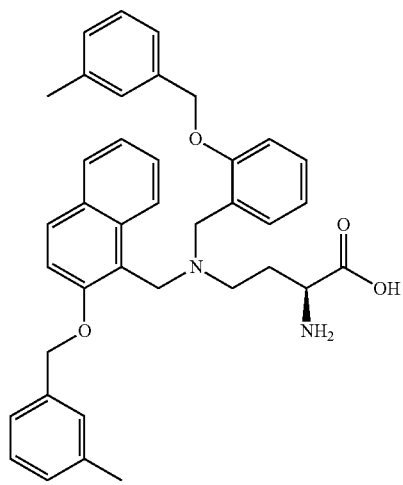

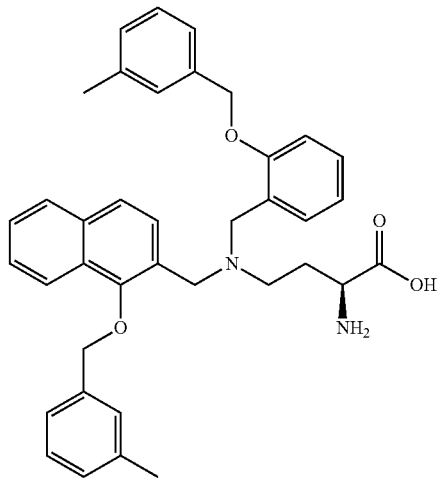

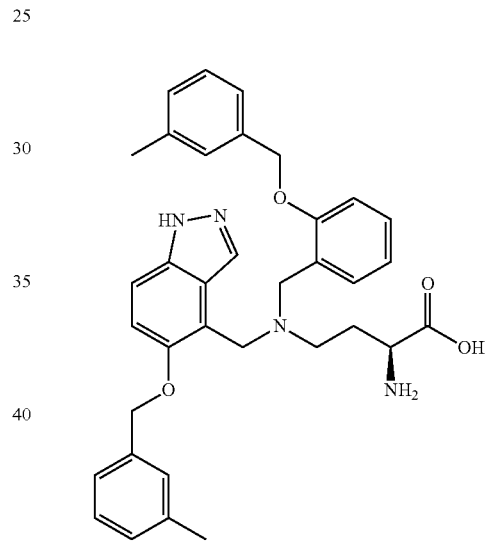

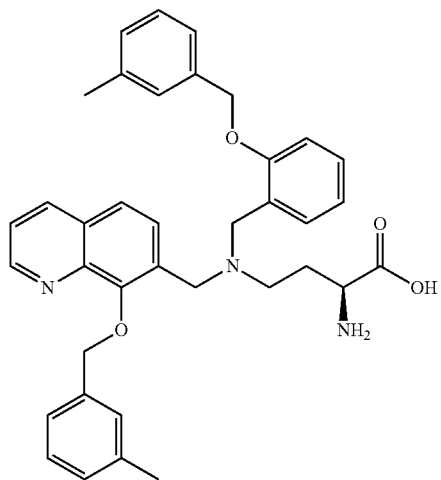

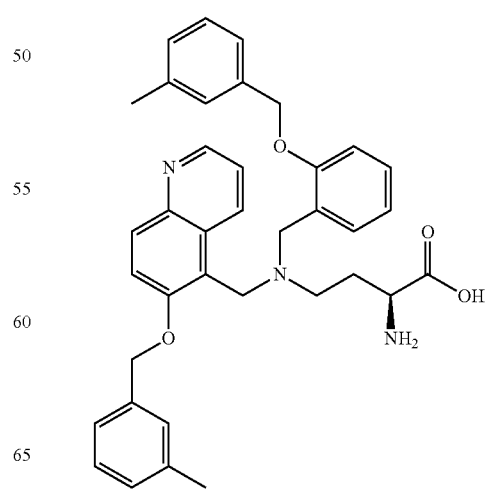

53
-continued
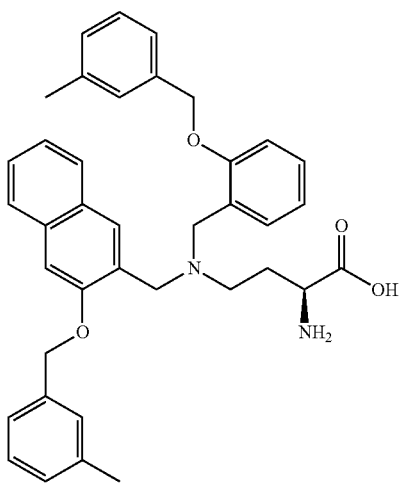
54
-continued
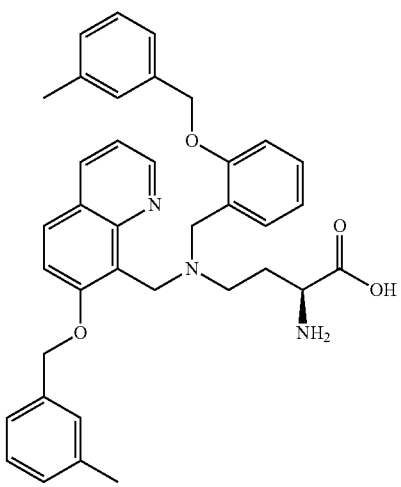
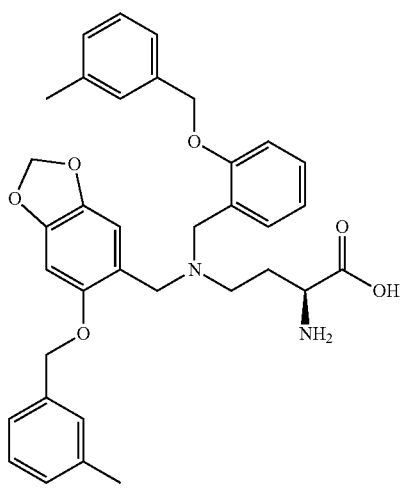
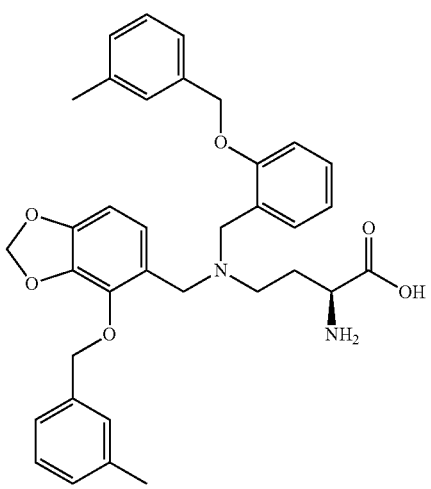 [SMILES: Cc1cccc(COc2ccccc2CN(CC[C@H](N)C(=O)O)Cc2ccc3ncoc3c2OCc2cccc(C)c2)c1]
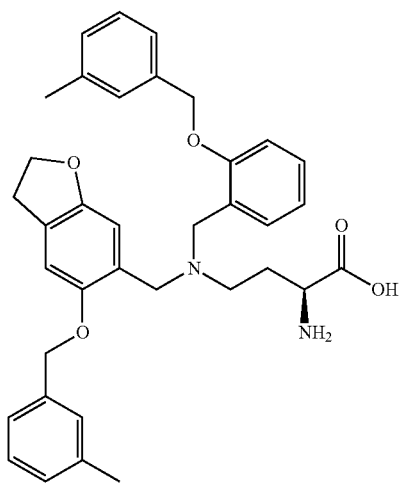
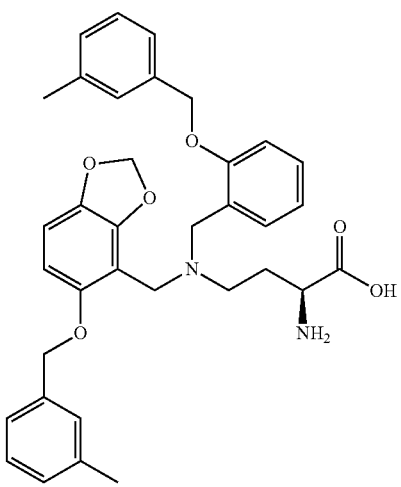

55
-continued
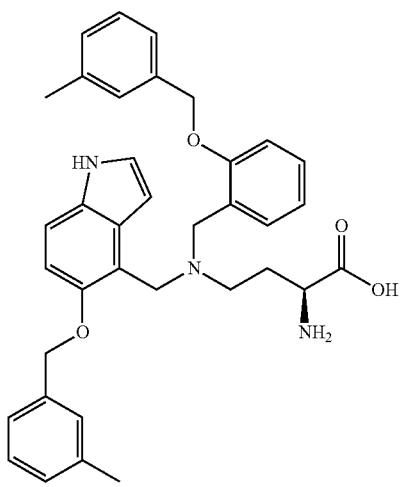
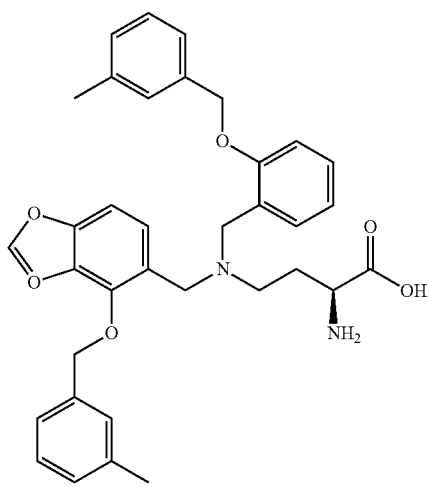
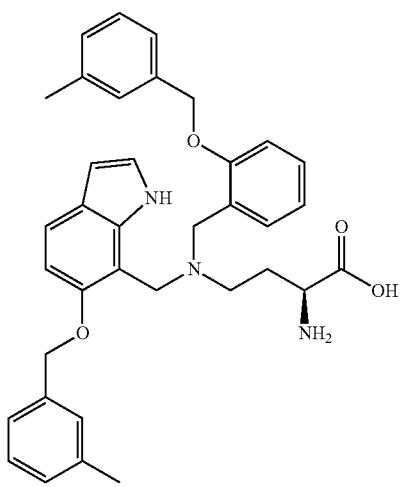
56
-continued
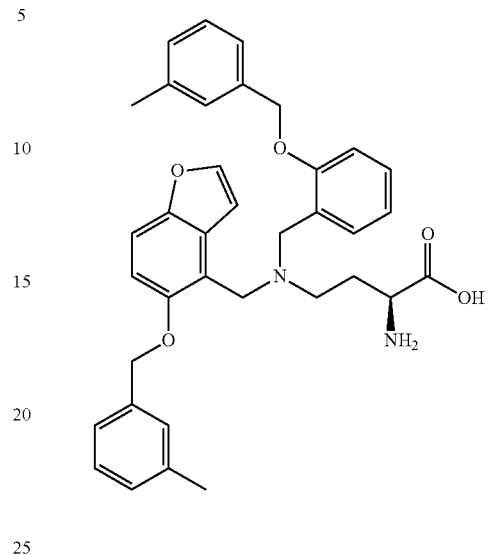
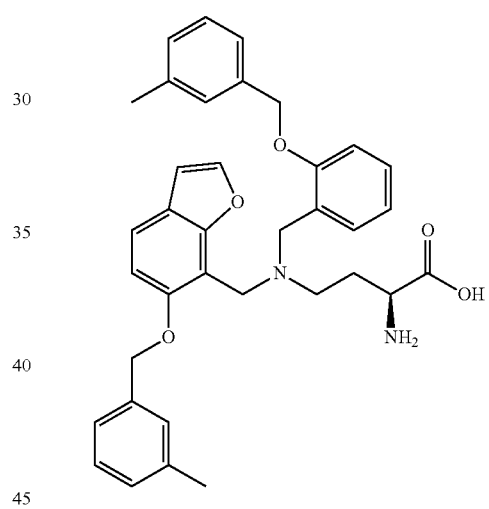
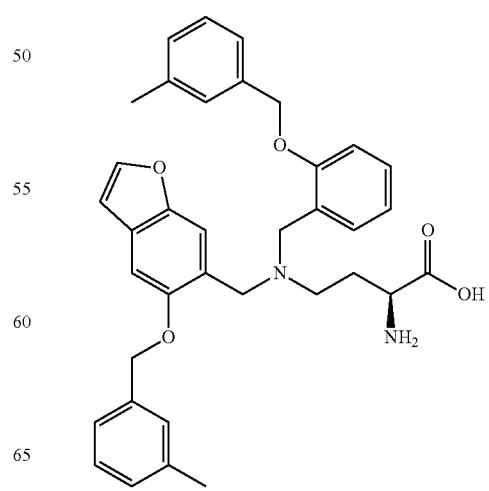

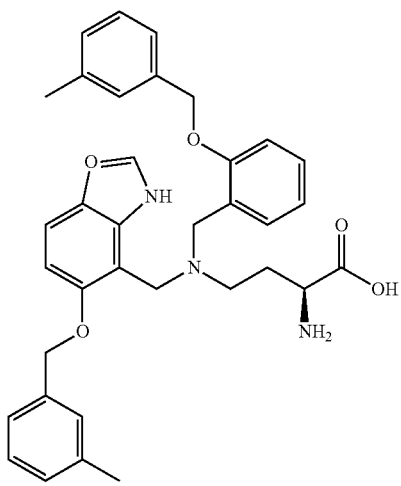
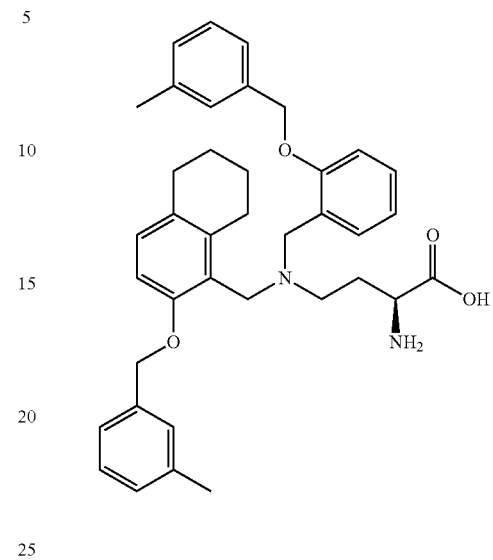
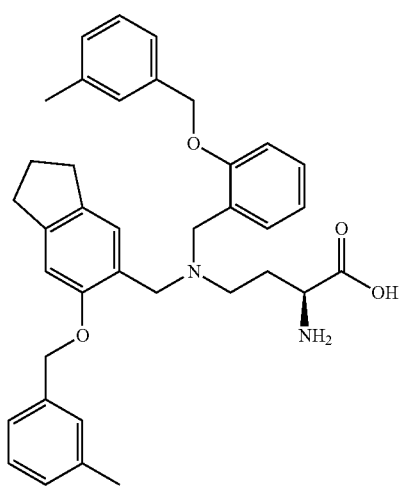
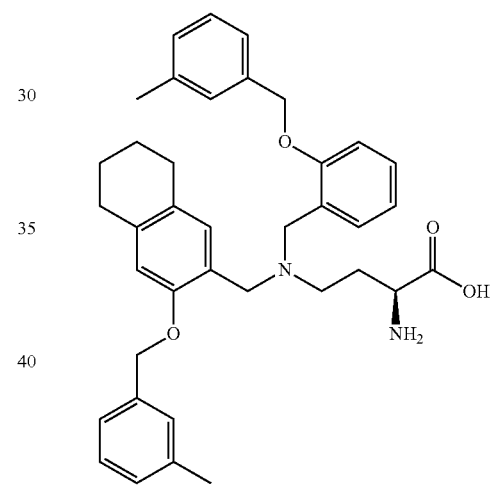
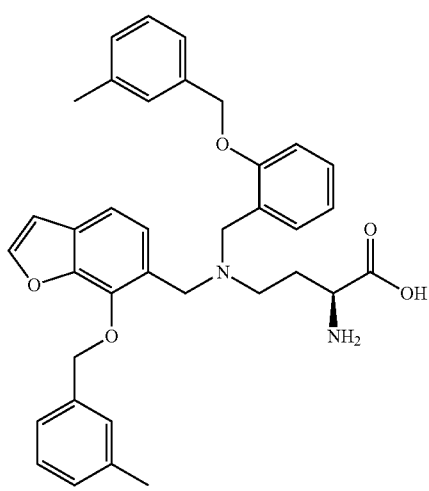
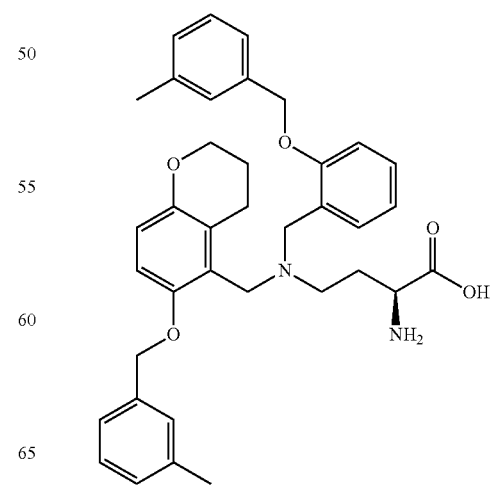

59
-continued
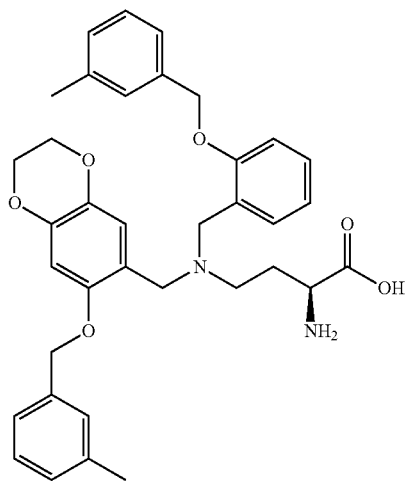
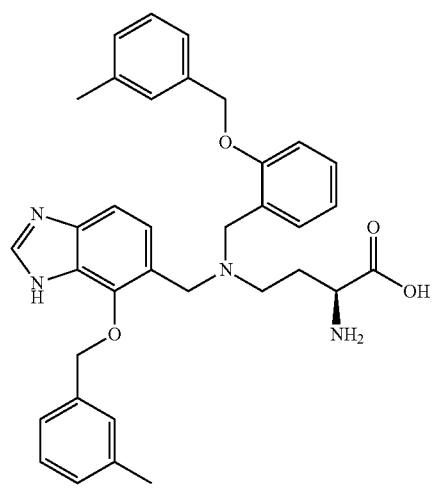
60
-continued
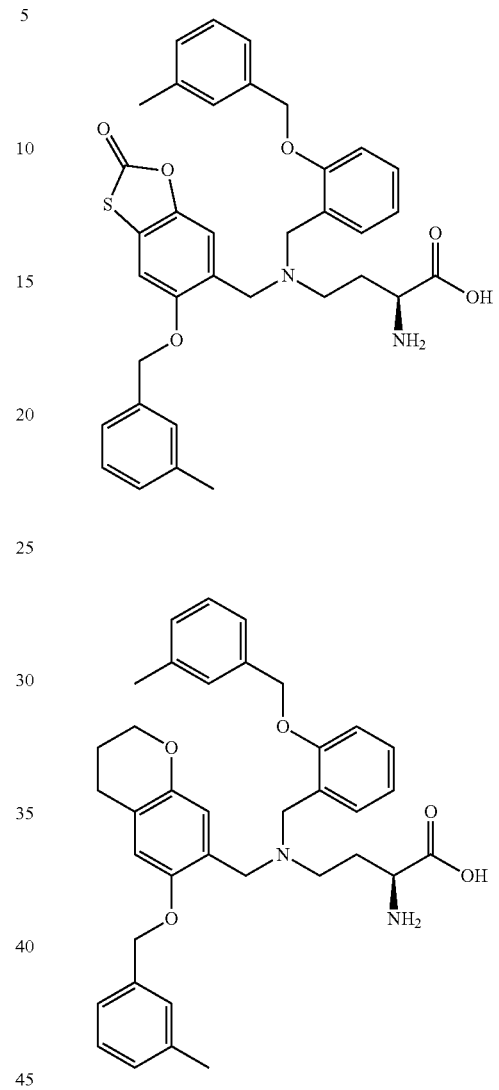
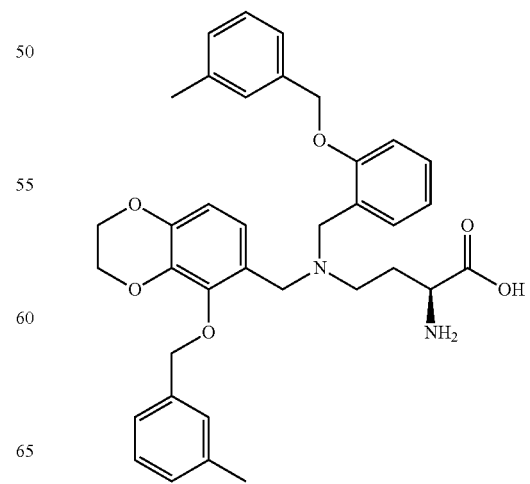

61
-continued
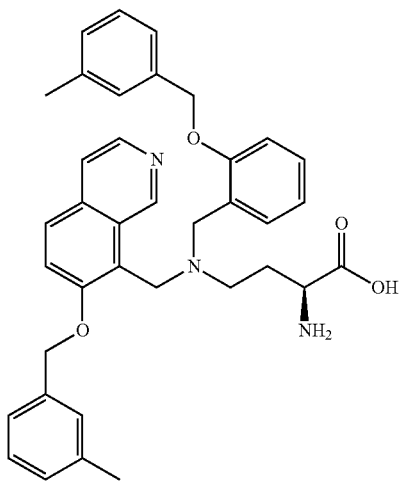
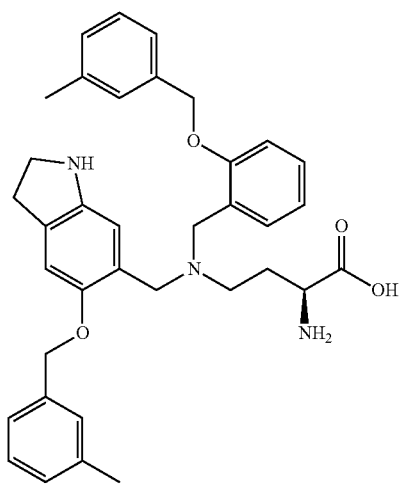
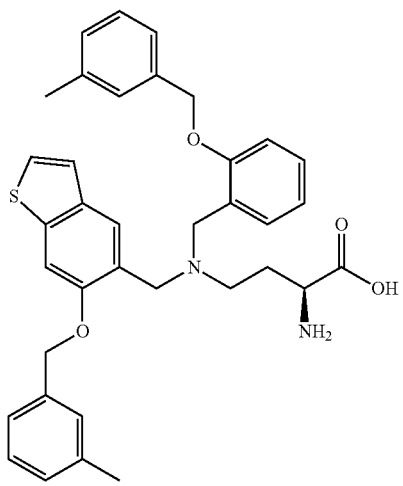
62
-continued
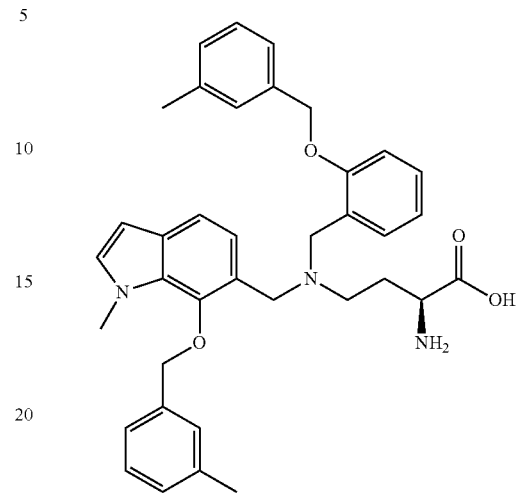
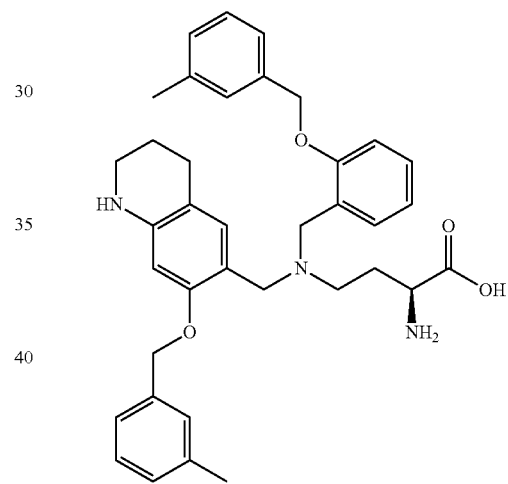
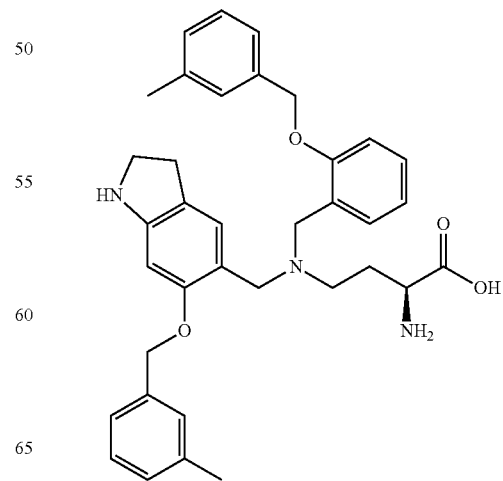

63
-continued
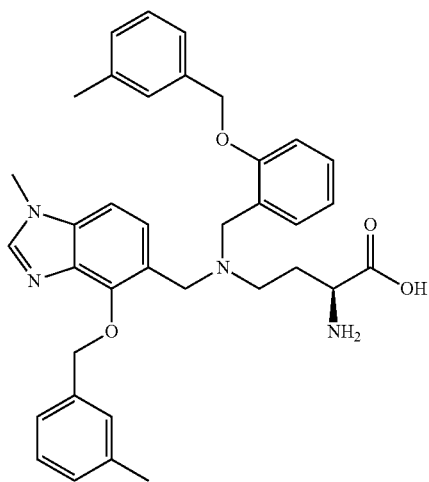
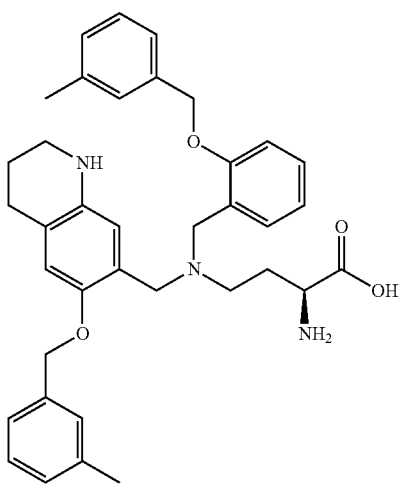
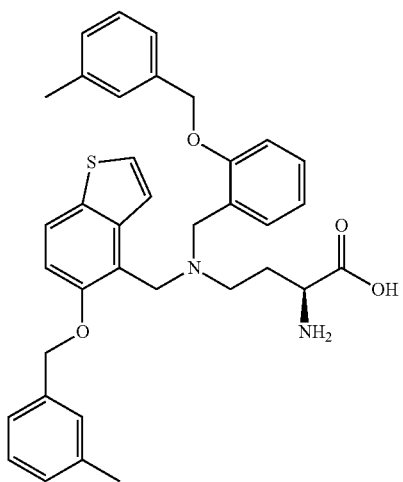
64
-continued
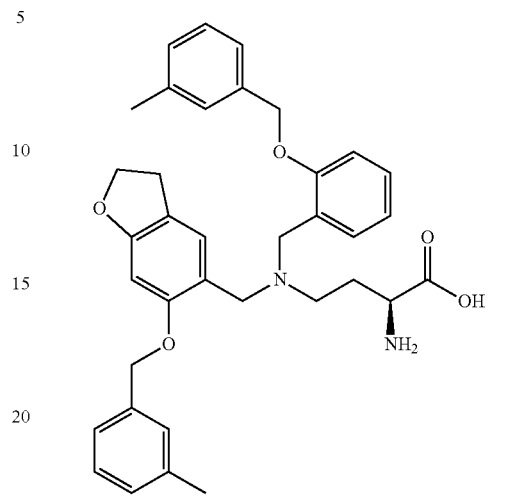
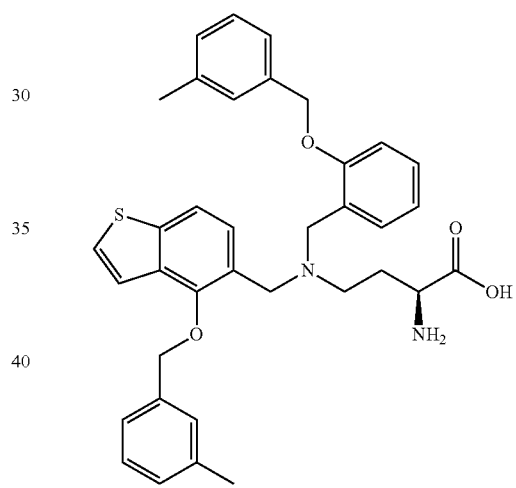
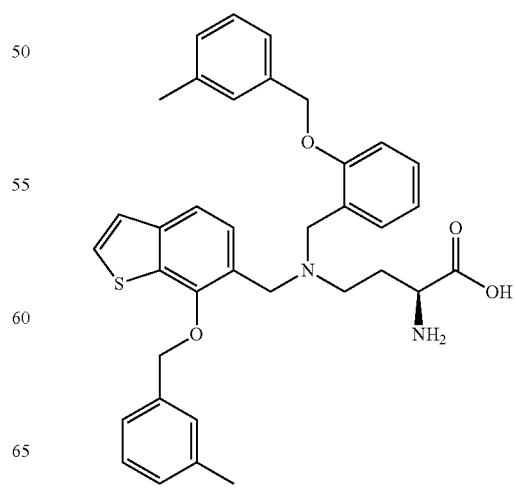

65
-continued
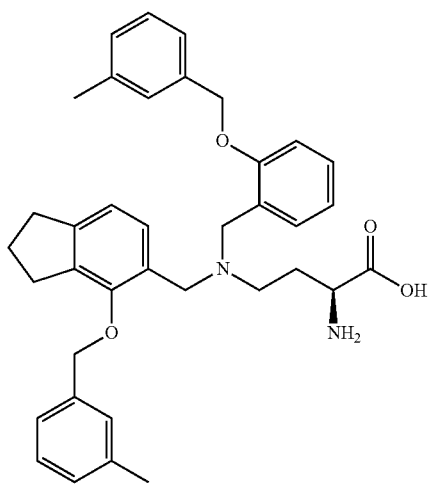
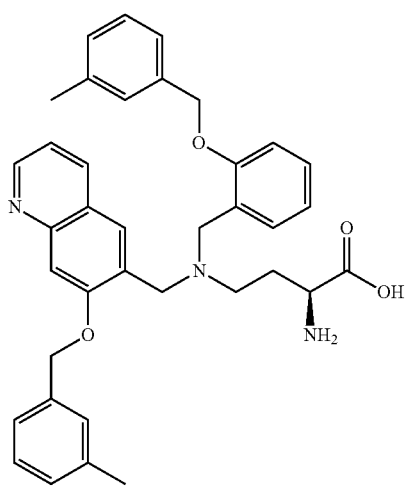
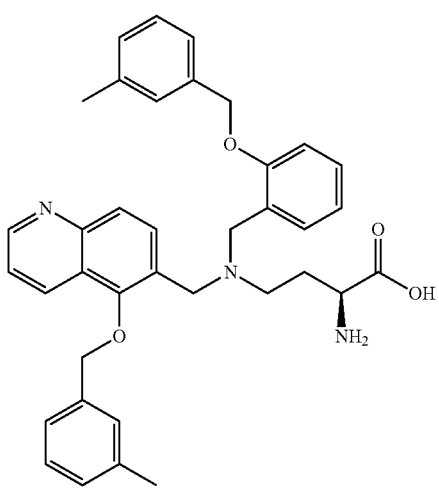
66
-continued
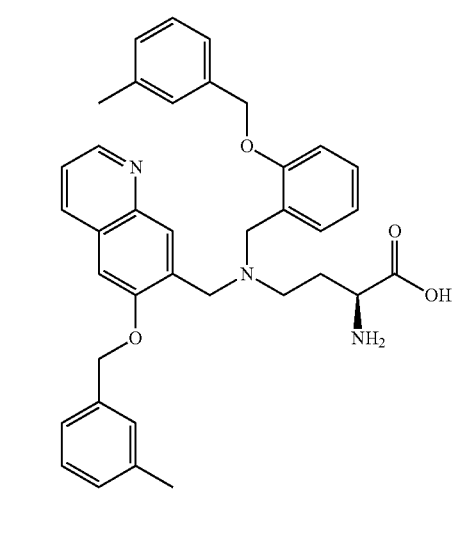
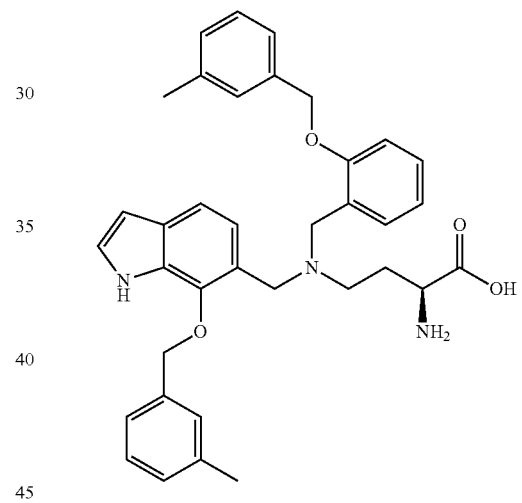

67
-continued
68
-continued
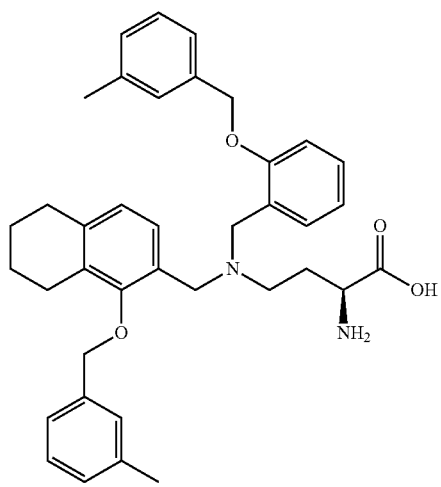
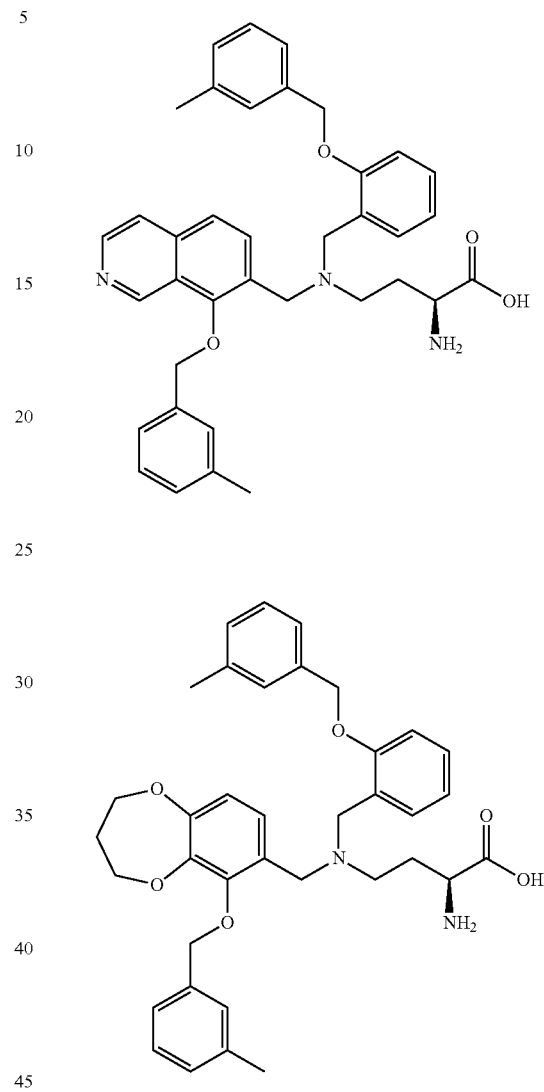
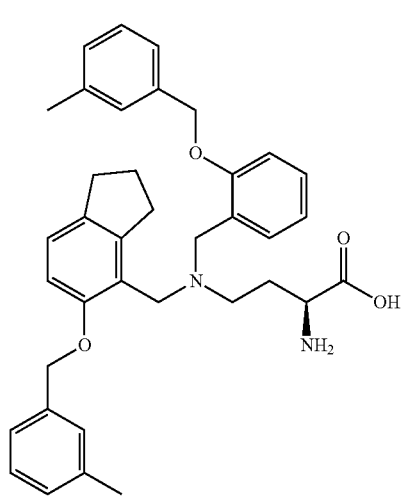

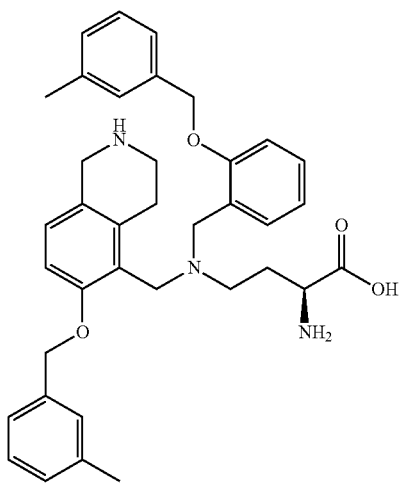
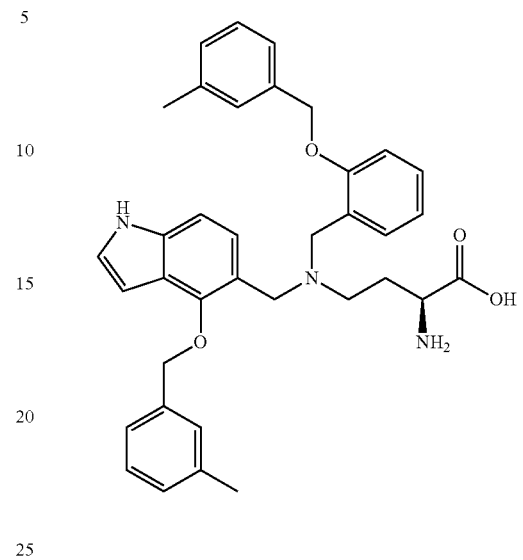
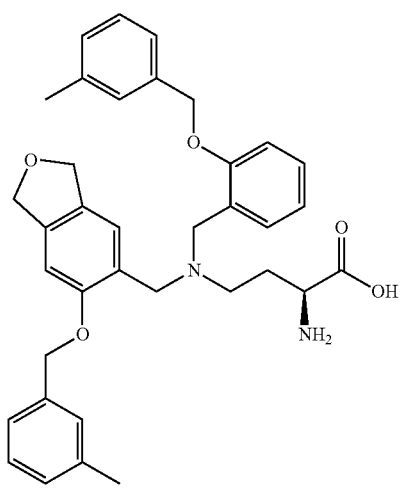
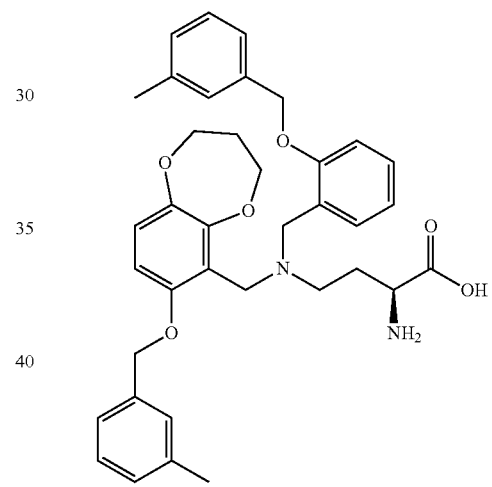
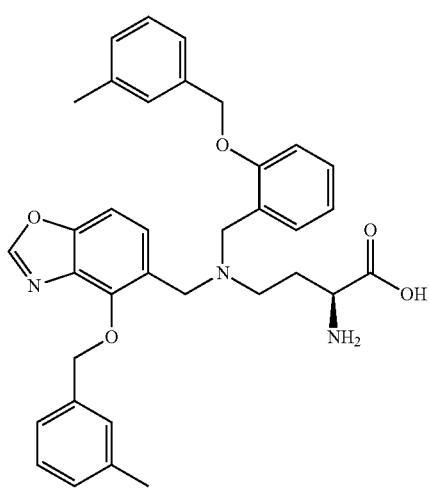
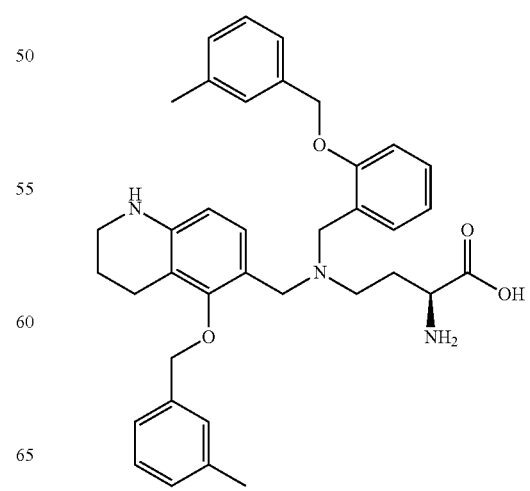

-continued

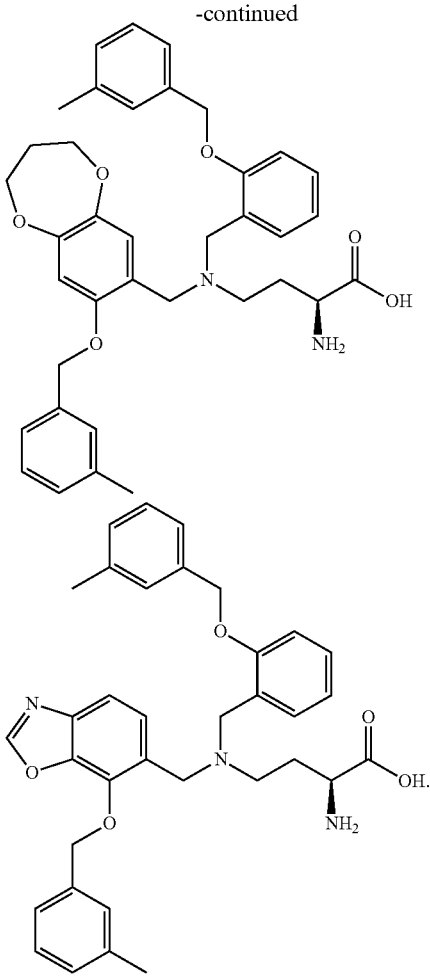

Pharmaceutical Compositions

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethyl enediamine, diethylamine, 2-diethyl aminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

Further disclosed herein are pharmaceutical compositions comprising one or more of the disclosed inhibitors of ASCT2 activity and a pharmaceutically acceptable carrier.

Accordingly, the pharmaceutical compositions of the present invention include those that contain one or more other active ingredients, in addition to a compound of the present invention.

The above combinations include combinations of a disclosed compound not only with one other active compound, but also with two or more other active compounds. Likewise, disclosed compounds may be used in combination with other drugs that are used in the prevention, treatment, control, amelioration, or reduction of risk of the diseases or conditions for which disclosed compounds are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient can be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent may be co-administered, either in concomitant therapy or in a fixed combination.

In one aspect, the compound can be employed in combination with at least one additional therapeutic agent. In one aspect of the invention the at least one additional therapeutic agent may be a cancer chemotherapeutic agent. In one aspect, the chemotherapeutic agent(s) may be platinum compounds, topoisomerase inhibitors, peptide antibiotics, alkylators, anthrcyclines, taxenes, histone deacetylase inhibitors, epothilones, kinase inhibitors, nucleotide analogues, retinoids, vinca alkaloids and derivatives, or any combination of chemotherapeutics. The platinum compound(s) may be carboplatin, cisplatin, or oxaliplatin. The topoisomerase inhibitor(s) may be irinotecan, topotecan, etoposide, teniposide, or tafluposide. The peptide antibiotic(s) may be bleomycin or actinomycin. The alkylator(s) may be cyclophosphamide, mechlorethamine, chlorambucil, or melphalan. The anthracycline(s) may be daunorubicin, doxorubicin, epirubicin, mitoxntrone, or valirubicin. The taxene(s) may be paclitaxel or docetaxel. The histone deacetylase inhibitor(s) may be vorinostat or romidepsin. The epothilone(s) may be ixabepilone, patupilone, or sagopilone. The kinase inhibitor(s) may be bortezomib, dabrafenib, erlotinib, gefitinib, imatinib, tremetinib, vemurafenib, or vismodegib. The nucleotide analogue(s) may be azacitidine, azathioprine, capecitabine, cytarabine, flurouracil, gemcitabine, hydroxyurea, mercaptopurine, methotrexate, or tioguanine.

In one aspect, the invention relates to pharmaceutical compositions comprising a compound having a structure represented by a formula:

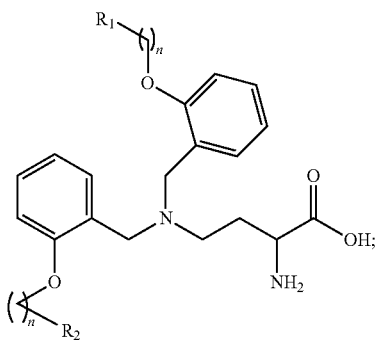

wherein:

$R_1$ is phenyl (optionally substituted with at least one $R_3$), benzyl (optionally substituted with at least one $R_3$), pyridinyl (optionally substituted with at least one $R_3$);

$R_2$ is phenyl (optionally substituted with at least one $R_3$), benzyl (optionally substituted with at least one $R_3$), pyridinyl (optionally substituted with at least one $R_3$);

$R_3$ is independently H, Me, alkyl, methoxy, alkoxy, halogen, $CF_3$; and n is 0-6;

and pharmaceutically acceptable salts and pharmaceutically acceptable derivatives thereof; and a pharmaceutically acceptable carrier.

Another embodiment relates to a pharmaceutical composition comprising a compound of the following formula:

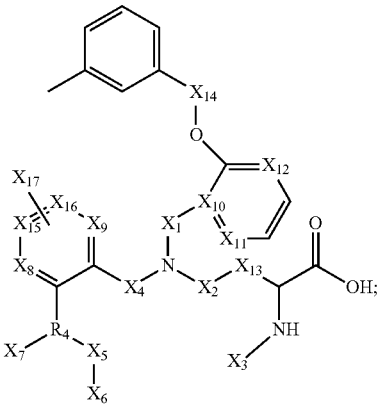

wherein:

$R_4$ is O or N;

$X_1$ is $CH_2$, or is CH and forms a ring with $X_9$ (substituted or unsubstituted), or is absent when $X_9$ forms a ring with $X_{10}$ and at the same time $X_{11}$ forms a ring with $X_2$;

$X_2$ is $CH_2$, or forms a ring with $X_3$ (substituted or unsubstituted), $X_3$ is H, or forms a ring with $X_2$ (substituted or unsubstituted), $X_4$ is $CH_2$, or forms a ring with $X_5$ or $X_7$ (substituted or unsubstituted), $X_5$ is absent; $CH_2$; or forms a ring with $X_4$ (substituted or unsubstituted);

$X_6$ is absent, H, or phenyl (substituted or unsubstituted), $X_7$ is H, absent, benzyl (substituted or unsubstituted) or forms a ring or bicyclic ring with $X_8$ or $X_4$ (substituted or unsubstituted);

$X_8$ is C, CH, $CH_2$, N, or forms a ring or bicyclic ring with $X_7$ (substituted or unsubstituted);

$X_9$ is C, CH, $CH_2$, N, or forms a ring or bicyclic ring with $X_1$, $X_{10}$, or $X_{11}$ (substituted or unsubstituted);

$X_{10}$ is CH, or forms a ring with $X_1$ or $X_9$ (substituted or unsubstituted);

$X_{11}$ is CH, or $CH_2$, or forms a ring with $X_2$ or $X_{13}$ (substituted or unsubstituted);

$X_{12}$ is CH or $CH_2$, or forms a ring with $X_{14}$ (substituted or unsubstituted);

$X_{13}$ is $CH_2$, or forms a ring with $X_{11}$ (substituted or unsubstituted);

$X_{14}$ is $CH_2$, or forms a ring with $X_{12}$ (substituted or unsubstituted);

$X_{15}$ is C, CH, $CH_2$, N;

$X_{16}$ is C, CH, $CH_2$, N;

$X_{17}$ is optionally present and is H, methyl, alkyl, halogen, methoxy, alkoxy, CN, $—CF_3$, $—OCF_3$, or Cyc;

and pharmaceutically acceptable salts and pharmaceutically acceptable derivatives thereof; and a pharmaceutically acceptable carrier.

Another embodiment relates to a pharmaceutical composition comprising a compound of the following formula:

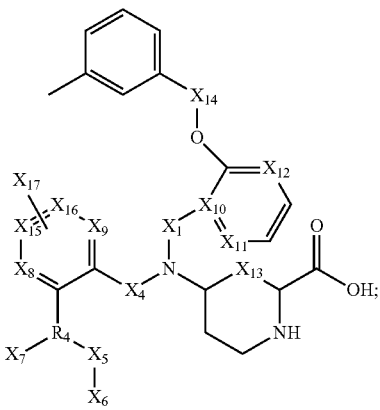

wherein:
$R_4$ is O;
$X_1$ is $CH_2$;
$X_4$ is $CH_2$;
$X_5$ is $CH_2$;
$X_6$ is phenyl (substituted or unsubstituted);
$X_7$ is absent;
$X_8$ is CH;
$X_9$ is CH;
$X_{10}$ is C;
$X_{11}$ is CH;
$X_{12}$ is CH;
$X_{13}$ is $CH_2$;
$X_{14}$ is $CH_2$;
$X_{15}$ is CH;
$X_{16}$ is CH; and
$X_{17}$ is H, alkyl, halogen, alkoxy, CN, —$CF_3$, or —$OCF_3$;
or pharmaceutically acceptable salt thereof.

Another embodiment relates to a pharmaceutical composition comprising a compound of the following formula:

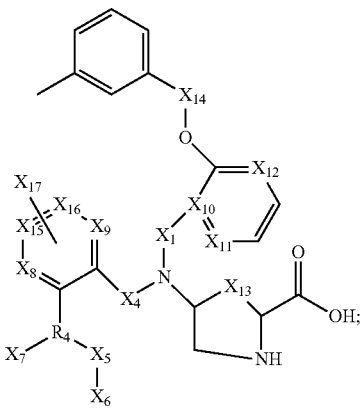

wherein:
$R_4$ is O;
$X_1$ is $CH_2$;
$X_4$ is $CH_2$;
$X_5$ is $CH_2$;
$X_6$ is phenyl (substituted or unsubstituted);
$X_7$ is absent;
$X_8$ is CH;
$X_9$ is CH;
$X_{10}$ is C;
$X_{11}$ is CH;
$X_{12}$ is CH;
$X_{13}$ is $CH_2$;
$X_{14}$ is $CH_2$;
$X_{15}$ is CH;
$X_{16}$ is CH; and
$X_{17}$ is H, alkyl, halogen, alkoxy, CN, —$CF_3$, or —$OCF_3$;
or pharmaceutically acceptable salt thereof.

Another embodiment relates to a pharmaceutical composition comprising a compound of the following formula:

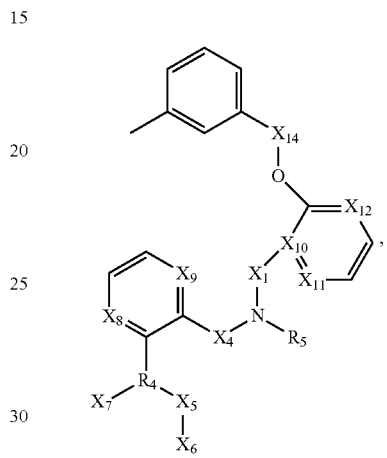

wherein:
$R_4$ is O or N;
$X_1$ is $CH_2$;
$X_4$ is $CH_2$;
$X_5$ is $CH_2$;
$X_6$ is phenyl (substituted or unsubstituted),
$X_7$ is H or absent;
$X_8$ is CH, $CH_2$;
$X_9$ is CH, $CH_2$;
$X_{10}$ is CH;
$X_{11}$ is CH, or $CH_2$;
$X_{12}$ is CH or $CH_2$;
$X_{14}$ is $CH_2$;
$R_5$ is chosen from:

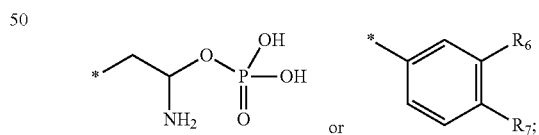

$R_6$ is NH C, CH, or $CH_2$;
$R_7$ is NH C, CH, or $CH_2$; and
$R_6$ and $R_7$ form a 5 or 6-membered heteroring optionally substituted by H, OH, amino, phosphonic acid, carbonyl, acetic acid;
and pharmaceutically acceptable salts and pharmaceutically acceptable derivatives thereof; and a pharmaceutically acceptable carrier.

Another embodiment of the present invention is a pharmaceutical composition comprising a compound of the following formula:

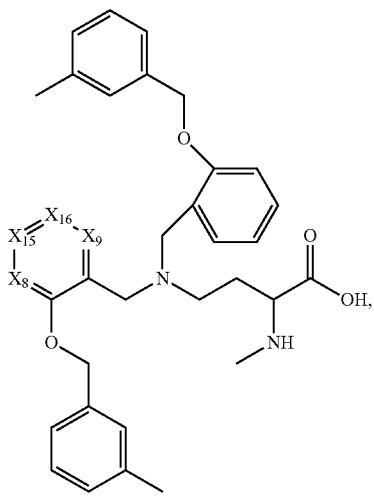

wherein:

$X_{16}$ and $X_9$ join to form a bicyclic ring (substituted or unsubstituted);

$X_{15}$ and $X_8$ join to form a bicyclic ring (substituted or unsubstituted); or $X_{16}$ and $X_{15}$ join to form a bicyclic ring (substituted or unsubstituted);

and pharmaceutically acceptable salts and pharmaceutically acceptable derivatives thereof; and a pharmaceutically acceptable carrier.

Another embodiment of the present invention is a pharmaceutical composition comprising a compound of the following formula:

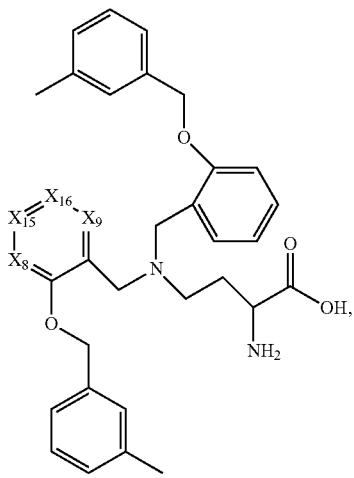

wherein:

$X_{16}$ and $X_9$ join to form a bicyclic ring (substituted or unsubstituted);

$X_{15}$ and $X_8$ join to form a bicyclic ring (substituted or unsubstituted); or $X_{16}$ and $X_{15}$ join to form a bicyclic ring (substituted or unsubstituted);

and pharmaceutically acceptable salts and pharmaceutically acceptable derivatives thereof; and a pharmaceutically acceptable carrier.

Another embodiment of the present invention relates to a pharmaceutical composition comprising a compound of the following formula:

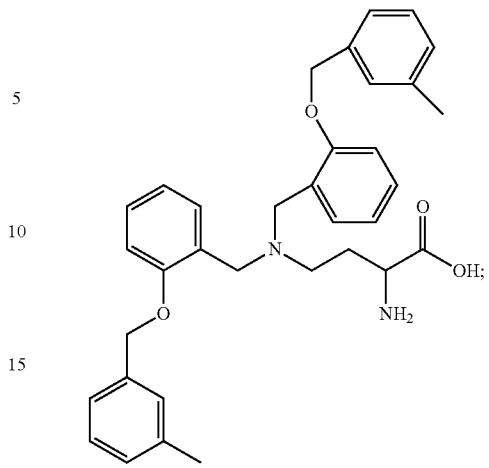

and pharmaceutically acceptable salts and pharmaceutically acceptable derivatives thereof; and a pharmaceutically acceptable carrier.

Methods of Use

The compounds of the invention can be used to treat a patient (e.g., a human) that suffers from or is at risk of suffering from a disease, disorder, condition, or symptom caused by or related to ASCT2 functional abnormality, including, but not limited to, cancer, microbial infections, and ischemia-related central nervous system injuries. The compounds of the invention can be used alone or in combination with other agents and compounds to treat such diseases, disorders, conditions, and symptoms. Each such treatment described herein includes the step of administering to a patient in need thereof a therapeutically effective amount of a compound of the invention described herein to delay, reduce or prevent such disease, disorder, condition, or symptom.

Besides being useful for human treatment, the compounds and formulations of the present invention are also useful for the treatment of ASCT2 functional abnormality in animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

It is known that ASCT2 plays a role in several disease processes, including cancer and ischemia-related central nervous system injuries. Accordingly, inhibition of ASCT2 is known to be effective to prevent or treat these disease processes. For example, targeting the ASCT2 transporter has been identified as a therapy to inhibit cancer cells (reviewed in: Nakanishi et al., J. Pharm. Sci. 100:3731 (2011)). Antisense mRNA to specifically down-regulate ASCT2 effectively inhibits survival of human hepatoma cells (Fuchs et al., Am. J. Physiol. Cell. Physiol. 293 C55 (2007)).

The involvement of ASCT2 glutamine transport abnormality or dysfunction is involved in a broad spectrum of cancer types and subtypes. For example, glutamine metabolism and glutamine transport by the ASCT2 transporter is up-regulated in a wide variety of tumor cell types, which gives them a growth advantage over normal cells (Fuchs et al., Sem. Cancer Biol., 15:254-266 (2005)). Specifically, ASCT2 was upregulated (statistically significant) in brain, colon, eye, kidney, liver, lung, lymph node, mammary gland, muscle, pancreas, placenta, skin, and stomach. Other studies show the broad expression and dependence of various cancer cells on the obligate glutamine transporter ASCT2, such as in breast cancer (Collins et al., J. Cell Physiol., 176:166-178 (1998)) and colon carcinoma (Wasa et al., Ann. Surg., 22:189-97 (1996)).

Ischemia-Related Central Nervous System Injury

It is known that ASCT2 glutamine transport abnormalities also play a role in ischemia-related central nervous system injuries. For example, Wolosker et al. (FEBS Journal, 275: 3514-3526 (2008)) describes the role that glutamate transporters play in the regulation of NMDAR receptors. NMDAR receptor activity has been correlated with neuronal damage following ischemia (i.e., stroke). One way to control NMDAR activity is to limit the availability of its agonist ligand, D-serine. Glutamate ASCT 2 inhibition, as provided by the compounds and methods of the present invention, limits the level of D-serine available to NMDAR receptors, thereby limiting NMDAR activity and conferring a neuroprotective benefit.

In other embodiments of the present invention, the compounds disclosed herein are also useful for the treatment of ASCT2 functional abnormality in animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents).

Methods of Diagnostic Imaging

Compounds of the invention that contain a radionuclide, such as fluorine-18, can also be used, alone or in combination with other agents and compounds, in radiographic medical imaging applications in a patient (e.g., a human) to diagnose or follow the progression of diseases, disorders, conditions or symptoms related to a disease, disorder, condition, or symptom caused by or related to ASCT2 functional abnormality, including, but not limited to, cancer, microbial infections, and ischemia-related central nervous system injuries. This use of ASCT2 inhibitors is shown in US Published Patent Application No. 2015/0056138, incorporated herein by reference. Radiologists and other medical clinicians are skilled in the use of radiographic imaging devices, such as positron emission tomography (PET) scanners, and methods of imaging diagnostic compounds, such as the radionuclide compounds of the invention, in a patient are widely known (e.g., Saha, Basics of PET Imaging: Physics, Chemistry, and Regulations, Springer (2010) ISBN 978-1-4419-0804-9, hereby incorporated by reference).

The radionuclide compounds and formulations of the present invention are also useful for the medical imaging of animals, e.g., the veterinary treatment of domesticated animal, companion animals (e.g., dogs and cats), exotic animals, farm animals (e.g., ungulates, including horses, cows, sheep, goats, and pigs), and animals used in scientific research (e.g., rodents and non-human primates).

Methods of Radionuclide Compound Synthesis

The radionuclide diagnostic compounds of the invention can be synthesized by several techniques known to persons skilled in the art. For example, for the substitution of a carbon atom by a carbon-11, several derivatives such as [$^{11}$C]methyl iodide or [$^{11}$C]methyl triflate (Welch et al., In Handbook of Radiopharmaceuticals-Radiochemistry and Applications (Welch M J, Redvanly C S Eds.), New York-Chichester-Brisbane-Toronto, Wiley-Interscience Pub., 1-848 (2003)).

In the case of a labeling with fluorine-18, the radioisotope may be directly attached to a core structure by nucleophilic aliphatic or aromatic (including heteroaromatic (Dolle et al., Curr. Pharm. Design 11:3221-3235 (2005)) substitutions or electrophilic substitutions or linked through the addition of a spacer group, both techniques known to persons skilled in the art (Kilbourn, In fluorine-18 Labeling of Radiopharmaceuticals, Nuclear Science Series (Kilbourn M R Ed.), National Academy Press, Washington, D.C., 1-149 (1990); Lasne et al., Topics in Current Chemistry 222:201-258 (2002); Cai et al., Eur. J. Org. Chem. 17:2853-2873 (2008); and Dolle et al., In Fluorine and Health: Molecular Imaging, Biomedical Materials and Pharmaceuticals, Tressaud A, Haufe G (Eds). Elsevier 3-65 (2008)). An alkyl, alkenyl or alkynyl linker may also be used for the addition of the fluorine-18 atom (Damont et al., J. Label. Compds Radiopharm. 51:286-292 (2008); Dolle et al., Bioorg. Med. Chem. 14:1115-1125 (2006); and Dolle et al., J. Label. Compds Radiopharm. 50:716-723 (2007)). Additional methods of producing radionuclide (e.g., fluorine-18) labeled compounds are described in U.S. Patent Application Publications No. 2006/0100465, 2010/0292478, and 2011/0184159, each hereby incorporated by reference.

In the case of a labeling with other halogens (e.g., bromine-76, iodine-123 or iodine-124), the radioisotope may also be directly attached by nucleophilic or electrophilic substitutions to a core structure or linked through the addition of a spacer group, both techniques known to persons skilled in the art (Maziere et al., Curr. Pharm. Des. 7:1931-1943 (2001); and Coenen et al., In Radioiodination reactions for pharmaceuticals-Compendium for effective synthesis strategies, Coenen H. H., Mertens J., Maziere B. (Eds), Springer Verlag, Berlin-Heidelberg, 1-101 (2006)).

In the case of the labeling with metal radioisotopes (e.g., gallium-68, copper-64 or technetium-99m), the preferred approach used, which will be considered by a person skilled in the art, is the use of a bifunctional chelating agent based on, for example, the open-chain polyaminocarboxylates ethylenediamine tetraacetic acid (EDTA) and diethylenetriamine pentaacetic acid (DTPA), the polyaminocarboxylic macrocycle 1,4,7,10-tetraazacyclododecane-1,4,7,10-tetraacetic acid (DOTA), mercaptoacetyldi- and triglycine (MAG2, MAG3), bis-(S-benzoyl-thioglycoloyl)diaminopropanoate ((SBT)$_2$DAP) and hydrazinonicotinic acid (HYNIC), facilitating the complexation of the radiometal cation at one function and the covalent attachment to a core molecule at another (Brunner et al., (1995) Radiotracer production-Radiometals and their chelates In Principle of Nuclear Medecine, Wagner H. N. (Ed). Saunders: Philadelphia, 220-228 (1995); Weiner R. E. et al., Chemistry of gallium and indium radiopharmaceuticals In Handbook of Radiopharmaceuticals-Radiochemistry and Applications (Welch M J, Redvanly C S Eds.), New York-Chichester-Brisbane-Toronto, Wiley-Interscience Pub., 363-400 (2003); Anderson et al., Chemistry of copper radionucleides and radiopharmaceutical products In Handbook of Radiopharmaceuticals-Radiochemistry and Applications (Welch M J, Redvanly C S Eds.), New York-Chichester-Brisbane-Toronto, Wiley-Interscience Pub., 401-422 (2003); and Mahmood et al., Technetium radiopharmaceuticals In Handbook of Radiopharmaceuticals-Radiochemistry and Applications (Welch M J, Redvanly C S Eds.), New York-Chichester-Brisbane-Toronto, Wiley-Interscience Pub., 323-362 (2003)).

The diagnostic compounds of the invention described herein that include a radionuclide (e.g., fluorine-18) can be synthesized to adjust the specific activity of the compound. Specific activity is defined as the radioactivity per unit mass of a radionuclide or a labeled compound. For example, if a 50 mg sample contains 100 mCi (370 MBq), then the specific activity of the sample is given as 100/50=2 mCi/mg or 74 MBq/mg. Specific activity should not be confused with the concentration of a compound containing a radionuclide, which are generally expressed in mCi/mL or MBq/mL. The specific activity is an important parameter to consider in radiolabeling and in vivo biodistribution of tracers, such as the radionuclide compounds of the invention. Cold molecules in low specific activity radiopharmaceuticals compete with radioactive molecules and lower the uptake of the tracer in the target tissue(s). Similarly, low specific activity radionuclides yield poor radiolabeling, and hence, poor radiography (e.g., PET). For these reasons, the diagnostic compounds of the invention containing fluorine-18 are synthesized having a specific activity of at least 1.0, 1.2, 1.4, 1.8, 2.0, 2.2, 2.4, or 2.6 Ci/mmol. In one embodiment of the invention, the fluorine-18 diagnostic compound has a specific activity of at least 1.0 Ci/mmol.

Persons having skill in the art are aware of methods that can increase or decrease the specific activity of a desired radionuclide compound of the invention. For example, electrophilic fluorination of palladium aryl complexes can be used to yield diagnostic compounds of the invention containing fluorine-18 with high specific activity (Lee et al., (2011)).

Co-Administration

The invention further relates to the use of a first amount of an ASCT2 inhibitor of the present invention and a second amount of an anti-cancer agent in a method of treating cancer.

In particular embodiments of this invention, the combination of a compound of the present invention is anti-cancer agent is additive, i.e. the combination treatment regimen produces a result that is the additive effect of each constituent when it is administered alone. In accordance with this embodiment, the amount of an ASCT2 inhibitor of the present invention and the amount of the anti-cancer together constitute an effective amount to treat cancer.

In another particular embodiment of this invention, the combination of a compound of the present invention and anti-cancer agent is considered therapeutically synergistic when the combination treatment regimen produces a significantly better anticancer result (e.g., cell growth arrest, apoptosis, induction of differentiation, cell death) than the additive effects of each constituent when it is administered alone at a therapeutic dose. Standard statistical analysis can be employed to determine when the results are significantly better. For example, a Mann-Whitney Test or some other generally accepted statistical analysis can be employed.

The treatment procedures can take place sequentially in any order, simultaneously or a combination thereof. For example, the first treatment procedure, administration of a compound of the present invention, can take place prior to the second treatment procedure, i.e. the anti-cancer agent, after the second treatment with the anticancer agent, at the same time as the second treatment with the anticancer agent, or a combination thereof. For example, a total treatment period can be decided for the compound of the present invention. The anti-cancer agent can be administered prior to onset of treatment with the compound of the present invention or following treatment with a compound of the present invention. In addition, treatment with the anti-cancer agent can be administered during the period of administration of the compound of the present invention but does not need to occur over the entire treatment period for the ASCT2 inhibitor of the present invention. Similarly, treatment with the compound of the present invention can be administered during the period of anti-cancer agent administration but does not need to occur over the entire anti-cancer agent treatment period. In another embodiment, the treatment regimen includes pre-treatment with one agent, either the compound of the present invention or the anti-cancer agent, followed by the addition of the second agent for the duration of the treatment period.

Non-limiting examples of anticancer compounds of the present invention include compounds selected from carboplatin, gemcitabine, cisplatin, 5-fluorouracil, cyclophosphamide, etoposide, vincristine, doxorubicin and irinotecan.

PARTICULAR EMBODIMENTS

The present disclosure is also drawn to the following particular embodiments.

Embodiment 1

A compound of the following formula:

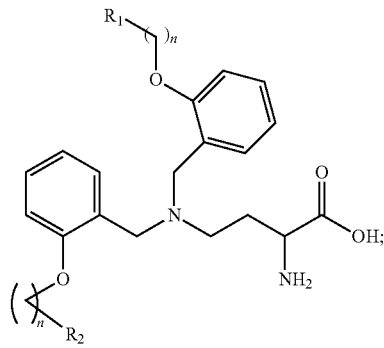

wherein:
R$_1$ is phenyl (optionally substituted with at least one R$_3$), benzyl (optionally substituted with at least one R$_3$), pyridinyl (optionally substituted with at least one R$_3$);
R$_2$ is phenyl (optionally substituted with at least one R$_3$), benzyl (optionally substituted with at least one R$_3$), pyridinyl (optionally substituted with at least one R$_3$);
R$_3$ is independently H, Me, alkyl, methoxy, alkoxy, halogen, CF$_3$; and
n is 0-6;
and pharmaceutically acceptable salts and pharmaceutically acceptable derivatives thereof.

Embodiment 2

A compound of Embodiment 1, of the following formula:

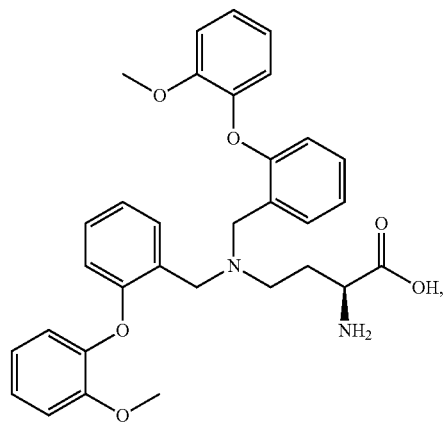

85
-continued
86
-continued
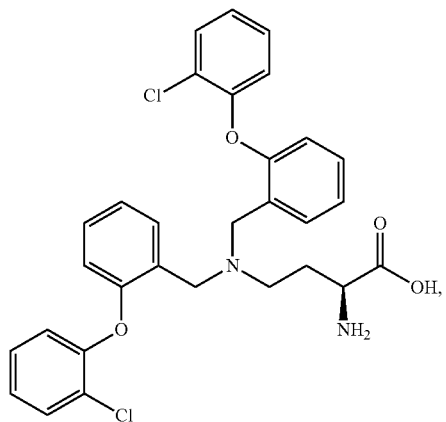
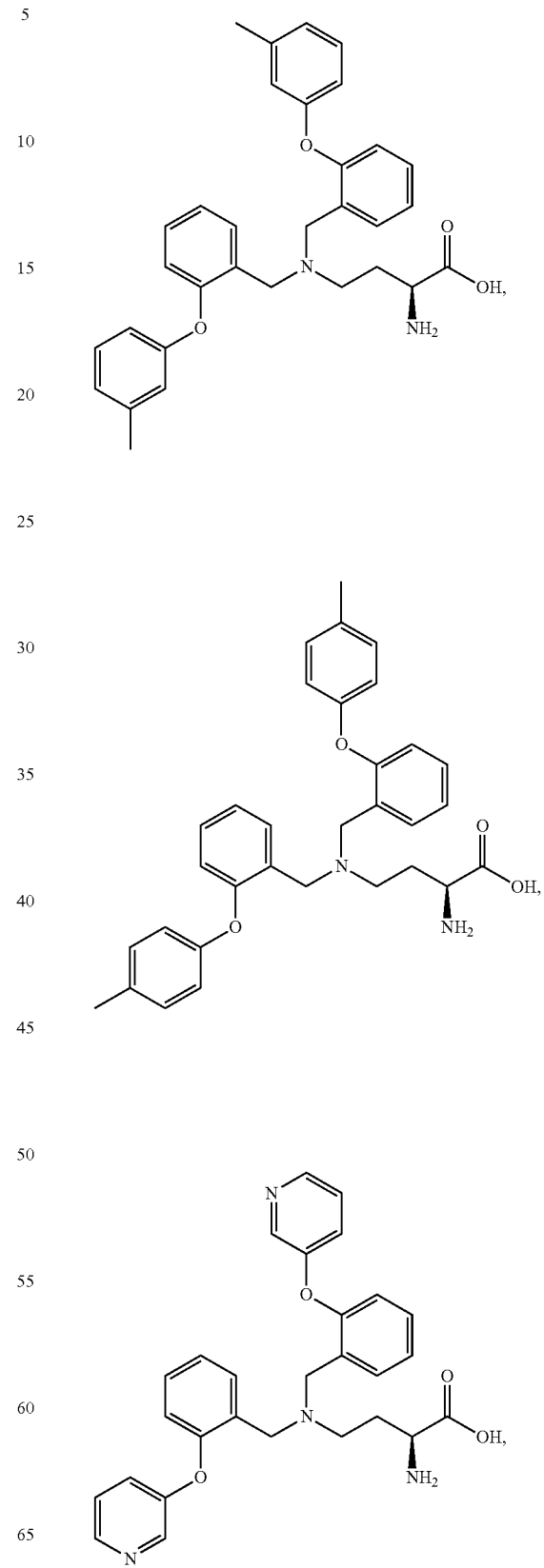

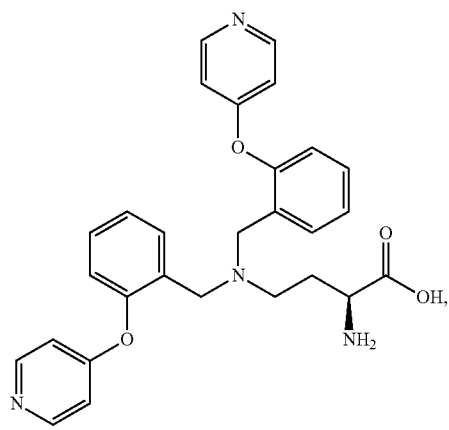
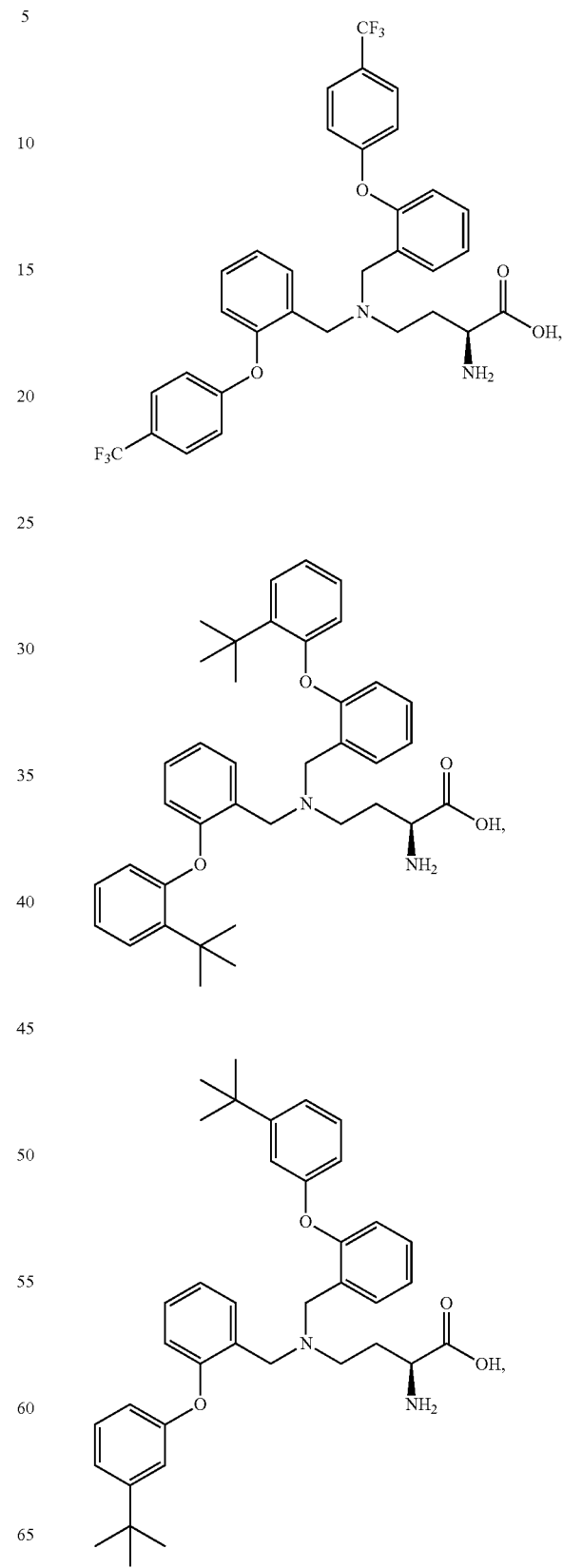

89
-continued
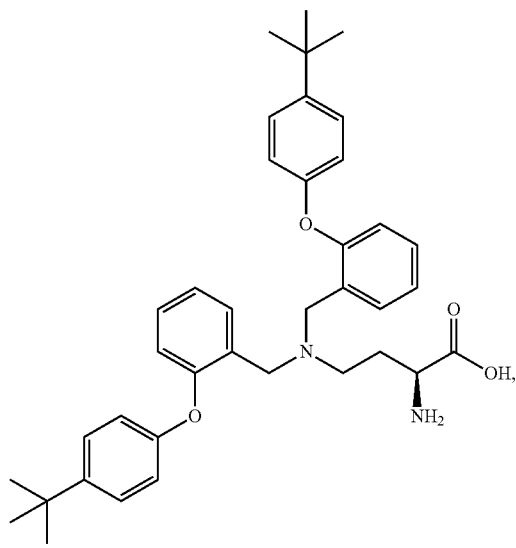
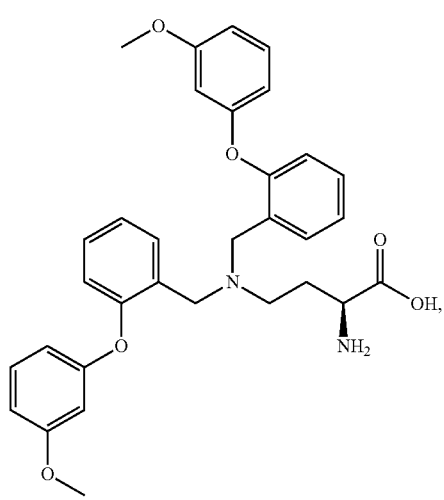
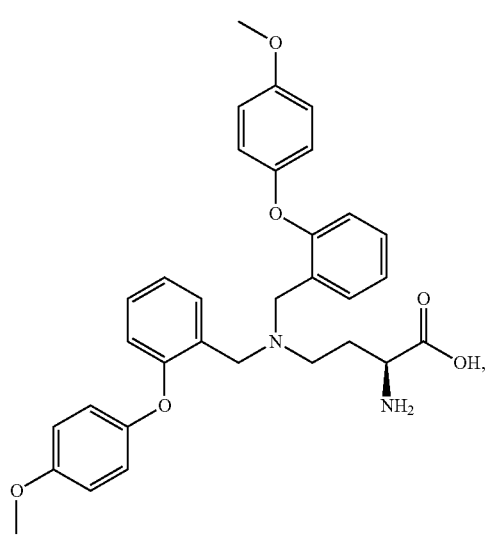
90
-continued
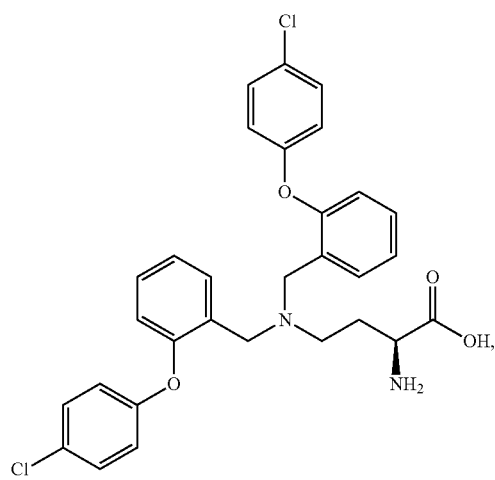
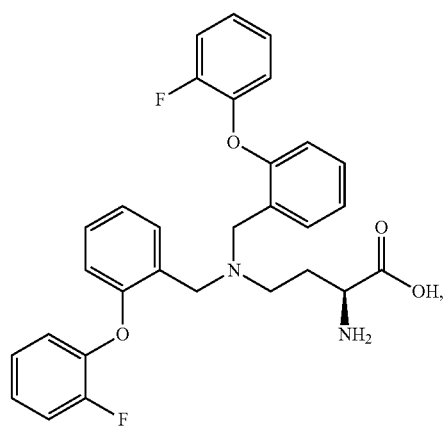
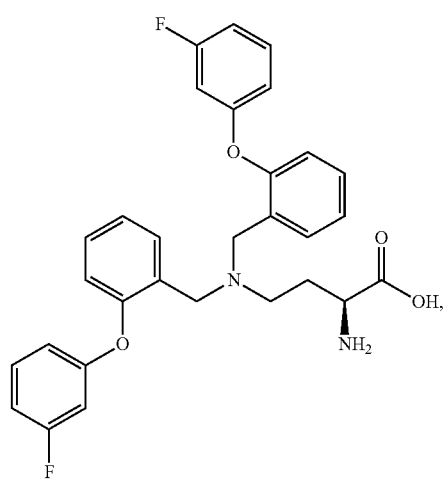

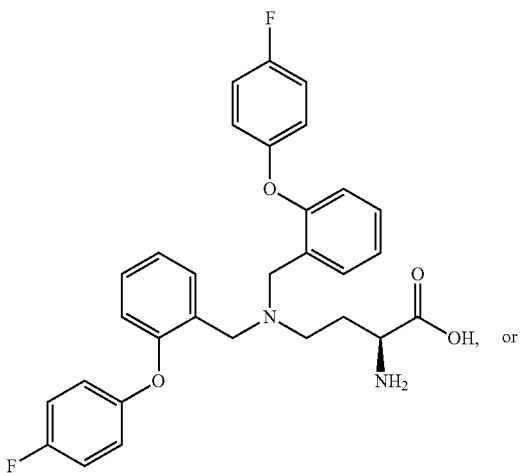

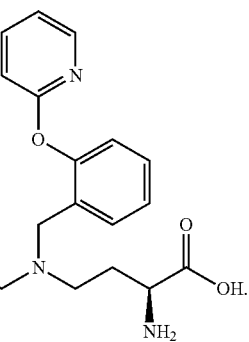

Embodiment 3

A compound of Embodiment 1, of the following formula:

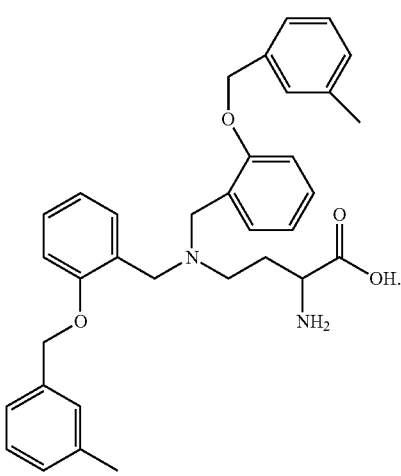 [SMILES: Cc1cccc(COc2ccccc2CN(CCC(N)C(=O)O)Cc2ccccc2OCc2cccc(C)c2)c1]

Embodiment 4

A compound of Embodiment 1, of the following formula:

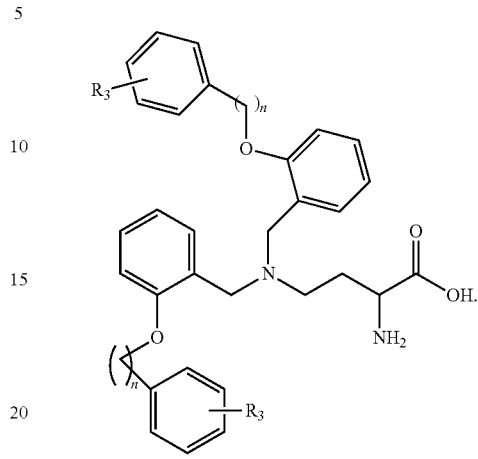

Embodiment 5

A compound of the following formula:

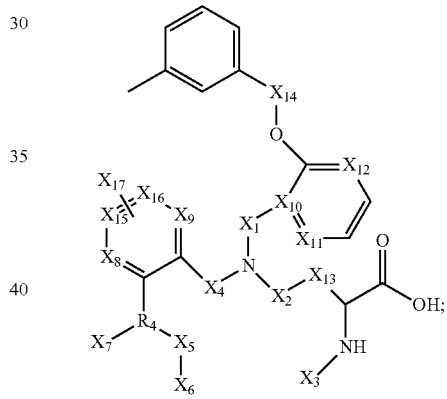

wherein:

$R_4$ is O or N;

$X_1$ is $CH_2$, or is CH and forms a ring with $X_9$ (substituted or unsubstituted), or is absent when $X_9$ forms a ring with $X_{10}$ and at the same time $X_{11}$ forms a ring with $X_2$;

$X_2$ is $CH_2$, or forms a ring with $X_3$ (substituted or unsubstituted), $X_3$ is H, or forms a ring with $X_2$ (substituted or unsubstituted), $X_4$ is $CH_2$, or forms a ring with $X_5$ or $X_7$ (substituted or unsubstituted), $X_5$ is absent; $CH_2$; or forms a ring with $X_4$ (substituted or unsubstituted);

$X_6$ is absent, H, or phenyl (substituted or unsubstituted), $X_7$ is H, absent, benzyl (substituted or unsubstituted) or forms a ring or bicyclic ring with $X_8$ or $X_4$ (substituted or unsubstituted);

$X_8$ is C, CH, $CH_2$, N, or forms a ring or bicyclic ring with $X_7$ (substituted or unsubstituted);

$X_9$ is C, CH, $CH_2$, N, or forms a ring or bicyclic ring with $X_1$, $X_{10}$, or $X_{11}$ (substituted or unsubstituted);

93

$X_{10}$ is CH, or forms a ring with $X_1$ or $X_9$ (substituted or unsubstituted);

$X_{11}$ is CH, or CH$_2$, or forms a ring with $X_2$ or $X_{13}$ (substituted or unsubstituted);

$X_{12}$ is CH or CH$_2$, or forms a ring with $X_{14}$ (substituted or unsubstituted);

$X_{13}$ is CH$_2$, or forms a ring with $X_{11}$ (substituted or unsubstituted);

$X_{14}$ is CH$_2$, or forms a ring with $X_{12}$ (substituted or unsubstituted);

$X_{15}$ is C, CH, CH$_2$, N;

$X_{16}$ is C, CH, CH$_2$, N;

$X_{17}$ is optionally present and is H, methyl, alkyl, halogen, methoxy, alkoxy, CN, —CF$_3$, —OCF$_3$, or Cyc;

and pharmaceutically acceptable salts and pharmaceutically acceptable derivatives thereof.

Embodiment 6

A compound of Embodiment 5, of the following formula:

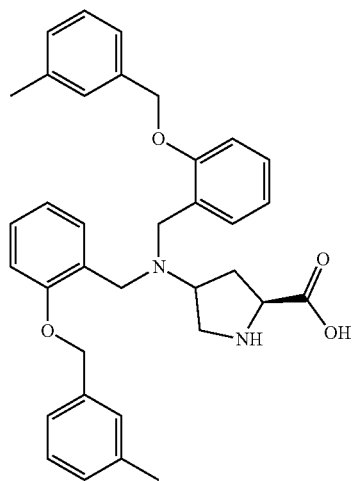

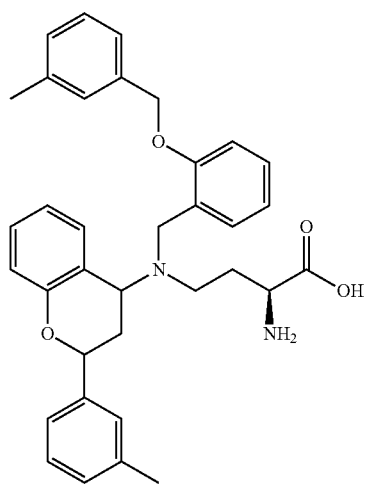

94

-continued

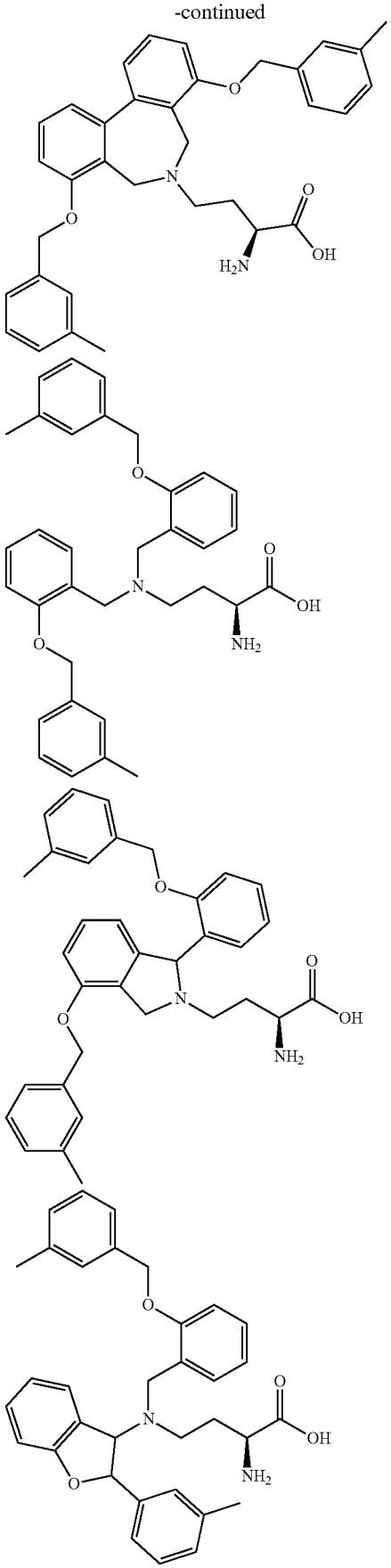

95
-continued
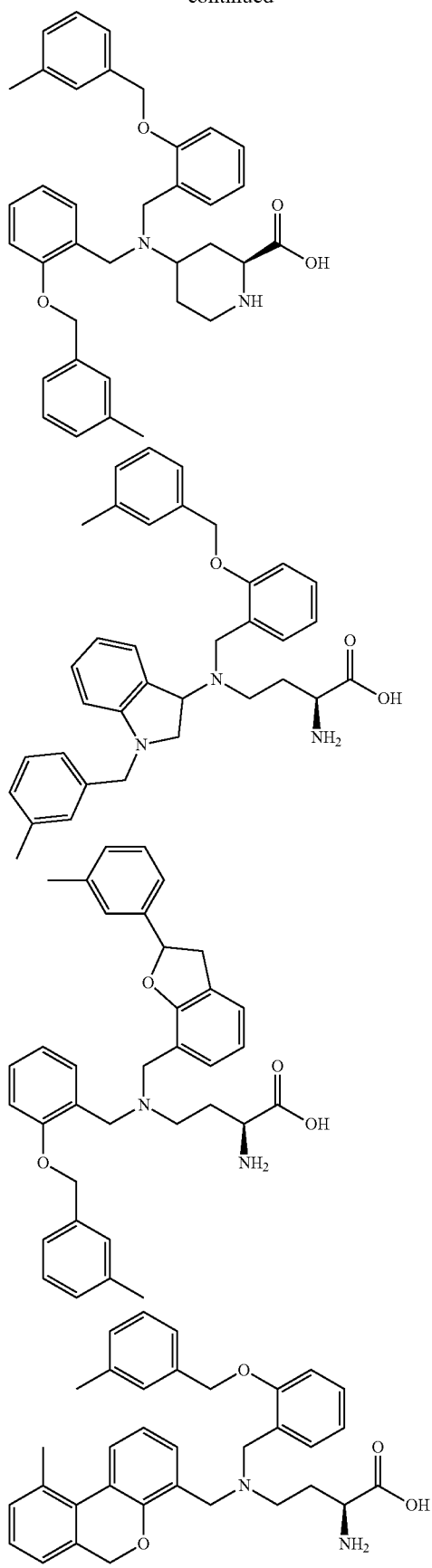
96
-continued
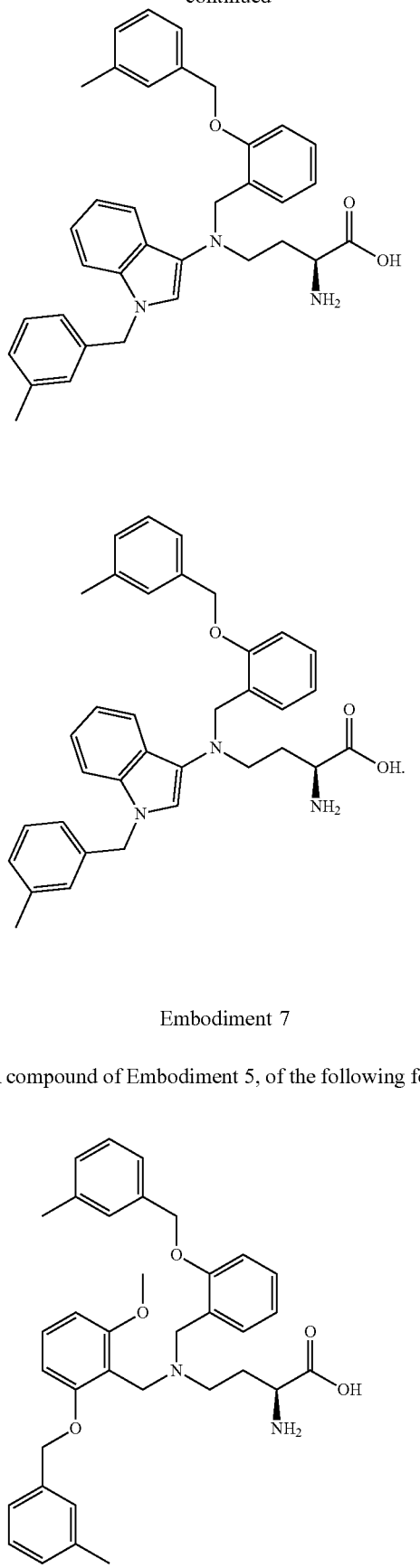
Embodiment 7
A compound of Embodiment 5, of the following formula:
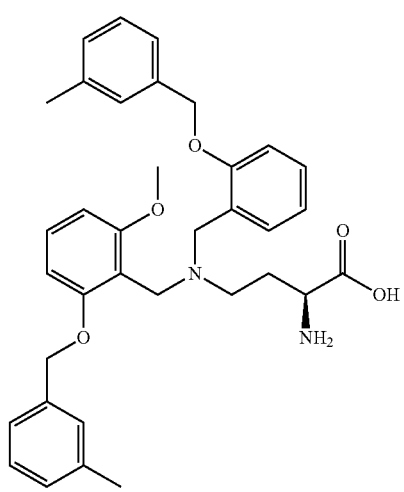

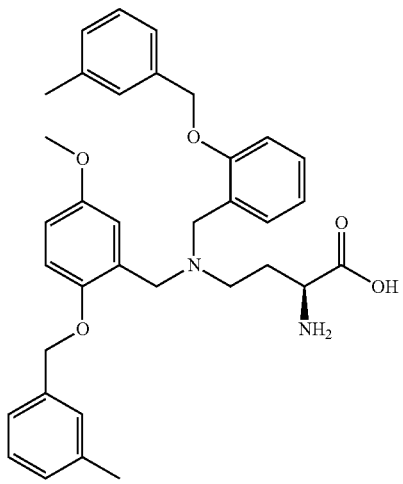
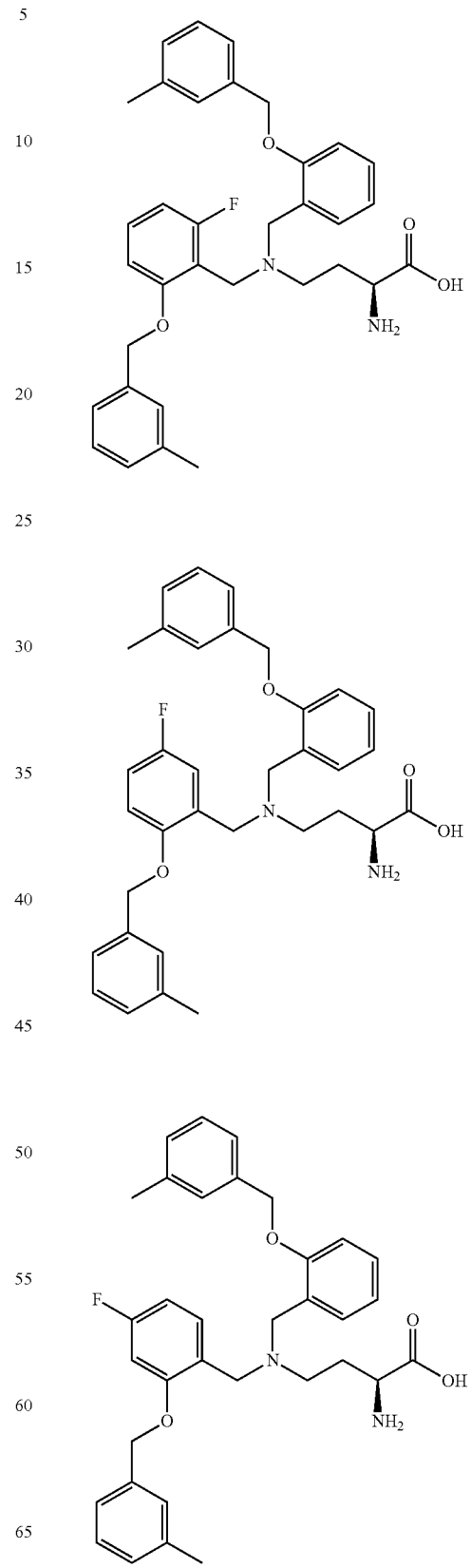

99
-continued
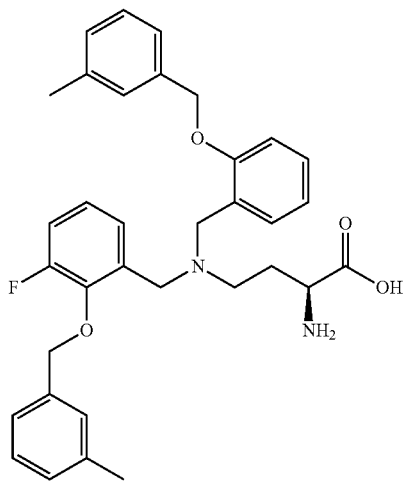
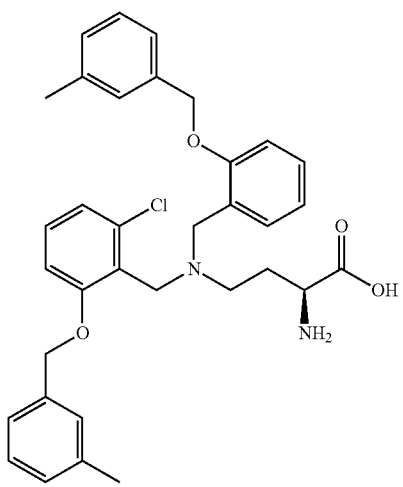
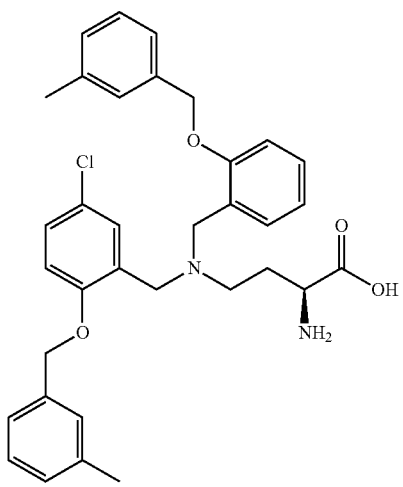
100
-continued
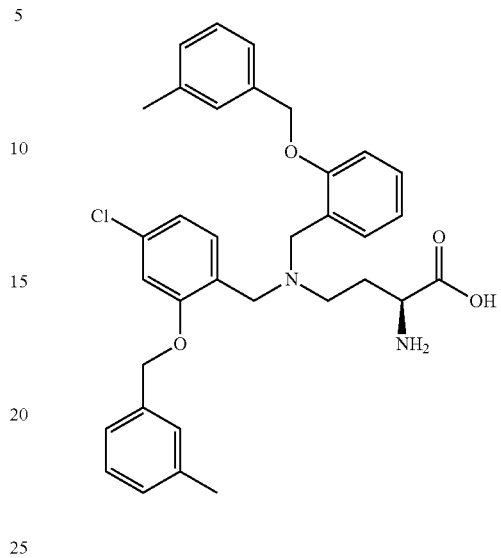
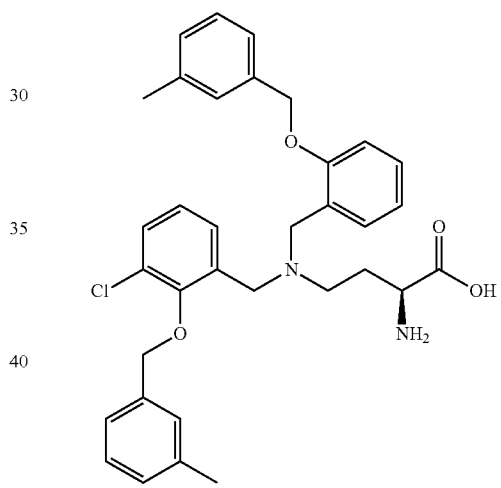
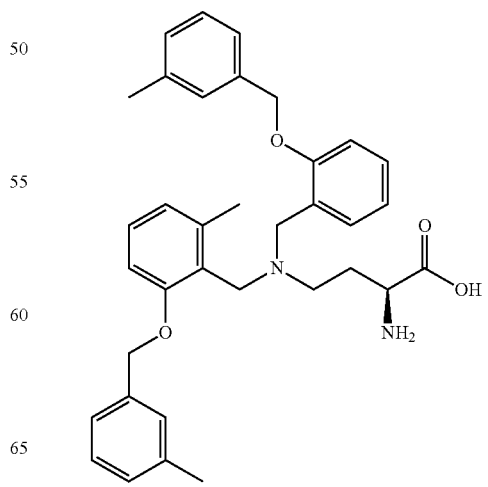

101
-continued
102
-continued
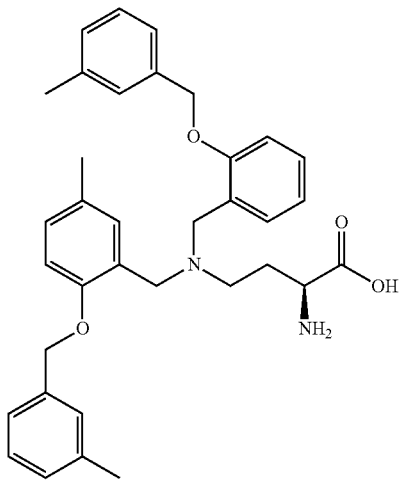
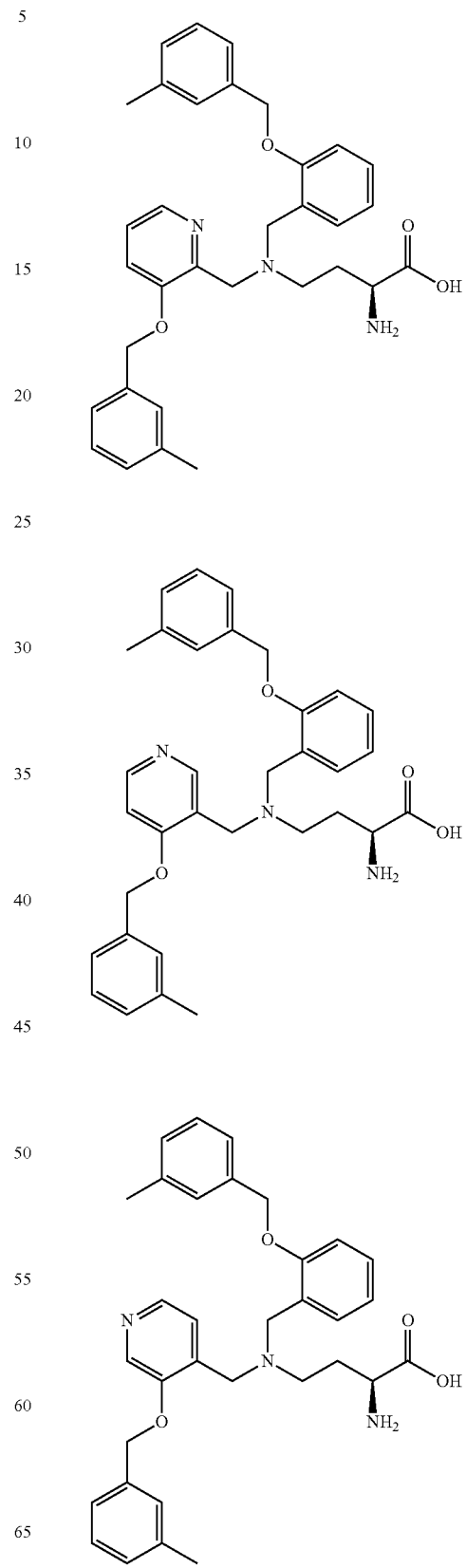

103
-continued
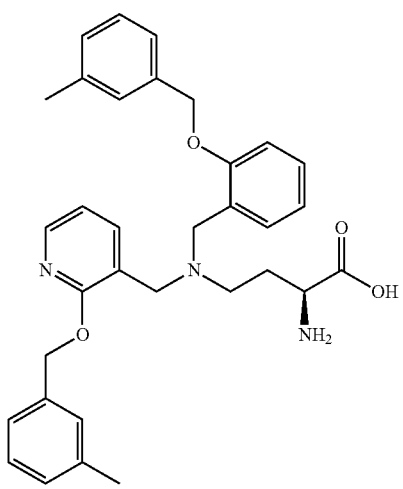
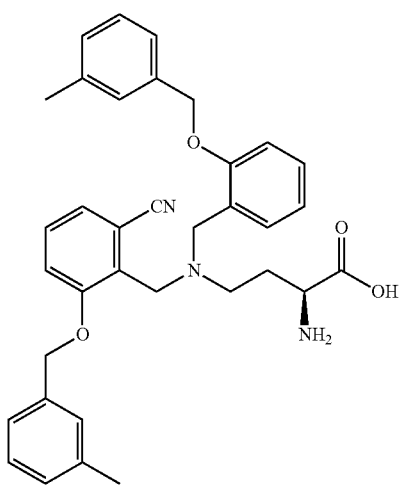
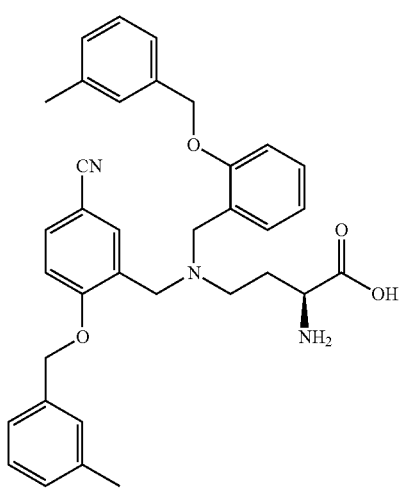
104
-continued
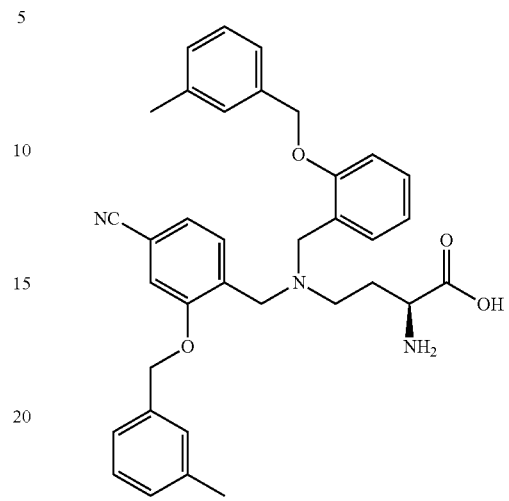
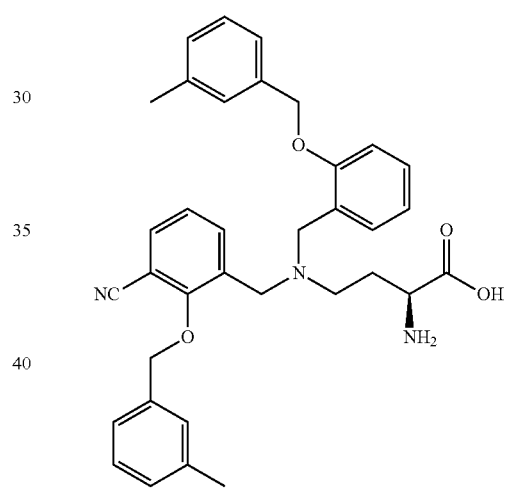
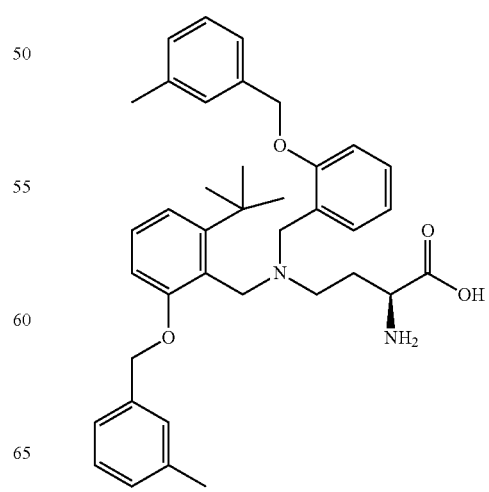

105
-continued
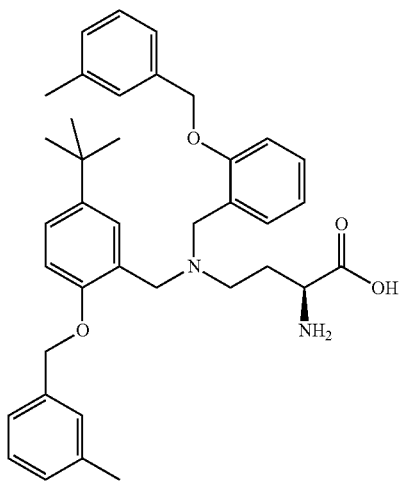
106
-continued
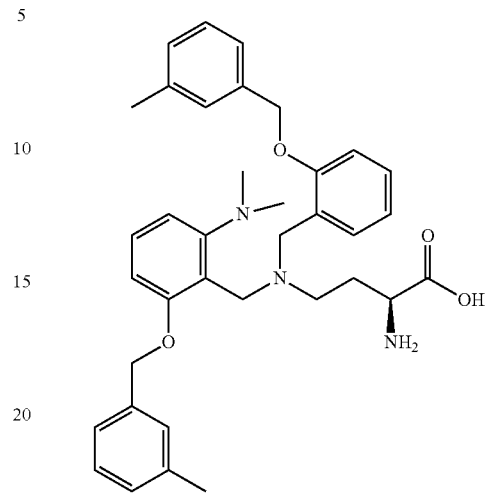
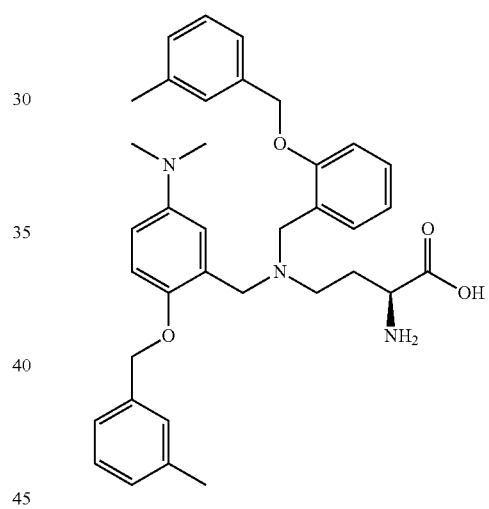
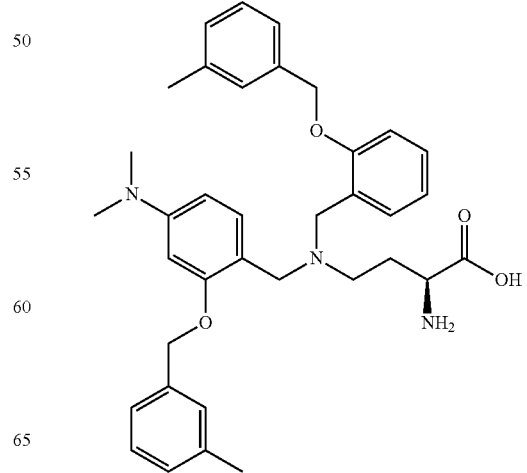

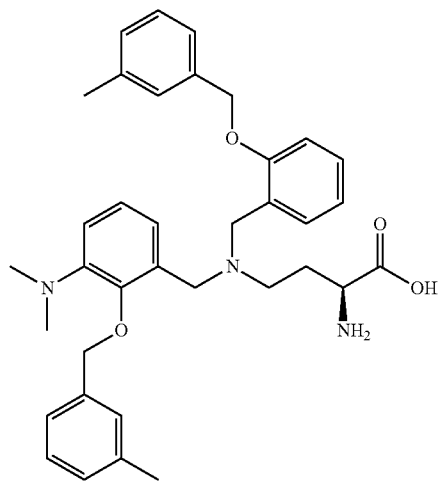
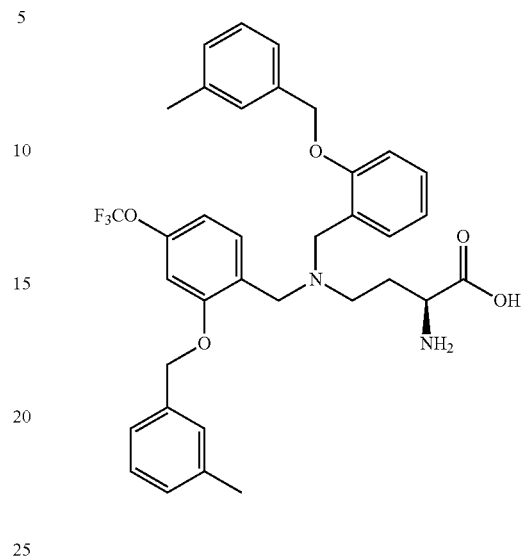
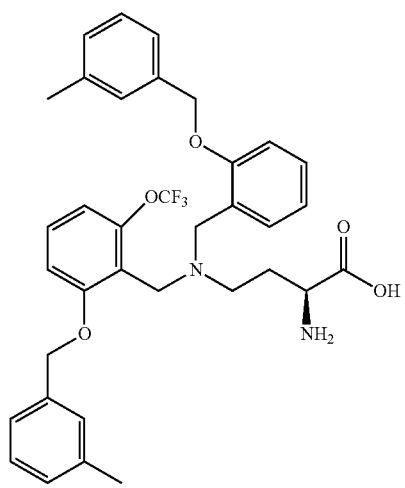
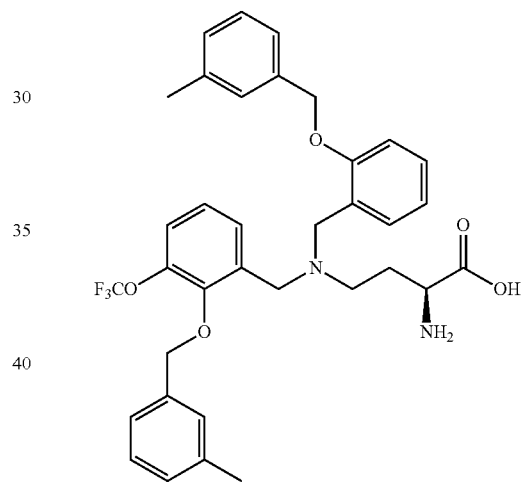
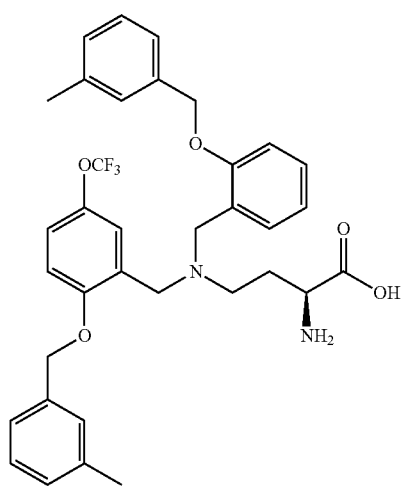
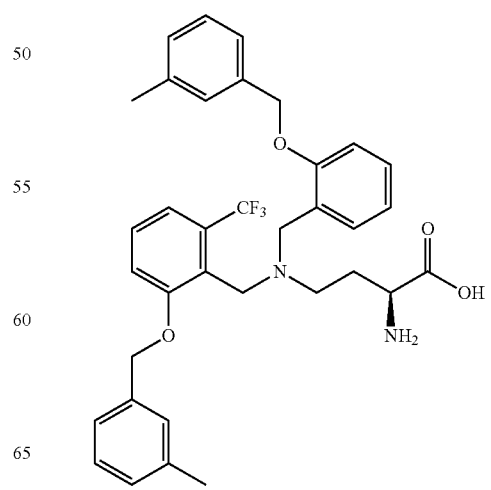

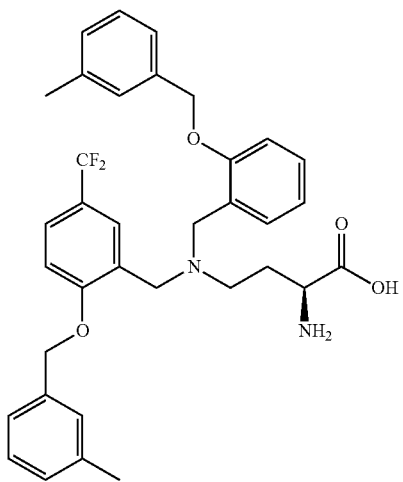
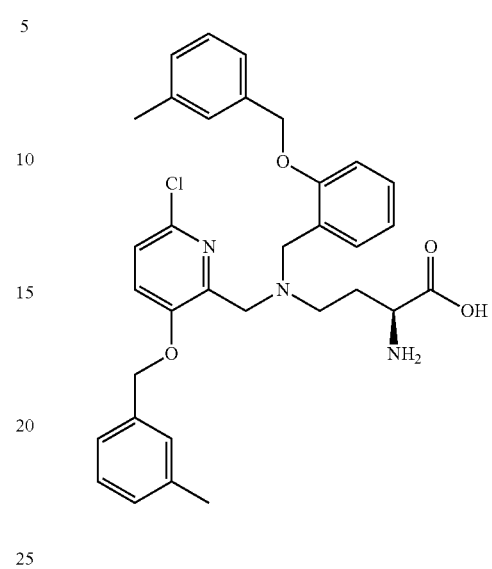
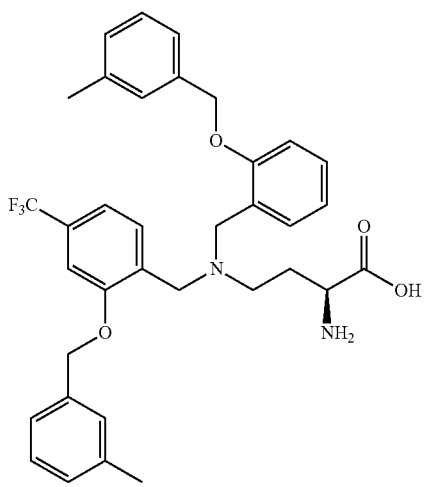
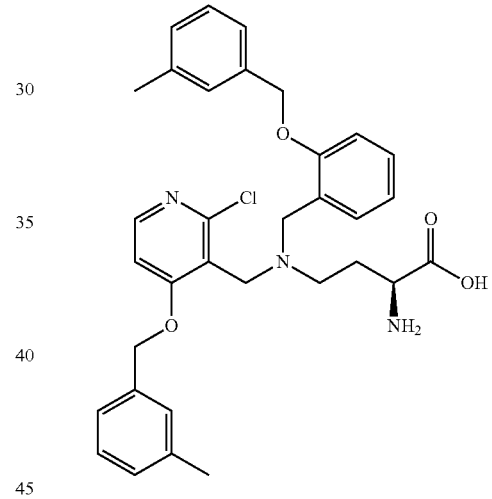
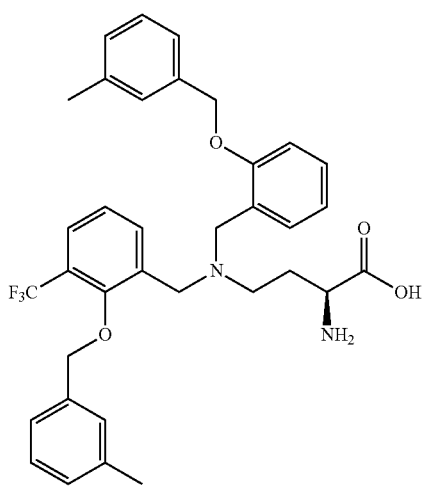
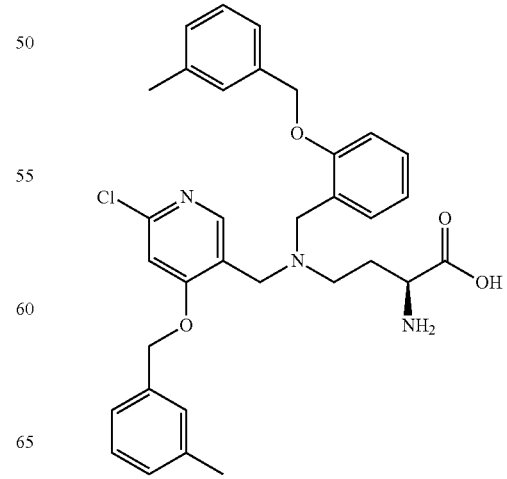

111
-continued
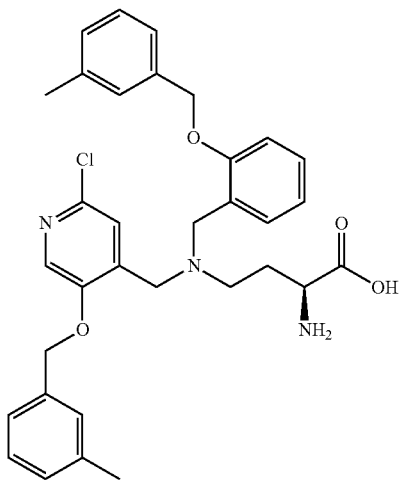
112
-continued
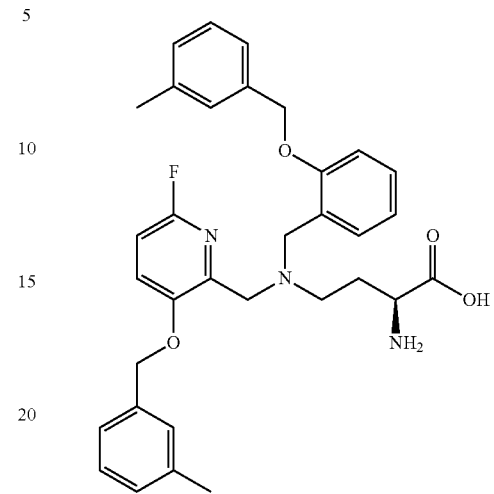
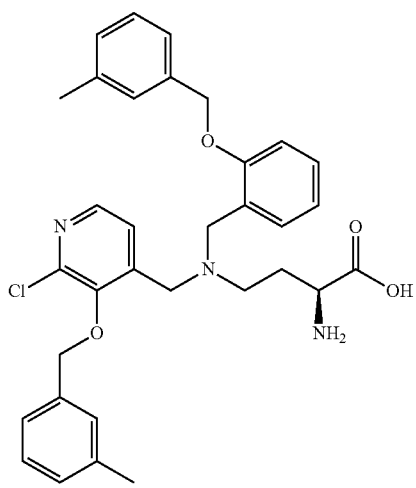
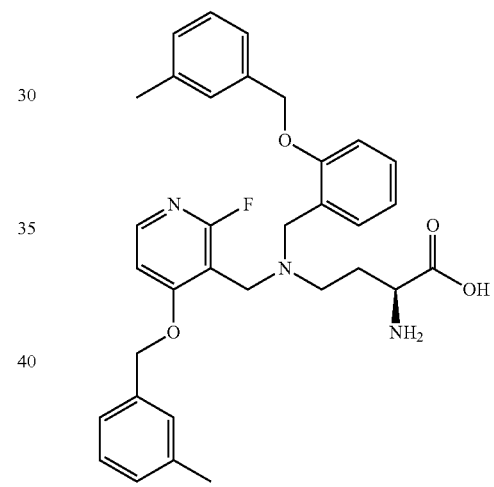
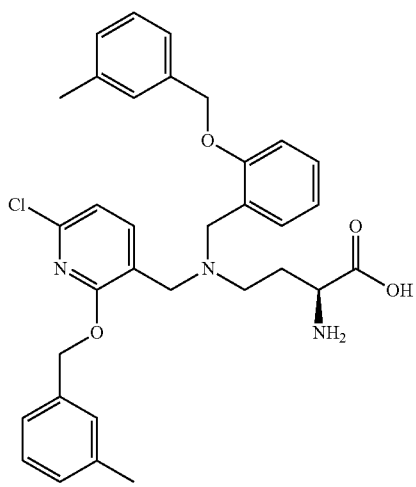
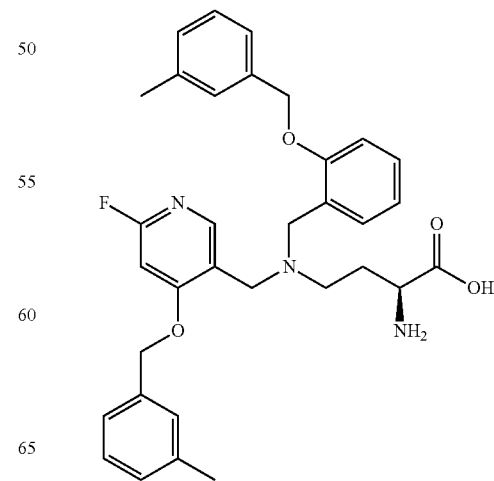

113
-continued
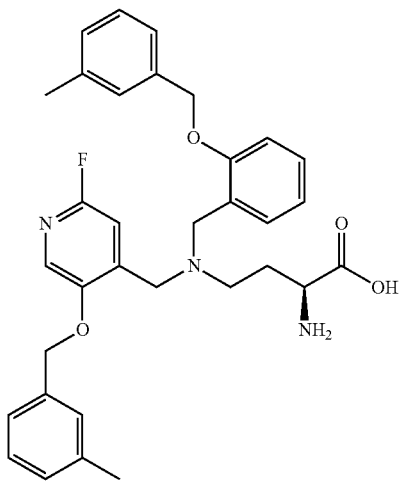
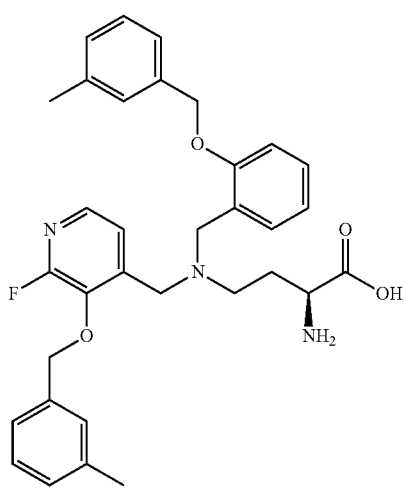
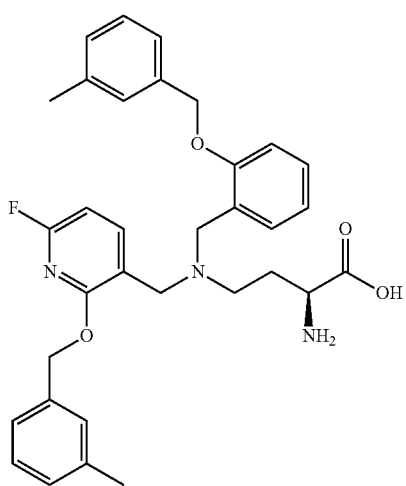
114
-continued
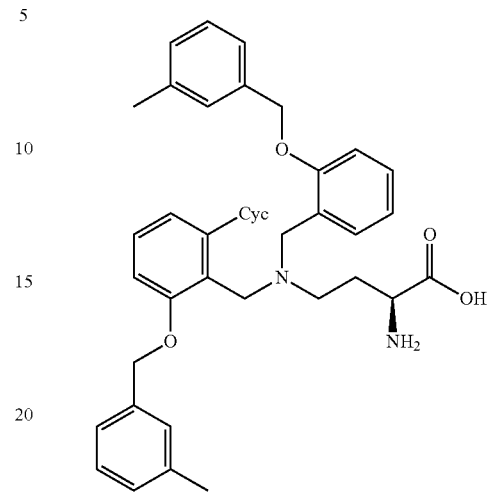
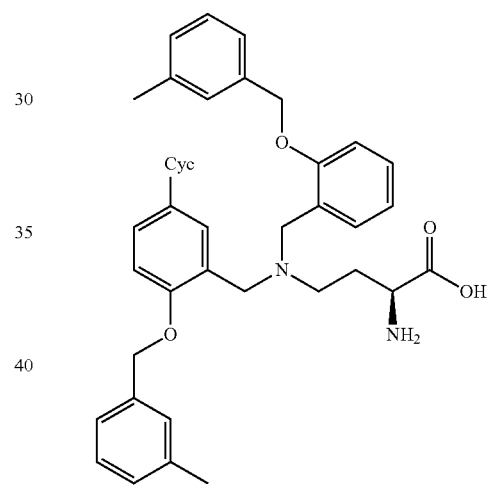
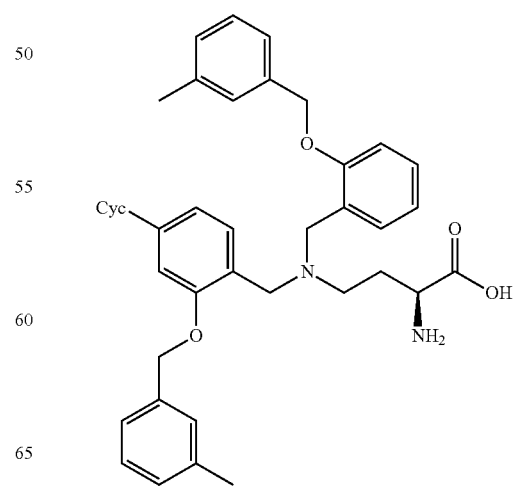

-continued

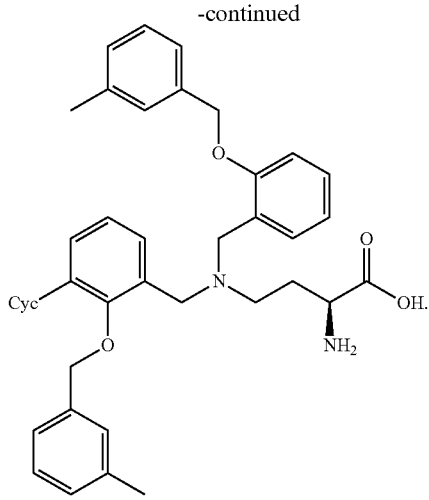

Cyc = cycles (examples: cycloalkyl, heterocycles)

Embodiment 8

A compound of Embodiment 5, of the following formula:

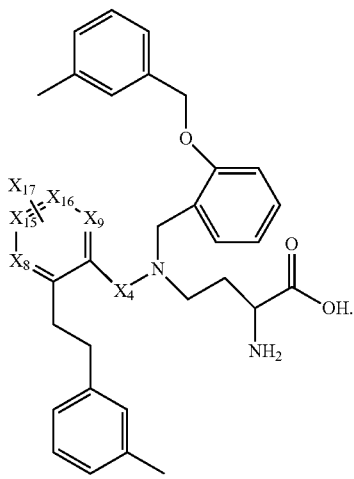

Embodiment 9

A compound of the following formula:

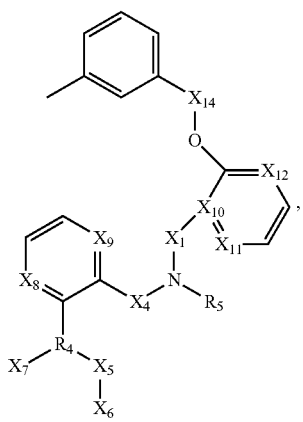

wherein:

$R_4$ is O or N;
$X_1$ is $CH_2$;
$X_4$ is $CH_2$;
$X_5$ is $CH_2$;
$X_6$ is phenyl (substituted or unsubstituted),
$X_7$ is H or absent;
$X_8$ is CH, $CH_2$;
$X_9$ is CH, $CH_2$;
$X_{10}$ is CH;
$X_{11}$ is CH, or $CH_2$;
$X_{12}$ is CH or $CH_2$;
$X_{14}$ is $CH_2$;
$R_5$ is chosen from:

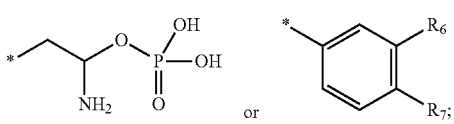

$R_6$ is NH C, CH, or $CH_2$;
$R_7$ is NH C, CH, or $CH_2$; and
$R_6$ and $R_7$ form a 5 or 6-membered heteroring optionally substituted by H, OH, amino, phosphonic acid, carbonyl, acetic acid;

and pharmaceutically acceptable salts and pharmaceutically acceptable derivatives thereof.

Embodiment 10

A compound of Embodiment 9, of the following formula:

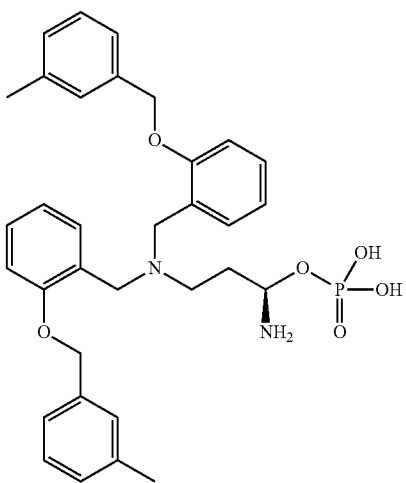

117
-continued
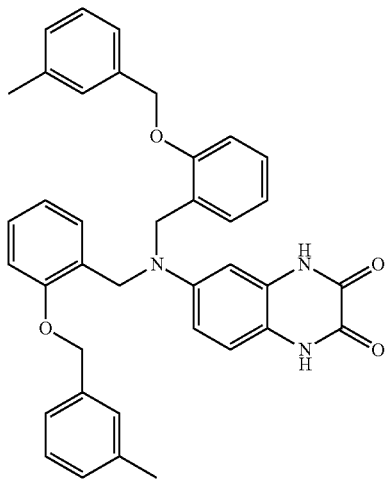
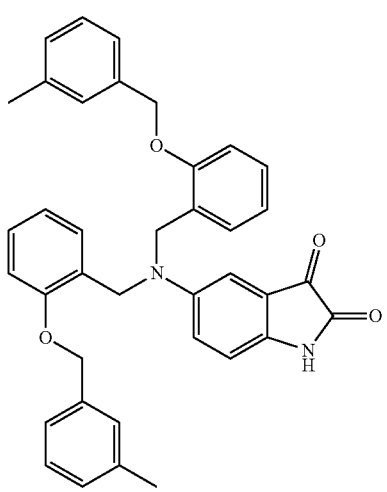
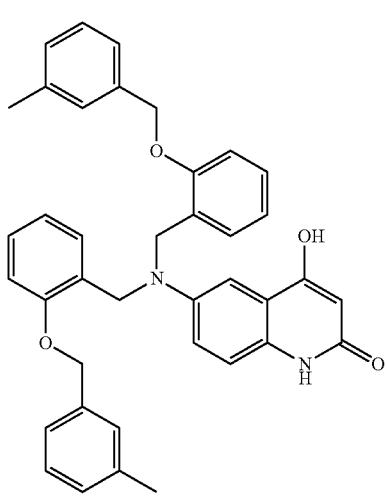
118
-continued
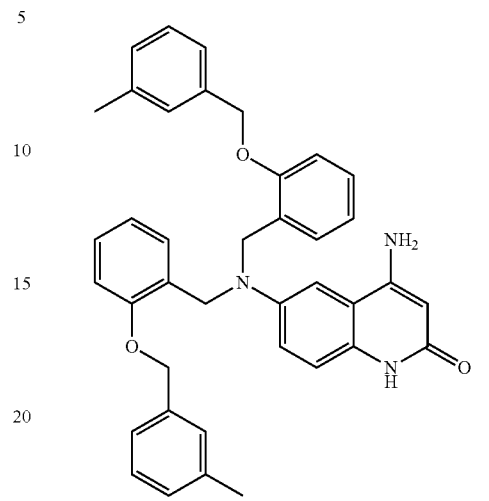
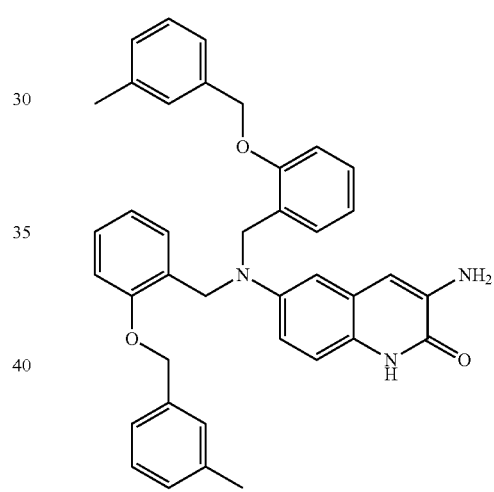
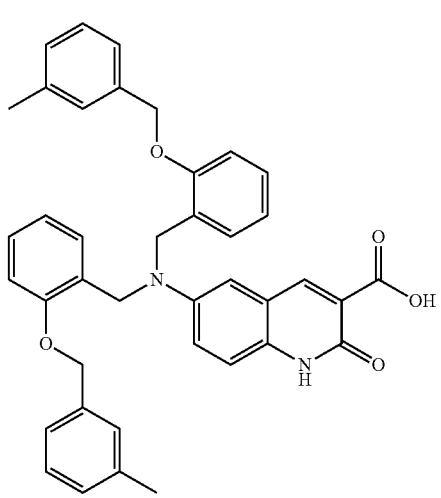

-continued

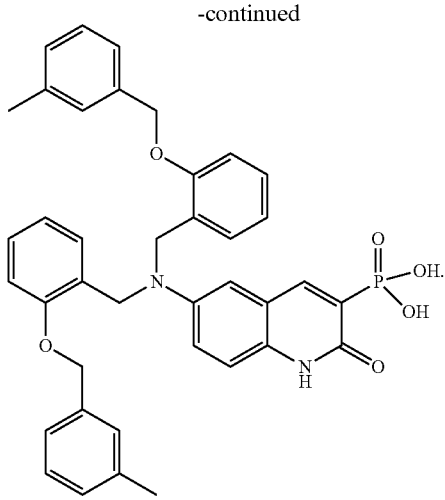

Embodiment 11

A compound of Embodiment 9, wherein $R_6$ and $R_7$ are C, CH, $CH_2$, N, or NH, and form a ring. In other embodiments, $R_6$ and $R_7$ are both NH and form a ring.

Embodiment 12

A compound of the following formula:

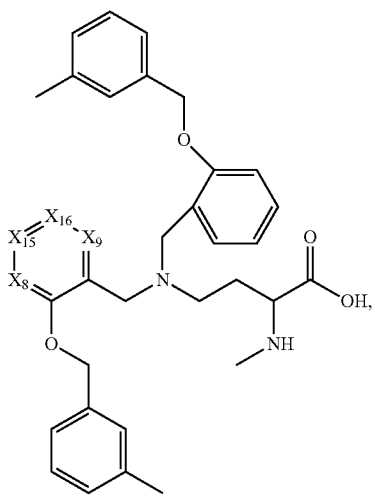

wherein:
$X_{16}$ and $X_9$ join to form a bicyclic ring (substituted or unsubstituted);
$X_{15}$ and $X_8$ join to form a bicyclic ring (substituted or unsubstituted); or
$X_{16}$ and $X_{15}$ join to form a bicyclic ring (substituted or unsubstituted);
and pharmaceutically acceptable salts and pharmaceutically acceptable derivatives thereof.

Embodiment 13

A compound of Embodiment 12, wherein: $X_{16}$ and $X_9$, $X_{15}$ and $X_8$, or $X_{16}$ and $X_{15}$ join together to form pyrazole, pyrrole, pyridine, pyrrolidine, piperidine, phenyl, cyclohexane, cyclopentene, tetrahydropyran, pyran, furan, dioxolane, dioxane, oxazole, imidazole, thiophene, oxathiolane, dioxepane, dioxepine.

Embodiment 14

A compound of Embodiment 12, of the following formula:

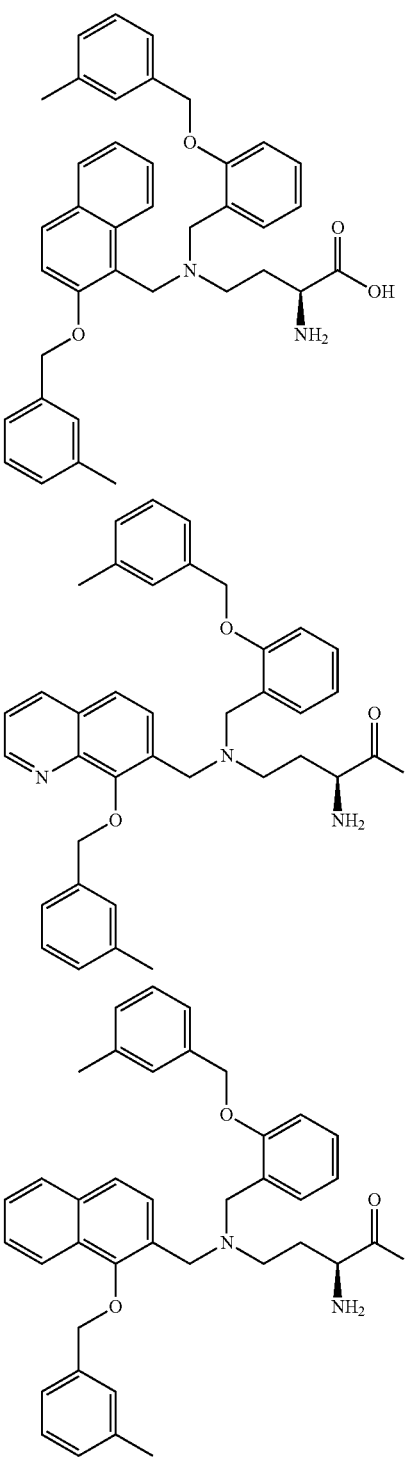

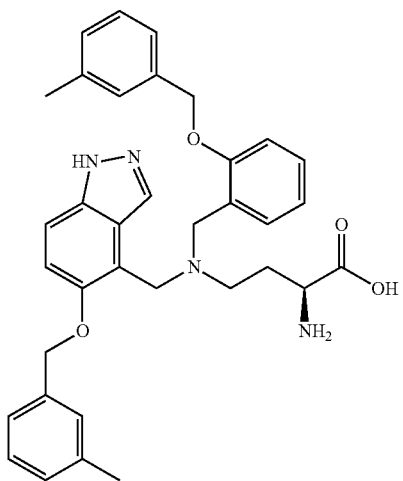
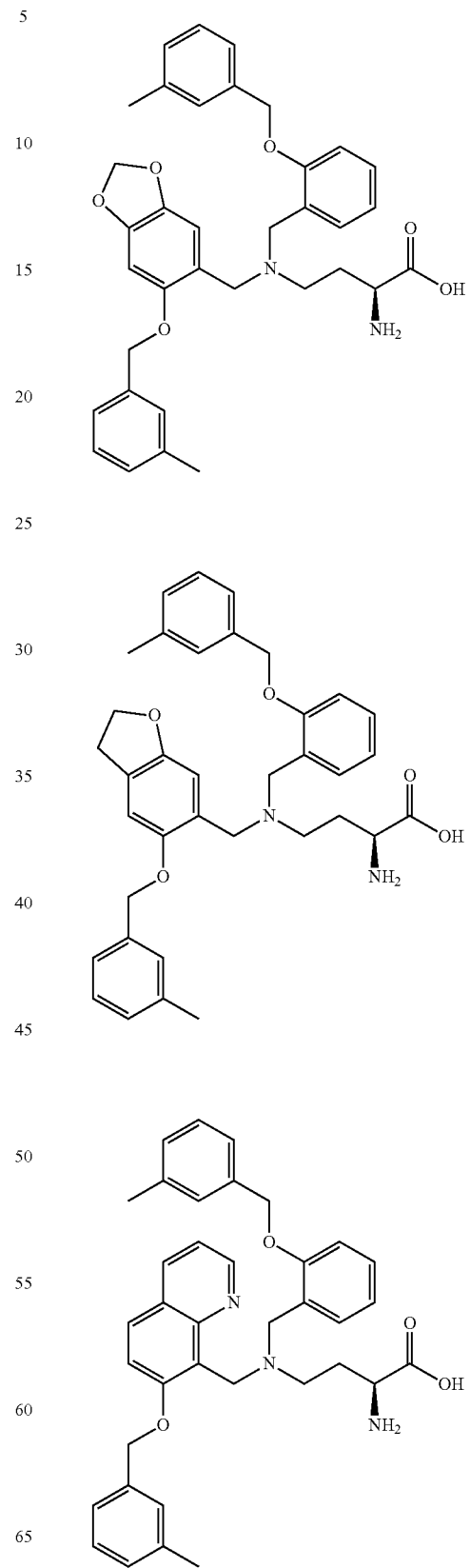

123
-continued
124
-continued
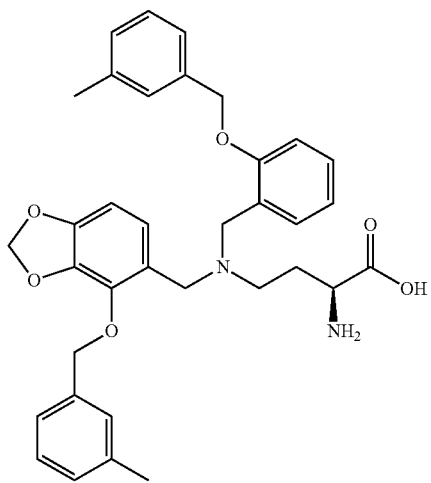 [SMILES: Cc1cccc(COc2ccccc2CN(CC[C@H](N)C(=O)O)Cc2ccc3ncoc3c2OCc2cccc(C)c2)c1]
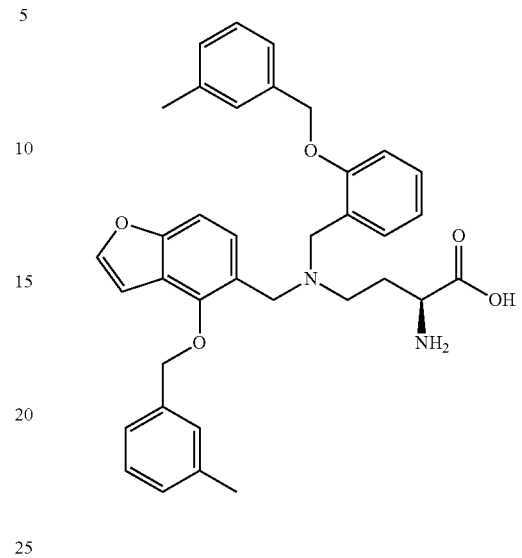
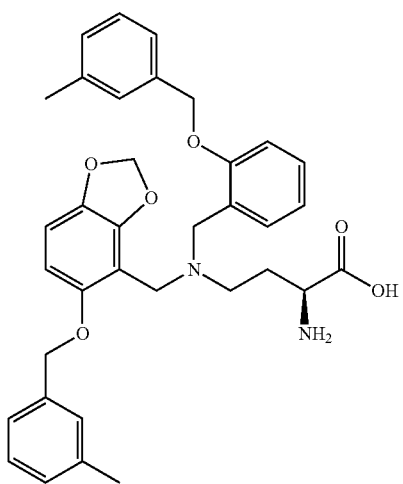
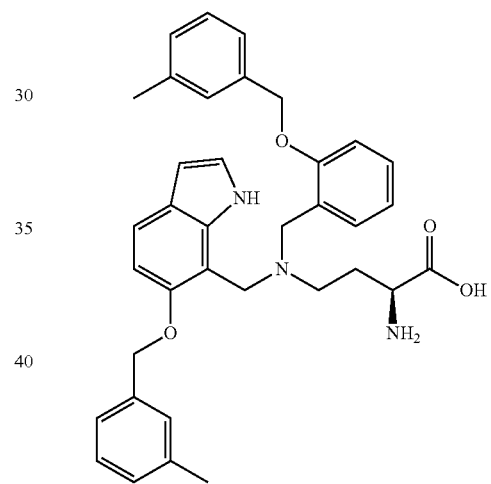
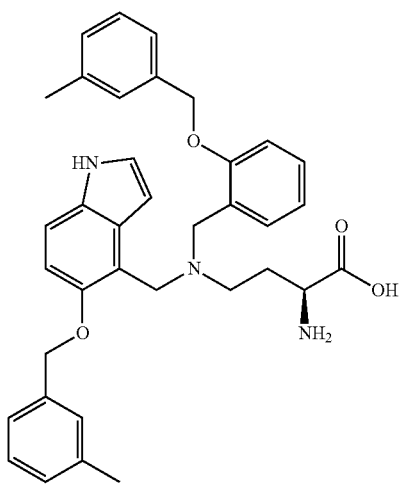
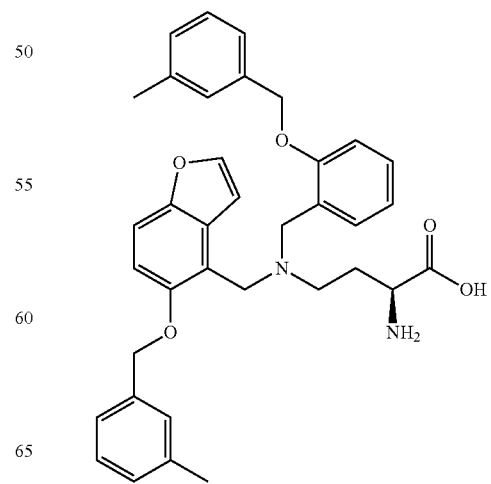

125
-continued
126
-continued
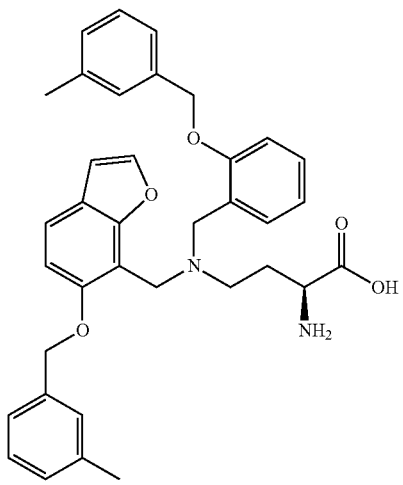
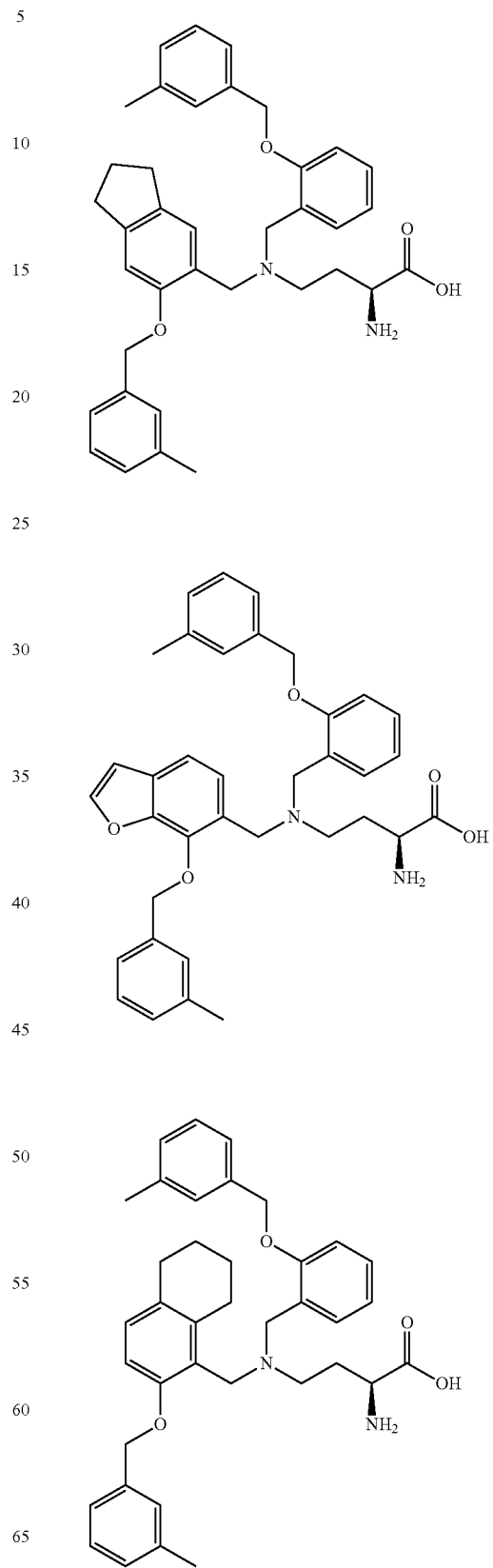

127
-continued
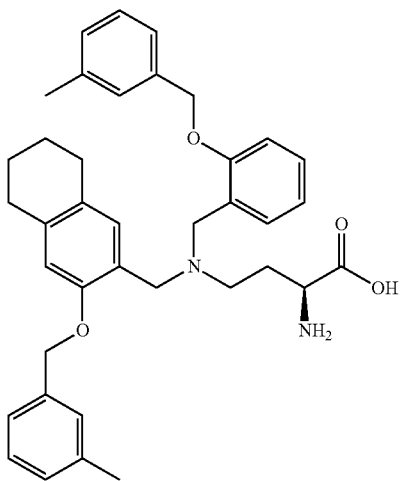
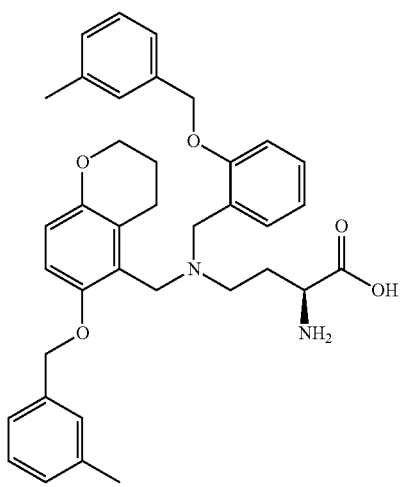
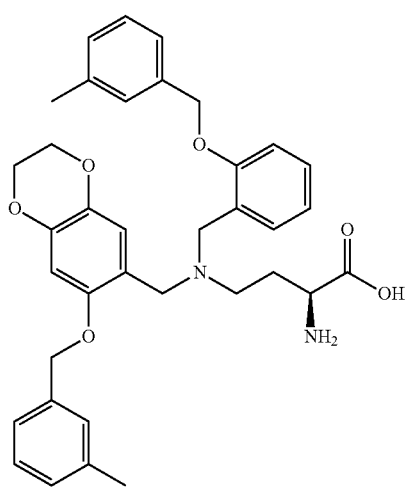
128
-continued
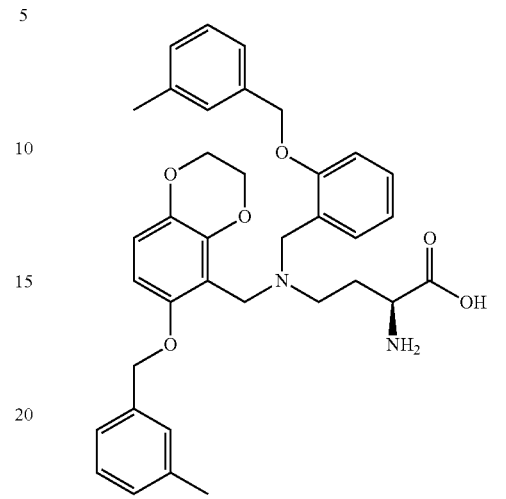
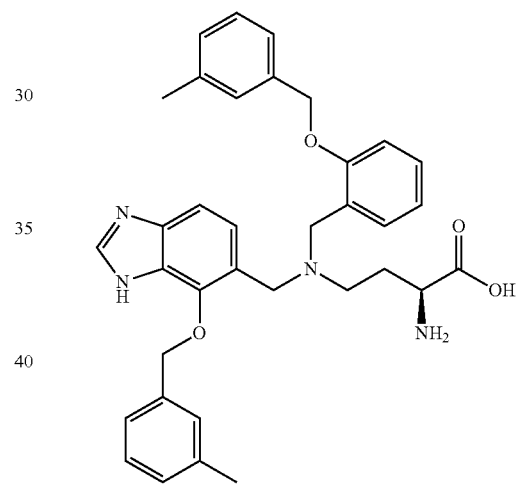
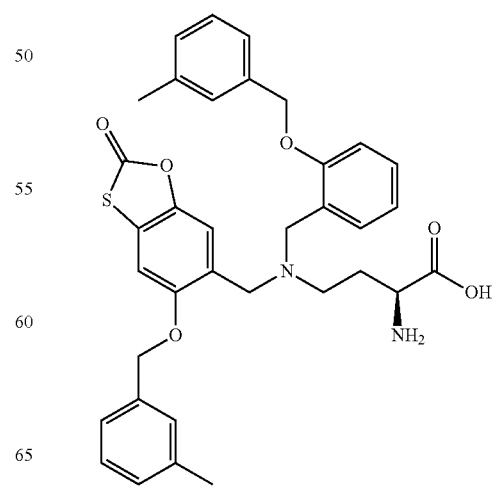

129
-continued
130
-continued
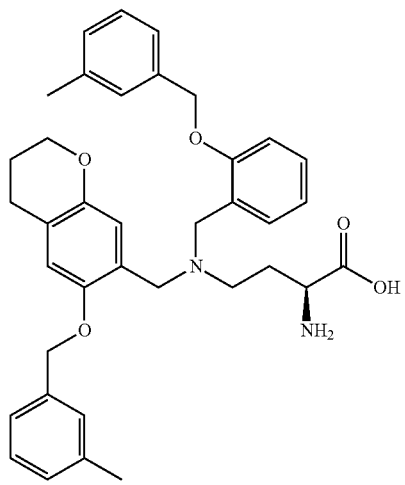
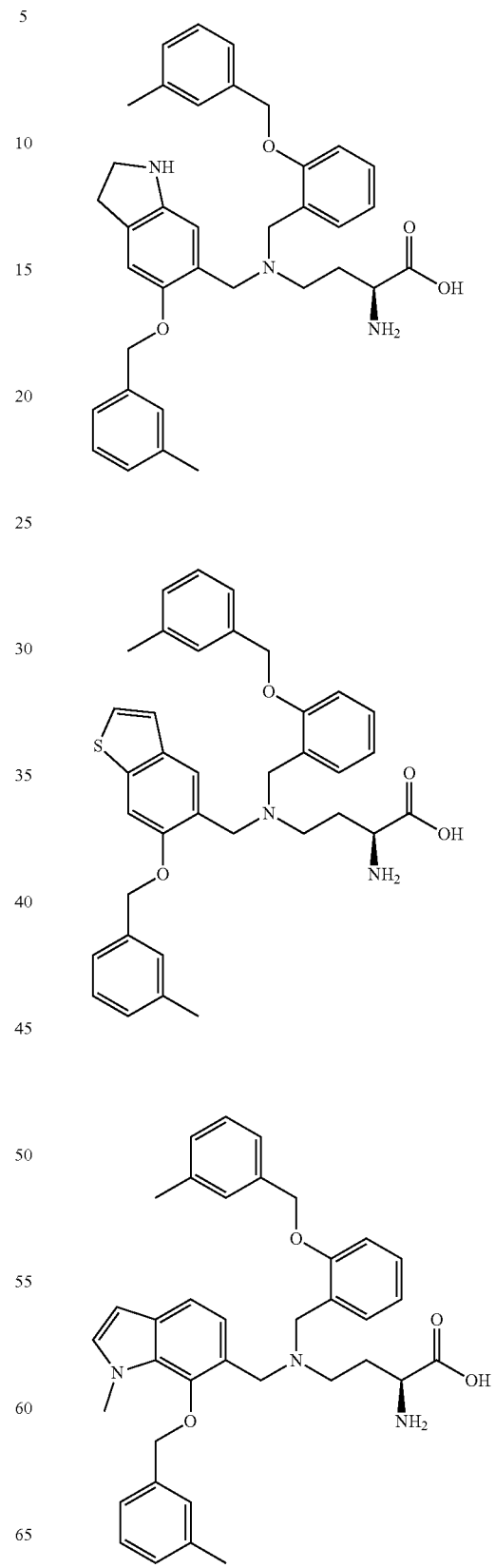

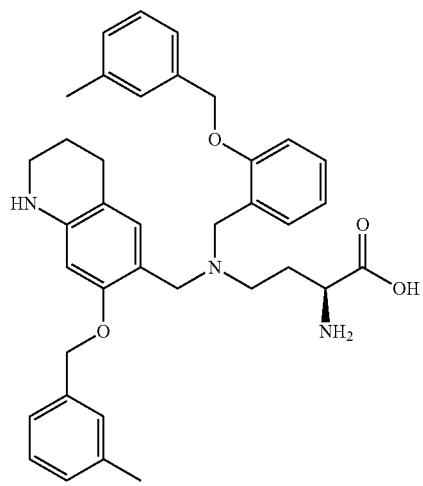
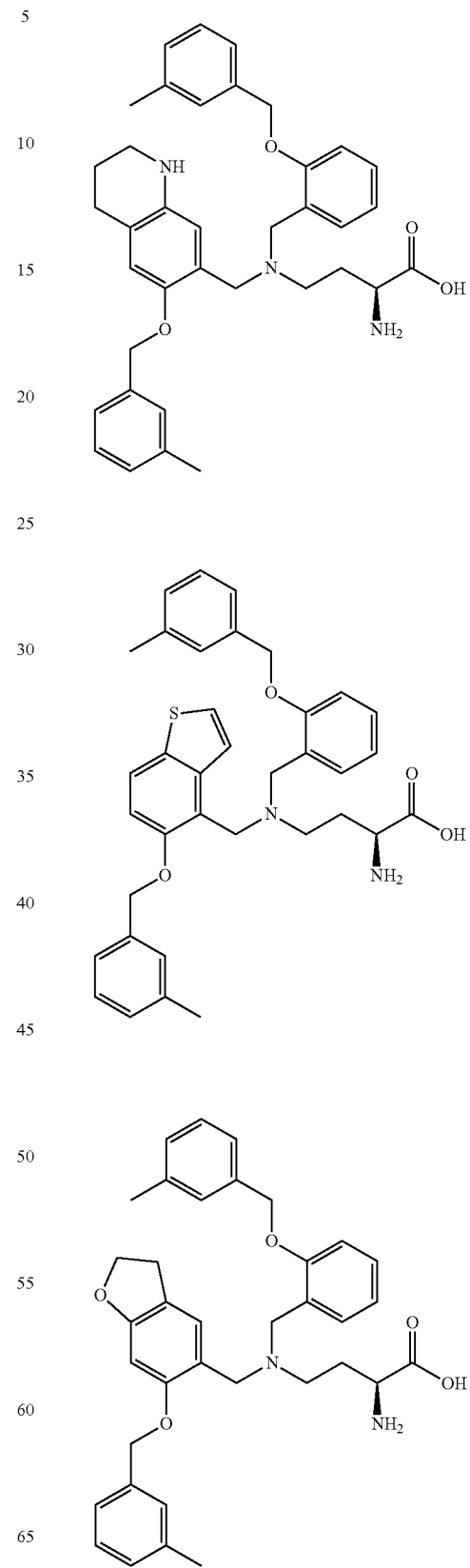

133
-continued
134
-continued
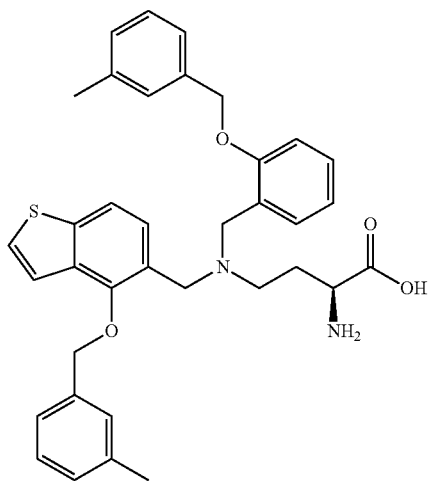
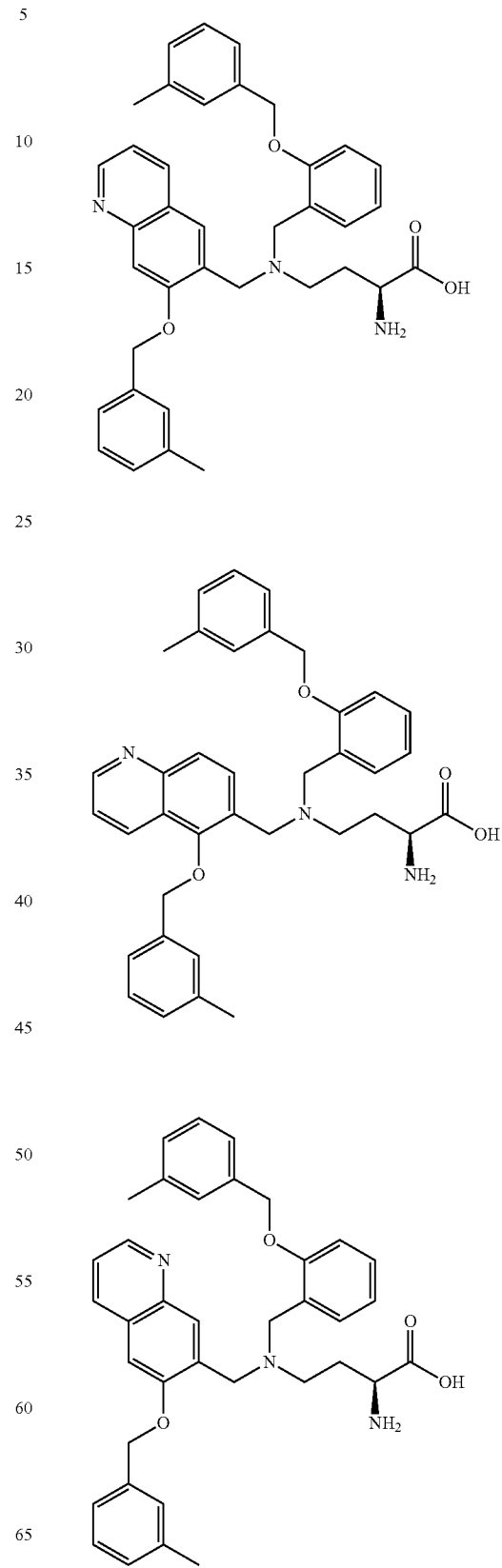

135
-continued
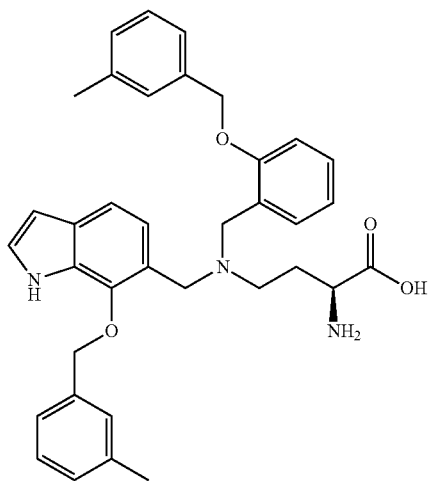
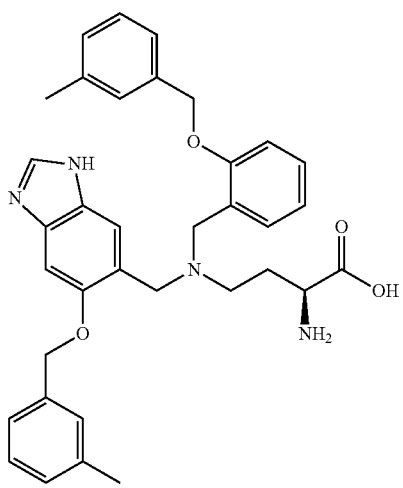
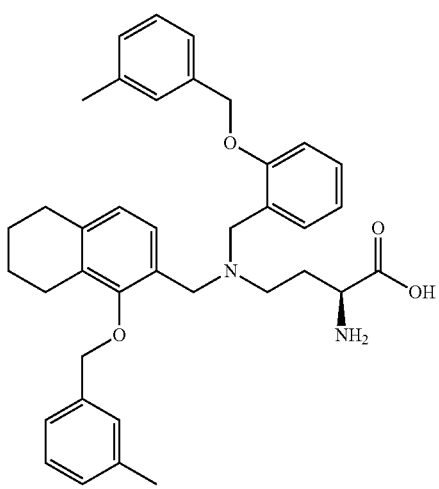
136
-continued
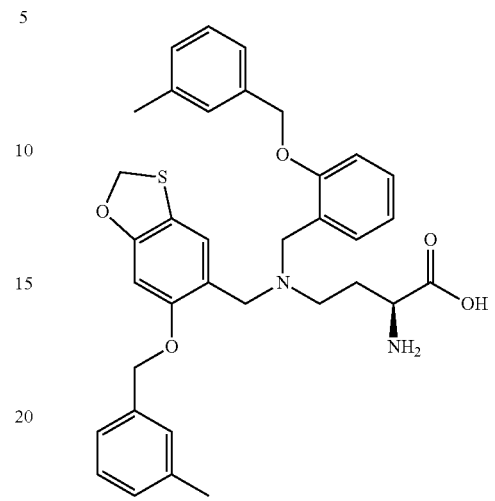
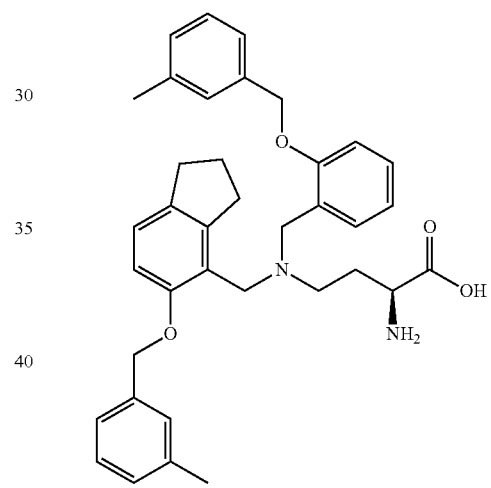
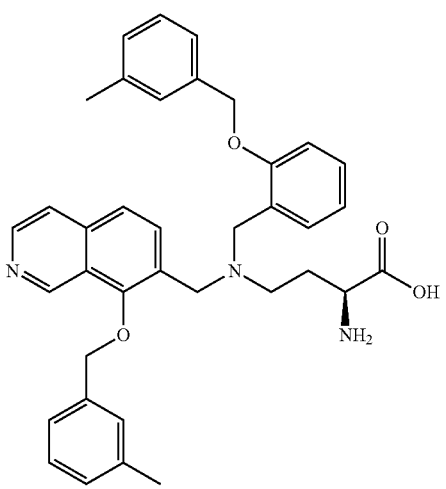

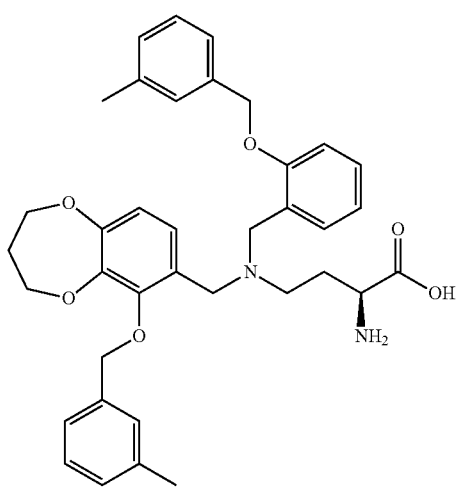
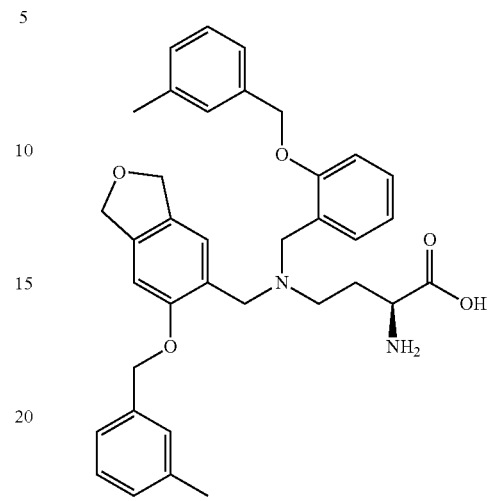
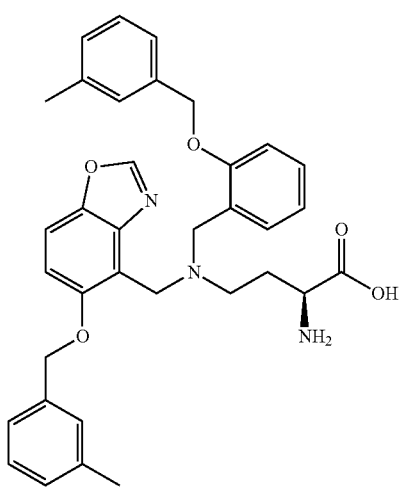
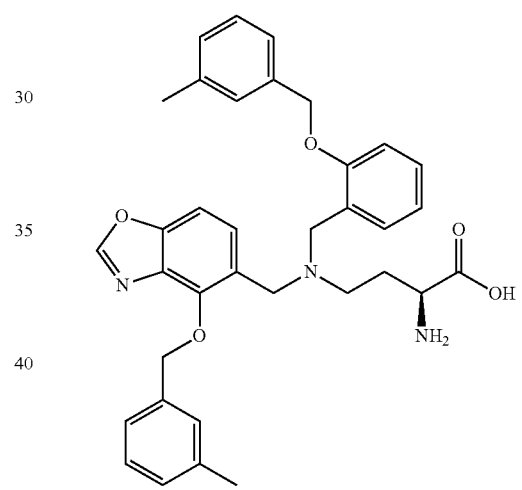
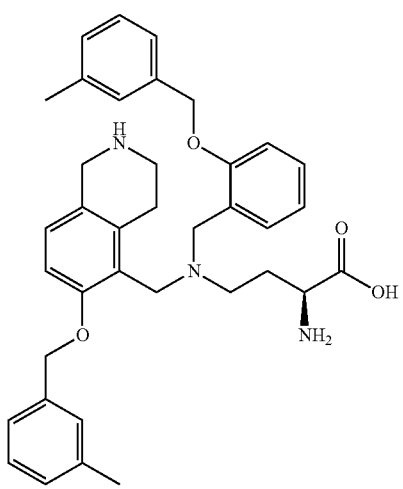
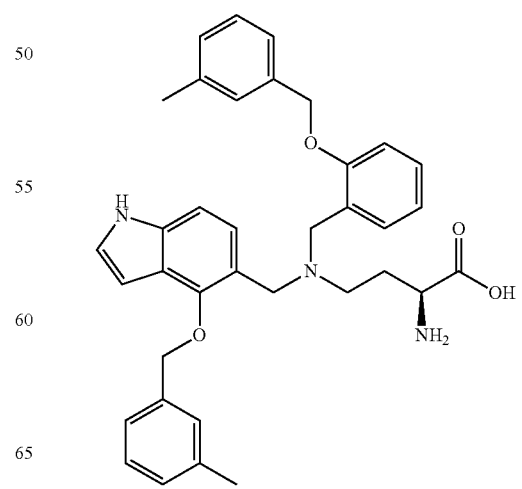

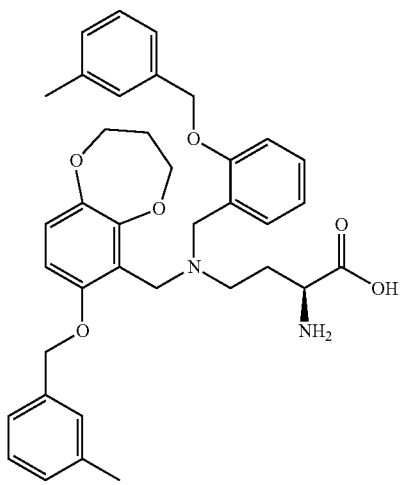

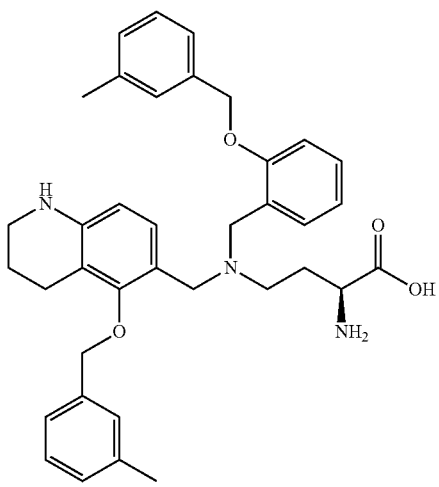

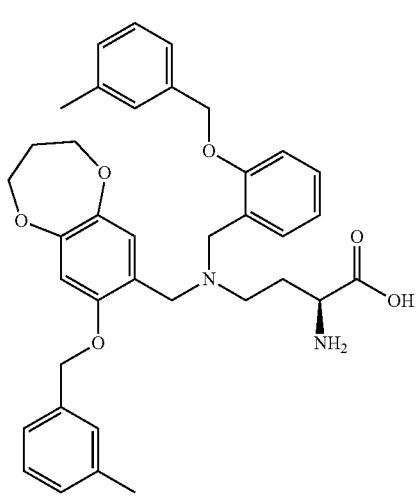

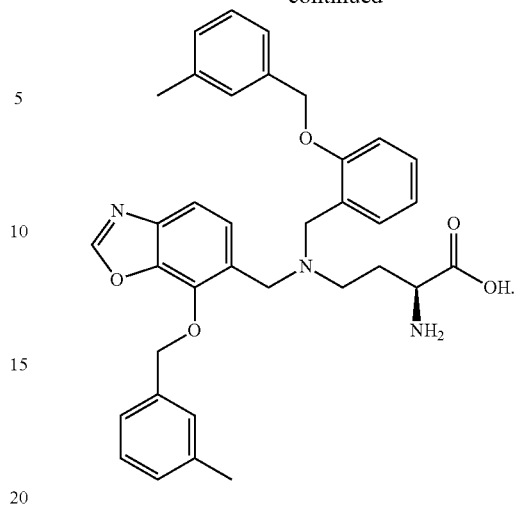

Embodiment 16

A method of modulating ASCT2 function in a patient in need thereof, comprising administering to the patient an effective ASCT2 function modulating amount of a composition of one of Embodiments 1-14.

Embodiment 17

A compound of one of Embodiments 1-14, for use in the treatment of cancer.

Embodiment 18

The use of Embodiment 17, wherein the cancer is lung cancer, colon cancer, breast cancer, or pancreas cancer.

Embodiment 19

A method of modulating angiogenesis, tumor progression, and/or metastasis, comprising the step of administering to a tissue or a subject associated with a disease condition a therapeutically effective amount of a compound of one of Embodiments 1-14.

Embodiment 20

The method of Embodiment 19, wherein said modulating inhibits angiogenesis, tumor progression, and/or metastasis.

Embodiment 21

The method of Embodiment 20, wherein said inhibiting involves inhibiting cellular glutamine uptake via ASCT2.

Embodiment 22

A compound of one of Embodiments 1-14, and an imaging agent coupled thereto.

Embodiment 23

A compound of Embodiment 22, wherein the imaging agent is a radionuclide.

Examples and Data

Embodiments of the present invention include the series of small-molecule glutamine transport antagonists described herein. These examples show compounds in that series are potent inhibitors of live-cell glutamine uptake reported to date.

To continue efforts towards novel ASCT2 inhibitors, the present inventors focused work around elaborating the glutamylanilide scaffold, particularly the amide linker. After screening multiple iterations of this scaffold, the present inventors arrived at a series of substituted 2,4-diaminobutanoic acids. Surprisingly, embodiments of the present invention demonstrated up 10 fold better activity against ASCT2 compared with GPNA and had tractable structural elements for further development.

Screening of the synthesized amino acids 5-11 (Table 1), in both C6 (rat) and HEK293 (human) cell lines revealed that compounds 6, 7, and 11 displayed roughly equal potencies in both cells lines. Interestingly, other compounds in this series, (Table 1, Compounds 8, 10) demonstrated some preference for blocking glutamine transport in the rat cell line. A potent exemplary compound in the rat cell line (Table 1, Compound 5) also exhibited this preference and blocked ASCT2-mediated glutamine uptake in C6 cells with an $IC_{50}$ of 1.3 µM.

TABLE 1

Structures and activities of phenoxybenzyl analogues. All $IC_{50}$ values are reported as the mean of at least 3 biological replicates.

| Compound | R = | $IC_{50}$ (rat) | SEM | $IC_{50}$ (human) | SEM |
|---|---|---|---|---|---|
| 5 | 3-methoxyphenoxy | 1.3 µM | ±0.7 µM | 57.2 µM | ±20.8 µM |
| 6 | 4-methoxyphenoxy | 8.7 µM | ±0.5 µM | 11.9 µM | ±0.4 µM |
| 7 | 4-chlorophenoxy | 24.3 µM | ±2.8 µM | 26.0 µM | ±4.0 µM |
| 8 | 2-fluorophenoxy | 1.8 µM | ±0.6 µM | 33.8 µM | ±7.2 µM |
| 9 | 3-fluorophenoxy | 36.3 µM | ±10.9 µM | 11.5 µM | ±2.2 µM |
| 10 | 4-fluorophenoxy | 10.5 µM | ±2.7 µM | 141.7 µM | ±14.2 µM |
| 11 | 2-pyridyloxy | 68.2 µM | ±10.3 µM | 59.6 µM | ±4.9 µM |

To further investigate the SAR of this scaffold, the present inventors prepared a library of 2-amino-4-bis(benzyloxybenzyl)aminobutanoic acids with various substitutions around the distal aromatic ring. Overall, it was discovered that this addition of a rotatable bond between the two aromatic groups improved activity against glutamine uptake in both C6 and HEK293 cells. Two particularly potent compound of the present invention (Table 2, Compounds 12, 19) blocked ASCT2-mediated glutamine uptake with potencies of 5.1 and 3.3 µM in C6 cells and 7.2 and 7.9 µM in HEK293 cells respectively. One compound in the benzyloxy series (Table 2, Compound 18) demonstrated significant preference for inhibiting glutamine uptake in the human form of ASCT2 (HEK293) over the rat form (C6). Full concentration response curves for the most potent compounds in each form of ASCT2 are shown in FIG. 2.

TABLE 2

Structures and activities of benzyloxybenzyl analogues. All $IC_{50}$ values are reported as the mean of at least 3 biological replicates.

| Compound | R = | $IC_{50}$ (rat) | SEM | $IC_{50}$ (human) | SEM |
|---|---|---|---|---|---|
| 12 | 3-methoxybenzyloxy | 5.1 µM | ±1.0 µM | 7.2 µM | ±0.5 µM |
| 13 | 2-chlorobenzyloxy | 18.4 µM | ±3.3 µM | 40.1 µM | ±4.8 µM |
| 14 | 3-chlorobenzyloxy | 12.7 µM | ±1.6 µM | 50.8 µM | ±16.1 µM |
| 15 | 4-chlorobenzyloxy | 20.1 µM | ±3.8 µM | 33.7 µM | ±9.7 µM |
| 16 | 2-methylbenzyloxy | 41.7 µM | ±5.0 µM | 25.6 µM | ±2.0 µM |
| 17 | 3-methylbenzyloxy | 9.0 µM | ±3.3 µM | 9.6 µM | ±0.1 µM |
| 18 | 4-methylbenzyloxy | 86.4 µM | ±13.0 µM | 17.5 µM | ±3.0 µM |

TABLE 2-continued

Structures and activities of benzyloxybenzyl analogues. All IC$_{50}$ values are reported as the mean of at least 3 biological replicates.

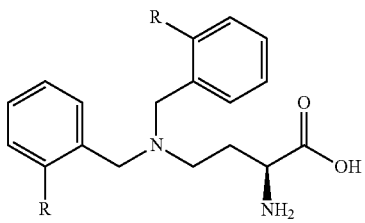

| Compound | R = | IC$_{50}$ (rat) | SEM | IC$_{50}$ (human) | SEM |
|---|---|---|---|---|---|
| 19 | 2-F-benzyloxy | 3.3 μM | ±1.4 μM | 7.9 μM | ±1.9 μM |
| 20 | 4-F-benzyloxy | 11.2 μM | ±2.3 μM | 13.7 μM | ±1.7 μM |
| 21 | 2-pyridylmethoxy | 8.4 μM | ±1.1 μM | 48.3 μM | ±10.8 μM |
| 22 | 3-pyridylmethoxy | 17.3 μM | ±8.5 μM | 89.1 μM | ±11.5 μM |
| 23 | 3-CF$_3$-benzyloxy | 22.5 μM | ±5.2 μM | 17.6 μM | ±3.4 μM |

Biologically active compounds were also evaluated in silico in a human ASCT2 model. The present inventors employed computational approaches similar to the approach of Albers et al. and our previously published work[11] to explore potential points of intermolecular interaction and binding pockets accessible to candidate probes. From a homology model based on the open structure of the bacterial aspartate transporter GltPh in complex with the inhibitor D,L-threo-benzyloxyaspartate (TBOA), PDB ID 2NWW, a number of targetable structural motifs were identified including a lipophilic pocket adjacent to the amino acid zwitterion binding site and potential hydrophilic points of contact within a loop region that was displaced by the inhibitor GPNA in the open form of the transporter. The best scoring poses for the most potent compounds identified demonstrated a compatible fit with the human ASCT2 model and interestingly, a tendency to exhibit points of interaction with both the amino acid zwitterion binding sites, particularly Ser353, Ser351, and Asp464, as well as the adjacent hydrophobic pocket, with possible pi-stacking and hydrogen bonding interactions with Trp461.

I. General Experimental

All reagents were purchased from commercial suppliers and purified as needed. Analytical thin-layer chromatography (TLC) was performed on 250 mM silica gel plates from Sorbent Technologies. Visualization was accomplished via UV light, and/or the use of ninhydrin and potassium permanganate solution followed by application of heat. Chromatography was performed using Silica RediSep Rf flash columns on a CombiFlash Rf automated chromatography system. All $^1$H and $^{13}$C NMR spectra were recorded on a Burker AV-400 (400 mHz and 100 MHz respectively). All $^1$H and $^{13}$C chemical shifts are reported in ppm relative to residual solvent peaks as a internal standard set to d 7.26 and d 77.16 (CDCl$_3$). Data are reported as follows: chemical shift, multiplicity (s=singlet, d=doublet, t=triplet, q=quartet, dd=doublet of doublets, br=broad, m=multiplet), coupling constant (Hz), integration. Low resolution mass spectra were obtained on an Agilent 1200 LCMS with electrospray ionization.

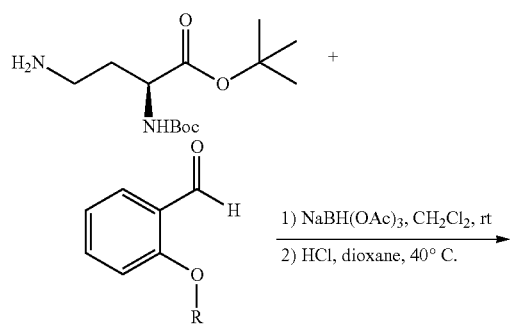

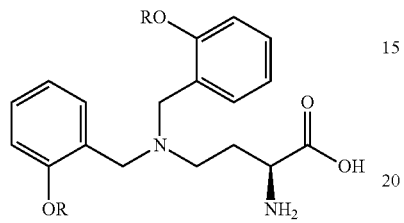

General Procedure for the Synthesis of 2-amino-4-bis(aryloxybenzyl)aminobutanoic Acids To a vial equipped with a magnetic stir bar was added $N^\alpha$-Boc-L-2,4-diaminobutyric acid tert-butyl ester hydrochloride (0.16 mmol, 1.0 eq) followed by methylene chloride (1.6 mL). The appropriate aryloxybenzaldehyde (0.40 mmol, 2.5 eq) was added followed by sodium triacetoxyborohydride (0.56 mmol, 3.5 eq). The reaction stirred at rt for 12-18 hours. Upon completion, the reaction is partitioned between water and methylene chloride, extracted with methylene chloride (3×), dried over anhydrous $MgSO_4$, and concentrated in vacuo. The products were purified by flash silica column chromatography (hexanes/ethyl acetate) to afford pure 2-N-Boc-4-N-bis(aryloxybenzyl) tert-butyl esters. Products were deprotected by treatment with excess HCl in dioxane at 40° C. for 4-7 h followed by concentration under vacuum to afford analytically pure products in yields ranging from 52-75% over two steps.

This exemplary compound was prepared according to the general procedure and purified via reverse phase chromatography (5-95% acetonitrile/water) to afford the product as a clear oil (62%). $^1$H NMR (400 MHz, $CDCl_3$) (ppm): 7.71 (d, J=7.4 Hz, 2H); 7.31 (t, J=7.7 Hz, 2H); 7.20 (t, J=8.1 Hz, 2H); 7.13 (t, J=7.5 Hz, 2H); 6.82 (d, J=8.1 Hz, 2H); 6.69 (dd, $J_1$=2.1 Hz, $J_2$=8.3 Hz, 2H); 6.54-6.50 (m, 2H); 6.46 (d, J=6.45 Hz, 2H); 4.50 (s, 4H); 4.14-4.04 (m, 1H); 3.75 (s, 6H); 3.38-3.22 (m, 2H); 2.53-2.40 (m, 1H); 2.22-2.09 (m, 1H); 1.35 (s, 9H); 1.33 (s, 9H). $^{13}$C NMR (100 MHz, $CDCl_3$) (ppm): 170.09; 161.31; 161.04; 160.66; 156.74; 155.98; 133.64; 131.93; 130.59; 124.19; 119.45; 117.87; 111.34; 110.30; 105.60; 83.24; 80.34; 55.54; 51.96; 51.75; 49.64; 28.32; 27.87; 27.82. HRMS (TOF, ES+) $C_{41}H_{50}N_2O_8$ $[M+H]^+$ calc mass 699.3645, found 699.3628.

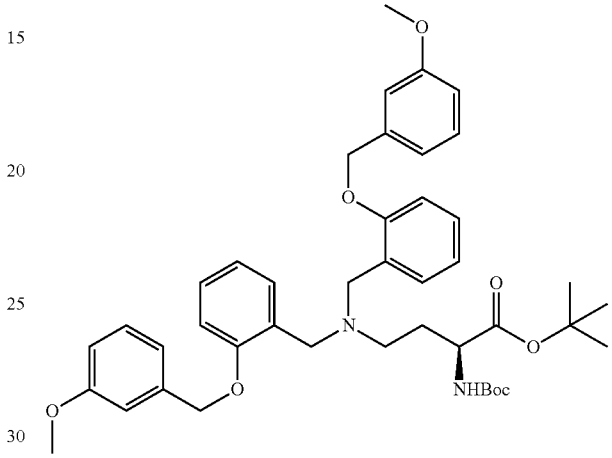

Compound was prepared according to the general procedure and purified via reverse phase chromatography (5-95% acetonitrile/water) to afford the product as a clear oil (67%). $^1$H NMR (400 MHz, $CDCl_3$) (ppm): 7.52 (d, J=7.3 Hz, 2H); 7.28 (t, J=7.8 Hz, 2H); 7.17 (t, J=7.6 Hz, 2H); 7.02-6.82 (m, 12H); 5.06 (s, 4H); 4.16-4.07 (m, 1H); 3.78 (s, 6H); 3.77-3.66 (m, 4H); 2.70-2.59 (m, 1H); 2.59-2.47 (m, 1H); 2.08-1.95 (m, 1H); 1.91-1.79 (m, 1H); 1.44 (s, 9H); 1.34 (s, 9H). $^{13}$C NMR (100 MHz, $CDCl_3$) (ppm): 171.68; 159.72; 156.72; 155.44; 138.96; 130.15; 129.52; 127.82; 127.63; 120.78; 119.33; 113.20; 112.58; 111.68; 81.16; 79.05; 69.80; 55.13; 53.45; 52.26; 50.75; 29.23; 28.37; 27.83. HRMS (TOF, ES+) $C_{43}H_{54}N_2O_8$ $[M+H]^+$ calc mass 727.3958, found 727.3942.

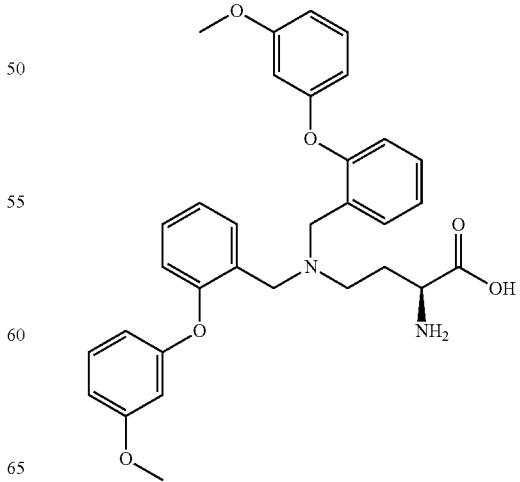

Compound was deprotected according to the general procedure and used without further purification (quant yield). $^1$H NMR (400 MHz, CDCl$_3$) (ppm): 7.81 (dd, J$_1$=6.7 Hz, J$_2$=16.4 Hz, 2H); 7.18-7.12 (m, 2H); 7.10 (td, J$_1$=2.1 Hz, J$_2$=7.1 Hz, 2H); 7.01 (d, J=7.0 Hz, 2H); 6.69 (t, J=8.8 Hz, 2H); 6.60 (d, J=8.2 Hz, 2H); 6.49 (s, 2H); 6.41 (d, J=7.6 Hz, 2H); 4.55 (s, 4H); 4.28 (s, 1H); 3.78-3.73 (m, 1H); 3.67 (s, 3H); 3.66 (s, 3H); 3.65-3.60 (m, 1H); 2.76 (s, 2H). $^{13}$C NMR (100 MHz, CDCl$_3$) (ppm): 169.94; 160.92; 156.38; 156.29; 133.81; 131.64; 130.25; 123.82; 118.96; 117.20; 111.50; 110.14; 105.58; 55.38; 52.21; 50.95; 49.89; 24.74. HRMS (TOF, ES+) C$_{32}$H$_{34}$N$_2$O$_6$ [M+H]$^+$ calc mass 543.2495, found 543.2476.

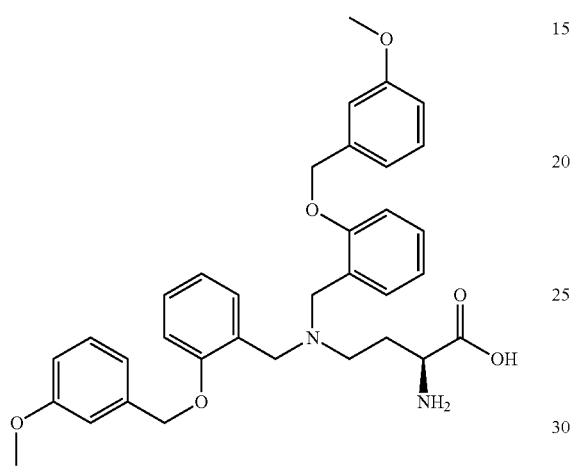 [SMILES: COc1cccc(COc2ccccc2CN(CC[C@H](NC(=O)OC(C)(C)C)C(=O)OC(C)(C)C)Cc2ccccc2OCc2cccc(OC)c2)c1]

Compound was deprotected according to the general procedure and used without further purification (quant yield). $^1$H NMR (400 MHz, CDCl$_3$) (ppm): 7.60-7.49 (m, 2H); 7.23-7.11 (m, 4H); 6.90-6.69 (m, 10H); 5.07-4.89 (m, 4H); 4.46 (br s, 4H); 4.13-4.04 (br s, 1H); 3.65 (s, 6H); 3.64-3.62 (m, 1H); 3.55-3.45 (m, 1H); 2.61 (br s, 2H). $^{13}$C NMR (100 MHz, CDCl$_3$) (ppm): 169.68; 159.70; 156.92; 137.74; 133.43; 131.65; 129.93; 129.89; 119.66; 117.55; 113.58; 112.99; 112.38; 70.30; 55.24; 53.24; 50.89; 50.13; 24.72. HRMS (TOF, ES+) C$_{32}$H$_{34}$N$_2$O$_6$ [M+H]$^+$ calc mass 571.2808, found 571.2784.

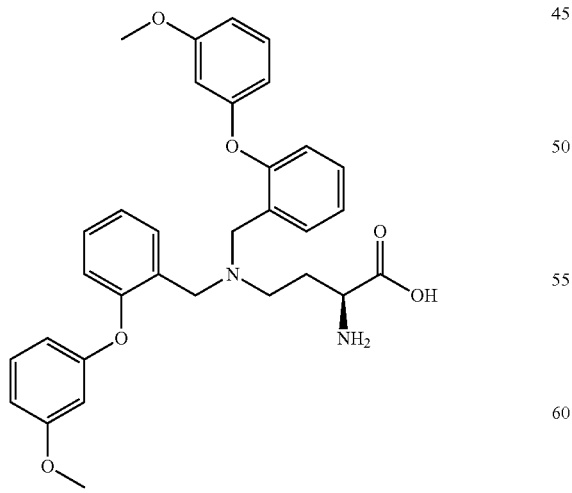

MLS-A-148-13
rat IC$_{50}$ = 1.3 μM
human IC$_{50}$ = 57.2 μM

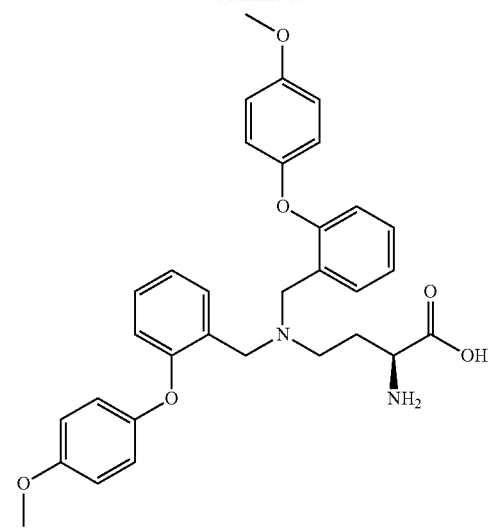

MLS-A-148-14
rat IC$_{50}$ = 8.7 μM
human IC$_{50}$ = 11.9 μM

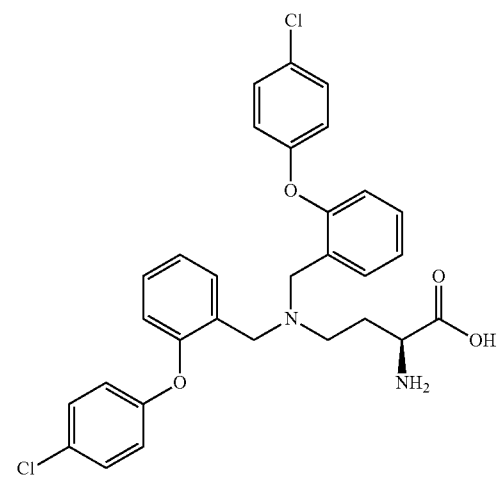

MLS-A-148-15
rat IC$_{50}$ = 24.3 μM
human IC$_{50}$ = 26.0 μM

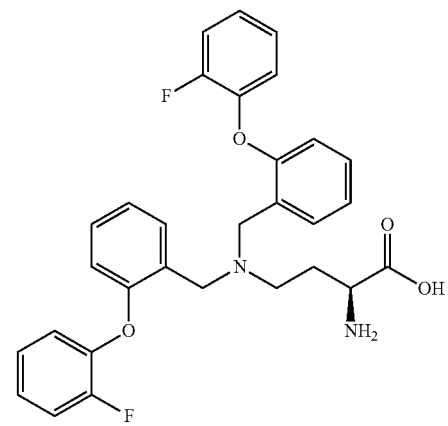

MLS-A-148-16
rat IC$_{50}$ = 1.8 μM
human IC$_{50}$ = 33.8 μM

151
-continued

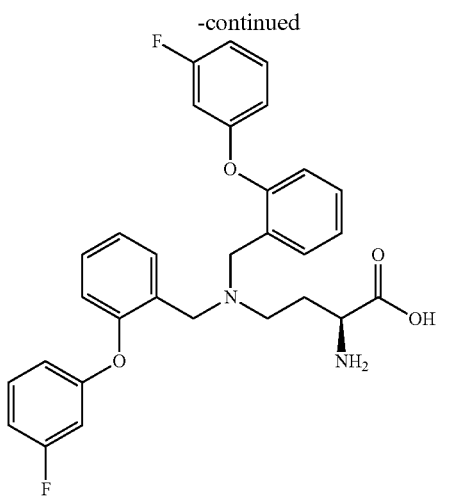

MLS-A-148-17
rat IC$_{50}$ = 36.3 µM
human IC$_{50}$ = 11.5 µM

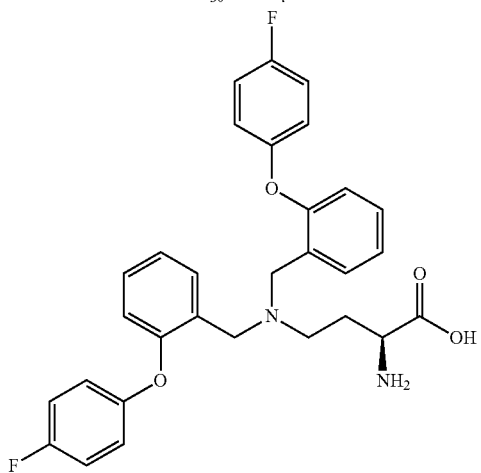

MLS-A-148-18
rat IC$_{50}$ = 10.5 µM
human IC$_{50}$ = 141.7 µM

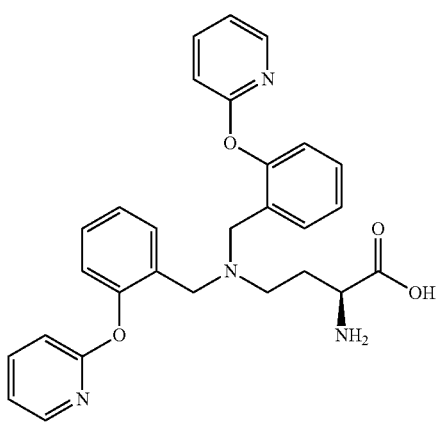

MLS-A-148-19
rat IC$_{50}$ = 68.2 µM
human IC$_{50}$ = 59.6 µM

152

Synthesis of (2S)-4-(Bis(2-((3-methylbenzyl)oxy)benzyl)amino)pyrrolidine-2-carboxylic Acid

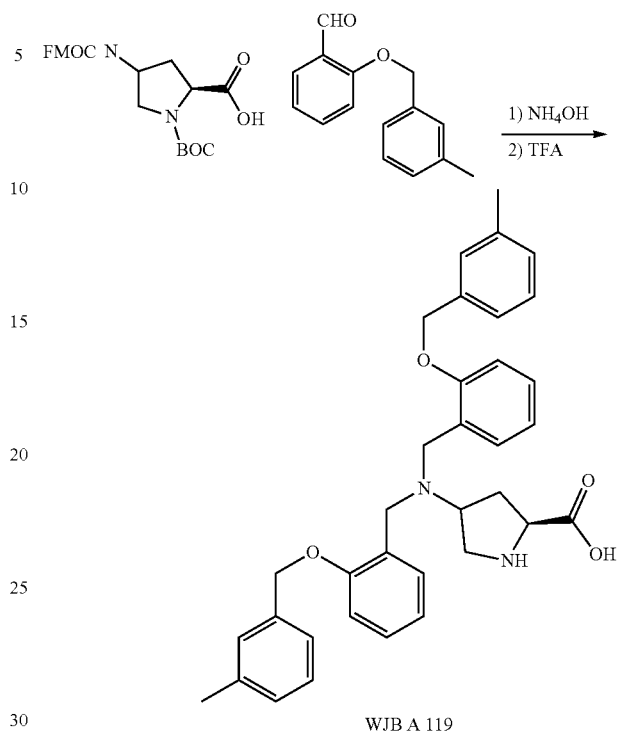

WJB A 119

To 4-amino-FMOC protected N—BOC protected proline, ammonium hydroxide was added with heating to 50 degrees C. for 20 minutes followed by azeotropic distillation from ACN and MeOH. Subsequently, the aldehyde was added in 2 mL DMA followed by NaBH$_3$CN. Reaction proceeded for 48 hrs followed by quenching with water, extraction with EtOAC (3x). The organic layers were combined, washed in brine, dried over Na$_2$SO$_4$, concentrated and purified by RP chromatography (gilson). WJB A 119 was obtained following TFA deprotection and purification by RP chromatography (gilson). This compound was characterized by LCMS for identity and purity.

Synthesis of (2S)-4-(Bis(2-((3-methylbenzyl)oxy)benzyl)amino)piperidine-2-carboxylic Acid

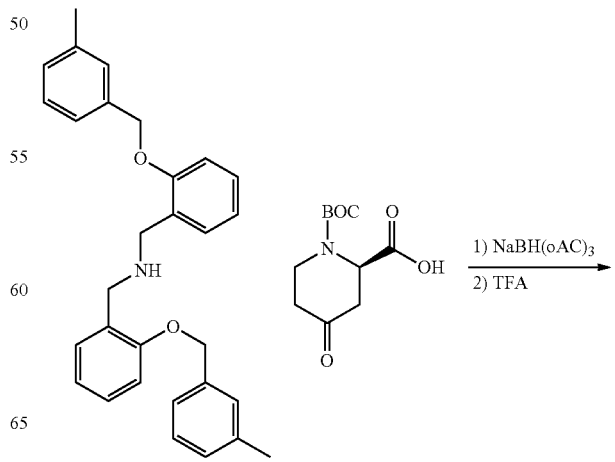

-continued

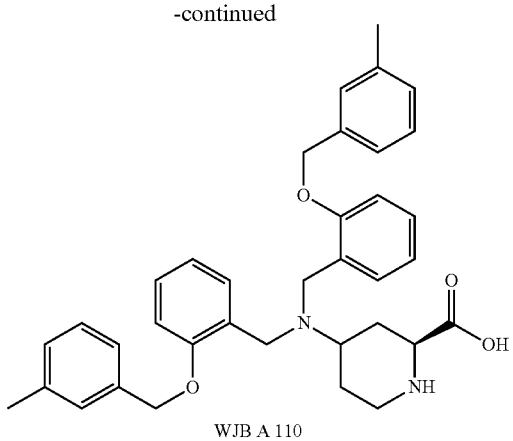

WJB A 110

To the secondary amine was added the corresponding BOC-protected piperidine in DMA and the borohydride (2.5 eq.). The reaction was heated to 50 degrees C. for 6 hrs followed by quenching with water and extraction with EtOAC (3×). The organic layers were combined, washed in brine, dried over $Na_2SO_4$, concentrated and purified by RP chromatography (gilson). WJB A 119 was obtained from the by TFA deprotection and purification by RP chromatography (gilson). The compound was characterized by LCMS for identity and purity.

Exemplary compound V-9302 (see FIGS. 3A and 3B), inhibited ASCT2-mediated glutamine uptake in human cells in a concentration-dependent fashion and exhibited a 100-fold improvement in potency ($IC_{50}$ V-9302=9.6 μM) over gamma-L-glutamyl-p-nitroanilide (GPNA; $IC_{50}$=1000 μM), a previously reported inhibitor of glutamine uptake. Using a panel of $^3$H-labeled amino acids transported by multiple transporter systems, including glutamine and other solutes not transported by ASCT2 (FIG. 9), the present inventors observed that V-9302 preferentially inhibited glutamine transport at up to 10-fold the $IC_{50}$ concentration (FIG. 3C/3D). Similarly, V-9302 was found to be capable of inhibiting the uptake of another ASCT2 substrate, leucine (FIG. 3D/E.), suggesting that the amino acid transport inhibitory profile was ASCT2-selective but not restricted to glutamine. To confirm that V-9302 binds ASCT2, the present inventors employed the Drug Affinity Responsive Target Stability (DARTS) technique[15] using HEK-293 cells expressing a tetracycline-inducible ASCT2 vector. The DARTS technique is a target identification strategy that capitalizes upon reduction in protease susceptibility of a target protein upon drug binding. The present inventors observed that ASCT2 was protected from proteolysis in a V-9302 concentration-dependent manner (FIG. 3F, FIG. 10), indicating a stable V-9302-ASCT2 interaction and, thus, implicating ASCT2 as a putative target of the compound. Interestingly, the ASCT2 paralog, ASCT1 (SLC1A4), was not stabilized in the presence of V-9302 (FIG. 10), suggesting that V-9302 exhibits ASCT2 selectivity.

Figures 4D, 4E, 4F:
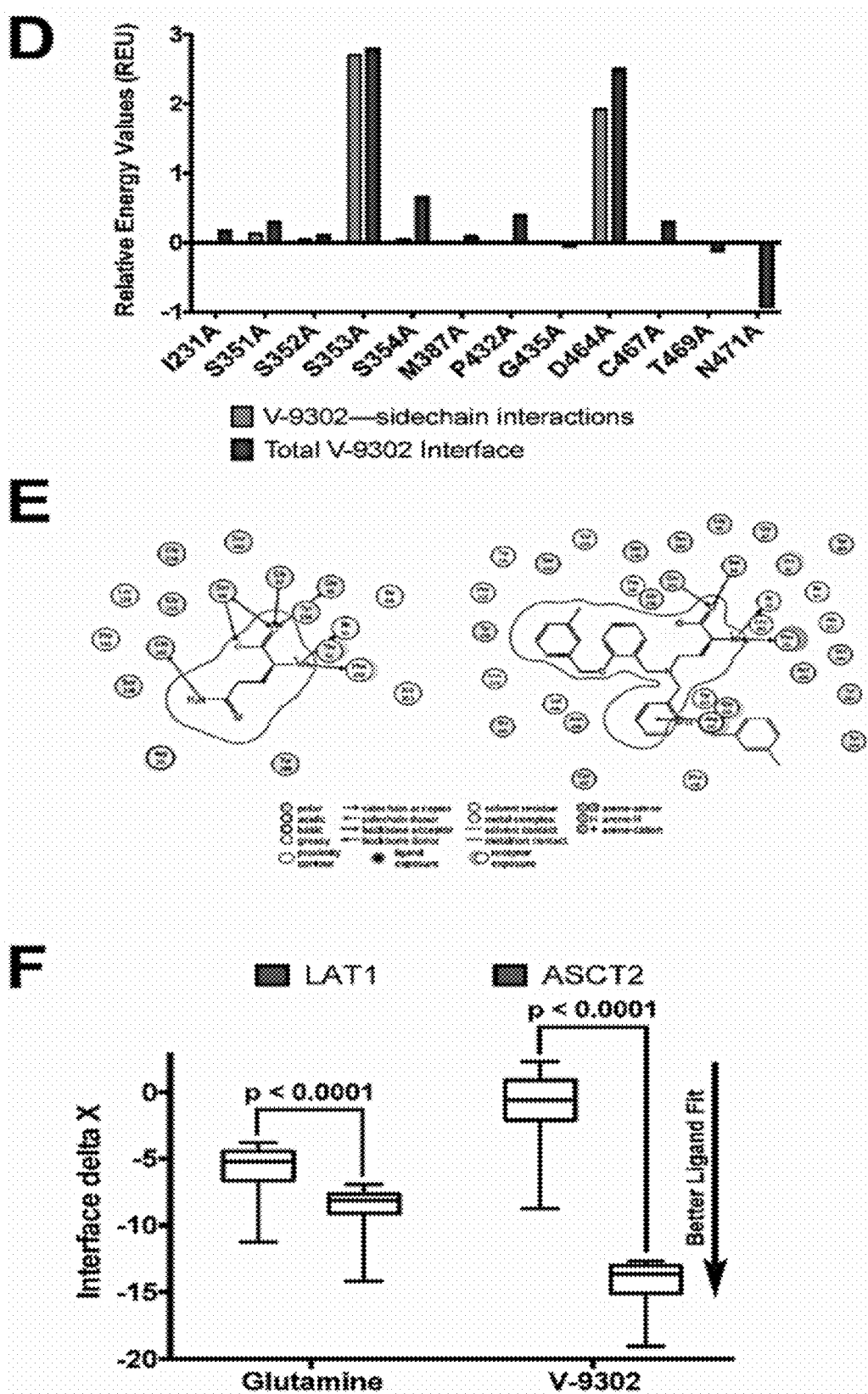

To model points of interaction between V-9302 and ASCT2, the present inventors utilized an in silico homology model of human ASCT2 (hASCT2). The present inventors found that V-9302 was compatible with the orthosteric amino acid binding pocket of hASCT2, which is localized within the transmembrane region of the protein (FIG. 4A). The conserved alpha-amino acid head group of V-9302 appeared to form key interactions within the zwitterion recognition site (FIG. 4B), which has been shown through crystallographic data to recognize amino acids and derivatives thereof. Similarly, docking glutamine into ASCT2 resulted in direct overlap with the putative binding pocket occupied by V-9302 (FIG. 4C). To validate the specific interactions observed, the present inventors performed an in silico alanine scan of residues located within the putative V-9302 binding pocket (FIG. 4D). Overall docking scores with mutation of S353 and D464 suggested strong corresponding sidechain interactions at these residues (FIG. 4D). Consistent with the amino acid selectivity assay (FIG. 3C/D), V-9302 interactions with LAT1, another transporter of glutamine, suffered steric hindrance penalties (FIG. 10E/F). In contrast to V-9302, interface scores for glutamine in ASCT2 and LAT1 were favorable in both models (Extended Data FIG. 10F). These two neutral amino acid transporters are frequently co-expressed and exhibit overlapping substrate specificity, which has led some to propose cooperatively between ASCT2 and LAT1 in certain cancers.

To evaluate the effects of V-9302 on human cancer cells, the present inventors conducted an in vitro efficacy screen of 29 human cancer cell lines spanning three disease states (FIG. 5). Given the anaplerotic nature of glutamine, the present inventors utilized an ATP-dependent assay of viability as a primary screen, which was validated in independent follow-up screening. In the primary screen, the present inventors observed that V-9302 exposure reduced in vitro viability by at least 20% in more than half of the cell lines screened, with sensitivity to V-9302 exposure not obviously linked to select mutational status (FIG. 11). Follow-up screening was carried out in a subset of colorectal cancer (CRC) cell lines that exhibited variable sensitivities to V-9302 in the primary screen. Using three independent assays lacking ATP-dependency, the present inventors confirmed that V-9302 exposure led to reduced cellular viability and increased cell death (FIG. 12). While V-9302 impacted either viability or cell death to varying degrees across the panel of cell lines screened, certain particularly sensitive cell lines exhibited dramatically decreased viability and increased cell death, including RKO, SW620, and LIM2537. To elucidate biological correlates of V-9302 sensitivity, the present inventors compared cell line sensitivity with ASCT2 levels (FIG. 13), as well as viability in media depleted of ASCT2 substrates (FIG. 14). Neither membranous nor total ASCT2 levels correlated with V-9302-dependent changes in viability. However, cell lines sensitive to V-9302 exposure exhibited reduced viability and increased cell death when propagated in glutamine-depleted or ASCT2-substrate-depleted media. Finally, the present inventors compared cellular viability with exposure to V-9302 or CB-839 in four human CRC cell lines (FIG. 5B). The $EC_{50}$ concentrations for the four CRC cell lines exposed to V-9302 ranged from approximately 9-15 μM, while CB-839 did not exhibit appreciable activity under identical conditions. Glutamine plays critical roles in T-cell proliferation and activation. The present inventors evaluated the effects of V-9302 on activated CD8-positive T-cells in vitro and found T-cell viability unchanged relative to vehicle (FIG. 15A). T-cell activation was also not impaired with V-9302 exposure (FIG. 15B).

The cell viability (HCC1806 cells) with exposure (48 hrs) to WJB-A-110 and WJB-A-119 was also evaluated to give $IC_{50}$ values of 32 μM and 23 μM, respectively.

Figure 17:
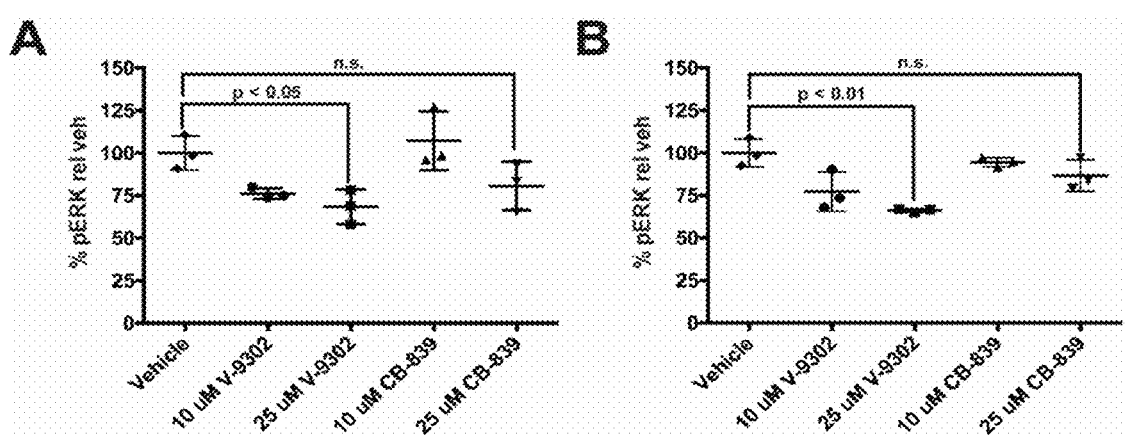
Figure 18:
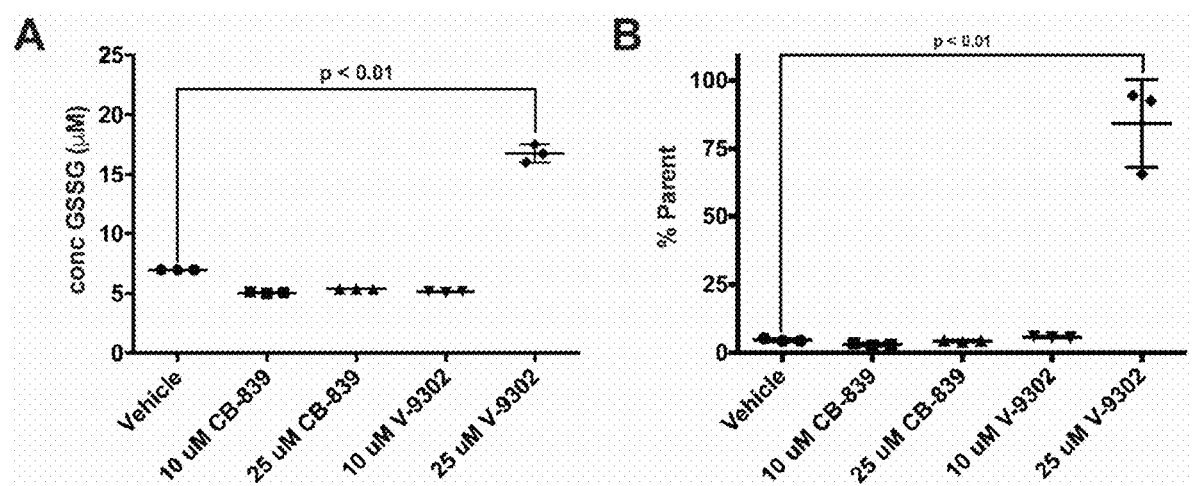
Figure 20:
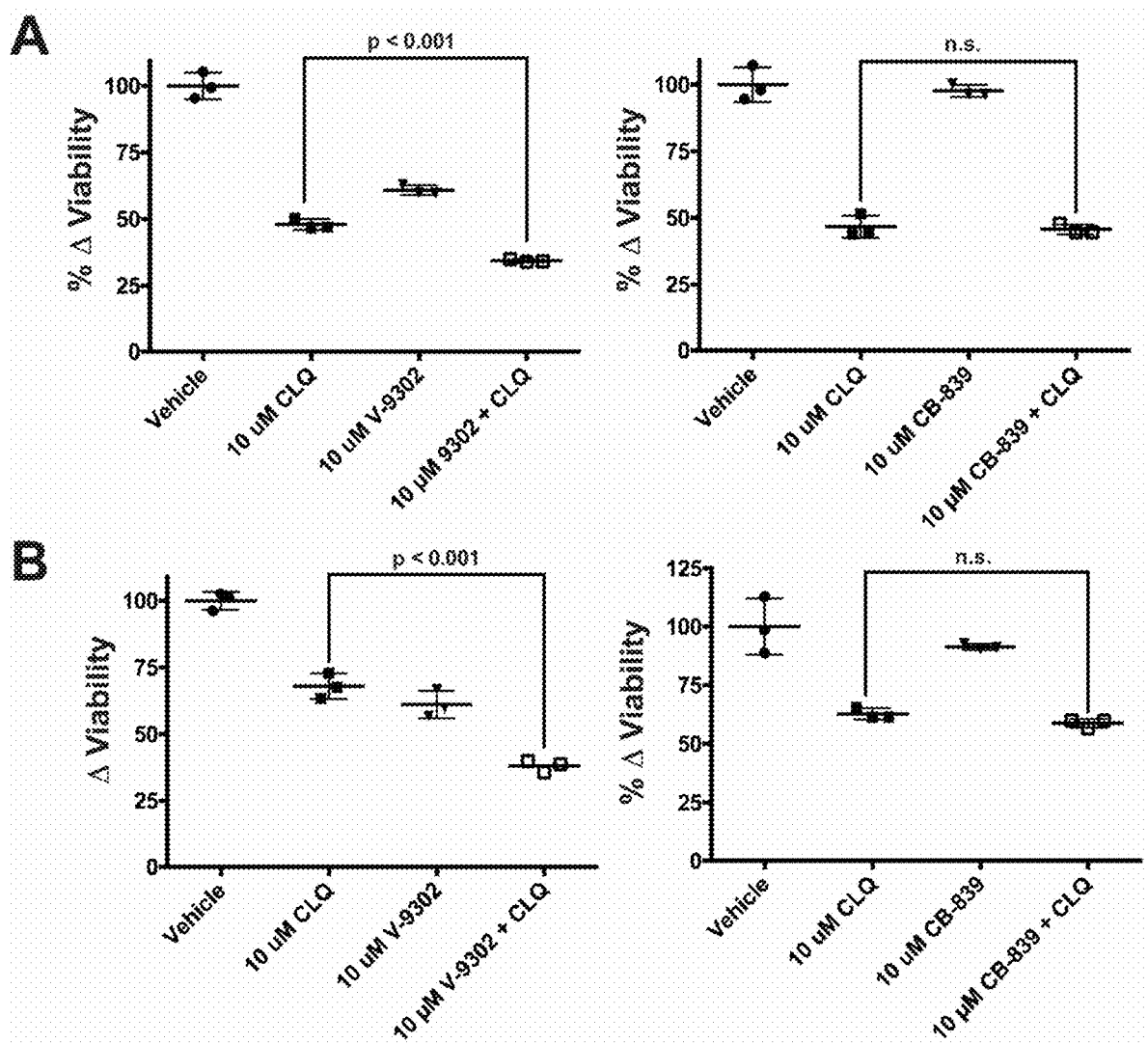
Figure 22:
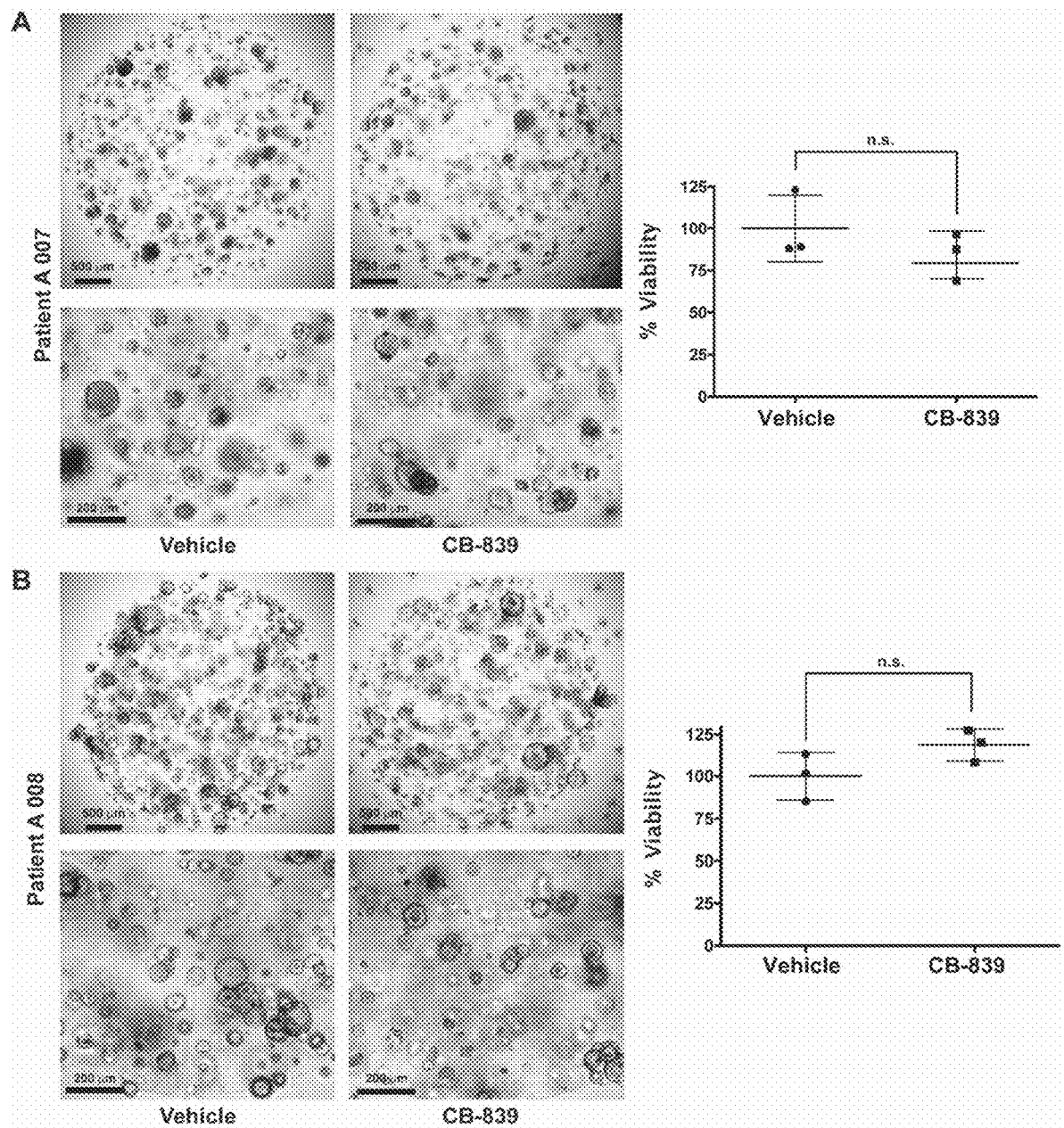

To elucidate determinants of response to V-9302 in vitro, we carried out shRNA knockdown of ASCT2 in HCC1806 cells, as previously shown, to enable direct comparison with silencing the target. Silencing ASCT2 (FIG. 6A) and V-9302 exposure (FIG. 6B) in HCC1806 cells resulted in analogous downstream effects, including significantly decreased pS6 and a modest decrease in pERK. A similar inhibition profile was observed in V-9302-treated HT29 cells (FIG. 16). Using an independent biochemical assay of pERK activity, the present inventors validated that V-9302 exposure resulted in a statistically significant, concentration-dependent decrease in pERK not observed with CB-839 in HCC1806 or HT29 cells (FIG. 17). In addition, in vitro V-9302 exposure in HCC1806 cells led to increased levels of oxidized glutathione (GSSG) at the expense of reduced glutathione (GSH) (FIG. 6C), and a corresponding increase in intracellular reactive oxygen species (ROS) (FIG. 6D). Like HCC1806 cells, V-9302 exposure led to elevated GSSG levels and ROS in HT29 cells, features not observed with CB-839 (FIG. 18). Autophagy following V-9302 exposure was observed in multiple cell lines, which was not unexpected given the relationship between amino acid withdrawal, regulation of mTOR, and autophagy. Immunofluorescence (FIG. 6E) revealed that V-9302 exposure in HCC1806 cells led to elevated LC3B, a marker of autophagy. In the same cell line as well as HT29, autophagic flux was elevated with V-9302 exposure in a concentration-dependent manner (FIG. 19A/B). Combining V-9302 with the lysosomal inhibitor, chloroquine, further increased the number of autophagic vesicles in HT29 cells (FIG. 19B). In contrast, CB-839 exposure did not lead to elevated autophagic flux, with or without the addition of chloroquine (FIG. 19C). In HT29 and HCT-116 cells, combined exposure of chloroquine and V-9302 further decreased cell viability compared with single agent exposure or vehicle control. In contrast, CB-839 did not decrease cell viability in these cell lines under identical conditions, nor exhibit a combinatorial effect with chloroquine (FIG. 20). Consistent with modulated oxidative stress and increased oxidation of NAD(P)H by glutathione reductase, V-9302 exposure led to decreased optical redox ratio in HCC1806 cells (ratio of NAD(P)H to FAD) (FIG. 6F) and decreased the fluorescent lifetimes of both NAD(P)H and FAD (FIG. 21). The optical redox ratio of a cell is well-conserved and has been highly validated with independent measurements, including glycolytic activity and oxygen consumption. The changes in optical redox ratio following V-9302 exposure, and their magnitude, are consistent with prior studies correlating these measures with PI3K/Akt/mTOR pathway inhibition in human breast cancer cells. The efficacy of V-9302 was further evaluated in two CRC organoids developed at Vanderbilt University Medical Center expressing activating mutations in KRAS and BRAF. The viability of both organoid A-008 (KRAS$^{G12V}$; p53$^{R248Q}$; PTEN$^{L140Y}$) and A-007 (BRAF$^{V600E}$, FIG. 25) were significantly reduced with exposure to V-9302 (FIG. 4G). In contrast, the same organoids were not significantly affected by CB-839 exposure (FIG. 22).

Figure 24:
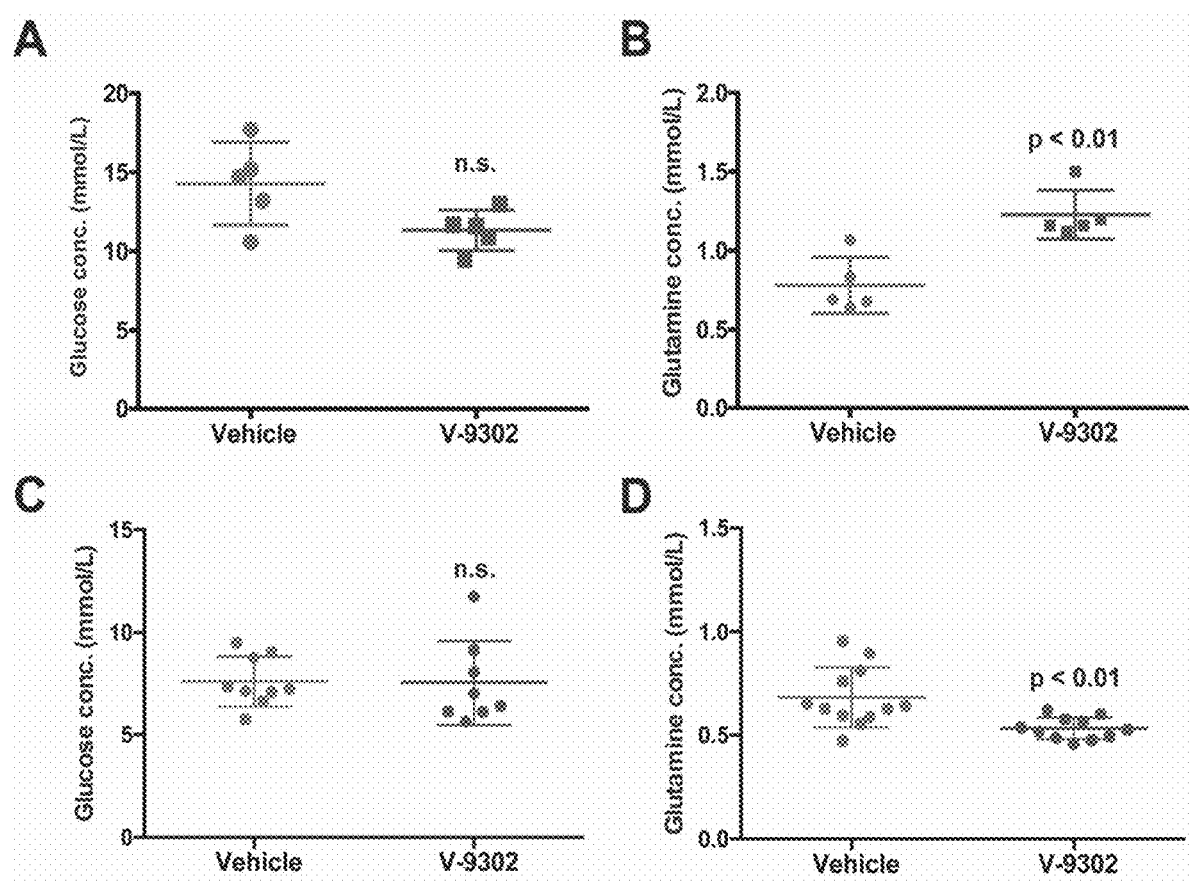
Figure 25:
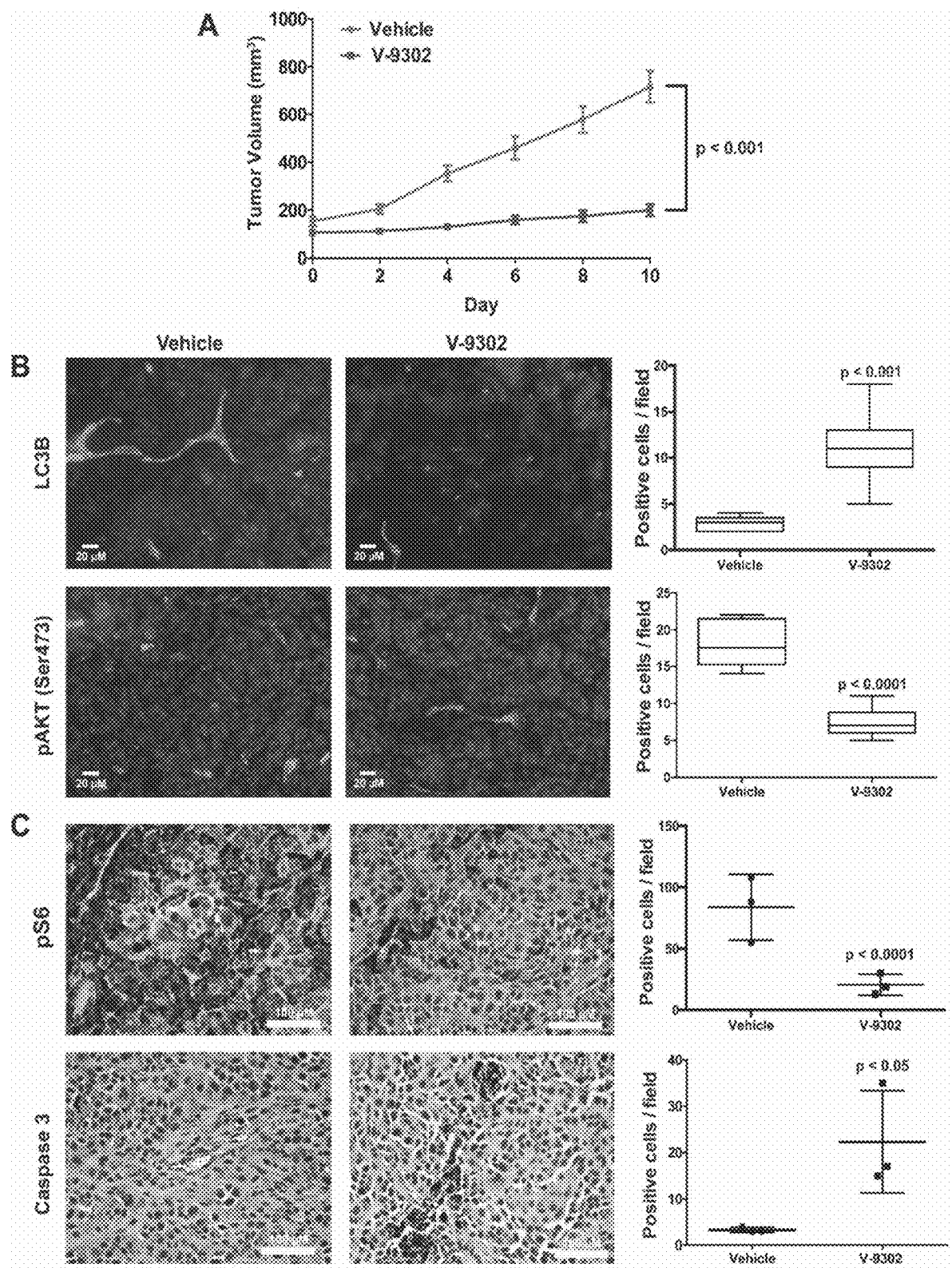
Figure 26:
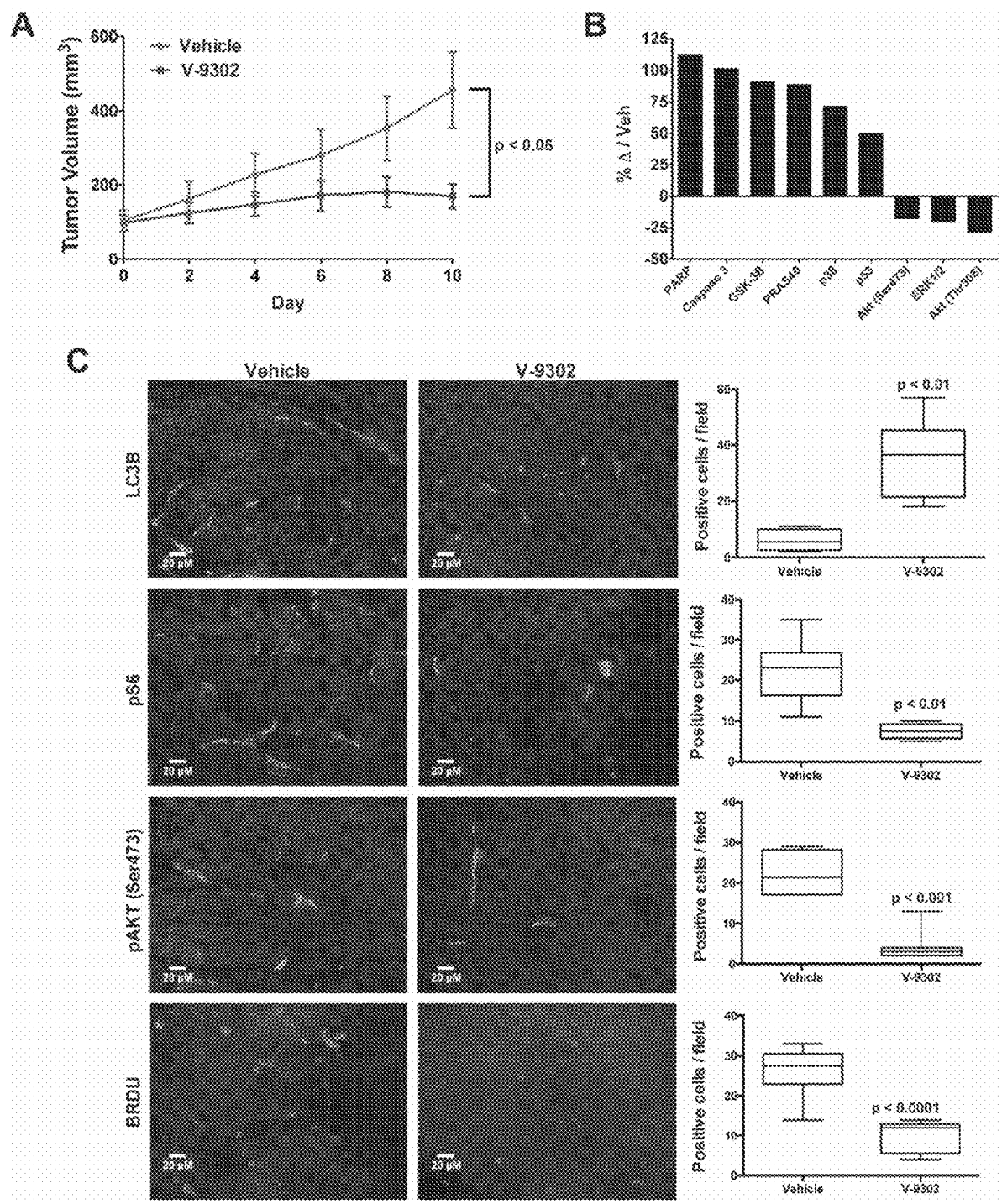

The present inventors next evaluated the performance of V-9302 in vivo, first establishing that steady-state plasma concentrations were achieved 4 h post-administration, with a half-life of approximately 6 h in healthy mice (FIG. 23). The effects of acute and chronic V-9302 exposure on plasma levels of glucose and glutamine were also evaluated in healthy mice. Following a single acute V-9302 exposure (4 h), plasma glucose levels were not significantly different than vehicle controls, yet plasma glutamine levels were elevated by approximately 50% in V-9302-treated mice compared to vehicle controls, likely a pharmacodynamic effect (FIG. 24A/B). Plasma glucose levels in mice chronically exposed to V-9302 or vehicle over a 21-day regimen were not significantly different, while plasma glutamine levels were slightly decreased (FIG. 24C/D). To evaluate the effect of V-9302 on glutamine levels in tumors, the present inventors employed non-invasive PET imaging using [$^{18}$F]-4F-glutamine$^5$. Following a single dose of V-9302 (75 mg/kg, 4 h), [$^{18}$F]-4F-glutamine uptake in tumors was reduced by approximately 50% to levels below background uptake in healthy muscle (FIG. 7A-C). Unlike tumors, [$^{18}$F]-4F-glutamine uptake in muscle was unaffected by V-9302 exposure (FIG. 7C), while [$^{18}$F]-4F-glutamine uptake in liver was modestly elevated (p=0.05) following V-9302. The present inventors next carried out chronic exposure studies in tumor-bearing mice. Athymic nude mice bearing HCT-116 (KRAS$^{G13D}$) or HT29 (BRAF$^{V600E}$) cell-line xenografts were treated with 75 mg/kg per day V-9302 for 21 days. Over the treatment course, V-9302 prevented tumor growth compared to vehicle controls in both HCT-116 (FIG. 7D) and HT29 (FIG. 7F) xenograft models. Consistent with in vitro mechanistic studies, V-9302 led to significantly decreased pS6 in tumor tissue in both HCT-116 (FIG. 7E) and HT29 xenografts (FIG. 7G). In addition to decreased pS6 IHC, V-9302 treatment led to elevated levels of cleaved caspase 3 in both HCT-116 (FIG. 7E) and HT29 xenografts (FIG. 7G). To evaluate V-9302 in a more clinically relevant model, the present inventors conducted a similar chronic exposure study in mice bearing a patient-derived xenograft (PDX) tumor (A-008, KRAS$^{G12V}$; p53$^{R248Q}$; PTEN$^{L140Y}$). Over the treatment course, V-9302 exposure led to a reduction in tumor volume compared to vehicle controls (FIG. 7H/I). To further elaborate in vivo determinants of response to V-9302, the present inventors carried out a 10-day exposure studies in aythumic nude mice bearing HCC1806 or Colo-205 xenografts (FIGS. 25 and 26). Both models exhibited V-9302-dependent tumor growth arrest analogous to that observed in HCT-116 and HT29 xenografts. Response to V-9302 in HCC1806 xenografts was characterized by elevated LC3B and cleaved caspase 3, along with decreased pAKT (Ser473) and pS6 (FIG. 25). Similarly, in Colo-205 xenografts, V9302 treatment led to elevated LC3B, cleaved caspase 3 and decreased pAKT (Ser473 and Thr308), as well as increased cleaved PARP and decreased and pERK (FIG. 26). Additional insights into V-9302-mediated response in Colo-205 xenografts included decreased tumor BRDU uptake, as well as elevated pGSK3B, pPRAS40, p38, and p53. Over the course of chronic exposure studies, no significant weight loss was observed in V-9302-treated cohorts compared to vehicle-treated controls (FIG. 27). Additionally, liver pathology was similar among mice chronically treated with V-9302 or vehicle control (FIG. 28).

To evaluate the in vivo effects of V-9302 on tumors globally, the present inventors carried out an unbiased metabolomic analysis of HT29 xenografts following 21 consecutive days of V-9302 exposure or vehicle treatment. A total of 782 metabolites of known identity that span 50 distinct metabolic pathways were quantitatively evaluated by LC/MS. Notably, V-9302 exposure significantly (P<0.05) impacted 239 metabolites that spanned seven metabolic categories (FIG. 8A), each attributable to various aspects of ASCT2 transport and glutamine metabolism. Certain metabolites impacted by V-9302 treatment were directly downstream of ASCT2 transport, such as N-acetylserine, which was reduced in V-9302-treated tumors by greater than 4-fold. Evidence of impacting ATP by V-9302 included significantly reduced creatine-phosphate levels in treated tumors. Confirming earlier in vitro studies that identified oxidative stress as a key impact of V-9302 treatment, oxidized glutathione (GSSG) and 4-hydroxy-nonenal-glutathione were significantly elevated. Other families of metabolites were elevated that appeared to indicate a compensatory metabolic shift to glucose metabolism, including various nucleotide sugars, aminosugars, and metabolites within the pentose phosphate pathway. Several metabolites impacted by V-9302 treatment were related to membrane biosynthesis and integrity. Numerous phospholipids, phosphatidylethanolamines, ceramides, and cholesterol metabolites were modulated by V-9302 exposure, which are largely consistent with an autophagic fingerprint.

The diversity of metabolic pathways upon which cancer cells are reliant represent key opportunities for drug development and precision medicine. It is well-recognized that energy production in cancer cells is uniquely dependent upon specific nutrients such as glucose and glutamine. Despite evidence illuminating the prominent role of glutamine in cancer cell growth and homeostasis, thus far, few efforts have resulted in therapies capable of effectively antagonizing glutaminolysis.

Mitochondrial glutaminase (GLS1), the enzyme responsible for catalyzing the conversion of glutamine to glutamate, represents a potentially promising target. Glutaminase is elevated in many tumors and tends to be associated with high-grade lesions. Studies evaluating genetic silencing of GLS1 activity encouraged the development of GLS1 inhibitors. One compound, CB-839 (Calithera Biosciences, San Francisco, Calif.), is a selective GLS1 inhibitor now being explored clinically in multiple solid and liquid tumors.

The present inventors discovered that blocking cellular glutamine transport would impart a greater impact on glutamine metabolism in cancer cells compared with targeting downstream enzyme activity (e.g., GLS1), particularly given the extensive biological plasticity leveraged by cancer cells to maintain intracellular glutamate pools. Compounds of the present invention, including V-9302 are distinct from investigational therapies targeting glutamine metabolism as it is designed to abrogate all facets of glutamine signaling and metabolism downstream of ASCT2-mediated import. This differs dramatically from glutaminase inhibitors, which largely overlook the role of glutamine on MAPK signaling, the activity of GLS2, and the activity of amino acid transporters that require glutamine antiport for their function (e.g., LAT1). Specifically antagonizing ASCT2, compounds of the present invention, including V-9302, also are distinguished in that they have the ability to block ASCT2-mediated transport of additional neutral amino acids beyond glutamine (FIG. 8). Not being bound by theory or mechanism, it cannot be ruled out that the observed efficacy in vivo may be due, in part, to combinatorial blockade of multiple ASCT2 substrates. While the present inventors observed that glutamine withdrawal or combinatorial ASCT2-substrate withdrawal had essentially indistinguishable effects on cell viability in V-9302-sensitive cancer cells, combinatorial depletion of ASCT2 substrates led to enhanced cell death in a portion of the cell lines evaluated. Collectively, these factors may, at least in part explain the difference in efficacy between V-9302 and CB-839 observed in this study. Embodiments of the present invention also exhibit unique qualities compared with another reported inhibitor of glutamine uptake, GPNA. Previously reported as an ASCT2 inhibitor, GPNA exhibits poor potency and selectivity in human cells.

The present inventors identified several molecular determinants associated with response to V-9302; many of these affect facets of cancer cell growth and proliferation, cell death, and oxidative stress (FIG. 8B). In multiple models, V-9302 exposure resulted in decreased mTOR activity as assessed by pS6 and pAKT (Ser473) levels, which is consistent with diminished amino acid transport and metabolism. Indeed, the present inventors found that mice treated chronically with V-9302 exhibited decreased plasma glutamine levels, which suggests, in part, diminished exchange via LAT1. In support of this, mTOR activity following V-9302 appeared decreased in all models evaluated. In spite of this, the present inventors observed elevated pPRAS40 levels in V-9302-treated Colo-205 xenografts, suggesting pro-survival cap-dependent translation. Although AKT is known to be a major regulator of PRAS40 phosphorylation, data presented here point to AKT-independent PRAS40 regulation, perhaps through PIM1 kinase. Interestingly, the observed increase in pGSK-30 in Colo-205 xenografts following V-9302 treatment could also be explained by PIM1 activity, suggesting potential synergy between V-9302 and an inhibitor of PIM1 kinase. Data stemming from global metabolomic analysis was also consistent with impaired amino acid transport in V-9302-treated tumors, with significant impacts on metabolites related to the ASCT2 substrates, glutamine and serine. Given the anaplerotic nature of glutamine, it was not surprising that metabolites related to ATP production were diminished in V-9302-treated tumors. Potentially related to an extra-mitochondrial role of glutamine, the present inventors consistently observed that V-9302 exposure led to diminished pERK levels in tumor cells in vitro and in vivo. While V-9302 treatment did not fully abolish pERK levels, it was intriguing to observe that V-9302-treated Colo-205 xenografts exhibited both decreased pERK and decreased BRDU incorporation, suggesting diminished proliferation. Indeed, prior studies have shown that glutamine can activate MAPK signaling independently of EGFR ligand activation, suggesting that glutamine deprivation as shown here may exert anti-proliferative effects.

Elevated autophagy was another notable characteristic of V-9302-mediated response in vitro and in vivo. Likely a pro-survival response to substrate starvation, combining V-9302 with an autophagy inhibitor further decreased the viability of V-9302-sensitive cells, potentially illuminating a future combination strategy. In addition to autophagy, significantly elevated apoptosis was frequently observed in V-9302-treated tumors.

A third feature of response to V-9302 was elevated oxidative stress. Frequently derived from glutamine, glutathione is a key modulator of oxidative stress. The present inventors observed that V-9302 impacted the redox state of glutathione in multiple models, leading to correspondingly increased levels of ROS. Additional markers elevated in V-9302-treated Colo-205 xenografts attributable to oxidative stress included elevated cleaved PARP, p38, and p53.

In summary, the present inventors report the first pharmacological inhibitors of the glutamine transporter, ASCT2. These results illustrate the promising nature of the lead compound, V-9302, but also that the concept of antagonizing glutamine metabolism at the transporter level represents a potentially viable approach in precision cancer medicine. Pairing patients with glutamine-dependent tumors and this novel class of inhibitors will require validated biomarkers. Since the expression of a transporter alone does not necessarily correlate with its activity, the present inventors were not surprised that the response to V-9302 did not correlate with tumor levels of ASCT2. Furthermore, larger studies are needed to evaluate correlates of V-9302 response and oncogene status. However, the present inventors did note that tumor cells sensitive to V-9302 were also sensitive to glutamine withdrawal, as well as ASCT2 substrate withdrawal, suggesting that response to V-9302 is likely a function of transporter activity and a tumors reliance upon thereof. Furthermore, given that combining V-9302 with an inhibitor of autophagy resulted in a greater impact on cell viability, it can not be ruled out that sensitivity to V-9302 may be predicated by a cancer cell's ability to use autophagy as a means to rescue the ASCT2-substrate-deprived phenotype. Importantly, the activity of ASCT2 can be quantitatively assessed using non-invasive PET imaging of glutamine uptake, which may represent a translational biomarker reflective of tumors likely to respond to V-9302 and similar agents.

Methods

General Methods/Reagents and Supplies

All reagents and supplies were obtained from commercial suppliers and in some cases further purified, on an as needed basis. Analytical thin-layer chromatography (TLC) was performed on silica gel plates from Sorbent Technologies with direct visualization via UV light, and/or the use of ninhydrin or potassium permanganate staining. Chromatographic purification of intermediates was performed using silica or C-18 RediSep Rf flash columns on a CombiFlash Rf automated chromatography system. All $^1$H and $^{13}$C NMR spectra were recorded on a Bruker AV-400 (400 mHz and 100 MHz respectively). All $^1$H and $^{13}$C chemical shifts were reported in ppm relative to residual solvent peaks. CB-839 was obtained from Calithera Biosciences. Immortalized cell lines were purchased from commercial vendors (ATCC) authenticated using a commercial vendor (Genetica). Animals were purchased from Harlan and used in accordance with Institutional and Federal guidelines. Human CRC organoids were obtained from patients enrolled in a clinical trial at Vanderbilt University Medical Center in accordance with an IRB approved protocol. For all statistical comparisons, the variance between groups being compared was similar.

Synthesis of V-9302

V-9302 was prepared as previously described[13]. For this study, V-9302 was purified by reverse phase (C-18) column chromatography (10-90% acetonitrile in water gradient over 60 min) giving a final yield up to 72% over two steps. 1H-NMR (400 MHz, CDCl3) δ (ppm): 7.23 (d, J=7.36 Hz, 2H), 7.20-7.15 (m, 4H), 7.10-7.06 (m, 6H), 6.89-6.82 (m, 2H), 5.06-4.97 (m, 4H), 3.81 (d, J=12.92 Hz, 2H), 3.64 (d, J=12.88 Hz, 2H), 3.00 (dd, J=7.38 Hz, 4.90 Hz, 1H), 2.75 (s, 2H), 2.29 (s, 6H), 2.01-1.90 (m, 1H), 1.90-1.77 (m, 1H). 13C-NMR (100 MHz, CDCl3) δ (ppm): 172.66 156.91, 138.04, 136.86, 131.82, 129.14, 128.53, 128.42, 128.15, 124.53, 120.91, 112.38, 70.07, 55.75, 52.70, 52.11, 26.51, 21.34. HRMS (TOF, ES+) $C_{34}H_{38}N_2O_4$ [M+H]+ calc. mass 539.2904, found 539.2891.

General Procedure for $^3$H-Amino Acid Uptake Assays

Live-cell amino acid uptake assays using HEK293 cells were carried out in 96-well plates (CulturPlate-96, Perkin Elmer). 96-well plates were coated with poly-D-lysine prior to the assay. Cells were plated at a density of 35,000 cells per well 24 h prior to carrying out the assay. Each set of conditions was replicated at least three times, technically and biologically. Cells were washed three times with 100 µL of assay buffer (containing 137 mM NaCl, 5.1 mM KCl, 0.77 mM $KH_2PO_4$, 0.71 mM $MgSO_4.7H_2O$, 1.1 mM $CaCl_2$, 10 mM D-glucose, and 10 mM HEPES) to remove cell media. $^3$H-amino acid (500 nM) in the same buffer was added concomitantly with V-9302 and allowed to incubate for 15 min at 37° C. For ASCT2-mediated $^3$H-glutamine uptake assays, 5 mM of the system-L inhibitor 2-amino-2-norbornanecarboxylic acid (BCH) was added and the assay buffer was adjusted to pH 6.0. For selectivity studies, no BCH was added and the assay was conducted at pH 7.4.

Following the incubation period, the $^3$H-glutamine/inhibitor was removed and the cells were washed three times with assay buffer. The cells were then lysed by the addition of 50 µL of 1 M NaOH. For reading, 150 µL of scintillation fluid (Microscint 40, Perkin Elmer) was added and the plates were counted on a scintillation counter (Topcount, Perkin Elmer). Fifty percent inhibitory concentrations ($IC_{50}$) were calculated using GraphPad Prism version 6 for Mac OS X, GraphPad Software, San Diego Calif. USA, www.graphpad.com. Error is reported as standard deviation (SD).

Procedure for in Silico Docking Studies of V-9302

A model of an inhibitor-bound conformation of hASCT2 was used as a target for ligand docking of V-9302. Two-dimensional structures for all ligands were generated in ChemDraw and imported into Tripos Sybyl for conversion into three-dimensional structures using CONCORD and docking using RosettaLigand. Figures for docked complexes were generated and ray-traced using PyMol (The PyMOL Molecular Graphics System, Version 1.5.0.4, Schrodinger, LLC.). In addition, fragment constraints were utilized to encourage placement of the amino acid analog main chain atoms in a location analogous to the positions that were experimentally determined for (2S,3S)-3-[3-[4-(trifluoromethyl)benzoyl amino]-benzyloxy]aspartate (TFB-TBOA) in its co-crystal structure within the homologous human excitatory amino acid transporter 1 (hEAAT1, PDB: 5MJU) transporter protein Seeding the docking calculations in this way yielded better-scoring docking poses using the empirically derived scoring function, suggesting that this feature of the binding interaction may be conserved between these two systems.

For comparative studies of ASCT2 and LAT1, predictive structures used for docking were generated using homology modeling. To determine suitable template structures, the primary sequence of ASCT2 was extracted from gene SLC1A5 (UniProtKB: Q15758). Using the PDB Search tool within MOE (Molecular Operating Environment, Version 2014.09, Chemical Computing Group), ASCT2 alignments were generated with the crystal structure of hEAAT1, (PDB: 5MJU). The primary sequence of LAT1 used to determine predictive structures was extracted from gene SLC7A5 (UniProtKB: Q01650). LAT1 homology models structures were generated from crystal structures of the Arg+ bound conformation of *Escherichia coli* AdiC and the ApcT transporter derived from *Methanocaldococcus jannaschii* (PDB IDs: 3L1L and 3GIA, respectively.) Using the templates and respective sequence alignments, MOE's homology model application generated initial structures with a well-conserved binding pocket. All resulting ASCT2 and LAT1 structures underwent energy minimization using Amber12 force field potentials and protonation. In order to mimic the lipid bilayer environments of ASCT2 and LAT1, homology models were embedded and relaxed into the membrane using the RosettaMP framework. Upon further refinement, top scoring models of both ASCT2 and LAT1 were used for docking simulations of V-9302 and additional ligands according to the RosettaLigand protocol. Ligand rotational conformer libraries were generated using energy minimization in MMFF94x force field potentials then screened using the MOE conformer search tool. The binding site was identified using prior knowledge of homology binding sites and Surflex-Dock results. Each simulation consisted of 500 iterations while scoring the protein-ligand interface energies. Final models were sorted based on interface_delta_X scores while evidence regarding steric hindrance penalties was extracted based on if_X_fa_rep energies.

In Silico Alanine Scan

Docking studies were performed to place V-9302 into the amino-acid binding site of an ASCT2 homology model. The highest-scoring poses were found when the constraints were enabled, to favor poses that anchored the amino acid moiety of the ligands to a similar binding orientation as TFB-TBOA in the structure of the homologous protein hEAAT1. In-silico mutagenesis experiments were conducted by individually changing side chains to alanine, without otherwise changing the conformation of the protein or ligand in ROSETTA. RosettaLigand was then used to re-score the same V-9302 docking pose with each of these Ala mutants. The docking score for each mutant was then compared with the score for the WT model to assess the WT sidechain contribution to the overall score in this binding pose.

Generation of HEK293 Cells with Tetracycline-Inducible ASCT2 Expression

T-REx™-293 cells (Invitrogen R71007) were transfected with the plasmid pCDNA5-TO-h-SLC1A5 (Invitrogen V1033-20). The cloning sites consisted of Not1 and Xba; insert OriGene # SC 116600. Stably transfected clones were selected via hygromycin (150 µg/ml).

Drug Affinity Responsive Target Stability (DARTS) Assay

DARTS was carried out as previously described[15] using T-REx-293 cells with tetracycline-inducible expression of ASCT2 or lysate from 115 mg of homogenized mouse brain for ASCT1. Lysates were exposed to V-9302 at varying concentrations for 35-45 min at room temperature with shaking. Lysates were then incubated at room temperature with the protease Thermolysin (1:100 and 1:200 total enzyme to total substrate) for 30 min. ASCT2 was measured by immunoblotting (ASCT2 antibody: Millipore ABN73; ASCT1 antibody: Cell Signaling 8442).

shRNA

HCC1806 cells were transfected with a lentiviral vector (pLKO.1) containing control shRNA (Sigma SHC002V) or shRNA against ASCT2 (Sigma SHCLNV-NM_005628): 5'-CCGGCTGGATTATGAGGAATGGATACTCGAG-TATCCATTCCTCATAATCCAGTTT TTG-3'. ASCT2 expression was measured by immunoblotting (ASCT2 antibody: Millipore ABN73) at 72 h post transduction and after puromycin selection.

Cell Viability Screens

Viability was evaluated using a commercially available chemiluminescent reagents (CellTiter-Glo, Promega Corp. G7572; MultiTox Glo, Promega Corp. G9270) in 96-well plate format according to the manufacturers protocol. Cells were exposed to either vehicle, V-9302, CB-839, V-9302+chloroquine (CLQ), or CB-839+CLQ and incubated for a period of 48 h. Subsequently, CellTiter-Glo reagent was added and the plates were read using a plate reader (BioTek Synergy 4) with standard settings. Each set of conditions was replicated at least three times, technically and biologically. Error is reported as standard deviation (SD). The sulforhodamine B assay was run analogously to the above assays as previously described[19].

Measurement of Glutathione and Reactive Oxygen Species (ROS)

Glutathione levels were measured using a commercially available kit (Cayman Chemical 703002) according to the manufacturers protocol. Concurrently ROS was measured in cells using CM-H2DCFDA (Life Technologies C6827) coupled with flow cytometry in accordance with the manufacturers protocol. The assay was replicated replicated at least three times, technically and biologically. Significance was calculated using a t-test in Graphpad Prism. Error is reported as standard deviation (SD).

Measurement of pERK

Detection of activated ERK in cell lysates was enabled by the AlphaScreen SureFire ERK assay (Perkin Elmer) according to the manufacturers protocol. Cells were plated in 96-well plates for 24 hours prior to the assay. Cells were treated with either vehicle or indicated concentrations of V-9302 or CB-839 for 48 hours.

Measurement of Autophagic Flux

Autophagic flux was measure using the CYTO-ID autophagy detection kit (Enzo Life Sciences ENZ-51031). HCC1806 and HT29 cells were seeded in 96 well plates the day before the experiment. After overnight incubation, cells were treated with V-9302, CB-839, 500 nM rapamycin as a positive control, or the combinations thereof with 10 uM chloroquine for 18 hours. Following treatment, cells were gently washed with assay buffer followed by addition of the dual color detection solution and incubation at 37° C. for 30 min. The plate was analyzed on a fluorescence microplane reader (BioTek Synergy 4).

Immunoassays

For immunoreactivity studies, tissue samples were diluted to 100 mg/mL in lysis buffer (#7018s, Cell Signaling Technology) and subsequently homogenized, sonicated, and spun at 3.5K RPM for 1 min. Lysate samples were then screened against an array of target-specific capture antibodies using PathScan Intracellular Signaling Array Kits (#7323, Cell Signaling Technology) in accordance with the manufacturer's instructions and developed using HyBlot CL autoradiography film (# e3012, Denville Scientific Inc.). Processed films were digitized using an Epson Perfection V600 Photo scanner and the relative pixel intensities for each blot quantified using the image processing software ImageJ. Complementary western blot studies were performed by loading 20-40 µg of protein into 7.5-12% SDS PAGE gels, transferred to PVDF membranes (PerkinElmer), and resolved by electrophoresis. Membranes were blocked overnight at 4° C. in trisbuffered saline 0.1% Tween-20 (TBST) containing 5% w/v nonfat dry milk powder and subsequently incubated with antibodies to p-ERK 1/2 Thr202/Tyr204 (Cell Signaling, 4370), pS6 (Cell Signaling, #4858) LC3B, (anti LC3B, Cell signaling 2775), or b-tubulin (Novus Biologicals, NB600-936); Membrane chemiluminescence was imaged on a Xenogen IVIS 200 system.

Immunofluorescence

HCC1806 cells were treated V-9302 (25 µM aqueous, 1% DMSO) for 48 h. Following treatment, cells were fixed with 70% methanol for 5-10 min. LC3B was visualized with 1:100 primary antibody (anti LC3B, Cell signaling 2775) at 37° C. for 45 min followed by application of 1:600 secondary antibody (Rhodamine Red, Invitrogen R6394) at 37° C. for 30 min and DAPI for 4 min. Images were acquired with a fluorescence microscope at visualized at 40× magnification.

In Vivo BrdU Incorporation Assay

Four hours after the final treatment the mice were injected with bromodeoxyuridine (BrdU) labeling reagent (Zymed Laboratories, South San Francisco, Calif.). Six hours after injection mice were killed. The tumors were harvested, fixed in paraffin, and sectioned. Slides were stained with anti-BrdU primary antibody (mouse IgG) followed by rhodamine red-labeled goat anti-mouse secondary antibody (Invitrogen Molecular Probes, Carlsbad, Calif.). Sections were counter-stained with the nucleophilic dye 4',6-diamidino-2-phenylindole (DAPI). Photographs were obtained, scanned into Photoshop software, and quantified. The mean and standard error of BrdU incorporating cells were determined (n=3). To quantify endothelial cell proliferation in vivo, high-power photographs were taken. The endothelial cells surrounding blood vessels were confirmed by two separate observers and quantified for each treatment condition as stated above (n=6).

Immunohistochemistry (IHC)

For IHC, animals were sacrificed and tumor tissue samples were collected within 4 h of the final V-9302 dose, fixed in 10% formalin for 24 h then stored in 70% EtOH/PBS. Tissues were sectioned (5 µm thickness) and stained for pS6 (Cell Signaling, #4858) and caspase 3 (Cell Signaling #9661). Tissue slides were imaged at 20× magnification.

Fluorescence Redox Ratio Imaging

HCC1806 cells were plated on 35-mm glass-bottom petri dishes for imaging (MatTek Corp). Fluorescence intensity and lifetime images were acquired using a custom-built multiphoton fluorescence lifetime system (Bruker), with a 40× oil-immersion objective (1.3 NA) and an inverted microscope (TiE, Nikon). A titanium:sapphire laser (Chameleon Ultra II, Coherent) was tuned to 750 nm for two-photon excitation of NAD(P)H and tuned to 890 nm for two-photon excitation of FAD. A 440/80 nm bandpass filter was used to collect NAD(P)H fluorescence emission, and a 550/100 nm was used to collect FAD emission. A pixel dwell time of 4.8 µs was used to collect images that were 256×256 pixels, with a total integration time of 60 seconds. A GaAsP PMT (H7422P-40, Hamamatsu) detected emitted photons. The field of view acquired was 270 µm×270 µm, and 6 fields of view were acquired per treatment group. Time-correlated single photon counting electronics (SPC-150, Becker and Hickl) were used to acquire fluorescence decay curves. The second harmonic generated signal from urea crystals at 900 nm excitation was used to measure the instrument response function, which was found to have a full width at half maximum of 220 ps. Fluorescence lifetime validation was performed by imaging a fluorescent bead (Polysciences Inc) and confirming that the measured lifetime (2.1 ns) agreed with previously published values[22]. The assay was replicated at least three times, technically and biologically.

A histogram of photon counts per temporal bin (decay curve) was constructed for each pixel in the image and then deconvolved with the instrument response function. Decay curves were then fit to a two-component exponential decay to account for the distinct free and protein-bound lifetimes of NAD(P)H and FAD, using SPCImage software (Becker & Hickl). The decay fit is given by equation 1, where I(t) represents the fluorescence intensity measured at time t after the laser pulse, $\alpha_1$ and $\alpha_2$ represent the fractional contributions of the short and long lifetime components to the overall intensity, respectively, $\tau_1$ and $\tau_2$ represent the fluorescence lifetimes of the short and long lifetime components, respectively, and C $$I(t)=\alpha_1 \exp^{-t/\tau_1}+\alpha_2 \exp^{-t/\tau_2}+C \qquad \text{Eq}$$

represents a constant level of background light.

The mean lifetime ($\tau_m$) of NAD(P)H or FAD represents the weighted average of the $$\tau_m=\alpha_1*\tau_1+\alpha_2*\tau_2 \qquad \text{Eq}$$

short and long lifetime components (equation 2).

An automated cell segmentation routine was written using CellProfiler to identify individual cell cytoplasms and extract average fluorescence intensity and fluorescence lifetime values for each cell in the field of view. Intensity values for each pixel were calculated by integrating the decay curve for each pixel. Optical redox ratio values were calculated for each cell by dividing the average intensity of NAD(P)H by the average intensity of FAD. Optical redox ratio values were normalized to vehicle. For each imaging endpoint, values for all cells imaged in each treatment group were averaged together to generate mean and standard error values. An unpaired t-test with Welch's correction was performed for all comparisons of imaging values.

Organoid Culture and Viability Assay

Human CRC-derived organoids were prepared as reported method with modification[41]. Briefly, specimens from freshly resected tumors were minced and digested with 2 mg/ml type 2 collagenase (Worthington, N.J., USA). Samples were passed through 40 m filters (Greiner Bio One, NC, USA) and epithelial cells trapped on the filters were embed in Matrigel (Corning, MA, USA) and cultured with advanced DMEM/F12 supplemented with N2 and B27 supplements (Thermo Fischer, MA, USA), 50 ng/ml rhEGF (R&D systems, MN, USA) and 1% antibiotic-antimycotic (Corning). For viability assay, organoids were dissociated by TrypLE express (Thermo Fischer) and suspended in Matrigel. 5 µl of cell suspension in Matrigel drops were placed into non-treated 96 well plates (Corning) and overlaid with experimental medium, which consisted of either V-9302, CB-839, or vehicle at indicated concentration in advanced DMEM/F12 supplemented with N2 and B27 supplements, 1% antibiotic-antimycotic and 4 mM L-glutamine (GE Healthcare, OH, USA). After 4 days of culture, images of the organoids in Matrigel were captured and the number of viable cells were quantified with CellTiter Aqueous One Cell Proliferation Assay kit (Promega, WI, USA) and a Synergy 4 plate reader (BioTek, VT, USA). The assay was replicated at least three times, technically and biologically. Significance was calculated using a t-test in Graphpad Prism. Error is reported as standard deviation (SD).

V-9302 Plasma Stability Assay

Whole blood samples (n=5 mice) were assayed for V-9302 levels with time by Sano Informed Prescribing, Inc. (Franklin, Tenn.). Liquid chromatography-tandem mass spectroscopy (LC-MS/MS) analyses were performed via reverse phase chromatography using a Shimadzu Nexera X2 UPLC (Columbia, Md.) coupled with a QTrap® 5500 (Sciex, Framinghman, MA, USA). Standard curve and quality control samples were made by spiking V-9302 in fresh whole blood and then applying to 10 µL Mitra® Microsamplers (Neoteryx, LLC, Torrance, Calif.). Blank samples were made using fresh whole blood applied to Mitra® Microsamplers and allowed to dry for at least 24 h. All data were collected using Sciex Analyst 1.6.2 software and analyzed with MultiQuant 3.0 software. Error is reported as standard deviation (SD).

Plasma Metabolite Analysis

To quantify plasma glutamine and glucose, whole blood was collected from healthy mice (n=10) chronically exposed to V-9302 (75 mg/kg, daily) or vehicle with sacrifice 4 h after the final treatment. Following centrifugation, plasma was collected and 50 µL was added to a 96-well plate in triplicate. Plasma samples were diluted with 50 µL of assay buffer (YSI 2357) and glucose and glutamine were quantified directly using a YSI 2950D Biochemistry Analyzer (YSI Inc). Significance was calculated using a t-test in Graphpad Prism. Error is reported as standard deviation (SD).

CD8+Cell Studies:

CD8+ cells were isolated from the spleens of 8-12 week old C57BL6 mice on standard chow from Jackson Labs maintained under IACUC approved protocols. CD8+ cells were stained using the proliferative dye Cell Trace Violet (LifeTech) before stimulation as per manufacturer's protocol. Cells were stimulated on 5 ug/mL anti-CD3/CD28-coated plates in media containing IL-2 ('activated', 10 ng/mL), or in tissue-culture treated plates in media containing IL-7 ('naive', 1 ng/mL) for up to 7 days. Cells were removed at each day described for viability, cell counts, proliferation, and surface markers of activation. Cell surface markers used were CD62L-FITC and APC, CD44-PECy5 and CD25-PE. All data were acquired in triplicate on a MacsQuant Analyzer (Miltenyi Biotec) and analyzed using FlowJo V10 (TreeStar software).

Synthesis of 4-[$^8$F]-Fluoroglutamine

4-[$^{18}$F]fluoroglutamine and the requisite tosylate precursor were produced as reported[5].

PET Imaging and Analysis

Animal handling methods for PET imaging studies were conducted as reported[5,42] Prior to imaging, animals were allowed to acclimate to facility environment for at least 1 h in a warmed chamber at 31.5° C. Animals were administered 10.4-11.8 MBq 4-[$^{18}$F]fluoroglutamine via intravenous injection and imaged using a Concorde Microsystems Focus 220 microPET scanner (Siemens Preclinical Solutions). During imaging, animals were maintained under 2% isoflurane anesthesia in oxygen at 2 L/min and kept warm for the duration of the PET scan. PET images in xenograft-bearing mice were acquired as 60-minute dynamic data sets. Imaging was initiated three hours post-treatment following vehicle or V-9302 (75 mg/kg) administration. PET data were reconstructed using a three-dimensional (3D) ordered subset expectation maximization/maximum a posteriori (OSEM3D/MAP) algorithm. The resulting three-dimensional reconstructions had an x-y voxel size of 0.474 mm and inter-slice distance of 0.796 mm. ASIPro software (Siemens Preclinical Solutions) was used to manually draw 3D regions of interest (ROIs) surrounding the entire tumor volume. 4-[$^{18}$F]fluoroglutamine uptake was quantified as the percentage of the injected dose per gram of tissue (% ID/g). Significance was calculated using a t-test in Graphpad Prism. Error is reported as standard deviation (SD).

In Vivo Tumor Studies

For in vivo studies, cell-line xenograft tumors were propagated in 6-week old, female athymic nude mice from immortalized cell lines. For HCC-1806 ($10 \times 10^6$ cells), HCT-116 ($5 \times 10^6$), and HT29 ($10 \times 10^6$) cells were injected. Palpable tumors were typically visible within 2-3 weeks. For imaging studies (HCC-1806), tumors were propagated to approximately 500 mm$^3$. For treatment studies (HCT-116, HT29) tumors were propagated to approximately 200 mm$^3$ prior to therapy and were randomly assigned into treated and untreated cohorts. For generating the PDX, primary tumor tissue was obtained form a patient at Vanderbilt University Medical Center under an IRB approved protocol. The tumor tissue was genotyped within the VANTAGE core facility. Xenograft was generated as previously described 41. Briefly, tumor tissues were sectioned into approximately 125 cubic millimeter pieces then implanted subcutaneously without further manipulation. PDX tumors were propagated to the F3 generation for V-9302 treatment studies. For treatment, V-9302 was reconstituted in a vehicle of phosphate buffered saline supplemented with 2% DMSO and administered intraperitoneally. Tumor volumes were measured manually using calipers every third day and quantified using the formula V=W·L·(H/2).

Metabolomics

HT-29 (n=10) tumor samples were harvested and snap frozen within 4 h of the final dose of V-9302 or vehicle. Metabolomic data acquisition was outsourced to Metabolon, Inc. Samples were prepared using the automated MicroLab STAR® system from Hamilton Company. To remove protein, dissociate small molecules bound to protein or trapped in the precipitated protein matrix, and to recover chemically diverse metabolites, proteins were precipitated with methanol under vigorous shaking for 2 min (Glen Mills GenoGrinder 2000) followed by centrifugation. The resulting extract was divided into five fractions: two for analysis by two separate reverse phase (RP)/UPLC-MS/MS methods with positive ion mode electrospray ionization (ESI), one for analysis by RP/UPLC-MS/MS with negative ion mode ESI, one for analysis by HILIC/UPLC-MS/MS with negative ion mode ESI, and one sample was reserved for backup. Samples were placed briefly on a TurboVap® (Zymark) to remove the organic solvent. All methods utilized a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract was dried then reconstituted in solvents compatible to each of the four methods. Each reconstitution solvent contained a series of standards at fixed concentrations to ensure injection and chromatographic consistency. One aliquot was analyzed using acidic positive ion conditions, chromatographically optimized for more hydrophilic compounds. In this method, the extract was gradient eluted from a C18 column (Waters UPLC BEH C18-2.1×100 mm, 1.7 µm) using water and methanol, containing 0.05% perfluoropentanoic acid (PFPA) and 0.1% formic acid (FA). Another aliquot was also analyzed using acidic positive ion conditions, however it was chromatographically optimized for more hydrophobic compounds. In this method, the extract was gradient eluted from the same afore mentioned C18 column using methanol, acetonitrile, water, 0.05% PFPA and 0.01% FA and was operated at an overall higher organic content. Another aliquot was analyzed using basic negative ion optimized conditions using a separate dedicated C18 column. The basic extracts were gradient eluted from the column using methanol and water, however with 6.5 mM Ammonium Bicarbonate at pH 8. The fourth aliquot was analyzed via negative ionization following elution from a HILIC column (Waters UPLC BEH Amide 2.1×150 mm, 1.7 µm) using a gradient consisting of water and acetonitrile with 10 mM Ammonium Formate, pH 10.8. Raw data was extracted, peak-identified and QC processed using Metabolon's hardware and software. Compounds were identified by comparison to library entries of purified standards or recurrent unknown entities. Metabolon maintains a library based on authenticated standards that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library+/−10 ppm, and the MS/MS forward and reverse scores between the experimental data and authentic standards. The MS/MS scores are based on a comparison of the ions present in the experimental spectrum to the ions present in the library spectrum. Peaks were quantified using area-under-the-curve. For studies spanning multiple days, a data normalization step was performed to correct variation resulting from instrument inter-day tuning differences. For many studies, two types of statistical analysis are usually performed: significance tests and classification analysis. Standard statistical analyses are performed in ArrayStudio on log transformed data. For those analyses not standard in ArrayStudio, the programs R (http://cran.r-project.org) or JMP are used.

REFERENCES

Throughout this patent application, various publications are referenced. All such publications, including those listed below, are incorporated herein by reference.

1. Pochini, L., Scalise, M., Galluccio, M. & Indiveri, C. Membrane transporters for the special amino acid glutamine: structure/function relationships and relevance to human health. *Front Chem* 2, 61 (2014).
2. Jin, L., Alesi, G. N. & Kang, S. Glutaminolysis as a target for cancer therapy. *Oncogene* 35, 3619-3625 (2016).
3. Hassanein, M., et al. SLC1A5 mediates glutamine transport required for lung cancer cell growth and survival. *Clin Cancer Res* 19, 560-570 (2013).
4. van Geldermalsen, M., et al. ASCT2/SLC1A5 controls glutamine uptake and tumour growth in triple-negative basal-like breast cancer. *Oncogene* 35, 3201-3208 (2016).
5. Schulte, M. L., et al. Non-Invasive Glutamine PET Reflects Pharmacological Inhibition of BRAFV600E In Vivo. *Mol Imaging Biol* (2016).
6. Gao, P., et al. c-Myc suppression of miR-23a/b enhances mitochondrial glutaminase expression and glutamine metabolism. *Nature* 458, 762-765 (2009).
7. Watanabe, T., et al. Differential gene expression signatures between colorectal cancers with and without KRAS mutations: crosstalk between the KRAS pathway and other signalling pathways. *Eur J Cancer* 47, 1946-1954 (2011).
8. Shukla, K., et al. Design, synthesis, and pharmacological evaluation of bis-2-(5-phenylacetamido-1,2,4-thiadiazol-2-yl)ethyl sulfide 3 (BPTES) analogs as glutaminase inhibitors. *J Med Chem* 55, 10551-10563 (2012).
9. Harding, J. J., et al. Safety and tolerability of increasing doses of CB-839, a first-in-class, orally administered small molecule inhibitor of glutaminase, in solid tumors. *J Clin Oncol* 33(2015).
10. Rhoads, J. M., et al. Glutamine metabolism stimulates intestinal cell MAPKs by a cAMP-inhibitable, Raf-independent mechanism. *Gastroenterology* 118, 90-100 (2000).
11. Willems, L., et al. Inhibiting glutamine uptake represents an attractive new strategy for treating acute myeloid leukemia. *Blood* 122, 3521-3532 (2013).
12. Schulte, M. L., Khodadadi, A. B., Cuthbertson, M. L., Smith, J. A. & Manning, H. C. 2-Amino-4-bis(aryloxybenzyl)aminobutanoic acids: A novel scaffold for inhibition of ASCT2-mediated glutamine transport. *Bioorg Med Chem Lett* 26, 1044-1047 (2016).
13. Esslinger, C. S., Cybulski, K. A. & Rhoderick, J. F. N-gamma-Aryl glutamine analogues as probes of the ASCT2 neutral amino acid transporter binding site. *Bioorgan Med Chem* 13, 1111-1118 (2005).
14. Lomenick, B., et al. Target identification using drug affinity responsive target stability (DARTS). *Proc Natl Acad Sci USA* 106, 21984-21989 (2009).
15. Canul-Tec, J. C., et al. Structure and allosteric inhibition of excitatory amino acid transporter 1. *Nature* 544, 446-+ (2017).
16. Vichai, V. & Kirtikara, K. Sulforhodamine B colorimetric assay for cytotoxicity screening. *Nat Protoc* 1, 1112-1116 (2006).
17. Rathmell, J. C. T Cell Myc-tabolism. *Immunity* 35, 845-846 (2011).
18. Skala, M. & Ramanujam, N. Multiphoton redox ratio imaging for metabolic monitoring in vivo. *Methods Mol Biol* 594, 155-162 (2010).
19. Walsh, A. J., et al. Quantitative optical imaging of primary tumor organoid metabolism predicts drug response in breast cancer. *Cancer Res* 74, 5184-5194 (2014).
20. Deberardinis, R. J., Sayed, N., Ditsworth, D. & Thompson, C. B. Brick by brick: metabolism and tumor cell growth. *Curr Opin Genet Dev* 18, 54-61 (2008).
21. Hanover, J. A., Krause, M. W. & Love, D. C. The hexosamine signaling pathway: 0-GlcNAc cycling in feast or famine. *Biochim Biophys Acta* 1800, 80-95 (2010).
22. Obeid, L. M., Linardic, C. M., Karolak, L. A. & Hannun, Y. A. Programmed cell death induced by ceramide. *Science* 259, 1769-1771 (1993).
23. Tresse, E., Kosta, A., Giusti, C., Luciani, M. F. & Golstein, P. A UDP-glucose derivative is required for vacuolar autophagic cell death. *Autophagy* 4, 680-691 (2008).
24. Sentelle, R. D., et al. Ceramide targets autophagosomes to mitochondria and induces lethal mitophagy. *Nat Chem Biol* 8, 831-838 (2012).
25. Dall'Armi, C., Devereaux, K. A. & Di Paolo, G. The role of lipids in the control of autophagy. *Curr Biol* 23, R33-45 (2013).
26. Shatz, O., Holland, P., Elazar, Z. & Simonsen, A. Complex Relations Between Phospholipids, Autophagy, and Neutral Lipids. *Trends Biochem Sci* 41, 907-923 (2016).
27. Huang, F., Zhang, Q., Ma, H., Lv, Q. & Zhang, T. Expression of glutaminase is upregulated in colorectal cancer and of clinical significance. *Int J Clin Exp Pathol* 7, 1093-1100 (2014).
28. Xiang, Y., et al. Targeted inhibition of tumor-specific glutaminase diminishes cell-autonomous tumorigenesis. *J Clin Invest* 125, 2293-2306 (2015).
29. Seltzer, M. J., et al. Inhibition of glutaminase preferentially slows growth of glioma cells with mutant IDH1. *Cancer Res* 70, 8981-8987 (2010).
30. Gross, M. I., et al. Antitumor activity of the glutaminase inhibitor CB-839 in triple-negative breast cancer. *Mol Cancer Ther* 13, 890-901 (2014).
31. Suzuki, S., et al. Phosphate-activated glutaminase (GLS2), a p53-inducible regulator of glutamine metabolism and reactive oxygen species. *Proc Natl Acad Sci USA* 107, 7461-7466 (2010).
32. Nicklin, P., et al. Bidirectional transport of amino acids regulates mTOR and autophagy. *Cell* 136, 521-534 (2009).
33. Chiu, M., et al. GPNA inhibits the sodium-independent transport system L for neutral amino acids. *Amino Acids* 49, 1365-1372 (2017).
34. McKinley, E. T., Zhao, P., Coffey, R. J., Washington, M. K. & Manning, H. C. 3'-Deoxy-3'-[18F]-Fluorothymidine PET imaging reflects PI3K-mTOR-mediated pro-survival response to targeted therapy in colorectal cancer. *PLoS One* 9, e108193 (2014).
35. Wiza, C., Nascimento, E. B. & Ouwens, D. M. Role of PRAS40 in Akt and mTOR signaling in health and disease. *Am J Physiol Endocrinol Metab* 302, E1453-1460 (2012).
36. Santio, N. M., et al. The PIM1 kinase promotes prostate cancer cell migration and adhesion via multiple signalling pathways. *Exp Cell Res* 342, 113-124 (2016).
37. Rhoads, J. M., et al. L-glutamine stimulates intestinal cell proliferation and activates mitogen-activated protein kinases. *Am J Physiol* 272, G943-953 (1997).

38. Meiler, J. & Baker, D. ROSETTALIGAND: protein-small molecule docking with full side-chain flexibility. *Proteins* 65, 538-548 (2006).

39. Kondo, J., et al. Retaining cell-cell contact enables preparation and culture of spheroids composed of pure primary cancer cells from colorectal cancer. *Proc Natl Acad Sci USA* 108, 6235-6240 (2011).

40. McKinley, E. T., et al. 18FDG-PET predicts pharmacodynamic response to OSI-906, a dual IGF-1R/IR inhibitor, in preclinical mouse models of lung cancer. *Clin Cancer Res* 17, 3332-3340 (2011).

41. Schulte M L, Dawson E S, Saleh S A, Cuthbertson M L, Manning H C, "2-Substituted Nγ-glutamylanilides as novel probes of ASCT2 with improved potency", Bioorg Med Chem Lett., 2015 Jan. 1; 25(1):113-6. doi: 10.1016/j.bmcl.2014.10.098.

42. Jain, A. N. Surflex-Dock 2.1: Robust Performance from Ligand Energetic Modeling, Ring Flexibility, and Knowledge-Based Search, *J. Comput Aided Mol. Des.*, 21, 281-306 (2007).

43. Boudker, O., Ryan, R. M., Yernool, D., Shimamoto, K., Gouaux, E., "Crystal structure of GltPh in complex with TBOA", Nature 445: 387-393 (2007), PMID: 17230192, DOI: 10.1038/nature05455

44. Jain, A. N. Scoring noncovalent protein-ligand interactions: A continuous differentiable function tuned to compute binding affinities. J. Comput. Aided Mol. Des., 10, 427-40 (1996).

45. Dang, C. V. *Cancer Res.* 2010, 70, 859.

46. Dang, C. V.; Le, A.; Gao, P. *Clin. Cancer Res.* 2009, 15, 6479.

47. Gaglio, D.; Metallo, C. M.; Gameiro, P. A., et al. *Mol. Syst. Biol.* 2011, 7, 523.

48. Shimizu, K.; Kaira, K.; Yomizawa, Y.; Sunaga, N.; Kawashima, O.; Oriuchi, N.; Tominaga, H.; Nagamori, S.; Kanai, Y.; Yamada, M.; Oyama, T.; Takeyoshi, I. *Br. J. Cancer*, 2014, 110, 2030.

49. Witte, D.; Ali, N.; Carlson, N.; Younes, M. *Anticancer Res.* 2002, 22, 2555.

50. Kaira, K.; Sunrose, Y.; Arakawa, K.; Sunaga, N.; Shimizu, K.; Tominaga, H.; Oriuchi, N.; Nagamori, S.; Kanai, Y.; Oyama, T.; Takeyoshi, I. *Histopathology*, 2015, 66, 234.

51. Fuchs, B. C.; Perez, J. C.; Suetterlin, J. E.; Chaudhry, S. B.; Bode, B. P. Am. J. Physiol. Gastrointest. *Liver Physiol.* 2004, 286, G467.

52. Schulte, M. L.; Dawson, E. S.; Saleh, S. A.; Cuthbertson, M. L.; Manning, H. C. *Bioorg. Med. Chem. Lett.*, 2015, 25, 113.

53. Albers, T.; Marsiglia, W.; Thomas, T.; Gameiro, A.; Grewer, C. *Mol. Pharmacol.* 2012, 81, 356.

54. Oppedisano, F.; Catto, M.; Koutentis, P. A.; Nicolotti, O.; Pochini, L.; Koyioni, M.; Introcaso, A.; Michaelidou, S. S.; Carotti, A.; Indiveri *Toxicol. Appl. Pharmacol.* 2012, 265, 93-102.

55. Brown, J. M.; Hunihan, L.; Prack, M. M.; Harden, D. G.; Bronson, J.; Dzierba, C. D.; Gentles, R. G.; Hendricson, A.; Krause, R.; Macor, J. E.; Westphal, R. S. *J. Neurochem.* 2014, 129, 275.

We claim:

1. A compound of the following formula:

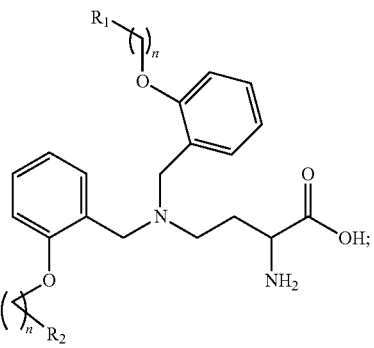

wherein:

$R_1$ is phenyl, substituted with at least one $R_3$; or pyridinyl, substituted with at least one $R_3$;

$R_2$ is phenyl, substituted with at least one $R_3$; or pyridinyl, substituted with at least one $R_3$;

each $R_3$ is independently H, alkyl, alkoxy, halogen, or $CF_3$; and n is 0, 1, 2, 3, 4, 5, or 6;

or a pharmaceutically acceptable salt thereof.

2. The compound of claim 1, of the following formula:

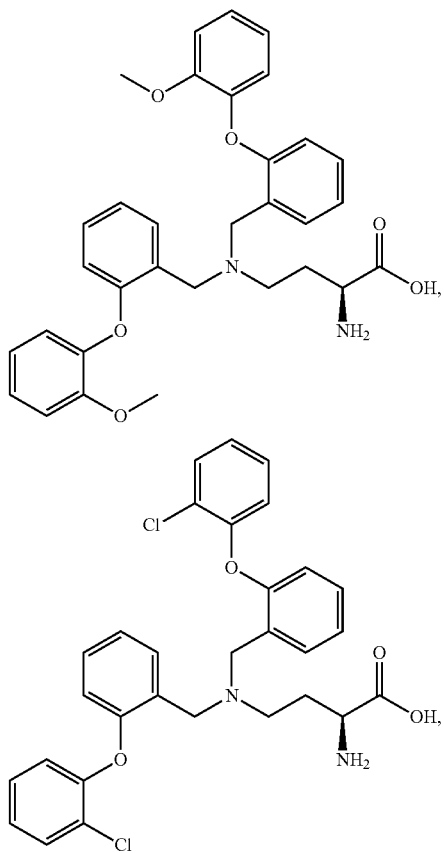

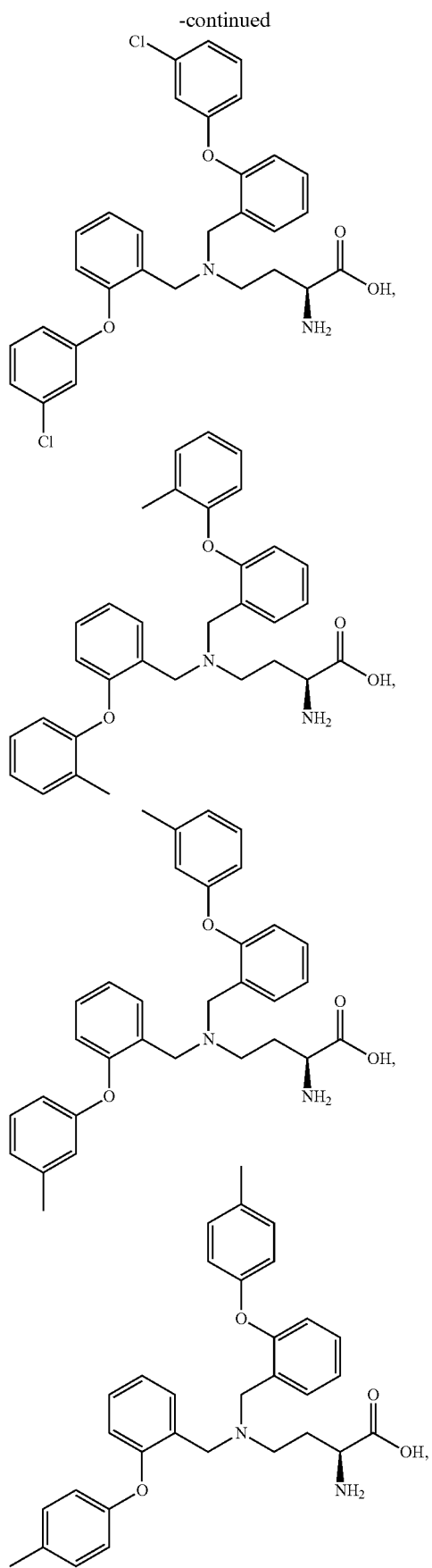
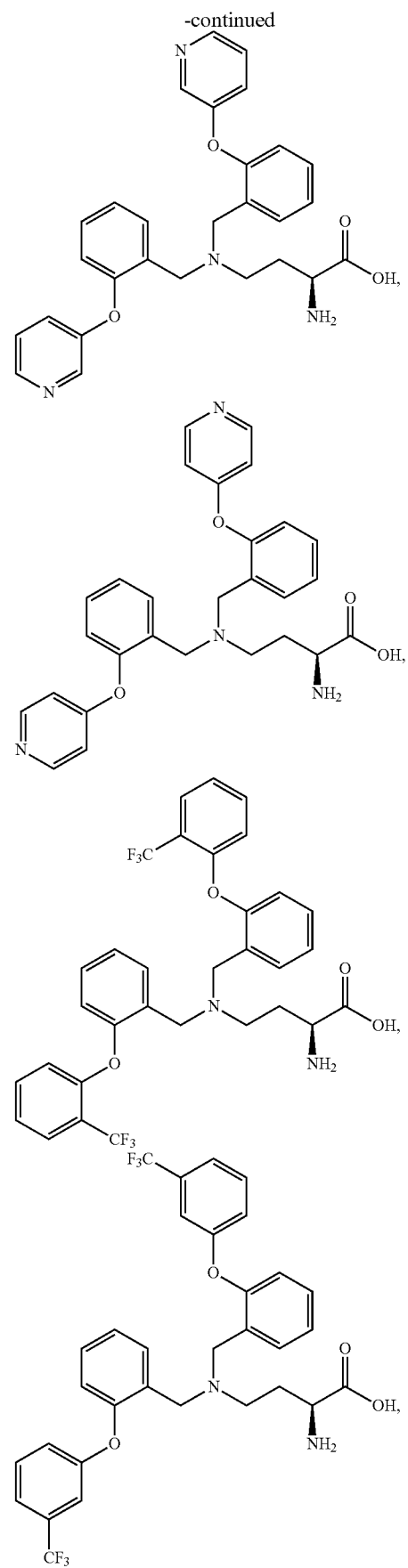

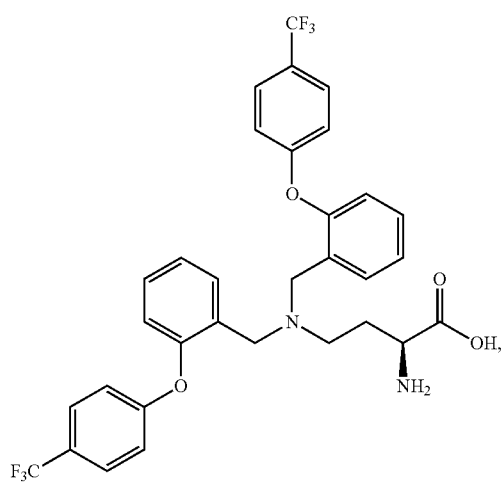
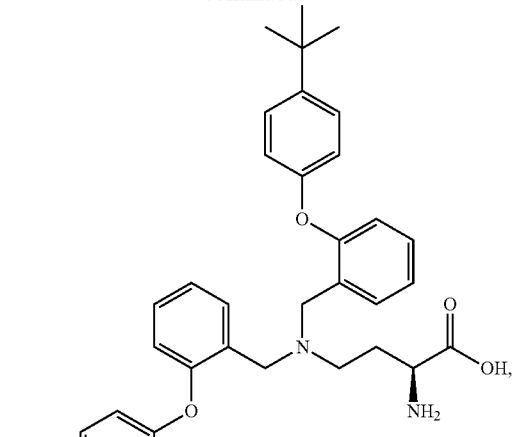
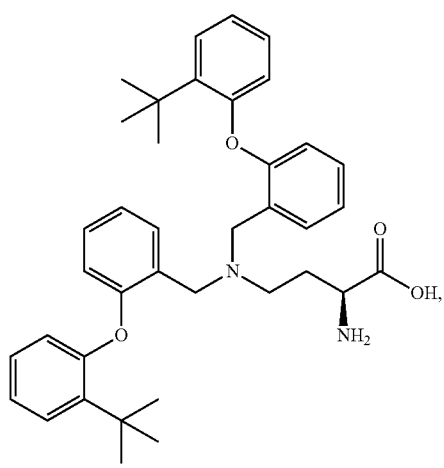
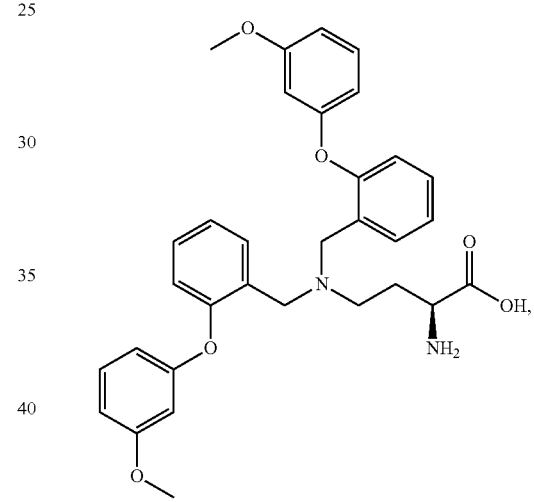
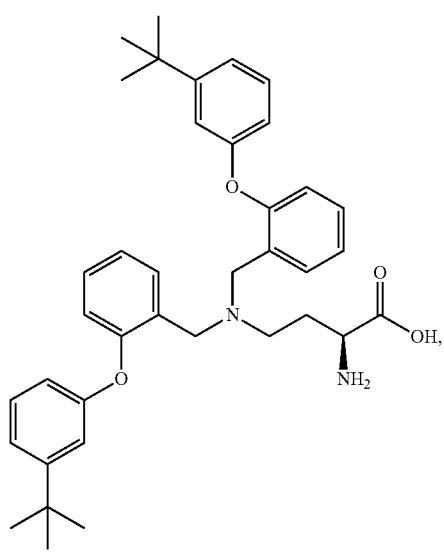
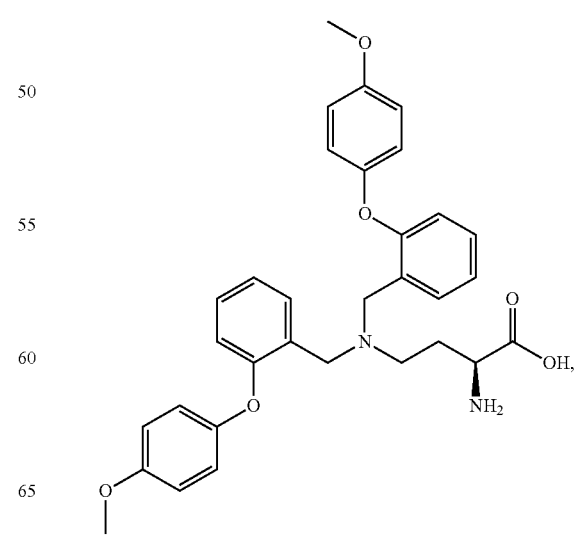

175
-continued
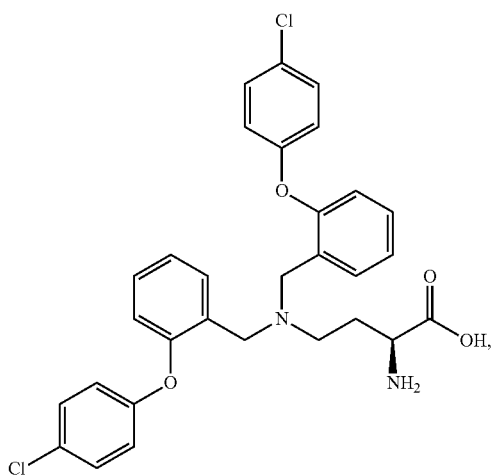
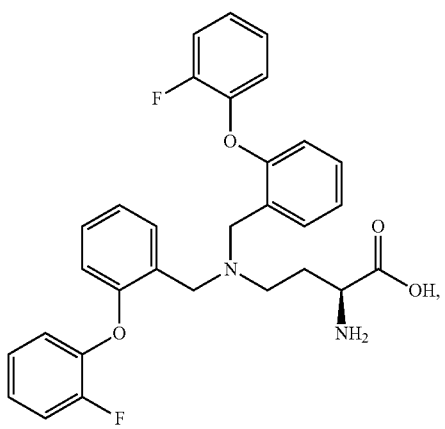
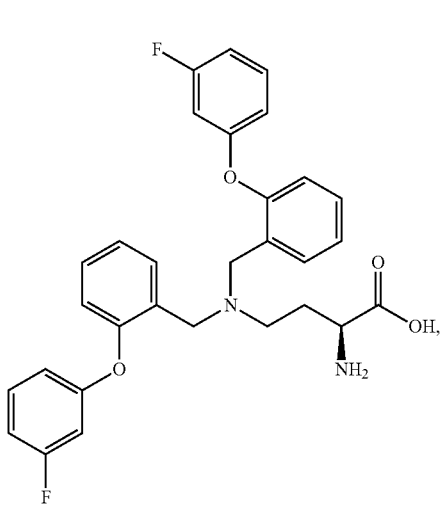
176
-continued
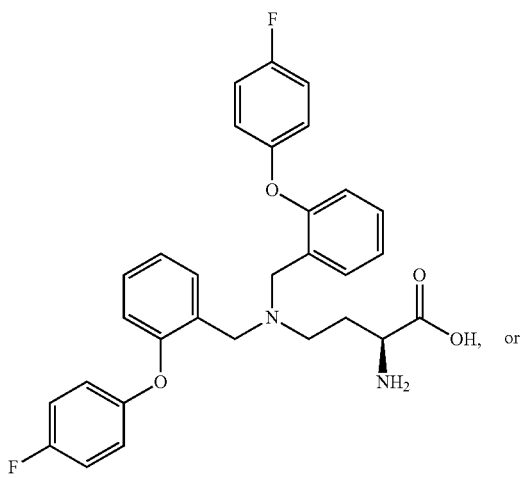
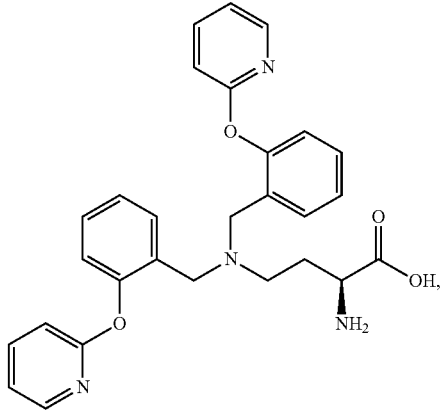
or a pharmaceutically acceptable salt thereof.
3. The compound of claim 1, of the following formula:
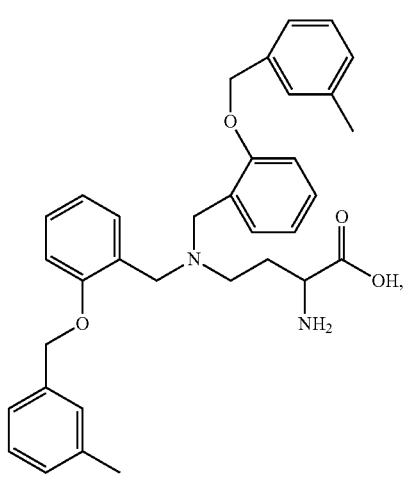 [SMILES: Cc1cccc(COc2ccccc2CN(CCC(N)C(=O)O)Cc2ccccc2OCc2cccc(C)c2)c1]
or a pharmaceutically acceptable salt thereof.

4. The compound of claim 1, of the following formula:

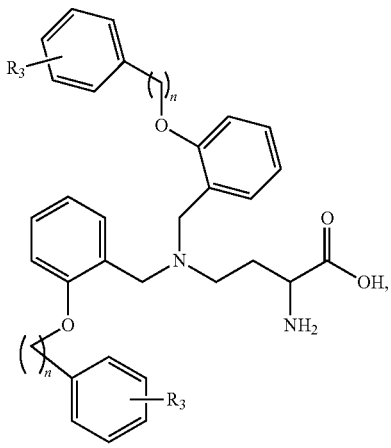

or a pharmaceutically acceptable salt thereof.

5. A compound of the following formula:

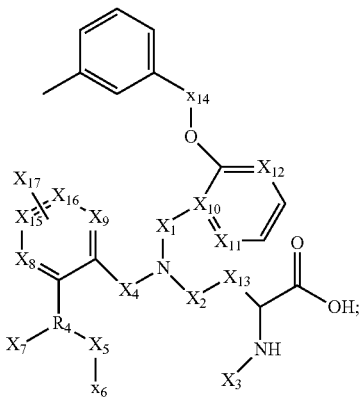

wherein:
$R_4$ is O or N;
$X_1$ is $CH_2$, or is CH and forms a ring with $X_9$ (substituted or unsubstituted), or is absent when $X_9$ forms a ring with $X_{10}$ and at the same time $X_{11}$ forms a ring with $X_2$;
$X_2$ is $CH_2$, or forms a ring with $X_3$ (substituted or unsubstituted),
$X_3$ is H, or forms a ring with $X_2$ (substituted or unsubstituted),
$X_4$ is $CH_2$, or forms a ring with $X_5$ or $X_7$ (substituted or unsubstituted),
$X_5$ is absent; $CH_2$; or forms a ring with $X_4$ (substituted or unsubstituted);
$X_6$ is absent, H, or phenyl (substituted or unsubstituted),
$X_7$ is H, absent, benzyl (substituted or unsubstituted) or forms a ring or bicyclic ring with $X_8$ or $X_4$ (substituted or unsubstituted);
$X_8$ is C, CH, or N, or forms a ring or bicyclic ring with $X_7$ (substituted or unsubstituted);

$X_9$ is C, CH, or N, or forms a ring or bicyclic ring with $X_1$, $X_{10}$, or $X_{11}$ (substituted or unsubstituted);
$X_{10}$ is C;
$X_{11}$ is CH, or forms a ring with $X_2$ or $X_{13}$ (substituted or unsubstituted);
$X_{12}$ is CH, or forms a ring with $X_{14}$ (substituted or unsubstituted);
$X_{13}$ is $CH_2$, or forms a ring with $X_{11}$ (substituted or unsubstituted);
$X_{14}$ is $CH_2$, or forms a ring with $X_{12}$ (substituted or unsubstituted);
$X_{15}$ is C, CH, or N;
$X_{16}$ is C, CH, or N;
$X_{17}$ is optionally present and is H, alkyl, halogen, alkoxy, CN, —$CF_3$, or —$OCF_3$;
or a pharmaceutically acceptable salt thereof.

6. The compound of claim 5, of the following formula:

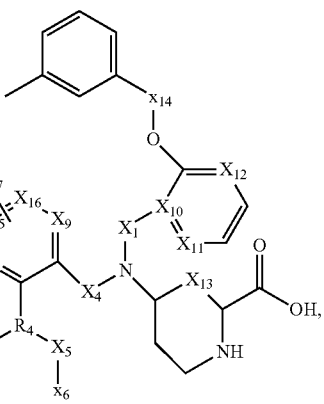

or a pharmaceutically acceptable salt thereof.

7. The compound of claim 5, of the following formula:

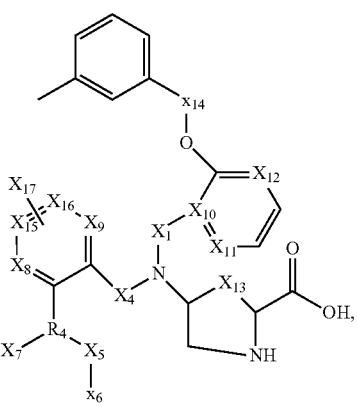

or a pharmaceutically acceptable salt thereof.

8. The compound of claim 5, of the following formula:
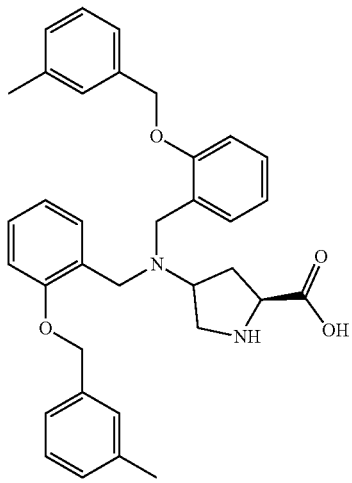
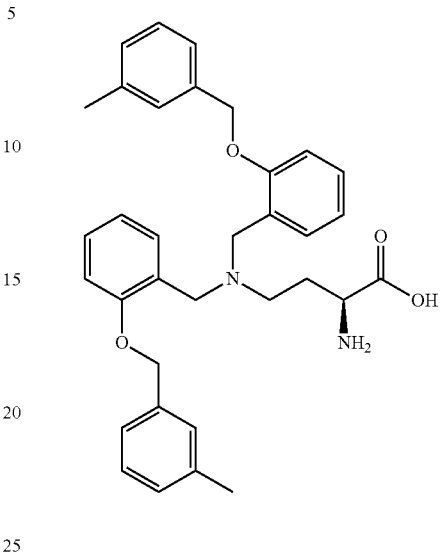
-continued
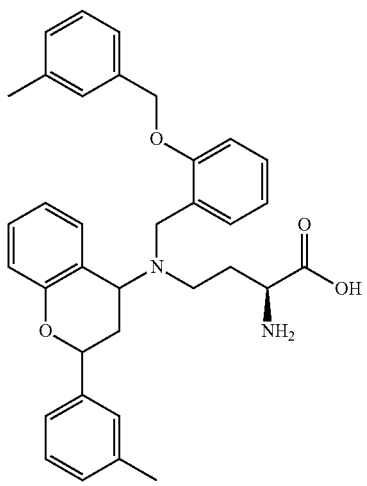
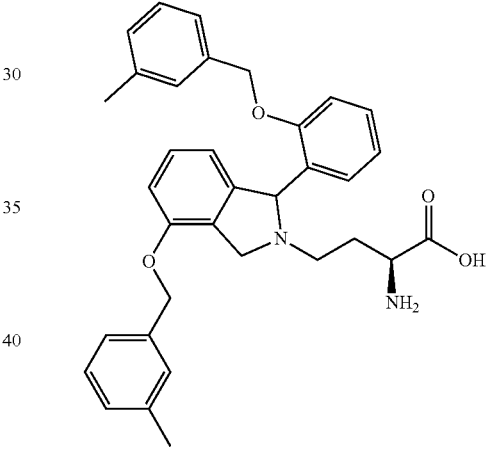
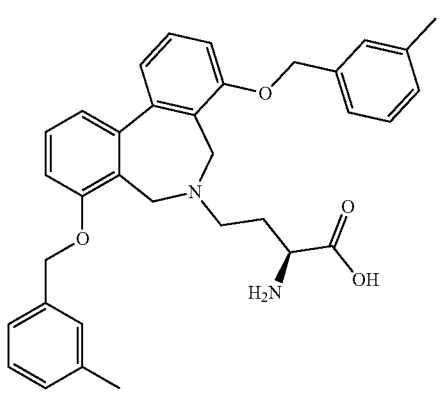
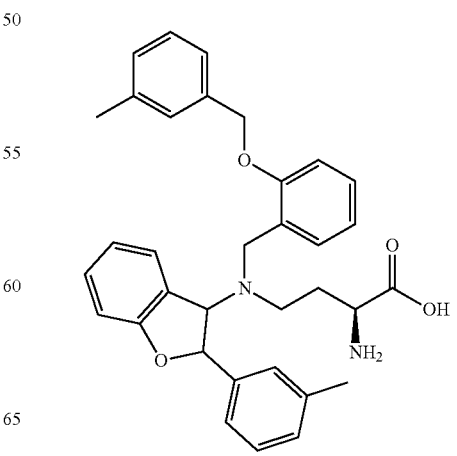

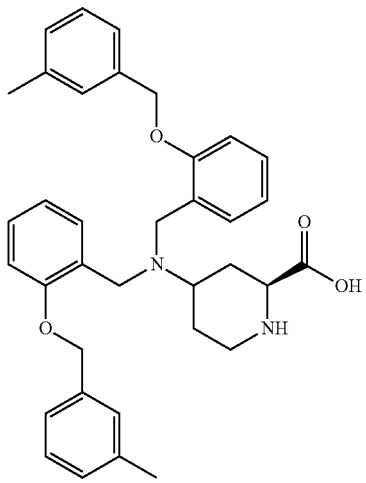
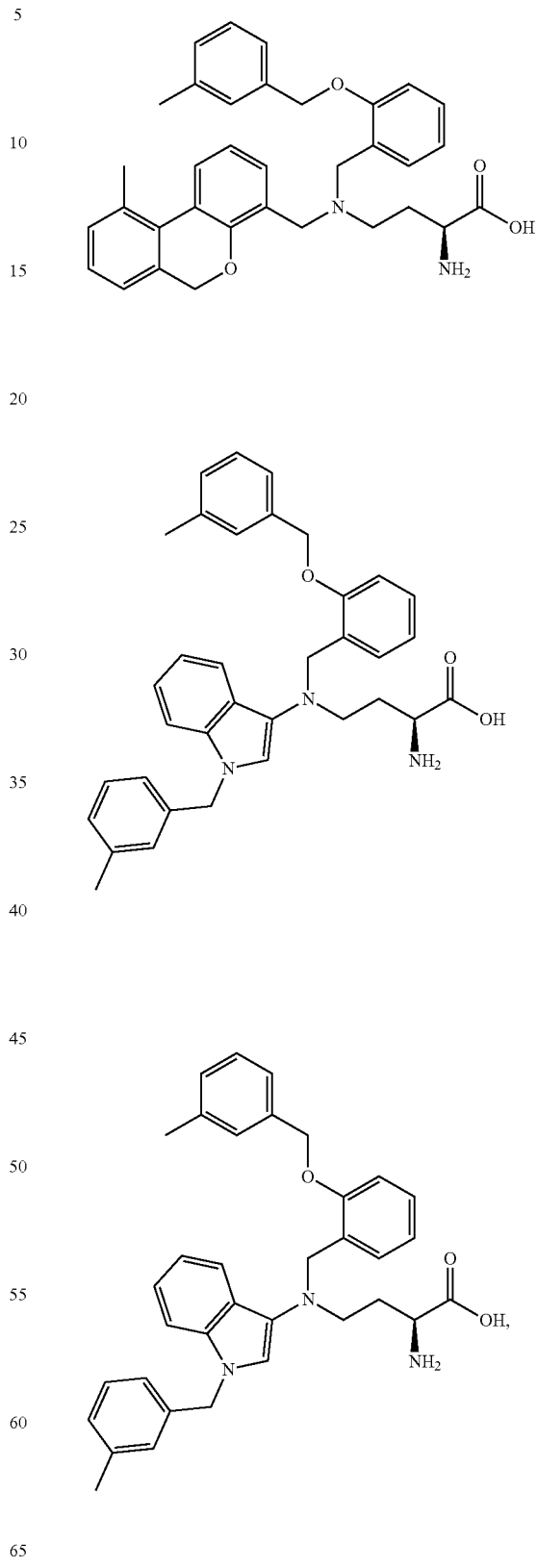
or a pharmaceutically acceptable salt thereof.

9. The compound of claim 5, of the following formula:
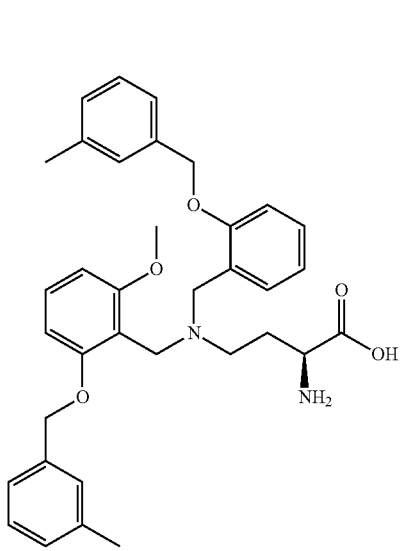
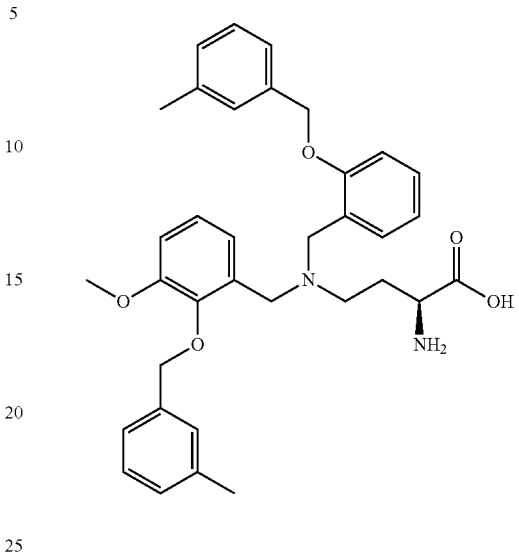
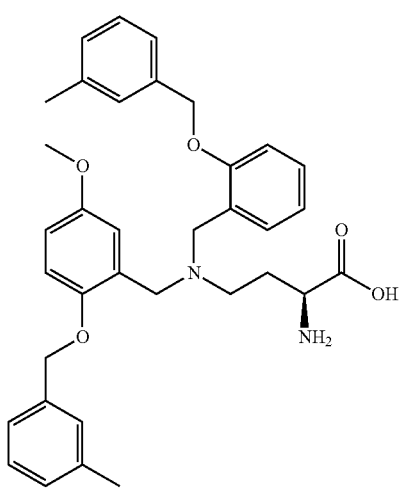
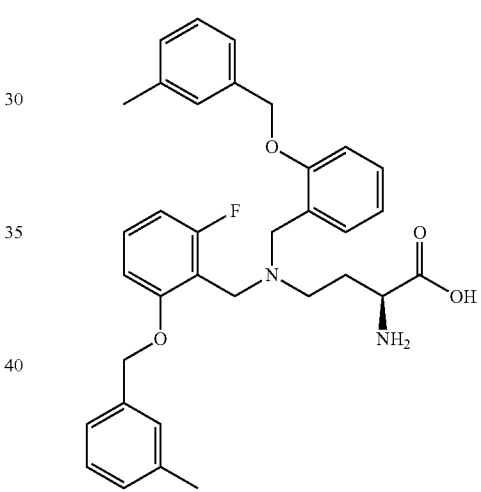
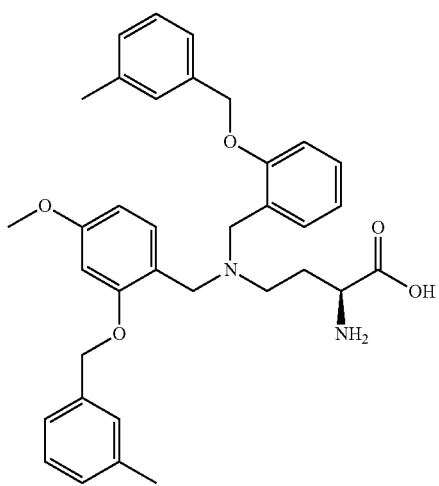
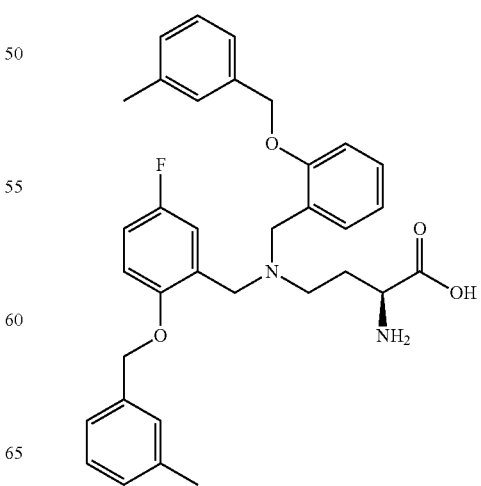

185
-continued
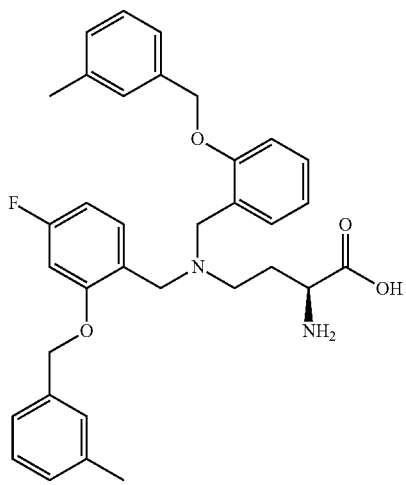
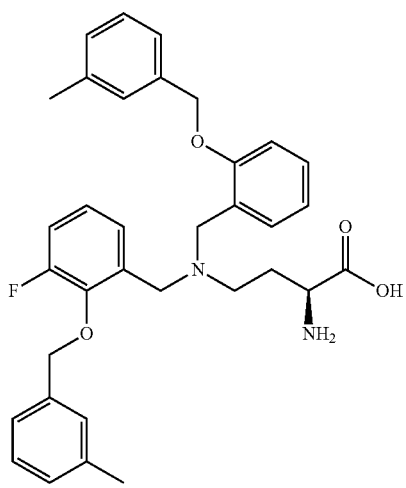
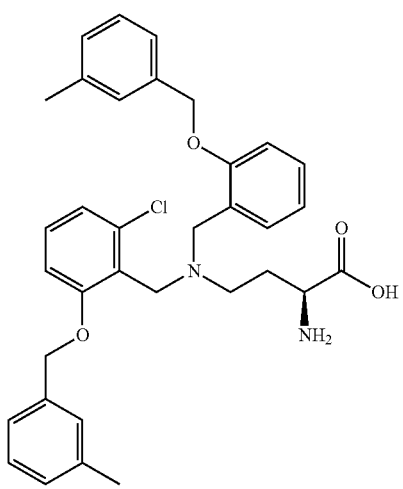
186
-continued
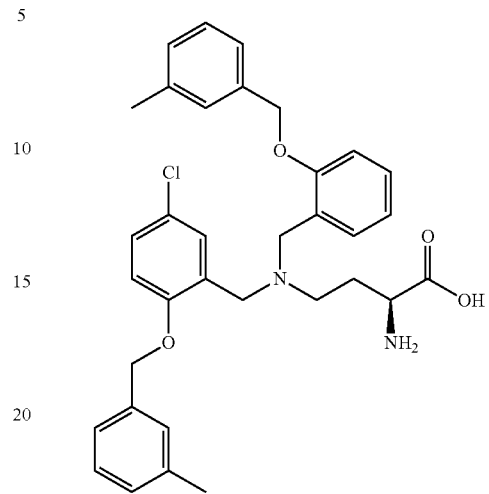
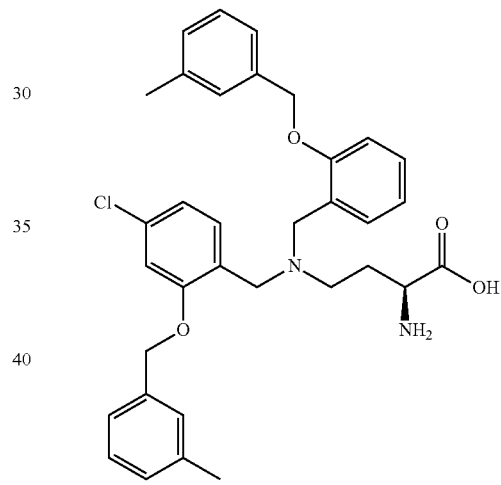
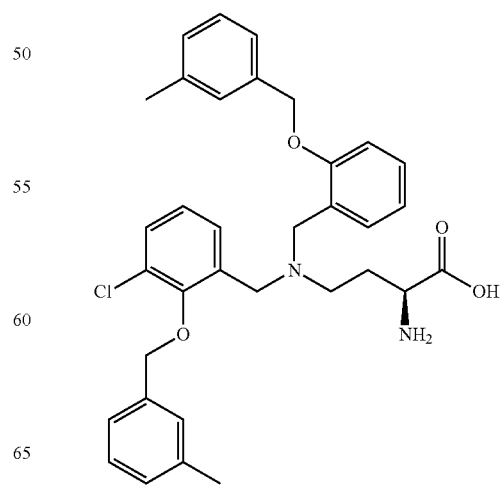

187
-continued
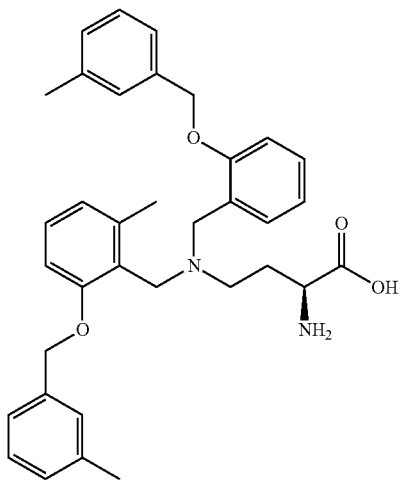
188
-continued
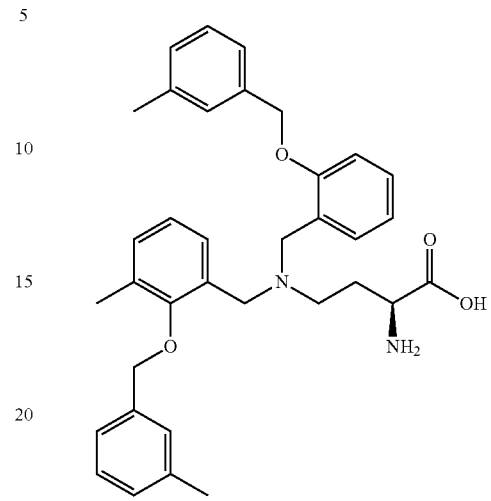
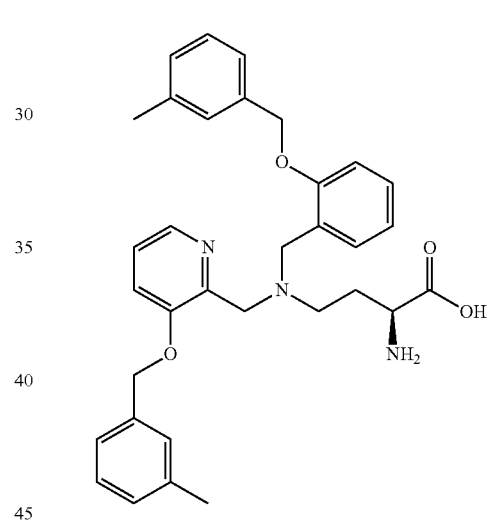
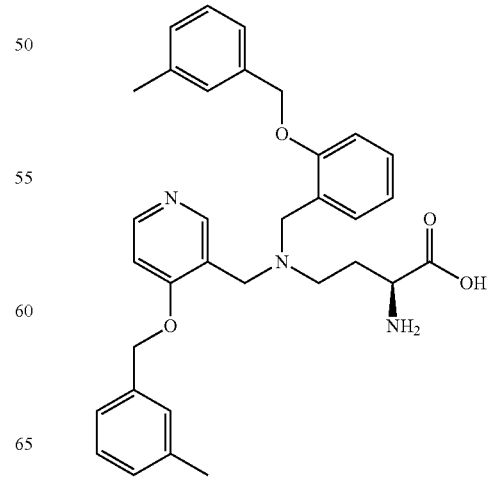

189
-continued
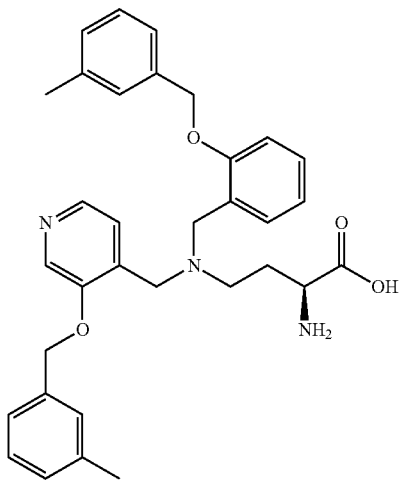
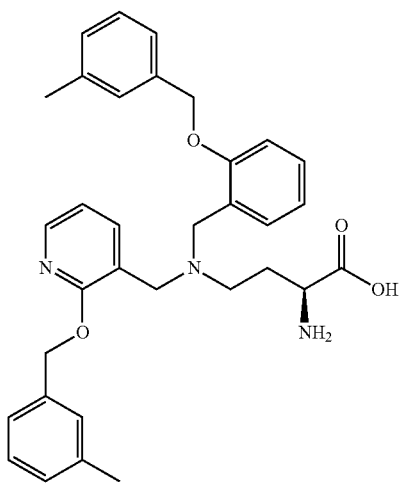
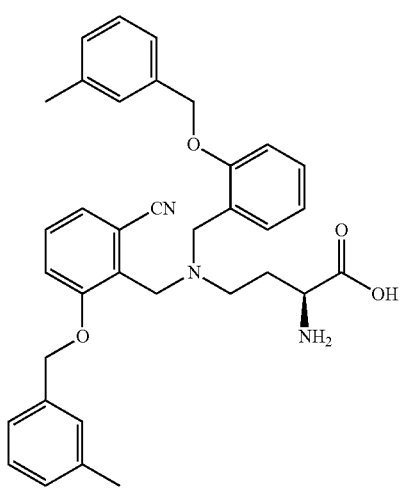
190
-continued
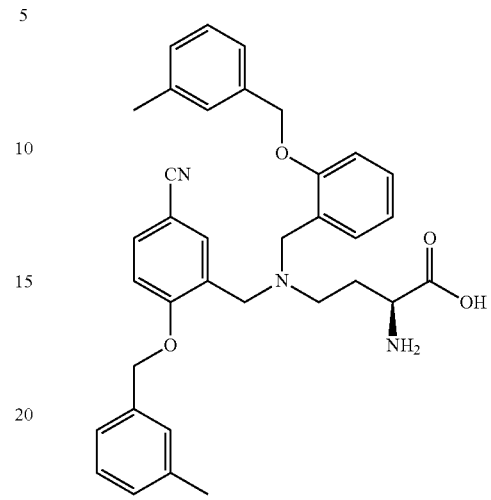
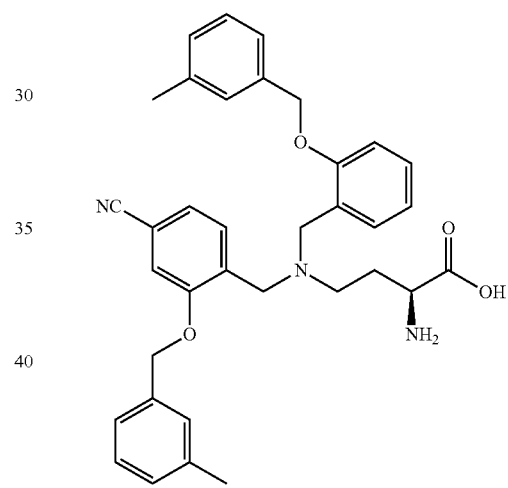
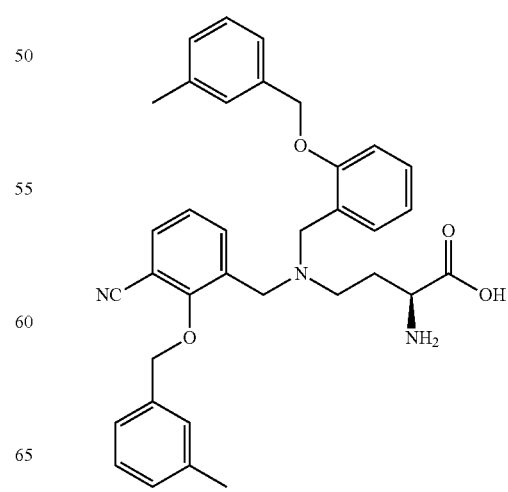

191
-continued
192
-continued
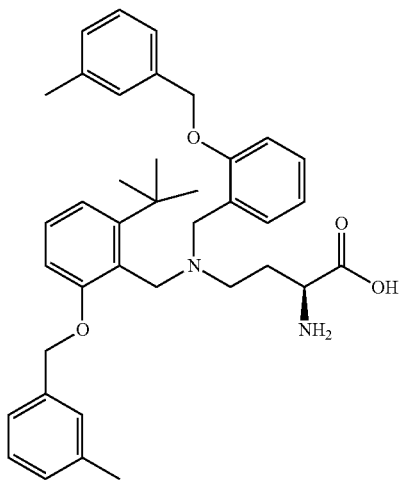
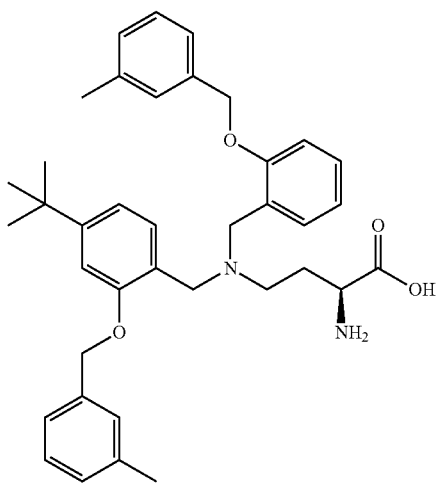
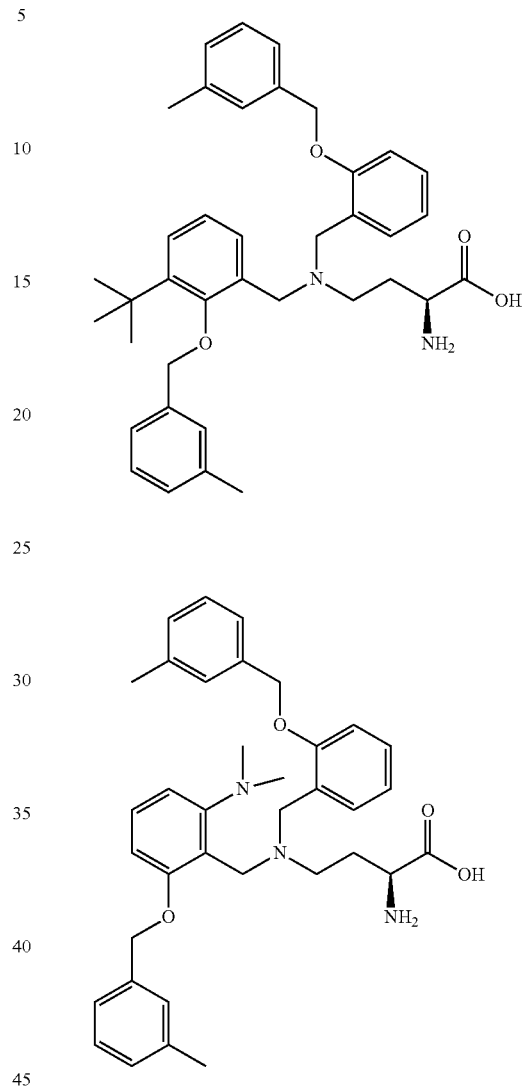
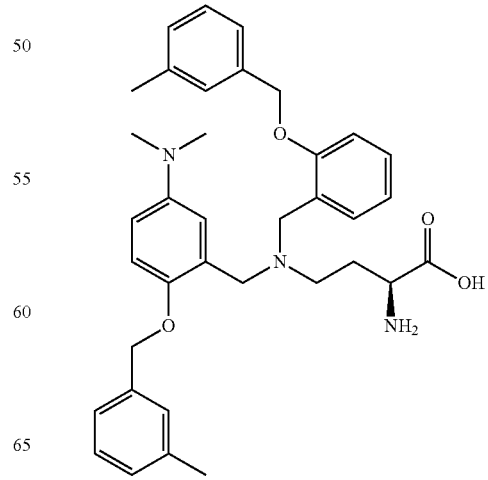

193
-continued
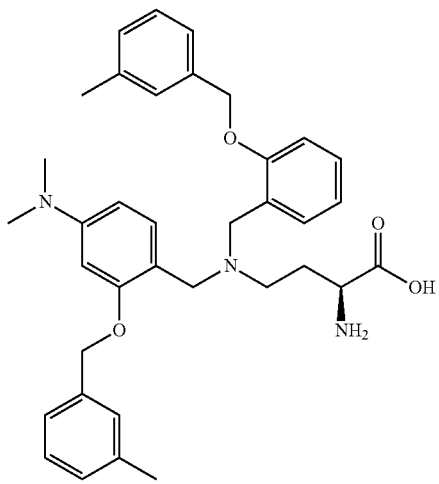
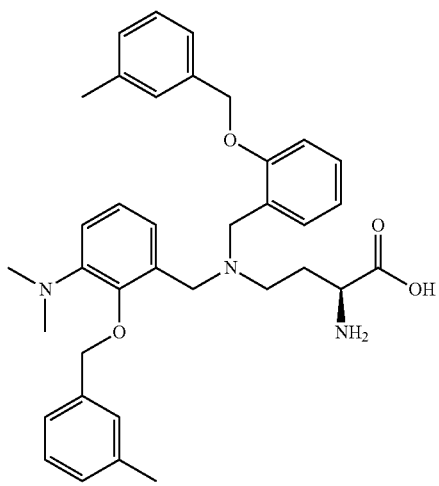
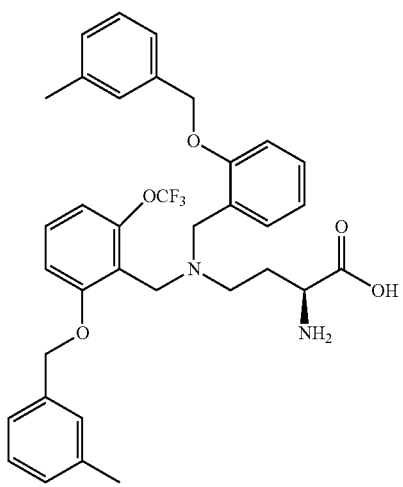
194
-continued
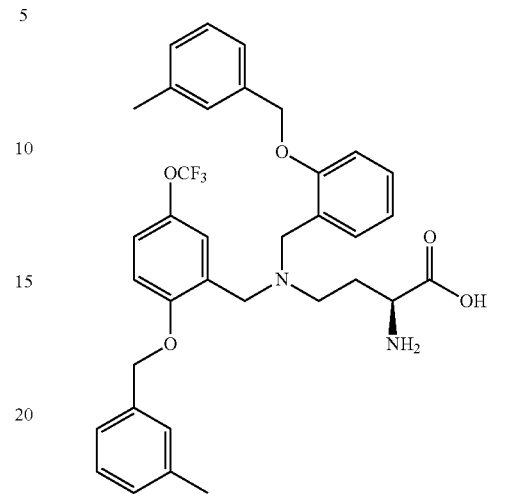
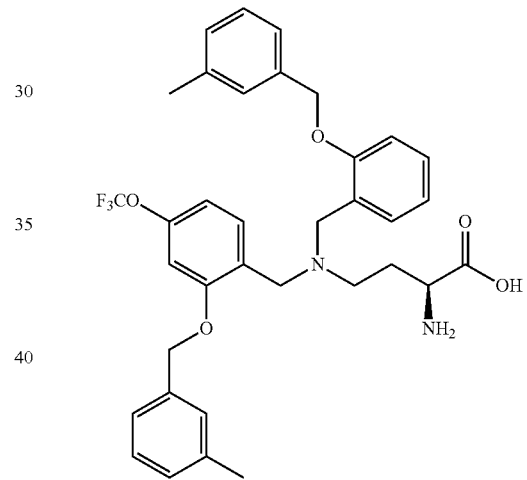
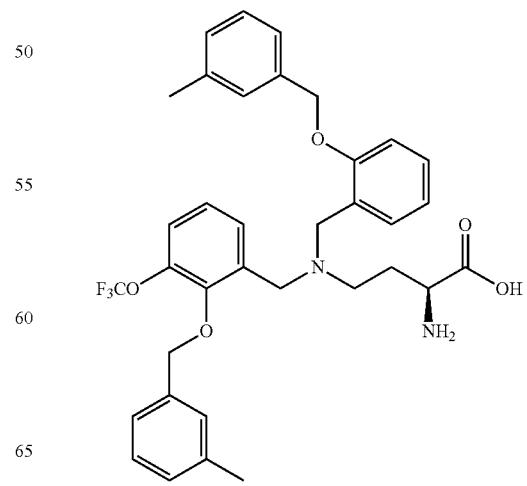

195
-continued
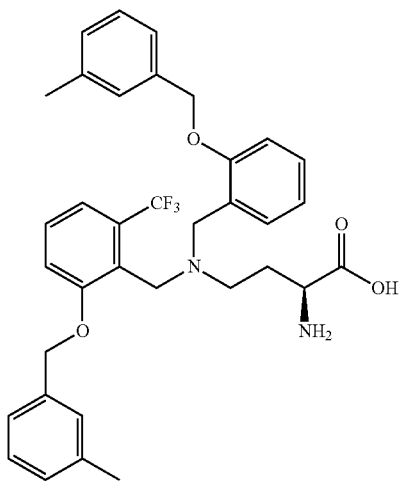
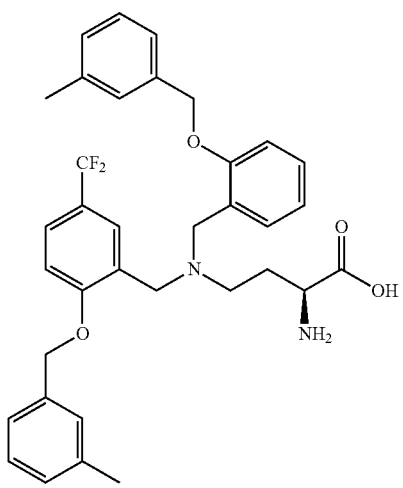
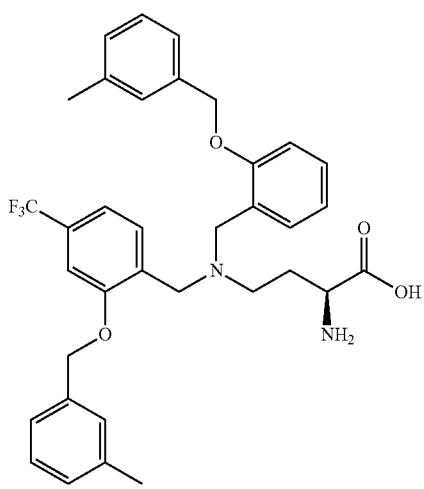
196
-continued
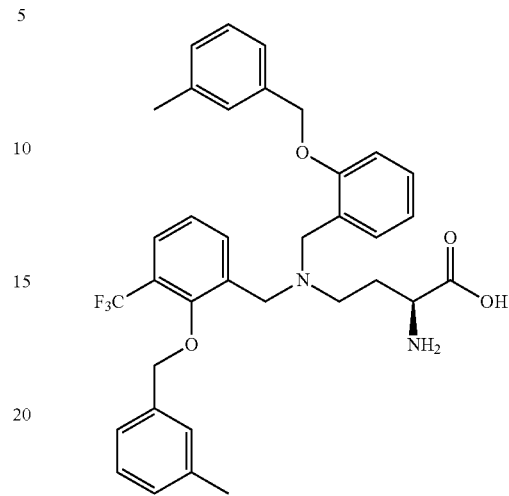
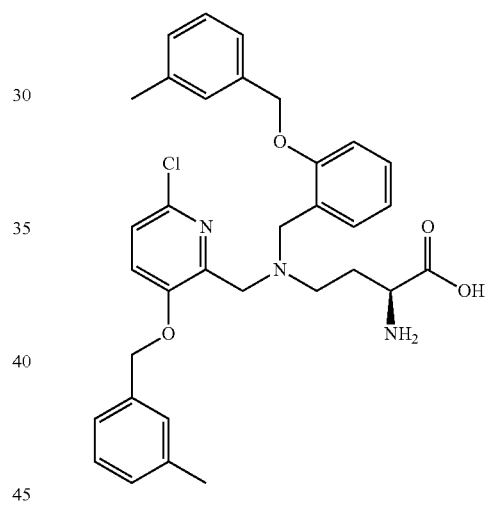
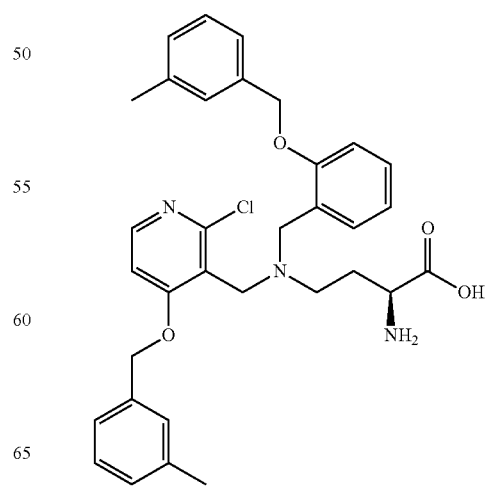

197
-continued
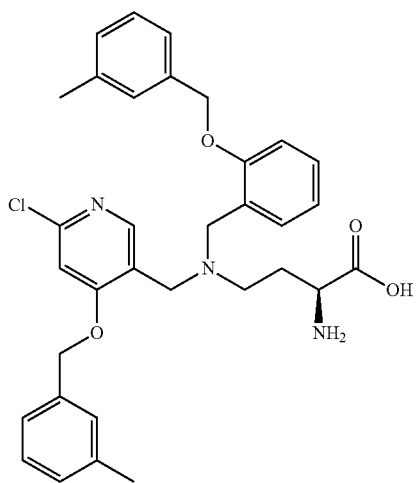
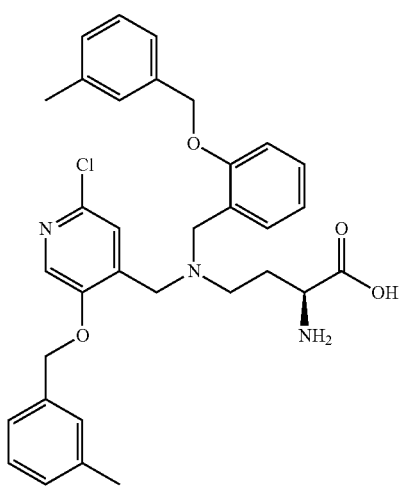
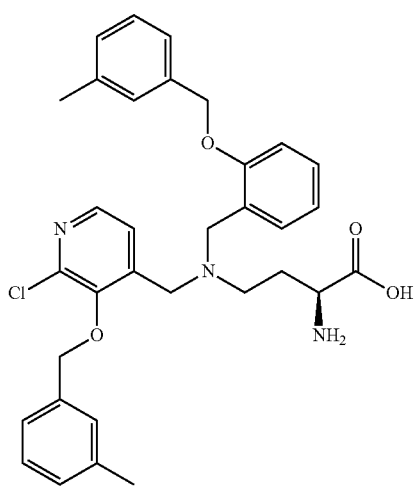
198
-continued
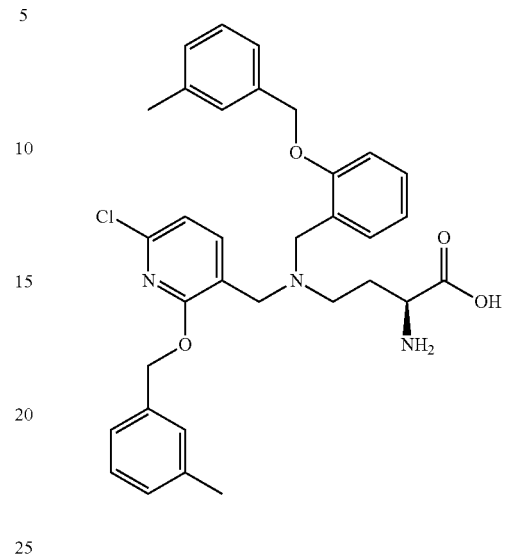
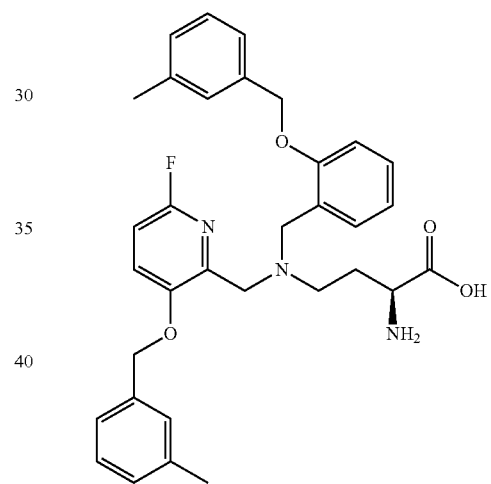
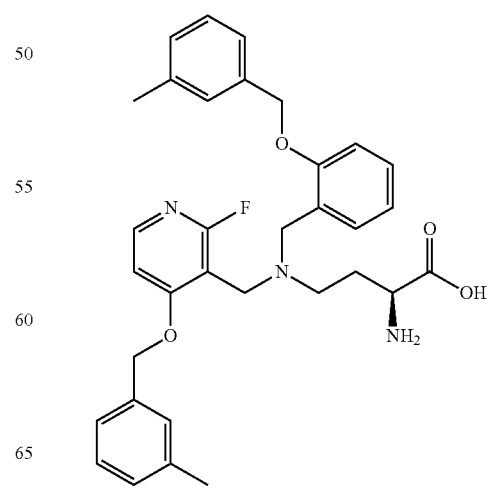

199
-continued
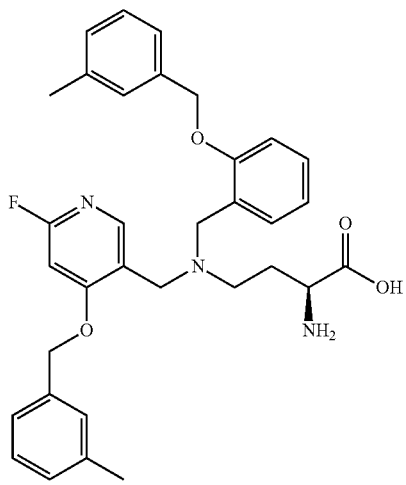
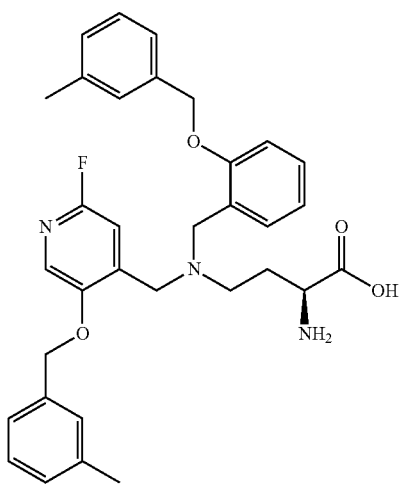
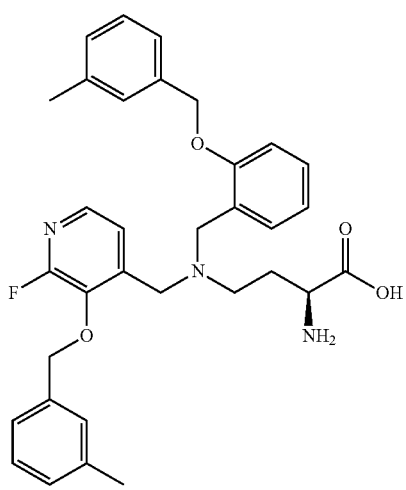
200
-continued
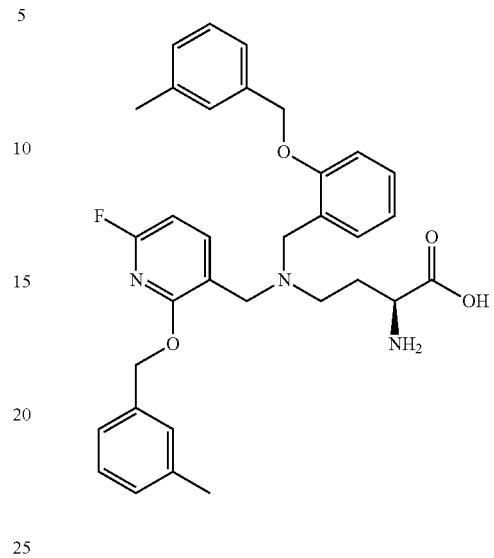
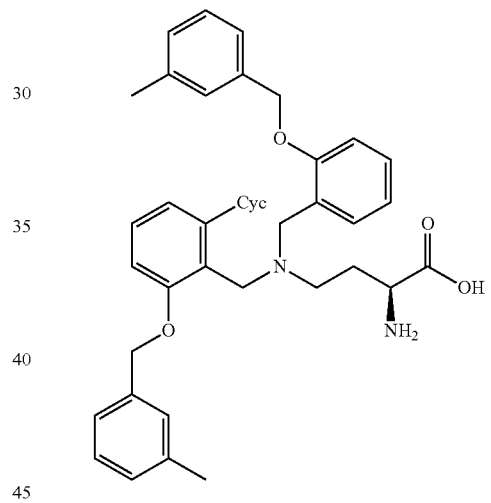
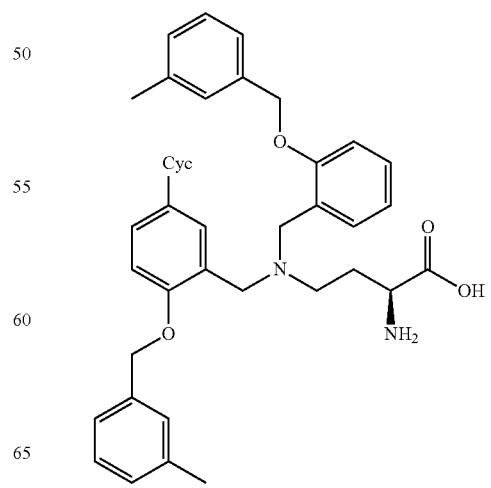

-continued

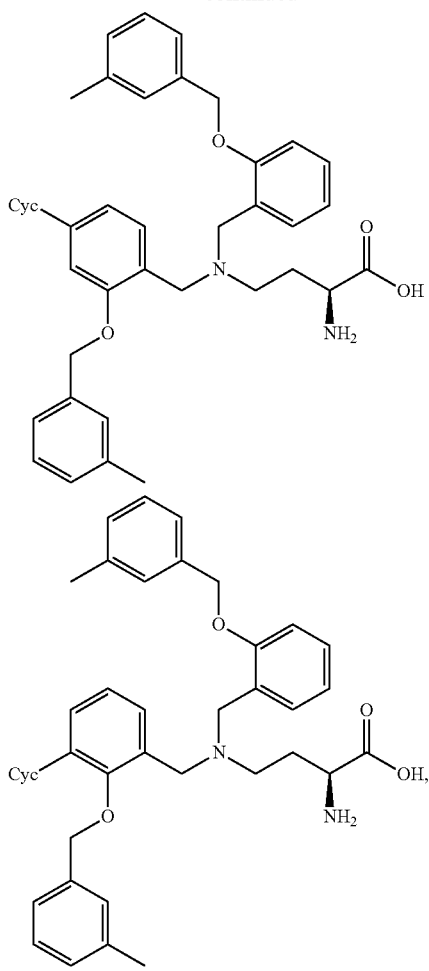

Cyc = cycles (examples: cycloalkyl, heterocycles)

or a pharmaceutically acceptable salt thereof.

10. The compound of claim 5, of the following formula:

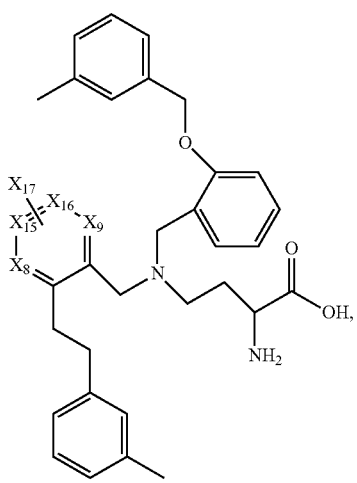

or a pharmaceutically acceptable salt thereof.

11. A compound of the following formula:

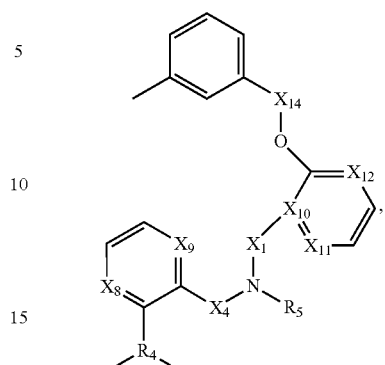

wherein:
$R_4$ is O or N;
$X_1$ is $CH_2$;
$X_4$ is $CH_2$;
$X_5$ is $CH_2$;
$X_6$ is phenyl (substituted or unsubstituted),
$X_7$ is H or absent;
$X_8$ is CH;
$X_9$ is CH;
$X_{10}$ is C;
$X_{11}$ is CH;
$X_{12}$ is CH;
$X_{14}$ is $CH_2$;
$R_5$ is:

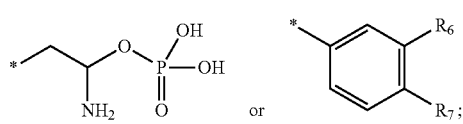

$R_6$ is NH C, CH, or $CH_2$;
$R_7$ is NH C, CH, or $CH_2$; and
$R_6$ and $R_7$ form a 5 or 6-membered heteroring optionally substituted by H, OH, amino, phosphonic acid, carbonyl, or acetic acid;
or a pharmaceutically acceptable salt thereof.

12. The compound of claim 11, of the following formula:

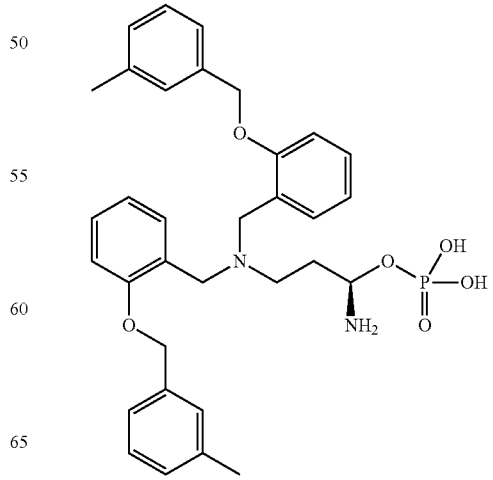

203
-continued
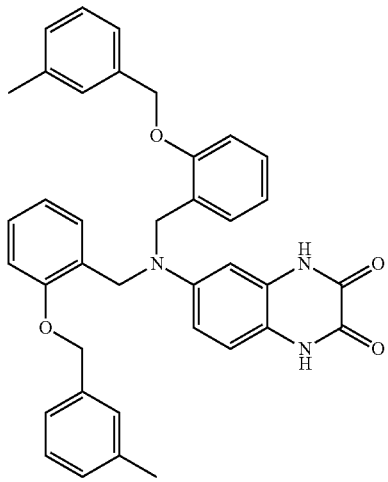
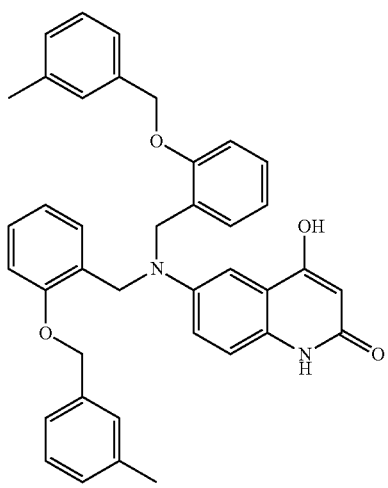
204
-continued
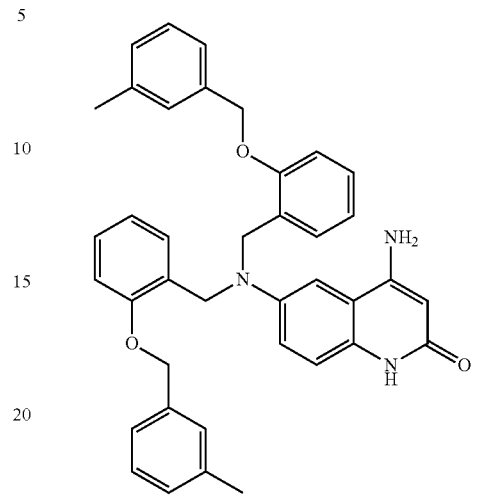
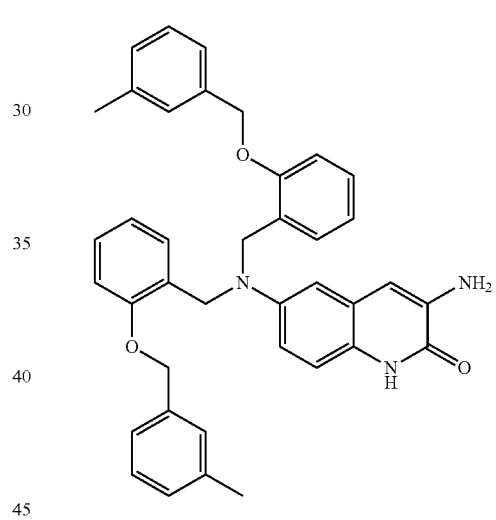
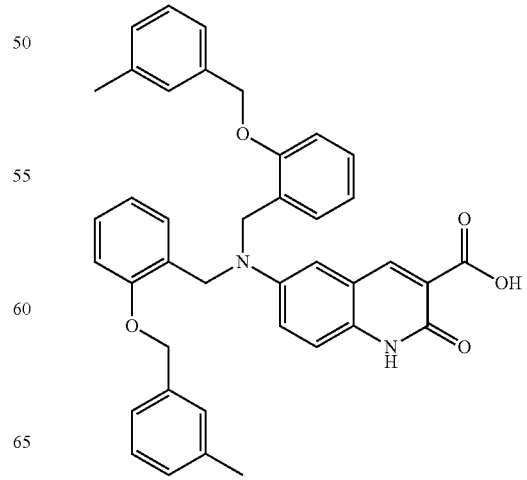

-continued

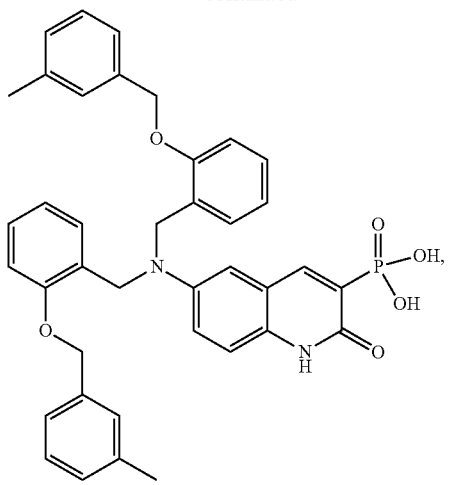

or a pharmaceutically acceptable salt thereof.

13. The compound of claim 11, wherein $R_6$ and $R_7$ are C, CH, $CH_2$, or NH, and form a ring.

14. A compound of the following formula:

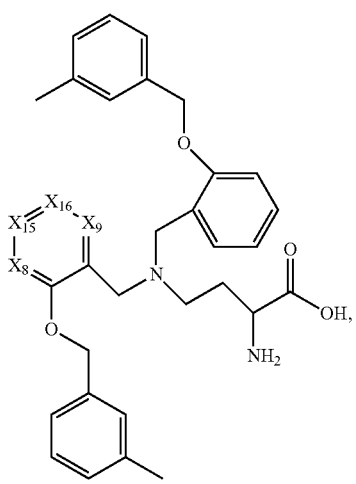

wherein:

$X_{16}$ and $X_9$ join to form a bicyclic ring (substituted or unsubstituted);

$X_{15}$ and $X_8$ join to form a bicyclic ring (substituted or unsubstituted); or $X_{16}$ and $X_{15}$ join to form a bicyclic ring (substituted or unsubstituted);

or a pharmaceutically acceptable salt thereof.

15. The compound of claim 14, wherein: $X_{16}$ and $X_9$, $X_{15}$ and $X_8$, or $X_{16}$ and $X_{15}$ join together to form pyrazole, pyrrole, pyridine, pyrrolidine, piperidine, phenyl, cyclohexane, cyclopentene, tetrahydropyran, pyran, furan, dioxolane, dioxane, oxazole, imidazole, thiophene, oxathiolane, dioxepane, or dioxepine.

16. The compound of claim 14, of the following formula:

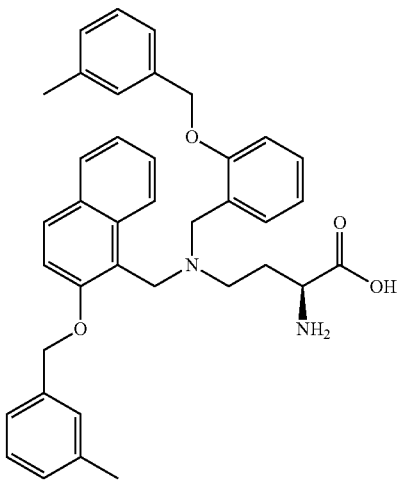

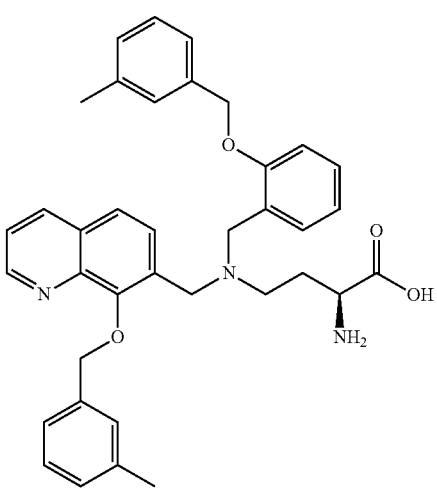

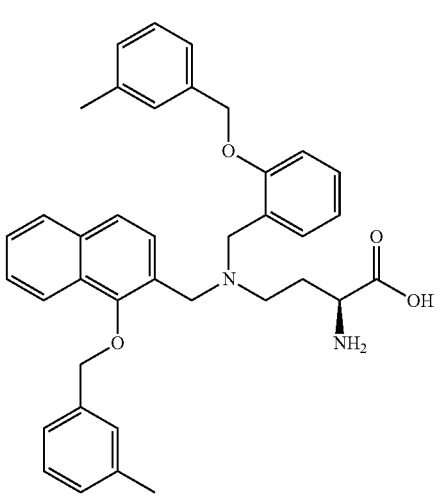

207
-continued
208
-continued
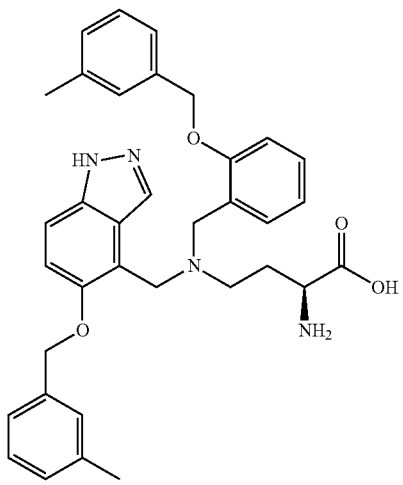
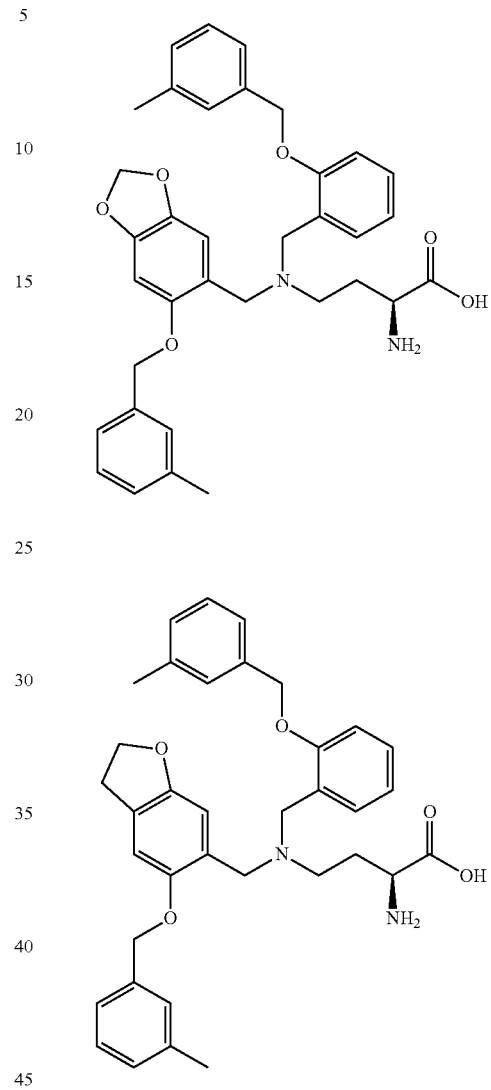
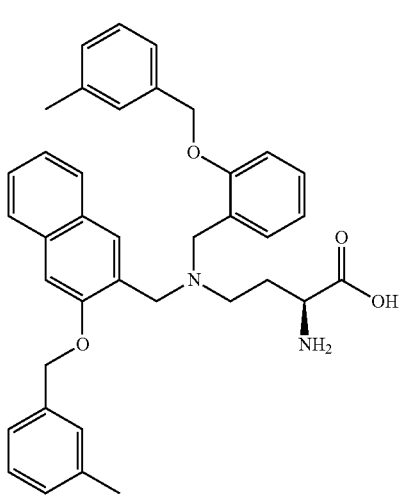

209
-continued
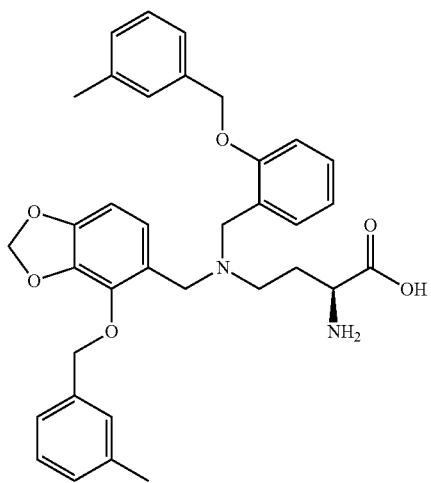
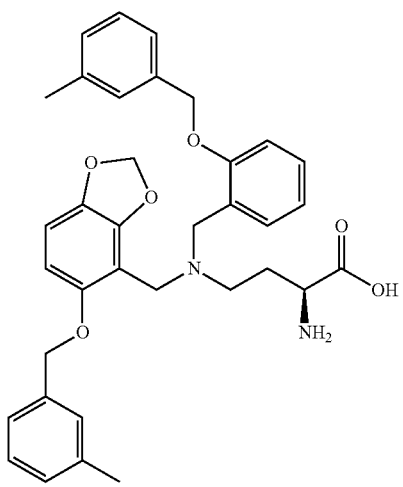
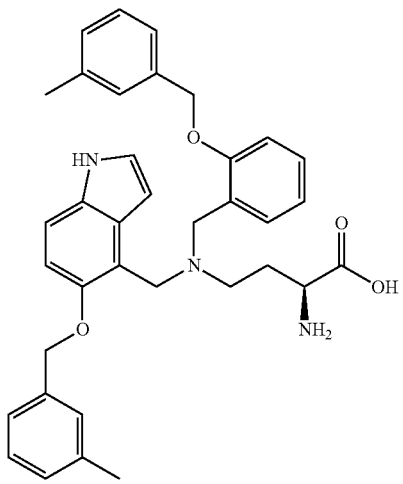
210
-continued
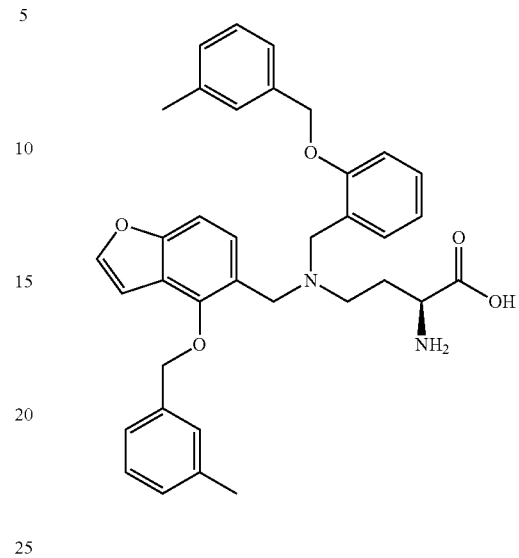
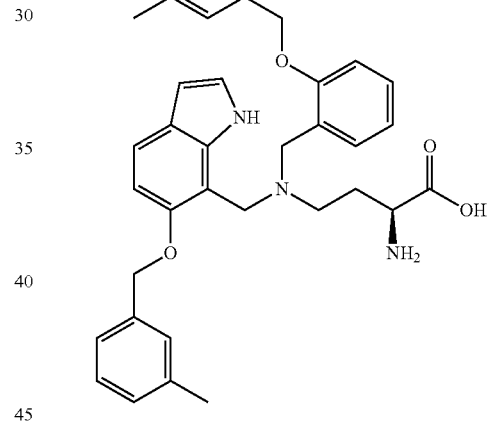
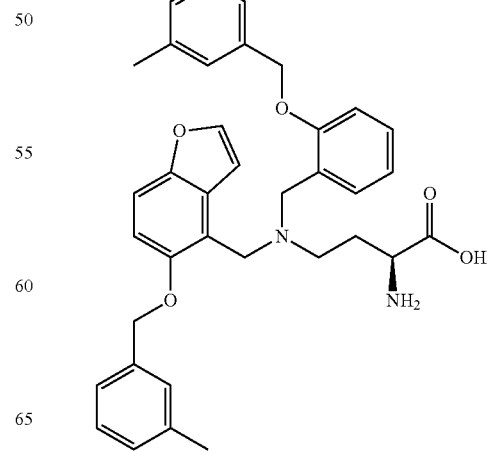

211
-continued
212
-continued
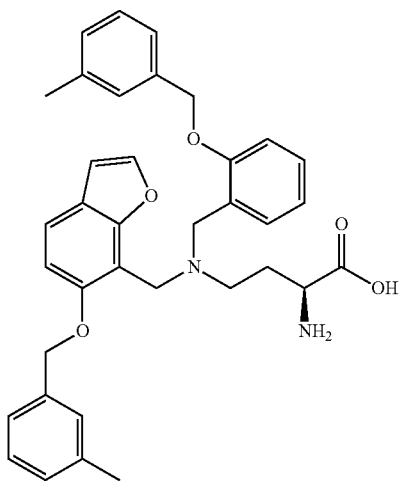
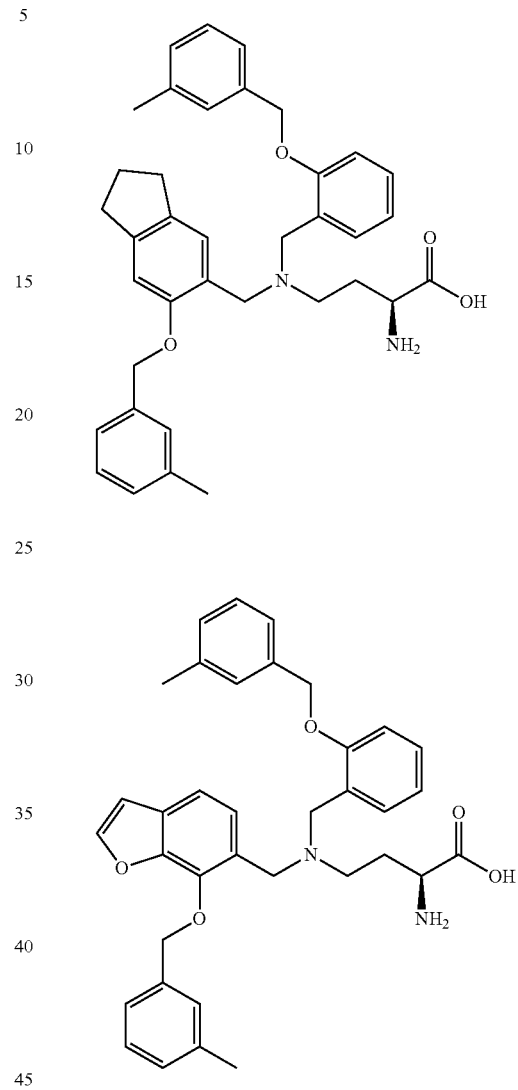
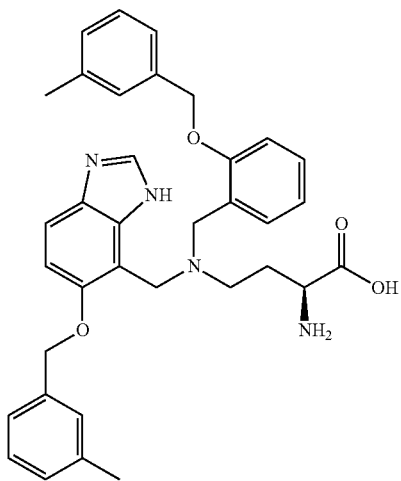
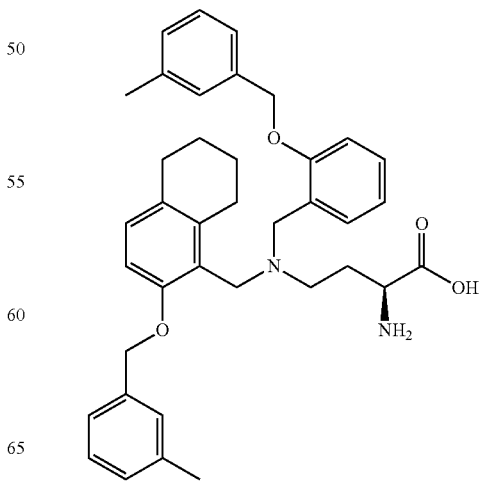

213
-continued
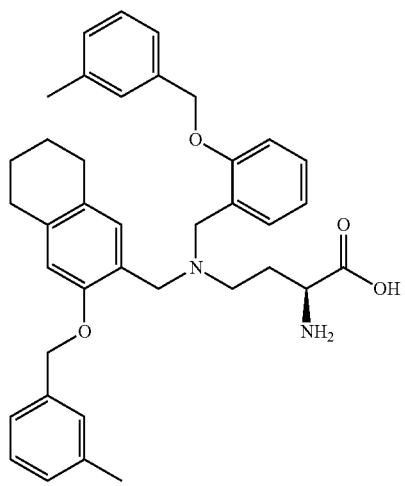
214
-continued
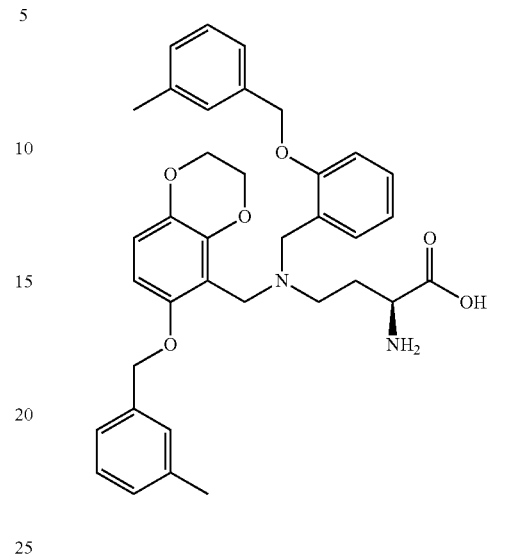
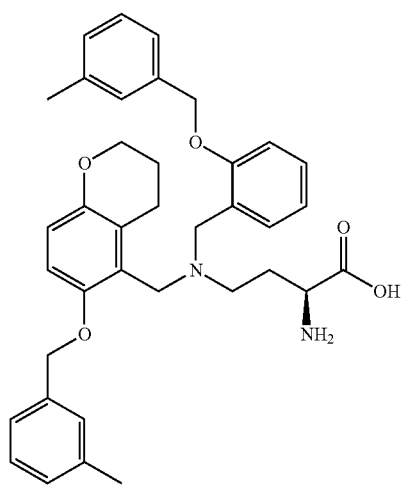
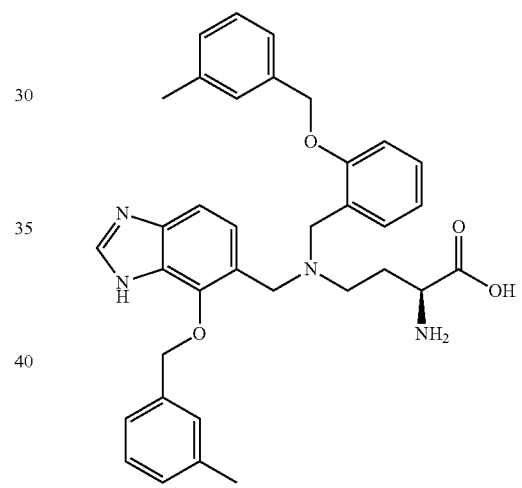
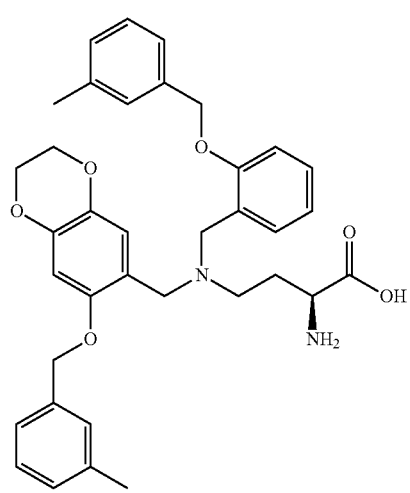
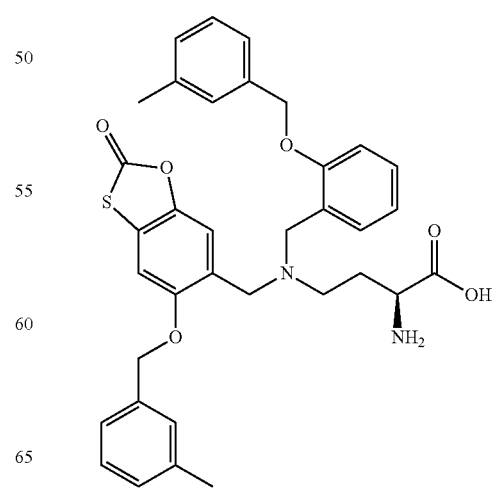

215
-continued
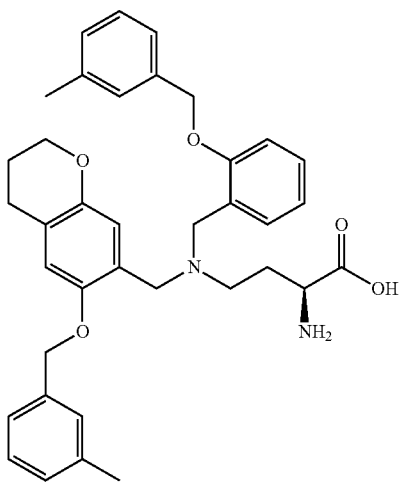
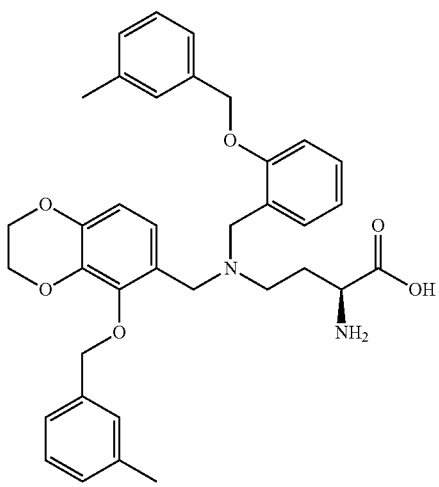
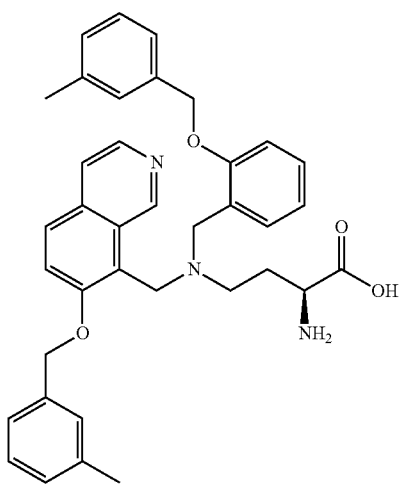
216
-continued
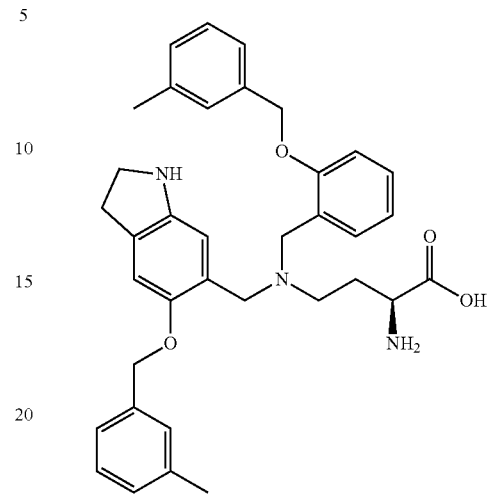
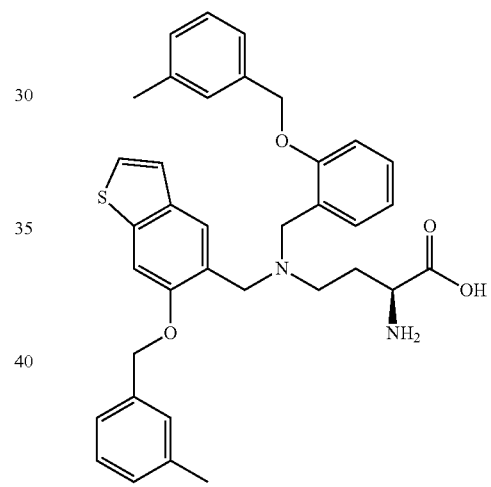
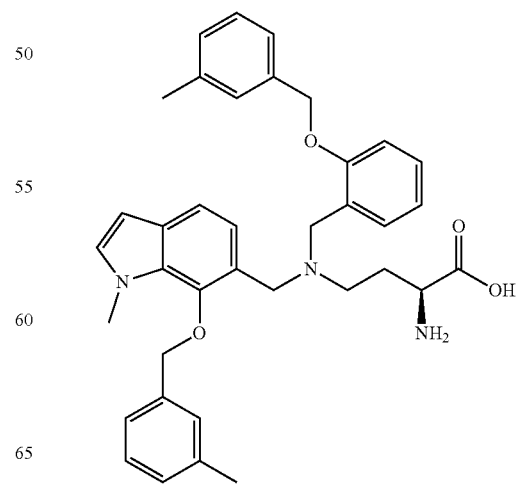

217
-continued
218
-continued
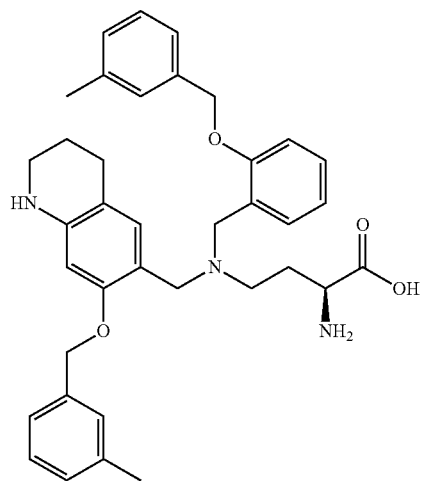
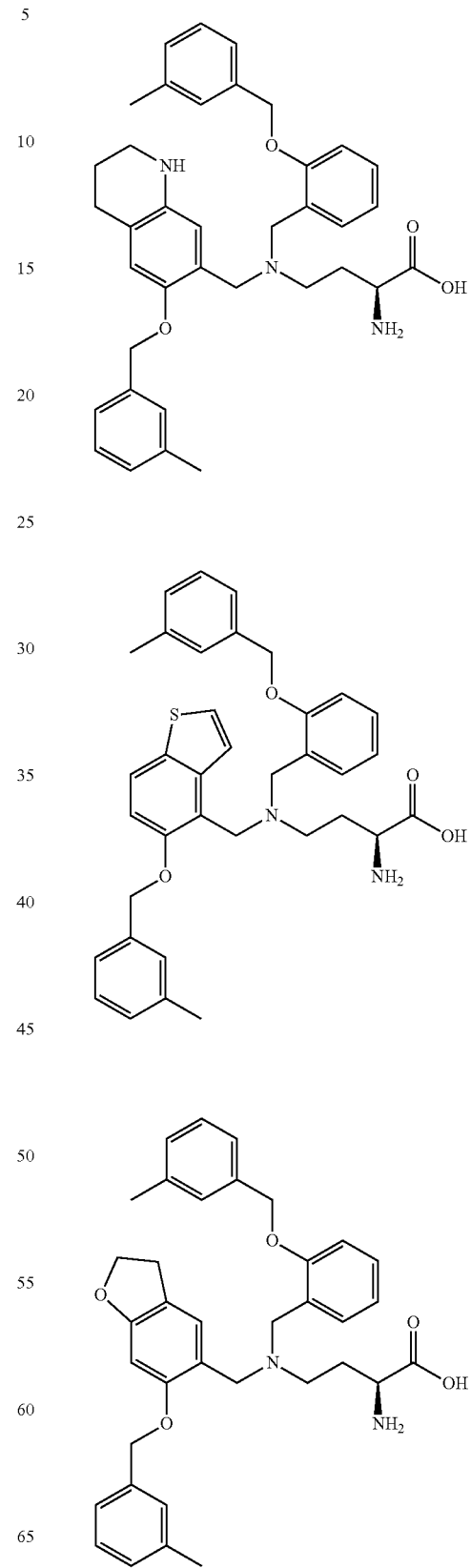

219
-continued
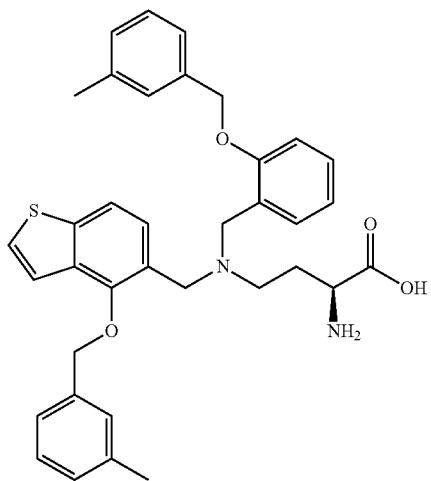
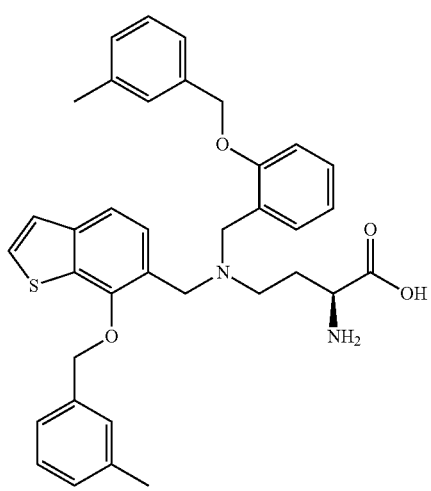 [SMILES: Cc1cccc(COc2ccccc2CN(CC[C@H](N)C(=O)O)Cc2ccc3ncoc3c2OCc2cccc(C)c2)c1]
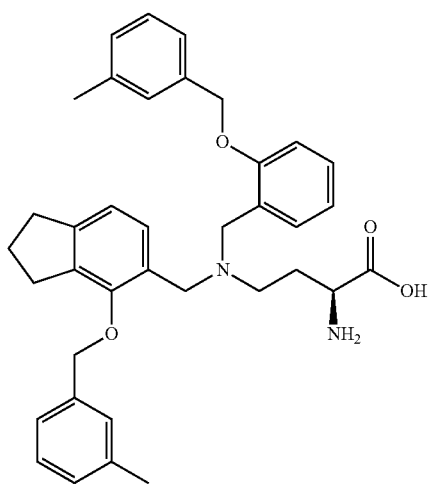
220
-continued
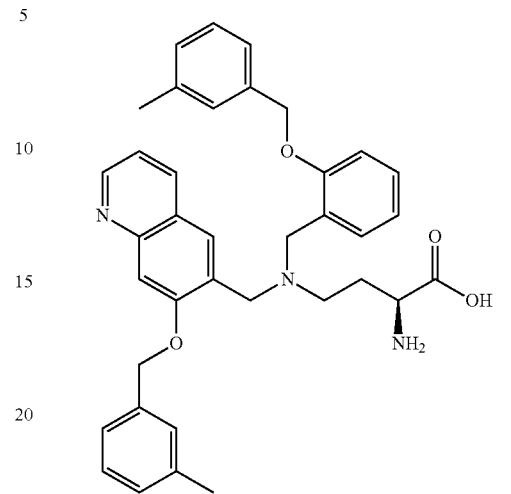
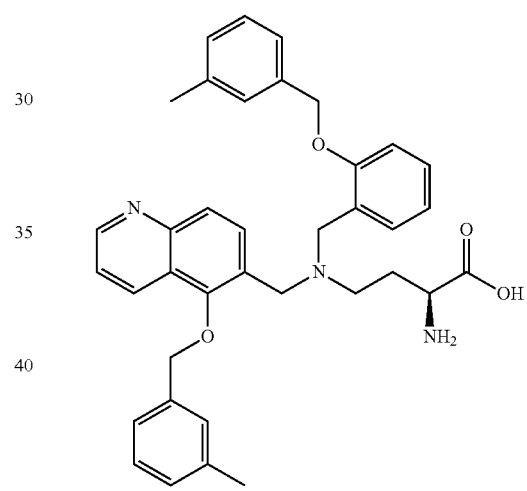
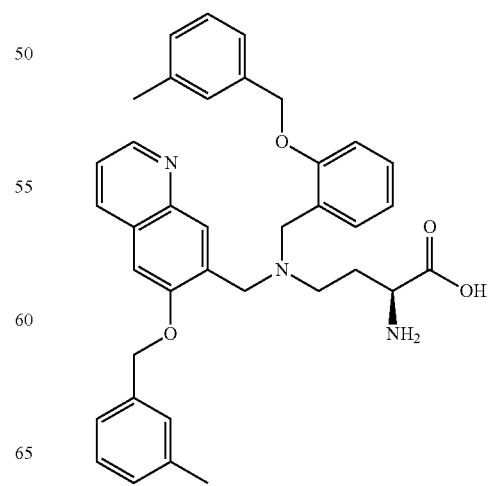

221
-continued
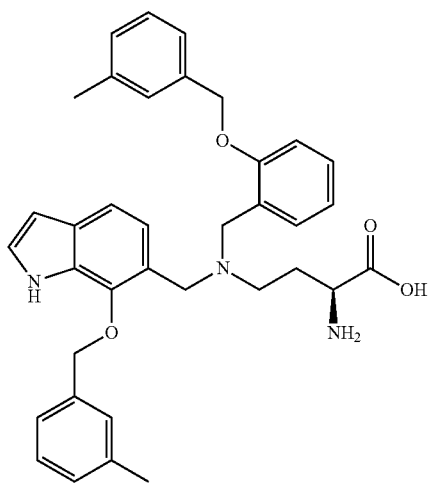
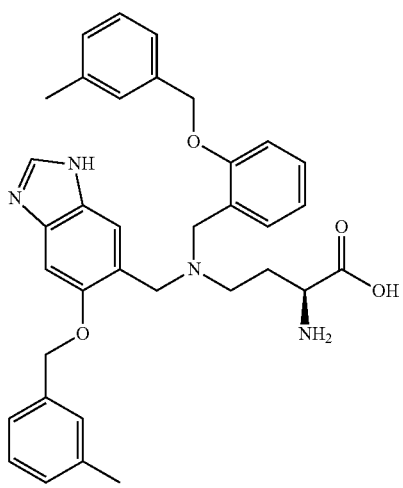
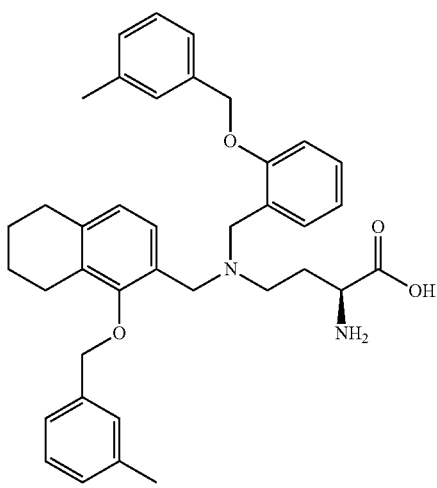
222
-continued
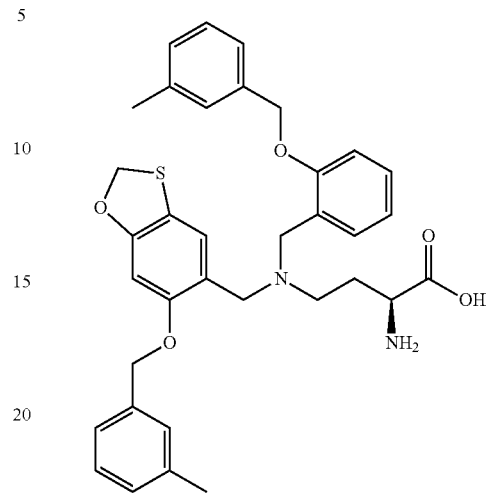
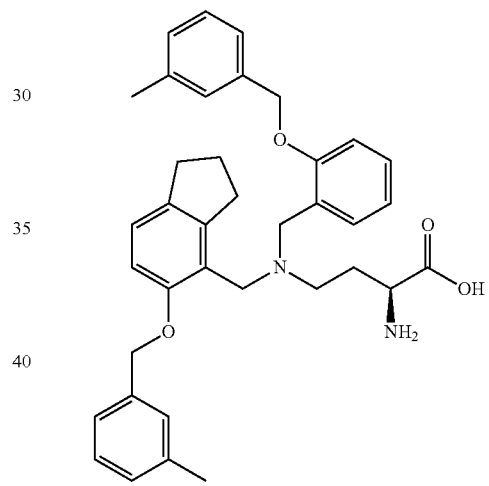
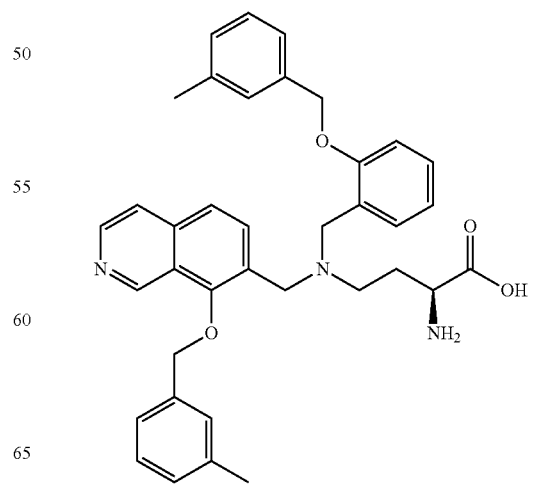

223
-continued
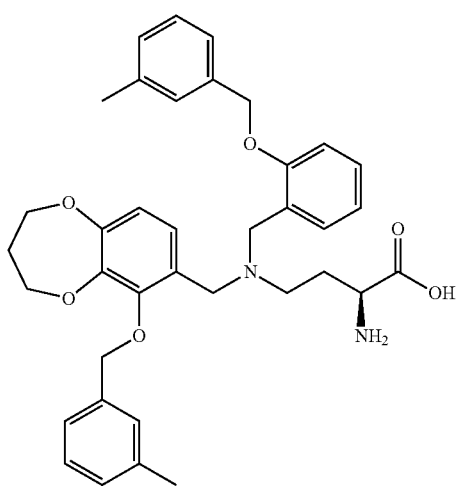
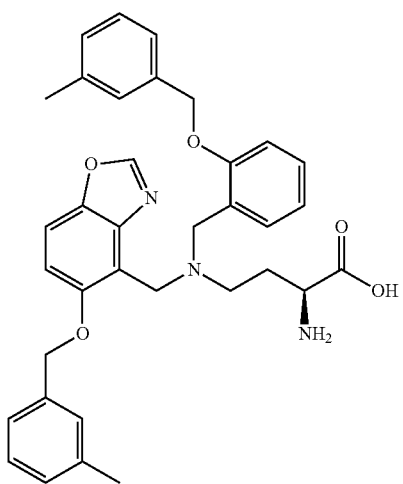
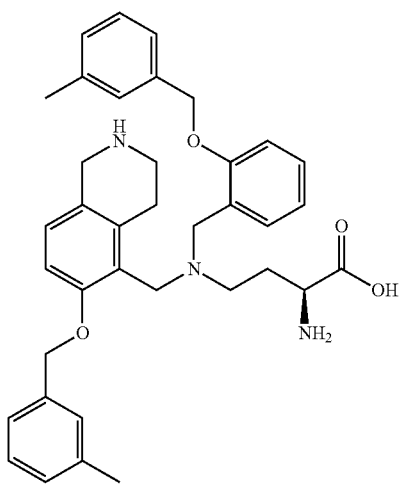
224
-continued
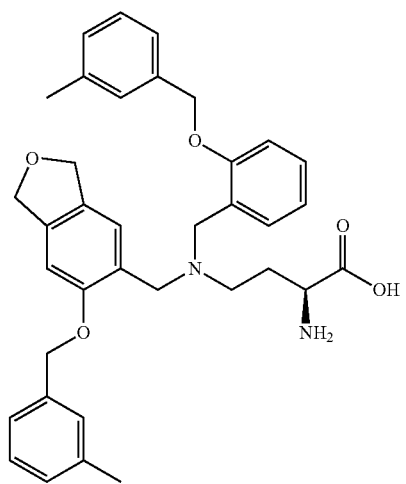
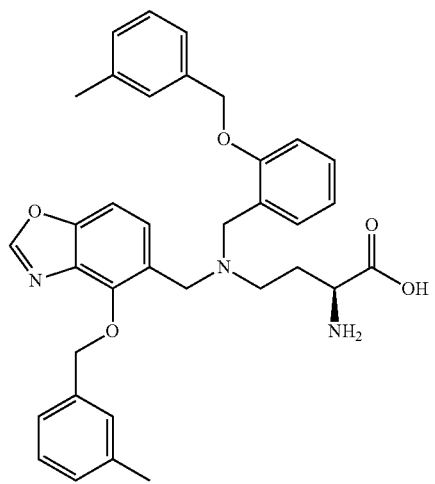
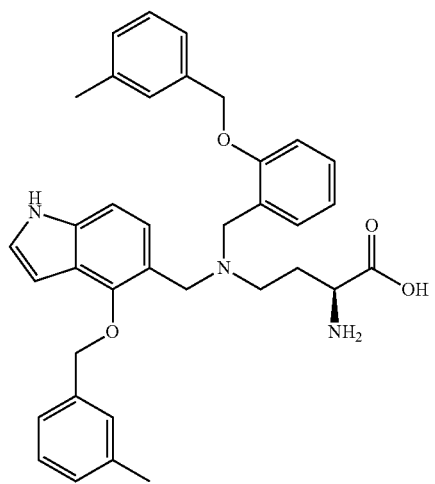

225
-continued

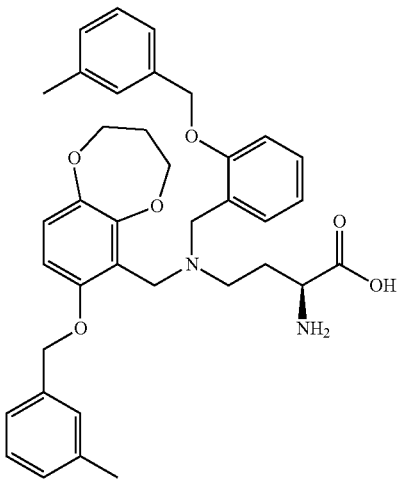

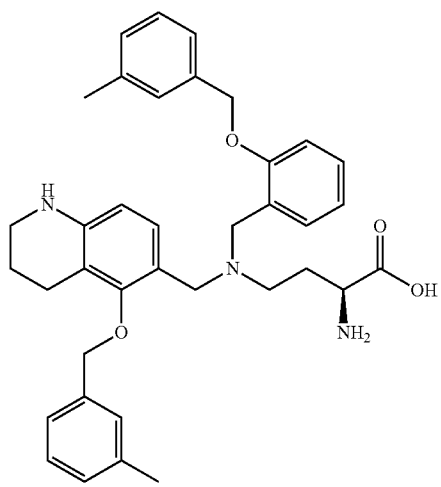

226
-continued

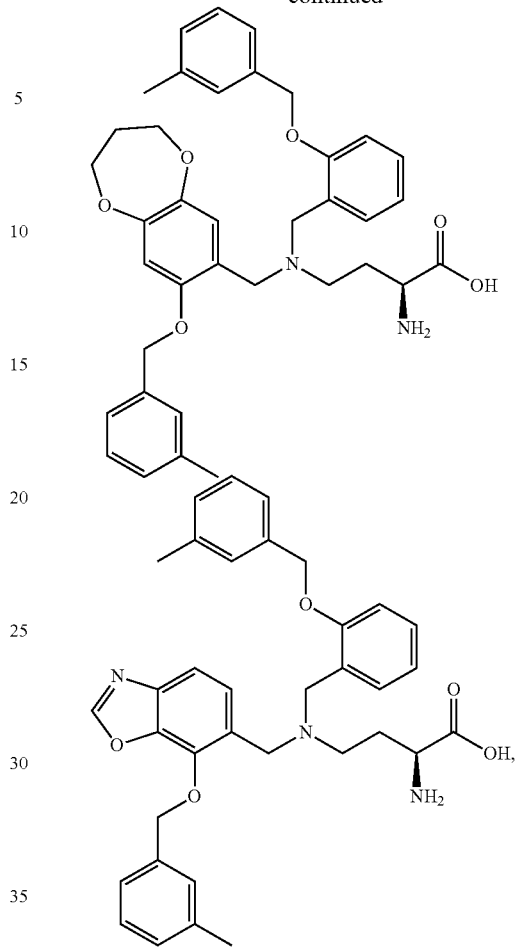

or a pharmaceutically acceptable salt thereof.

17. A pharmaceutical composition, comprising a compound of claim 1, or a pharmaceutically acceptable salt thereof, and a pharmaceutically acceptable carrier.

18. A method of treating cancer in a subject in need thereof, the method comprising administering a therapeutically effective amount of a compound of claim 1, or a pharmaceutically acceptable salt thereof, to the subject.

19. A method of treating cancer in a subject in need thereof, the method comprising administering a therapeutically effective amount of a compound of claim 5, or a pharmaceutically acceptable salt thereof, to the subject.

20. A method of treating cancer in a subject in need thereof, the method comprising administering a therapeutically effective amount of a compound of claim 14, or a pharmaceutically acceptable salt thereof, to the subject.

* * * * *